US010654769B2

(12) United States Patent
Cizeron et al.

(10) Patent No.: US 10,654,769 B2
(45) Date of Patent: May 19, 2020

(54) CATALYSTS FOR PETROCHEMICAL CATALYSIS

(71) Applicant: Siluria Technologies, Inc., San Francisco, CA (US)

(72) Inventors: Joel M. Cizeron, Redwood City, CA (US); Erik C. Scher, San Francisco, CA (US); Fabio R. Zurcher, Brisbane, CA (US); Wayne P. Schammel, Brisbane, CA (US); Greg Nyce, Pleasanton, CA (US); Anja Rumplecker, San Francisco, CA (US); Jarod McCormick, San Carlos, CA (US); Marian Alcid, Sunnyvale, CA (US); Joel Gamoras, Vallejo, CA (US); Daniel Rosenberg, San Francisco, CA (US); Erik-Jan Ras, Amsterdam (NL)

(73) Assignee: Siluria Technologies, Inc., San Francisco, CA (US)

(*) Notice: Subject to any disclaimer, the term of this patent is extended or adjusted under 35 U.S.C. 154(b) by 0 days.

(21) Appl. No.: 15/944,665

(22) Filed: Apr. 3, 2018

(65) Prior Publication Data
US 2019/0077728 A1 Mar. 14, 2019

Related U.S. Application Data

(63) Continuation of application No. 15/228,937, filed on Aug. 4, 2016, now Pat. No. 9,963,402, which is a (Continued)

(51) Int. Cl.
*B01J 23/30* (2006.01)
*C07C 2/84* (2006.01)
(Continued)

(52) U.S. Cl.
CPC ............. *C07C 2/84* (2013.01); *B01J 19/0046* (2013.01); *B01J 21/066* (2013.01); *B01J 21/08* (2013.01);
(Continued)

(58) Field of Classification Search
CPC . B01J 23/002; B01J 23/10; B01J 23/30; B01J 21/066; B01J 21/08; B01J 23/34;
(Continued)

(56) References Cited

U.S. PATENT DOCUMENTS 3,413,817 A 12/1968 Ludwig
3,596,473 A 8/1971 Streich
(Continued)

FOREIGN PATENT DOCUMENTS

CN 86104014 A 12/1986
CN 1073891 A 7/1993
(Continued)

OTHER PUBLICATIONS

Nam et al. "Virus-Enabled Synthesis and Assembly of Nanowires for Lithium Ion Battery Electrodes" Science (2006) 312(5775):885-888.
(Continued)

*Primary Examiner* — Patricia L. Hailey
(74) *Attorney, Agent, or Firm* — Seed IP Law Group LLP

(57) ABSTRACT

Metal oxide catalysts comprising various dopants are provided. The catalysts are useful as heterogenous catalysts in a variety of catalytic reactions, for example, the oxidative coupling of methane to C2 hydrocarbons such as ethane and ethylene. Related methods for use and manufacture of the same are also disclosed.

65 Claims, 13 Drawing Sheets

Related U.S. Application Data continuation of application No. 14/692,495, filed on Apr. 21, 2015, now Pat. No. 9,446,387, which is a continuation of application No. 14/517,524, filed on Oct. 17, 2014, now Pat. No. 9,040,762, which is a continuation of application No. 13/479,767, filed on May 24, 2012, now Pat. No. 8,921,256.

(60) Provisional application No. 61/564,832, filed on Nov. 29, 2011, provisional application No. 61/489,651, filed on May 24, 2011.

(51) Int. Cl.
| | |
|---|---|
| B01J 23/00 | (2006.01) |
| B01J 23/34 | (2006.01) |
| B01J 23/54 | (2006.01) |
| B01J 23/76 | (2006.01) |
| B01J 37/03 | (2006.01) |
| B01J 23/63 | (2006.01) |
| B01J 23/83 | (2006.01) |
| B01J 19/00 | (2006.01) |
| B01J 37/08 | (2006.01) |
| B01J 23/10 | (2006.01) |
| B01J 23/889 | (2006.01) |
| B01J 21/06 | (2006.01) |
| B01J 21/08 | (2006.01) |
| B01J 27/16 | (2006.01) |
| B01J 35/00 | (2006.01) |
| C07C 11/04 | (2006.01) |

(52) U.S. Cl.
CPC .......... *B01J 23/002* (2013.01); *B01J 23/10* (2013.01); *B01J 23/34* (2013.01); *B01J 23/54* (2013.01); *B01J 23/63* (2013.01); *B01J 23/76* (2013.01); *B01J 23/83* (2013.01); *B01J 23/8892* (2013.01); *B01J 27/16* (2013.01); *B01J 35/0006* (2013.01); *B01J 37/031* (2013.01); *B01J 37/035* (2013.01); *B01J 37/08* (2013.01); *C07C 11/04* (2013.01); *B01J 2219/00527* (2013.01); *B01J 2219/00536* (2013.01); *B01J 2219/00702* (2013.01); *B01J 2219/00747* (2013.01); *B01J 2523/00* (2013.01); *C07C 2521/10* (2013.01); *C07C 2521/14* (2013.01); *C07C 2523/10* (2013.01); *C07C 2523/18* (2013.01); *C07C 2523/34* (2013.01); *C07C 2529/072* (2013.01); *C07C 2529/076* (2013.01); *C07C 2529/89* (2013.01); *Y02P 20/52* (2015.11)

(58) Field of Classification Search
CPC ... B01J 23/54; B01J 23/63; B01J 23/76; B01J 23/83; B01J 23/8892; B01J 27/16; B01J 35/0006; B01J 37/031; B01J 37/035; B01J 37/08; C07C 11/04; C07C 2521/10; C07C 2521/14; C07C 2523/10; C07C 2523/18; C07C 2523/34; C07C 2529/072; C07C 2529/076; C07C 2529/89; Y02P 20/52
USPC .................................................. 502/305–355
See application file for complete search history.

(56) References Cited

U.S. PATENT DOCUMENTS

| | | |
|---|---|---|
| 4,105,641 A | 8/1978 | Buysch et al. |
| 4,126,580 A | 11/1978 | Lauder |
| 4,140,504 A | 2/1979 | Campbell et al. |
| 4,375,566 A | 3/1983 | Kawamata et al. |
| 4,554,395 A | 11/1985 | Jones et al. |
| 4,629,718 A | 12/1986 | Jones et al. |
| 4,636,378 A | 1/1987 | Pastor et al. |
| 4,695,668 A | 9/1987 | Velenyi |
| 4,751,336 A | 6/1988 | Jezl et al. |
| 4,754,091 A | 6/1988 | Jezl et al. |
| 4,754,093 A | 6/1988 | Jezl et al. |
| 4,777,313 A | 10/1988 | Sofranko et al. |
| 4,780,449 A | 10/1988 | Hicks |
| 4,814,539 A | 3/1989 | Jezl et al. |
| 4,826,796 A | 5/1989 | Erekson et al. |
| 4,844,803 A | 7/1989 | Urech et al. |
| 4,849,571 A | 7/1989 | Gaffney |
| 4,895,823 A | 1/1990 | Kolts et al. |
| 4,900,347 A | 2/1990 | McCue et al. |
| 4,939,311 A | 7/1990 | Washecheck et al. |
| 4,939,312 A | 7/1990 | Baerns et al. |
| 4,962,252 A | 10/1990 | Wade |
| 5,012,028 A | 4/1991 | Gupta et al. |
| 5,024,984 A | 6/1991 | Kaminsky et al. |
| 5,041,405 A | 8/1991 | Lunsford et al. |
| 5,057,478 A | 10/1991 | Abe et al. |
| 5,073,662 A | 12/1991 | Olbrich |
| 5,080,872 A | 1/1992 | Jezl et al. |
| 5,118,898 A | 6/1992 | Tyler et al. |
| 5,132,472 A | 7/1992 | Durante et al. |
| 5,134,103 A | 7/1992 | Lowery et al. |
| 5,137,862 A | 8/1992 | Mackrodt et al. |
| 5,149,516 A | 9/1992 | Han et al. |
| 5,179,056 A | 1/1993 | Bartley |
| 5,196,634 A | 3/1993 | Washecheck et al. |
| 5,198,596 A | 3/1993 | Kaminsky et al. |
| 5,263,998 A | 11/1993 | Mackrodt et al. |
| 5,276,237 A * | 1/1994 | Mieville .............. B01J 12/007 423/418.2 |
| 5,306,854 A | 4/1994 | Choudhary et al. |
| 5,312,795 A | 5/1994 | Kaminsky et al. |
| 5,316,995 A | 5/1994 | Kaminsky et al. |
| 5,328,883 A | 7/1994 | Washecheck et al. |
| 5,336,825 A | 8/1994 | Choudhary et al. |
| 5,336,826 A | 8/1994 | Brophy et al. |
| 5,371,306 A | 12/1994 | Woo et al. |
| 5,414,157 A | 5/1995 | Durante et al. |
| 5,500,149 A | 3/1996 | Green et al. |
| 5,523,493 A | 6/1996 | Cameron et al. |
| 5,599,510 A | 2/1997 | Kaminsky et al. |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,712,217 A | 1/1998 | Choudhary et al. |
| 5,714,657 A | 2/1998 | DeVries |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,789,339 A | 8/1998 | Ziebarth et al. |
| 5,817,904 A | 10/1998 | Vic et al. |
| 5,830,822 A | 11/1998 | Euzen |
| 5,849,973 A | 12/1998 | Van der Vaart |
| 5,866,737 A | 2/1999 | Hagemeyer et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Trubenbach et al. |
| 5,935,898 A | 8/1999 | Trubenbach et al. |
| 5,936,135 A | 8/1999 | Choudhary et al. |
| 5,959,170 A | 9/1999 | Withers |
| 5,968,866 A | 10/1999 | Wu |
| 6,020,533 A | 2/2000 | Lewis et al. |
| 6,037,298 A | 3/2000 | Hagen et al. |
| 6,087,545 A | 7/2000 | Choudhary et al. |
| 6,096,934 A | 8/2000 | Rekoske |
| 6,110,979 A | 8/2000 | Nataraj et al. |
| 6,114,400 A | 9/2000 | Nataraj et al. |
| 6,143,203 A | 11/2000 | Zeng et al. |
| 6,146,549 A | 11/2000 | Mackay et al. |

(56) References Cited

U.S. PATENT DOCUMENTS

| | | |
|---|---|---|
| 6,153,149 A | 11/2000 | Rabitz et al. |
| 6,262,325 B1 | 7/2001 | Narbeshuber et al. |
| 6,316,377 B1 | 11/2001 | Fulton et al. |
| 6,355,093 B1 | 3/2002 | Schwartz et al. |
| 6,403,523 B1 | 6/2002 | Cantrell et al. |
| RE37,853 E | 9/2002 | Detering et al. |
| 6,447,745 B1 | 9/2002 | Feeley et al. |
| 6,518,218 B1 | 2/2003 | Sun et al. |
| 6,518,476 B1 | 2/2003 | Culp et al. |
| 6,521,806 B1 | 2/2003 | Tamura et al. |
| 6,521,808 B1 | 2/2003 | Ozkan et al. |
| 6,576,200 B1 | 6/2003 | Yamamoto et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,696,388 B2 | 2/2004 | Kourtakis et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,761,838 B2 | 7/2004 | Zeng et al. |
| 6,764,602 B2 | 7/2004 | Shutt et al. |
| 6,800,702 B2 | 10/2004 | Wass |
| 6,821,500 B2 | 11/2004 | Fincke et al. |
| 6,821,656 B2 | 11/2004 | Dietrich et al. |
| 7,116,546 B2 | 10/2006 | Chow et al. |
| 7,166,267 B2 | 1/2007 | Villa |
| 7,176,342 B2 | 2/2007 | Bellussi et al. |
| 7,183,451 B2 | 2/2007 | Gattis et al. |
| 7,199,273 B2 | 4/2007 | Molinier et al. |
| 7,208,647 B2 | 4/2007 | Peterson et al. |
| 7,250,543 B2 | 7/2007 | Bagherzadeh et al. |
| 7,291,321 B2 | 11/2007 | Bagherzadeh et al. |
| 7,332,108 B2 | 2/2008 | Chartier |
| 7,361,622 B2 | 4/2008 | Benderly et al. |
| 7,396,798 B2 | 7/2008 | Ma et al. |
| 7,414,006 B2 | 8/2008 | McConville et al. |
| 7,438,887 B2 | 10/2008 | Suib et al. |
| 7,452,844 B2 | 11/2008 | Hu et al. |
| 7,473,814 B2 | 1/2009 | Basset et al. |
| 7,566,440 B2 | 7/2009 | Lim et al. |
| 7,576,030 B2 | 8/2009 | Benderly |
| 7,576,296 B2 | 8/2009 | Fincke et al. |
| 7,585,812 B2 | 9/2009 | Hu et al. |
| 7,589,246 B2 | 9/2009 | Iaccino et al. |
| 7,619,290 B2 | 11/2009 | Lieber et al. |
| 7,659,437 B2 | 2/2010 | Iaccino et al. |
| 7,667,085 B2 | 2/2010 | Gattis et al. |
| 7,683,227 B2 | 3/2010 | Iaccino et al. |
| 7,687,041 B2 | 3/2010 | Singh |
| 7,700,816 B2 | 4/2010 | Xu et al. |
| 7,728,186 B2 | 6/2010 | Iaccino et al. |
| 7,781,636 B2 | 8/2010 | Iaccino et al. |
| 7,795,490 B2 | 9/2010 | Iaccino et al. |
| 7,829,749 B2 | 11/2010 | Gao et al. |
| 7,867,938 B2 | 1/2011 | De et al. |
| 7,868,243 B2 | 1/2011 | Plissonnier et al. |
| 7,879,119 B2 | 2/2011 | Abughazaleh et al. |
| 7,902,113 B2 | 3/2011 | Zarrinpashne et al. |
| 7,910,670 B2 | 3/2011 | Knudsen et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,932,311 B2 | 4/2011 | Aymonier et al. |
| 7,943,106 B2 | 5/2011 | Robinson |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 8,039,681 B2 | 10/2011 | Krusic et al. |
| 8,071,498 B2 | 12/2011 | Aono et al. |
| 8,071,836 B2 | 12/2011 | Butler |
| 8,129,305 B2 | 3/2012 | Bagherzadeh et al. |
| 8,277,525 B2 | 10/2012 | Dalton |
| 8,293,805 B2 | 10/2012 | Khan et al. |
| 8,361,925 B2 | 1/2013 | Matsueda et al. |
| 8,399,527 B1 | 3/2013 | Brown et al. |
| 8,399,726 B2 | 3/2013 | Chinta et al. |
| 8,414,798 B2 | 4/2013 | Costello et al. |
| 8,435,920 B2 | 5/2013 | White et al. |
| 8,450,546 B2 | 5/2013 | Chinta et al. |
| 8,552,236 B2 | 10/2013 | Iaccino |
| 8,647,999 B2 | 2/2014 | Hayashi et al. |
| 8,669,171 B2 | 3/2014 | Perraud et al. |
| 8,710,286 B2 | 4/2014 | Butler |
| 8,729,328 B2 | 5/2014 | Chinta et al. |
| 8,759,598 B2 | 6/2014 | Hayashi et al. |
| 8,796,497 B2 | 8/2014 | Chinta et al. |
| 8,911,834 B2 | 12/2014 | Aktas et al. |
| 8,912,381 B2 | 12/2014 | Chinta et al. |
| 8,921,256 B2 | 12/2014 | Cizeron et al. |
| 8,932,781 B2 | 1/2015 | Yang et al. |
| 8,962,517 B2 | 2/2015 | Zurcher et al. |
| 9,040,762 B2 | 5/2015 | Cizeron et al. |
| 9,101,890 B2 | 8/2015 | Tonkovich et al. |
| 9,133,079 B2 | 9/2015 | Weinberger et al. |
| 9,446,387 B2 | 9/2016 | Cizeron et al. |
| 9,446,397 B2 | 9/2016 | Gamoras et al. |
| 9,469,577 B2 | 10/2016 | Schammel et al. |
| 9,527,784 B2 | 12/2016 | Weinberger et al. |
| 9,556,086 B2 | 1/2017 | Schammel et al. |
| 9,598,328 B2 | 3/2017 | Nyce et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,956,544 B2 | 5/2018 | Schammel et al. |
| 9,963,402 B2 | 5/2018 | Cizeron et al. |
| 10,183,900 B2 | 1/2019 | Nyce et al. |
| 10,195,603 B2 | 2/2019 | Scher et al. |
| 10,300,465 B2 | 5/2019 | Freer et al. |
| 10,308,565 B2 | 6/2019 | Schammel et al. |
| 2001/0044520 A1 | 11/2001 | Suzuki et al. |
| 2002/0150522 A1 | 10/2002 | Heim et al. |
| 2003/0135971 A1 | 7/2003 | Liberman et al. |
| 2003/0189202 A1 | 10/2003 | Li et al. |
| 2003/0207984 A1 | 11/2003 | Ding et al. |
| 2003/0233019 A1 | 12/2003 | Sherwood |
| 2004/0005723 A1 | 1/2004 | Empedocles et al. |
| 2004/0098914 A1 | 5/2004 | Balachandran et al. |
| 2004/0187963 A1 | 9/2004 | Tayu et al. |
| 2004/0220053 A1 | 11/2004 | Bagherzadeh et al. |
| 2005/0009686 A1 | 1/2005 | Julsrud et al. |
| 2005/0065391 A1 | 3/2005 | Gattis et al. |
| 2005/0199559 A1 | 9/2005 | Duby |
| 2005/0221083 A1 | 10/2005 | Belcher et al. |
| 2005/0255993 A1 | 11/2005 | Tanaka et al. |
| 2006/0018821 A1 | 1/2006 | Suzuki et al. |
| 2006/0083970 A1 | 4/2006 | Shibutani et al. |
| 2006/0125025 A1 | 6/2006 | Kawashima et al. |
| 2006/0135838 A1 | 6/2006 | Bagherzadeh et al. |
| 2006/0155157 A1 | 7/2006 | Zarrinpashne et al. |
| 2006/0177629 A1 | 8/2006 | Kunieda |
| 2006/0283780 A1 | 12/2006 | Spivey et al. |
| 2006/0284162 A1 | 12/2006 | Kurt et al. |
| 2007/0027030 A1 | 2/2007 | Cheung et al. |
| 2007/0043181 A1 | 2/2007 | Knudsen et al. |
| 2007/0073083 A1 | 3/2007 | Sunley |
| 2007/0083073 A1 | 4/2007 | Bagherzadeh et al. |
| 2007/0095445 A1 | 5/2007 | Gangopadhyay et al. |
| 2007/0106089 A1 | 5/2007 | Benderly et al. |
| 2007/0138082 A1 | 6/2007 | Connors et al. |
| 2007/0138459 A1 | 6/2007 | Wong et al. |
| 2007/0158611 A1 | 7/2007 | Oldenburg |
| 2008/0051279 A1 | 2/2008 | Klett et al. |
| 2008/0141713 A1 | 6/2008 | Verma |
| 2008/0262114 A1 | 10/2008 | Reynhout |
| 2008/0267852 A1 | 10/2008 | Schumacher et al. |
| 2008/0275143 A1 | 11/2008 | Malhotra et al. |
| 2008/0279744 A1 | 11/2008 | Robinson |
| 2008/0281136 A1 | 11/2008 | Bagherzadeh et al. |
| 2008/0293980 A1 | 11/2008 | Kiesslich et al. |

(56) References Cited

U.S. PATENT DOCUMENTS

| | | |
|---|---|---|
| 2008/0318044 A1 | 12/2008 | Tian et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0259076 A1 | 10/2009 | Simmons et al. |
| 2009/0267852 A1 | 10/2009 | Tahmisian et al. |
| 2009/0324470 A1 | 12/2009 | Alamdari et al. |
| 2010/0000153 A1 | 1/2010 | Kurkjian et al. |
| 2010/0003179 A1 | 1/2010 | Katusic et al. |
| 2010/0173070 A1 | 7/2010 | Niu |
| 2010/0183937 A1 | 7/2010 | Halloran et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0200501 A1 | 8/2010 | Hoag et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0049132 A1 | 3/2011 | Lee |
| 2011/0070139 A1 | 3/2011 | Kim et al. |
| 2011/0104588 A1 | 5/2011 | Kwon et al. |
| 2011/0124488 A1 | 5/2011 | Neltner et al. |
| 2011/0160508 A1 | 6/2011 | Ma et al. |
| 2011/0171629 A1 | 7/2011 | Swager et al. |
| 2011/0189559 A1 | 8/2011 | Baldanza et al. |
| 2011/0217544 A1 | 9/2011 | Young et al. |
| 2011/0240926 A1 | 10/2011 | Schellen et al. |
| 2011/0257453 A1 | 10/2011 | Chinta et al. |
| 2011/0275011 A1 | 11/2011 | Zhu et al. |
| 2012/0029218 A1 | 2/2012 | Kim et al. |
| 2012/0041246 A1 | 2/2012 | Scher et al. |
| 2012/0065412 A1 | 3/2012 | Abdallah et al. |
| 2012/0116094 A1 | 5/2012 | Swager et al. |
| 2012/0129690 A1 | 5/2012 | Larcher et al. |
| 2012/0136164 A1 | 5/2012 | Ying et al. |
| 2012/0153860 A1 | 6/2012 | Wang et al. |
| 2012/0164470 A1 | 6/2012 | Leschkies et al. |
| 2012/0172648 A1 | 7/2012 | Seebauer |
| 2012/0183770 A1 | 7/2012 | Bosnyak et al. |
| 2012/0198769 A1 | 8/2012 | Schirrmeister et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0264598 A1 | 10/2012 | Carpenter et al. |
| 2013/0023709 A1 | 1/2013 | Cizeron et al. |
| 2013/0025201 A1 | 1/2013 | Dalton |
| 2013/0039806 A1 | 2/2013 | Blinn et al. |
| 2013/0040806 A1 | 2/2013 | Dismukes et al. |
| 2013/0089739 A1 | 4/2013 | Polshettiwar et al. |
| 2013/0105305 A1 | 5/2013 | Yang et al. |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0178680 A1 | 7/2013 | Ha et al. |
| 2013/0225884 A1 | 8/2013 | Weinberger et al. |
| 2013/0252808 A1 | 9/2013 | Yamazaki et al. |
| 2013/0253248 A1 | 9/2013 | Gamoras et al. |
| 2013/0266809 A1 | 10/2013 | Nueraji et al. |
| 2013/0270180 A1 | 10/2013 | Zhang et al. |
| 2014/0050629 A1 | 2/2014 | Masuda et al. |
| 2014/0054516 A1 | 2/2014 | Moon et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0171707 A1 | 6/2014 | Nyce et al. |
| 2014/0178788 A1 | 6/2014 | Ha et al. |
| 2014/0194663 A1 | 7/2014 | Butler |
| 2014/0249339 A1 | 9/2014 | Simanzhenkov et al. |
| 2014/0274671 A1 | 9/2014 | Schammel et al. |
| 2014/0332733 A1 | 11/2014 | Joo et al. |
| 2014/0378728 A1 | 12/2014 | Davis et al. |
| 2015/0010467 A1 | 1/2015 | Ito et al. |
| 2015/0073192 A1 | 3/2015 | Cizeron et al. |
| 2015/0087875 A1 | 3/2015 | Zurcher et al. |
| 2015/0125383 A1 | 5/2015 | Yamazaki et al. |
| 2015/0224482 A1 | 8/2015 | Cizeron et al. |
| 2015/0314267 A1 | 11/2015 | Schammel et al. |
| 2015/0321974 A1 | 11/2015 | Schammel et al. |
| 2015/0368167 A1 | 12/2015 | Weinberger et al. |
| 2016/0074844 A1 | 3/2016 | Freer et al. |
| 2016/0107143 A1 | 4/2016 | Schammel et al. |
| 2016/0122261 A1 | 5/2016 | Schammel et al. |
| 2016/0340272 A1 | 11/2016 | Cizeron et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0341997 A1 | 11/2017 | Nyce et al. |
| 2018/0093931 A1 | 4/2018 | Schammel et al. |
| 2018/0117570 A1 | 5/2018 | Freer et al. |
| 2018/0118637 A1 | 5/2018 | Zurcher et al. |
| 2019/0010096 A1 | 1/2019 | Schammel et al. |
| 2019/0022626 A1 | 1/2019 | Schammel et al. |

FOREIGN PATENT DOCUMENTS

| | | |
|---|---|---|
| CN | 1087291 A | 6/1994 |
| CN | 1100669 A | 3/1995 |
| CN | 1321728 A | 11/2001 |
| CN | 1389293 A | 1/2003 |
| CN | 1403375 A | 3/2003 |
| CN | 1930333 A | 3/2007 |
| CN | 101224432 | 7/2008 |
| CN | 101387019 A | 3/2009 |
| CN | 101495429 A | 7/2009 |
| CN | 102125825 A | 7/2011 |
| CN | 103118777 A | 5/2013 |
| DE | 3406751 A1 | 8/1985 |
| EP | 0253522 A2 | 1/1988 |
| EP | 0595425 A1 | 5/1994 |
| EP | 0761307 B1 | 2/2003 |
| EP | 0764467 B1 | 2/2003 |
| EP | 1632467 A1 | 3/2006 |
| EP | 1749807 A1 | 2/2007 |
| EP | 2287142 A1 | 2/2011 |
| EP | 2374526 A1 | 10/2011 |
| EP | 2853521 A1 | 4/2015 |
| FR | 649429 A | 12/1928 |
| GB | 2191212 A | 12/1987 |
| JP | S6363626 A | 3/1988 |
| JP | H02218623 A | 8/1990 |
| JP | H03262535 A | 11/1991 |
| JP | H05238961 A | 9/1993 |
| JP | 2005161225 A | 6/2005 |
| JP | 2011032257 A | 2/2011 |
| RU | 2134675 C1 | 8/1999 |
| WO | 1986007351 A1 | 12/1986 |
| WO | 2000016901 A1 | 3/2000 |
| WO | 2004033488 A2 | 4/2004 |
| WO | 2005067683 | 12/2006 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2009071463 A2 | 6/2009 |
| WO | 2009115805 A1 | 9/2009 |
| WO | 2010005453 A2 | 1/2010 |
| WO | 2011050359 A1 | 4/2011 |
| WO | 2011149996 A2 | 12/2011 |
| WO | 2012162526 A2 | 11/2012 |
| WO | 2013186789 A1 | 12/2013 |
| WO | 2014043603 A1 | 3/2014 |
| WO | 2014049445 A2 | 4/2014 |

OTHER PUBLICATIONS

Natural Gas Spec Sheet, prepared by Florida Power and Light Company, 2003.

(56) References Cited

OTHER PUBLICATIONS

Neltner et al. "Production of Hydrogen Using Nanocrystalline Protein-Templated Catalysts on M13 Phage" ACS Nano (2010) 4(6): 3227-3235.
Neltner. Hybrid Bio-templated Catalysts. Doctoral Thesis, Massachusetts Institute of Technology, Jun. 2010, 156 pages.
O'Connor, C.T. et al. "Alkene oligomerization" Catalysis Today (1990) 6(3):329-349.
Pak et al., "Elementary Reactions in the Oxidative Coupling of Methane over Mn/Na2WO4/SiO2 and Mn/Na2WO4/MgO Catalysts," Journal of Catalysis (1998) 179:222-230.
Park, J-M et al. "Fabrication of metallic nano wires and nano ribbons using laser interference lithography and shadow lithography" Nanotechnology (2010) 21:1-6.
Peitz, S. et al. "An Alternative Mechanistic Concept for Homogeneous Selective Ethylene Oligomerization of Chromium-Based Catalysts: Binuclear Metallacycles as a Reason for 1-Octene Selectivity?" Chemistry—A European Journal (2010) 16(26):7670-7676.
Qiu et al., "Steady-state conversion of methane to aromatics in high yields using an integrated recycle reaction system," Catalysis Letters 48:11-15, 1997.
Ren, T. et al. "Basic petrochemicals from natural gas, coal and biomass: Energy use and CO2 emissions" Res Conserv Recycl (2009) 53(9):513-528.
Ryu, K-H et al. "Preparation of Porous LaFeO3 Nanowires using AAO Template and Their Catalytic Properties" Bull. Korean Chem Soc. (2011) 32(7):2457-2460.
Schaarschmidt, D. et al. "Ferrocenyl phosphane nickel carbonyls: Synthesis, solid state structure, and their use as catalysts in the oligomerization of ethylene" J. Organometallic Chem. (2010) 695(10-11):1541-1549.
Schweer et al., "OCM in a fixed-bed reactor: limits and perspectives," Catalysis Today 21:357-369, 1994.
Somorjai et al., "High technology catalysts towards 100% selectivity Fabrication, characterization and reaction studies," Catalysis Today 100:201-215, 2005.
Song, S. et al. "Synthesis, characterization and ethylene oligomerization behaviour of 8-(1-aryliminoethylidene)quinaldinylnickel dihalides" Catal. Sci. Technol. (2011) 1(1):69-75.
Spiniccia, R. et al. "Oxidative coupling of methane on LaAlO3 perovskites partially substituted with alkali or alkali-earth ions" J Molecular Catalysts (2001) 176:253-265.
Takanabe et al., "Mechanistic Aspects and eaction Pathways for Oxidative Coupling of Methane on Mn/Na2WO4/SiO2 Catalysts," J. Phys. Chem. C (2009) 113(23):10131-10145.
Takanabe et al., "Rate and Selectivity Enhancements Mediated by OH Radicals in the Oxidative Coupling of Methane Catalyzed by Mn/Na2WO4/SiO2," Angew. Chem. Int. Ed. (2008) 47:7689-7693.
Tana et al., "Morphology-dependent redox and catalytic properties of CeO2 nanostructures: Nanowires, nano rods and nanoparticles" Catalysis Today (Oct. 2009) 148(1-2):179-183.
Taylor et al. "Lanthanum Catalysts for CH4 Oxidative Coupling: A Comparison of the Reactivity of Phases" Ind. Eng. Chem. Res. (1991) 30:1016-1023.
Teymouri, M. et al. "Reactivity of perovskites on oxidative coupling of methane" J Mat Sci (1995) 30(11):3005-3009.
Theuerkauf et al. "Analysis of particle porosity distribution in fixed beds using the discrete element method" Powder Tech (Jul. 2006) 165(2):92-99.
Tian et al., "Catalytic reduction of NOx with NH3 over different-shaped MnO2 at low temperature" J Hazardous Mats (Jan. 2011) 188(1-3):105-109.
Tomishige, K. et al. "Reactivity and Characterization of Adsorbed Oxygen on SRTI1-SMGX03-D Catalysts for Oxidative Coupling of Methane" Physical Chemistry Chemical Physics, Royal Society of Chemistry (1999) 1 (12):3039-3045.
Tong et al. "Development Strategy Research of Downstream Products of Ethene in Tianjin" Tianjin Economy (1996) 37-40.
Trautmann et al., "Cyrogenic Technology for Nitrogen Rejection from Variable Content Natural Gas," XIV Convencion Internacional de Gas, Caracas, Venezuela May 10-12, 2000. (ref from client).
Tullo "Ethylene from Methane" Chemical and Engineering New (2011) 89(3):2021.
Valenzuela et al., "Nanostructured ceria-based catalysts for oxydehydrogenation of ethane with CO2" Topics in Catalysis (Jun. 2001) 15(2-4):181-188.
Van Santen, R.A. et al. "An introduction to molecular heterogeneous catalysis" New Trends in Material Chemistry (1997) pp. 345-363.
Wang et al., "Autothermal oxidative coupling of methane on the SrCO3/Sm2O3 catalysts," Catalysis Communications 10(6):807-810, 2009.
Wang et al., "Comparative study on oxidation of methane to ethane and ethylene over Na2WO4—Mn/SiO2 catalysts prepared by different methods," Journal of Molecular Catalysis A: Chemical (2006) 245:272-277.
Wang et al., "Low-temperature selective oxidation of methane to ethane and ethylene over BaCO3/La2O3 catalysts prepared by urea combustion method," Catalysis Communications 7(2):59-63, 2006.
Wang et al., "Nanostructured Sheets of Ti—O Nanobelts for Gas Sensing and Antibacterial Applications" Adv Functional Mats (Apr. 2008) 18(7):1131-1137.
Wang, X. et al. "Synthesis and Characterization of Lanthanide Hydroxide Single-Crystal Nanowires" Angew Chem Int Ed (2002) 41(24):4790-4793.
Wong et al., "Oxidative Coupling of Methane Over Alkali Metal Oxide Promoted LA2O3/BACO3 Catalysts," Journal of Chemical Technology and Biotechnology 65(4):351-354, 1996.
Yang et al., "Anisotropic syntheses of boat-shaped core-shell Au—Ag nanocrystals and nanowires," Nanotechnology 17(9): 2304-2310, 2006.
Yu, C et al. "Oxidative Coupling of Methane over Acceptor-doped SrTiO3: Corelation between p-type Conductivity an dC2 Silectivity and C2 Yield," J. Catalysis (1992) 13(5):338-344.
Zhang et al., "Relationship between packing structure and porosity in fixed beds of equilateral cylindrical particles" Chem Eng Sci (Dec. 2006) 61(24):8060-8074.
Zhang, Q. Journal of Natural Gas Chem., (2003) 12:81.
Zhang, X. et al."Single-Walled Carbon Nanotube-Based Coaxial Nanowires: Synthesis, Characterization, and Electrical properties" J Phys Chem (2005) 109(3):1101-1107.
Zhao X-W, "Technologies and Catalysts for Catalytic Preparation of Ethene," Industrial Catalysis (2004) 12 (Supplement):285-289.
Zhou, M et al., "Functionalization of lanthanum hydroxide nanowires by atom transfer radical polymerization," Nanotechnology (2007) 18(40): 7 pages.
Zhu, F. et al. "Recent Research Progress in Preparation of Ethylene Oligomers with Chromium-Based Catalytic Systems" Designed Monomers & Polymers (2011) 14(1):1-23.
Zimmerman et al., "Ethylene," Ullmann's Encyclopedia of Industrial Chemistry, Wiley-VCH Verlag GmbH & Co. K-GaA, Weinheim, Germany, 2009, 66 pages.
"Autothermal Partial Oxidative Coupling of Methane," IP.com, Prior Art Database Technical Disclosure, Jul. 29, 2008, 5 pages.
Agapie, T "Selective ethylene oligomerization: recent advances in chromium catalysis and mechanistic investigations" Coord Chem Rev (2011) 255:861-880.
Au et al., "A Comparison of BaF2/La2O3 and BaBr2/La2O3 Catalysts for the Oxidative Coupling of Methane" J Catalysis (Apr. 1996) 159(2):280-287.
Bergh, S. et al. "Combinatorial Heterogeneous Catalysis: Oxidative Dehydrogenation of Ethane to Ethylene, Selective Oxidation of Ethane to Acetic Acid, and Selective Ammoxidation of Propane to Acrylonitrile" Topics in Catalysis (2003) 23(1-4):65-79.
Carter, et al. "High activity ethylene trimerisation catalysts based on diphosphine ligands." Chem Commun (Camb). (Apr. 21, 2002) (8):858-9.
Cavani et al. "Oxidative dehydrogenation of ethane and propane: How far fro commercial implementation?" Catalysis Today (2007) 127:113-131.
Choudhary et al. "Aromatization of dilute ethylene over Ga-modified ZSM-5 type zeolite catalysts" Microporous and Mesoporous Materials (2001) 47:253-267.

(56) References Cited

OTHER PUBLICATIONS

Choudhary et al. "Oxidative conversion of methane/natural gas into higher hydrocarbons" Catalysis Surveys from Asia (2004) 8(1):15-25.

Choudhary et al. "Oxidative Coupling of Methane and Oxidative Dehydrogenation of Ethane over Strontium-Promoted Rare Earth Oxide Catalysts" J Chem Tech and Biotech (Feb. 1998) 71(2):167-172.

Choudhary et al. "Surface basicity and acidity of alkaline earth-promoted La2O3 catalysts and their performance in oxidative coupling of methane" J Chem. Technol. Biotechnol (1998) 72:125-130.

Choudhary, V.R. et al. "Oxidative Coupling of Methane over SrO Deposited on Different Commercial Supports Precoated with La2O3" Ind Eng Chem Res (1998) 37:2142-2147.

Christopher et al. "Engineering selectivity in heterogeneous catalysis: Ag nanowires as selective ethylene apoxidation catalysts" J Am Chem Soc. (2008) 130:11264-11265.

Dai, "Study on low temperature catalytic activation of methane," Thesis of graduate student for Master's Degree in Physical Chemistry, East China Normal University, May 2005, 8 pages. (with English Translation).

Debart et al., "Alpha-MnO2 Nanowires: A Catalyst for the O2 Electrode in Rechargeable Lithium Batteries," Angew. Chem. Int. Ed. (2008) 47:4521-4524.

Dedov, A.G. et al. "Oxidative coupling of methane catalyzed by rare earth oxides. Unexpected synergistic effect of the oxide mixtures" Applied Catalysis (2003) 245:209-220.

Devi et al. "College Inorganic Chemistry" Devi, K.V.S. Laxmi, Patel, N.C., and Venkatachalam, A.. College Inorganic Chemistry. Mumbai, IND: Himalaya Publishing House, 2010. Jan. 1, 2010 (Jan. 1, 2010), XP055242276, Retrieved from the Internet: URL:http://site.ebrary.com/lib/epo/reader.action?docID=10415159 [retried on Jan. 18, 2016] the whole document.

Dixon, J.T. et al. "Advances in selective ethylene trimerisation—a critical overview" J. Organometallic Chem. (2004) 689(23):3641-3668.

Dulai A. et al. "N,N'-Bis(diphenylphosphino)diaminophenylphosphine Ligands for Chromium-Catalyzed Selective Ethylene Oligomerization Reactions" Organometallics (2011) 30(5):935-941.

Enger et al., "A review of catalytic partial oxidation of methane to synthesis gas with emphasis on reaction mechanisms over transition metal catalysts," Applied Catalysis A: General 346:1-27, Aug. 2008.

Eskendirov et al., "Methane oxidative coupling on the Au/La2O3/CaO catalyst in the presence of hydrogen peroxide," (1995) Catalysis Letters 35:33-37.

Fallah, B. et al. "A New Nano-(2Li2O/MgO) Catalyst/Porous Alpha-Alumina Composite for the Oxidative Coupling of Methane Reaction" AIChE Journal (2010) 56(3):717-728.

Ferreira et al., "Effect of Mg, Ca, and Sr on CeO2 Based Catalysts for the Oxidative Coupling of Methane: Investigation on the Oxygen Species Responsible for Catalytic Performance" Indus and Eng Chem Res (Jul. 2012) 51 (32):10535-10541.

Galadima, A. et al. "Revisiting the oxidative coupling of methane to ethylene in the golden period of shale gas: A review" J Ind Eng Chem (Mar. 2016) http://dx.doi.org/10.1016/j.jiec.2016.03.027.

Gao et al., "A study on methanol steam reforming to CO2 and H2 over the La2CuO4 nanofiber catalyst," Journal of Solid State Chemistry 181:7-13, 2008.

Gao et al., "The direct decomposition of NO over the La2CuO4 nanofiber catalyst," Journal of Solid State Chemistry 181:2804-2807, 2008.

Gong et al., "Preparation of Carbon Nanotubes (CNTs)-Cordierite Monoliths by Catalytic Chemical Vapor Deposition as Catalyst Supports for Ammonia Synthesis" Catalysis Letts (May 2008) 122(3):287-294.

Guo et al. "Current Status and Some Perspectives of Rare Earth Catalytic Materials" J Chinese Rare Earth Soc (2007) 25(1):1-15.

Guo, X. et al. "Direct, Nonoxidative Conversion of Methane to Ethylene, Aromatics, and Hydrogen" Science (2014) 344:616-619.

Hess et al. (eds.) "Kirk-Othmer encyclopedia of chemical technology" New York, John Wiley & Sons Ltd. 1998, p. 171.

Hinson, P.G. Et al. "The oxidative coupling of methane on chlorinated Lithium-doped magnesium oxide" J Chem Soc, Chem Comm (1991) 20:1430-1432.

Huang et al., "Exploiting Shape Effects of La2O3Nanocatalysts for Oxidative Coupling of Methane Reaction," The Royal Society of Chemistry 2013, 7 pages (Electronic Supplementary Information).

Huang et al., "Exploiting Shape Effects of La2O3Nanocatalysts for Oxidative Coupling of Methane Reaction," The Royal Society of Chemistry 2013, 5 pages.

Istadi et al., "Synergistic effect of catalyst basicity and reducibility on performance of ternary CeO2-based catalyst for CO2 OCM to C2 hydrocarbons" J Mol Catalysis A: Chem (Nov. 2006) 259(1-2):61-66.

Jaramillo, P. et al. "Comparative analysis of the production costs and life-cycle GHG emissions of FT liquid fuels from coal and natural gas" Env. Sci. Tech (2008) 42:7559-7565.

Jiangrong Niu, et al. "Preparation and Characterization of La2O2CO3 Nanowires with High Surface Areas" J Chinese Rare Earth Soc (Dec. 2005) 23:33-36.

Kaminsky, M.P. et al. "Deactivation of Li-Based Catalysts for Methane Oxidative Coupling" Poster ACS Symposium on Natural Gas Upgrading II (Apr. 5-10, 1992).

Kaminsky, M.P. et al. "Oxygen X-Ray Absorption Near-Edge Structure Characterization of the Ba-Doped Yttria Oxidative Coupling Catalyst" J Catalysis (1992) 136:16-23.

Keller, et al. Synthesis of Ethylene via Oxidative Coupling of Methane. Journal of Catalysis 73: 9-19, 1982.

Krisfinadas, K.R. et al. "Pristine and Hybrid Nickel Nanowires: Template-, Magnetic Field-, and Surfactant-Free Wet Chemical Synthesis and Raman Studies" J Phys Chem (Feb. 25, 2011) 115:4483-4490.

Kuang, et al. "Grafting of PEG onto lanthanum hydroxide nanowires". Materials Letters (2008) 62:4078-4080.

Labinger, "Oxidative Coupling of Methane: An Inherent Limit to Selectivity?" Catalysis Letters (1988) 1:371-376.

Li, Y. et al. "Color control and white light generation of upconversion luminescence by operating dopant concentrations and pump densities in Yb3+, ER3+ and Tm3+ trip doped Lu2O3 nanocrystal" J Mater Chem (2011) 21:2895-2900.

Ling et al. "Preparation of Ag_coreAu_core Nanowires and Their Surface Enhanced Raman Spectroscopic Studies" Acta Chem Sinica (2007) 65(9):779-784.

Liu, et al. A novel Na_WO4-Mn.SiC monolithic foam catalyst with improved thermal properties for the oxidative coupling of methane. Catalysis Communications 9: 1302-1306, 2008.

Lunsford, "The Catalytic Oxidative Coupling of Methane," Angew. Chem. Int. Ed. Engl. (1995) 34:970-980.

Ma, et al. "Processing and properties of carbon nanotubes-non-SiC ceramic" J Mat Sci (Nov. 1998) 33 (21):5245-5246.

Matskevich, N.I. et al. "Synthesis and thermochemistry of new phase BaCe0.7Nd0.2In0.1O2.85" J Alloys and Compounds (2013) 577:148-151.

Miller, J.E. et al. "Oxidation reactions of ethane over Ba—Ce—O based perovskites" Applied Catalysis A: General (2000) 201:45-54.

Mileczko, et al. "Catalytic oxidative coupling of methane—reaction engineering aspects and process schemes" Fuel Processing Tech (1995) 42:217-248.

Nagamoto, H. et al. "Methane Oxidation over Perovskite-type Oxide Containing Alkaline-earth Metal" Chemistry Letts (1988) 17(2):237-240.

Tanaka et al., "Oxidative Coupling of Methane over Ba-incorporated LaInO$_3$ Perovskite Catalyst," *Journal of the Japan Petroleum Institute* 55(1):71-72, 2012.

* cited by examiner

CATALYSTS FOR PETROCHEMICAL CATALYSIS

BACKGROUND

Technical Field

This invention is generally related to novel catalysts and, more specifically, to doped metal oxide catalysts useful as heterogeneous catalysts in a variety of catalytic reactions, such as the oxidative coupling of methane to C2 hydrocarbons.

Description of the Related Art

Catalysis is the process in which the rate of a chemical reaction is either increased or decreased by means of a catalyst. Positive catalysts increase the speed of a chemical reaction, while negative catalysts slow it down. Substances that increase the activity of a catalyst are referred to as promoters or activators, and substances that deactivate a catalyst are referred to as catalytic poisons or deactivators. Unlike other reagents, a catalyst is not consumed by the chemical reaction, but instead participates in multiple chemical transformations. In the case of positive catalysts, the catalytic reaction generally has a lower rate-limiting free energy change to the transition state than the corresponding uncatalyzed reaction, resulting in an increased reaction rate at the same temperature. Thus, at a given temperature, a positive catalyst tends to increase the yield of desired product while decreasing the yield of undesired side products. Although catalysts are not consumed by the reaction itself, they may be inhibited, deactivated or destroyed by secondary processes, resulting in loss of catalytic activity.

Catalysts are generally characterized as either heterogeneous or homogeneous. Heterogeneous catalysts exist in a different phase than the reactants (e.g. a solid metal catalyst and gas phase reactants), and the catalytic reaction generally occurs on the surface of the heterogeneous catalyst. Thus, for the catalytic reaction to occur, the reactants must diffuse to and/or adsorb onto the catalyst surface. This transport and adsorption of reactants is often the rate limiting step in a heterogeneous catalysis reaction. Heterogeneous catalysts are also generally easily separable from the reaction mixture by common techniques such as filtration or distillation.

In contrast to a heterogeneous catalyst, a homogenous catalyst exists in the same phase as the reactants (e.g., a soluble organometallic catalyst and solvent-dissolved reactants). Accordingly, reactions catalyzed by a homogeneous catalyst are controlled by different kinetics than a heterogeneously catalyzed reaction. In addition, homogeneous catalysts can be difficult to separate from the reaction mixture.

While catalysis is involved in any number of technologies, one particular area of importance is the petrochemical industry. At the foundation of the modern petrochemical industry is the energy-intensive endothermic steam cracking of crude oil. Cracking is used to produce nearly all the fundamental chemical intermediates in use today. The amount of oil used for cracking and the volume of green house gases (GHG) emitted in the process are quite large: cracking consumes nearly 10% of the total oil extracted globally and produces 200M metric tons of $CO_2$ equivalent every year (Ren, T, Patel, M. *Res. Conserv. Recycl.* 53:513, 2009). There remains a significant need in this field for new technology directed to the conversion of unreactive petrochemical feedstocks (e.g. paraffins, methane, ethane, etc.) into reactive chemical intermediates (e.g. olefins), particularly with regard to highly selective heterogeneous catalysts for the direct oxidation of hydrocarbons.

While there are multistep paths to convert methane to certain specific chemicals using first; high temperature steam reforming to syngas (a mixture of $H_2$ and CO), followed by stochiometry adjustment and conversion to either methanol or, via the Fischer-Tropsch (F-T) synthesis, to liquid hydrocarbon fuels such as diesel or gasoline, this does not allow for the formation of certain high value chemical intermediates. This multi-step indirect method also requires a large capital investment in facilities and is expensive to operate, in part due to the energy intensive endothermic reforming step. For instance, in methane reforming, nearly 40% of methane is consumed as fuel for the reaction. It is also inefficient in that a substantial part of the carbon fed into the process ends up as the GHG $CO_2$, both directly from the reaction and indirectly by burning fossil fuels to heat the reaction. Thus, to better exploit the natural gas resource, direct methods that are more efficient, economical and environmentally responsible are required.

One of the reactions for direct natural gas activation and its conversion into a useful high value chemical, is the oxidative coupling of methane ("OCM") to ethylene: $2CH_4 + O_2 \rightarrow C_2H_4 + 2H_2O$. See, e.g., Zhang, Q., *Journal of Natural Gas Chem.*, 12:81, 2003; Olah, G. "Hydrocarbon Chemistry", Ed. 2, John Wiley & Sons (2003). This reaction is exothermic ($\Delta H = -67$ kcals/mole) and has typically been shown to occur at very high temperatures (>700° C.). Although the detailed reaction mechanism is not fully characterized, experimental evidence suggests that free radical chemistry is involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) is activated on the catalyst surface, forming methyl radicals which then couple in the gas phase to form ethane ($C_2H_6$), followed by dehydrogenation to ethylene ($C_2H_4$). Several catalysts have shown activity for OCM, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and combinations thereof, on various supports. A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction. Specifically, numerous publications from industrial and academic labs have consistently demonstrated characteristic performance of high selectivity at low conversion of methane, or low selectivity at high conversion (J. A. Labinger, *Cat. Lett.*, 1:371, 1988). Limited by this conversion/selectivity threshold, no OCM catalyst has been able to exceed 20-25% combined $C_2$ yield (i.e. ethane and ethylene), and more importantly, all such reported yields operate at extremely high temperatures (>800 C).

In this regard, it is believed that the low yield of desired products (i.e. $C_2H_4$ and $C_2H_6$) is caused by the unique homogeneous/heterogeneous nature of the reaction. Specifically, due to the high reaction temperature, a majority of methyl radicals escape the catalyst surface and enter the gas phase. There, in the presence of oxygen and hydrogen, multiple side reactions are known to take place (J. A. Labinger, *Cat. Lett.*, 1:371, 1988). The non-selective overoxidation of hydrocarbons to CO and $CO_2$ (e.g., complete oxidation) is the principal competing fast side reaction.

Other undesirable products (e.g. methanol, formaldehyde) have also been observed and rapidly react to form CO and $CO_2$.

In order to result in a commercially viable OCM process, a catalyst optimized for the activation of the C—H bond of methane at lower temperatures (e.g. 500-800° C.) higher activities, and higher pressures are required. While the above discussion has focused on the OCM reaction, numerous other catalytic reactions (as discussed in greater detail below) would significantly benefit from catalytic optimization. Accordingly, there remains a need in the art for improved catalysts and, more specifically, catalysts for improving the yield, selectivity and conversion of, for example, the OCM reaction and other catalyzed reactions. The present invention fulfills these needs and provides further related advantages.

BRIEF SUMMARY

In brief, heterogeneous metal oxide catalysts and related methods are disclosed. For example, catalysts comprising oxides of magnesium, manganese, tungsten and/or rare earth elements are provided. The disclosed catalysts find utility in any number of catalytic reactions, for example in the OCM reaction. In some embodiments, the catalysts are advantageously doped with one or more doping elements. The doping elements may be promoters such that the catalyst comprises an improved catalytic activity. For example, in certain embodiments, the catalytic activity is such that the C2 selectivity is 50% or greater and the methane conversion is 20% or greater when the catalyst is employed as a heterogenous catalyst in the oxidative coupling of methane at a temperature of 850° C. or less, 800° C. or less, for example 750° C. or less or 700° C. or less.

In one embodiment, the disclosure provides a catalyst comprising a mixed oxide of magnesium and manganese, wherein the catalyst further comprises lithium and boron dopants and at least one doping element from groups 4, 9, 12, 13 or combinations thereof, wherein the catalyst comprises a $C_2$ selectivity of greater than 50% and a methane conversion of greater than 20% when the catalyst is employed as a heterogenous catalyst in the oxidative coupling of methane at a temperature of 750° C. or less.

In another embodiment, a catalyst comprising a mixed oxide of manganese and tungsten, wherein the catalyst further comprises a sodium dopant and at least one doping element from groups 2, 16 or combinations thereof is provided.

In still another embodiment, the disclosure is directed to a catalyst comprising an oxide of a rare earth element, wherein the catalyst further comprises at least one doping element from groups 1-16, lanthanides, actinides or combinations thereof, wherein the catalyst comprises a $C_2$ selectivity of greater than 50% and a methane conversion of greater than 20% when the catalyst is employed as a heterogenous catalyst in the oxidative coupling of methane at a temperature of 750° C. or less.

In another embodiment, a catalyst comprising a mixed oxide of manganese and tungsten, wherein the catalyst further comprises a sodium dopant and at least one doping element from groups 2, 4-6, 8-15, lanthanides or combinations thereof, wherein the catalyst comprises a $O_2$ selectivity of greater than 50% and a methane conversion of greater than 20% when the catalyst is employed as a heterogenous catalyst in the oxidative coupling of methane at a temperature of 750° C. or less is provided.

In yet other embodiments, the disclosure provides a catalyst comprising a mixed oxide of a lanthanide and tungsten, wherein the catalyst further comprises a sodium dopant and at least one doping element from groups 2, 4-15, lanthanides or combinations thereof, wherein the catalyst comprises a $C_2$ selectivity of greater than 50% and a methane conversion of greater than 20% when the catalyst is employed as a heterogenous catalyst in the oxidative coupling of methane at a temperature of 750° C. or less.

Other embodiments are directed to a catalyst comprising a rare earth oxide and one or more dopants, wherein the catalyst comprises a $C_2$ selectivity of greater than 50% and a methane conversion of greater than 20% when the catalyst is employed as a heterogenous catalyst in the oxidative coupling of methane at a temperature of 750° C. or less, and wherein the dopant comprises Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ca/Cs, Ca/Mg/Na, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Gd/Ho/Sr, Ca/Sr, Ca/Sr/W, Na/Zr/Eu/Tm, Sr/Ho/Tm/Na, Sr/Pb, Ca, Sr/W/Li, Ca/Sr/W, Sr/Hf or combinations thereof.

Still other catalysts of the present invention include a catalyst comprising a mixed oxide of a rare earth element and a Group 13 element, wherein the catalyst further comprises one or more Group 2 elements.

Other embodiments of the present invention are directed to a catalyst comprising a lanthanide oxide doped with an alkali metal, an alkaline earth metal or combinations thereof, and at least one other dopant from groups 3-16.

Methods for use of the disclosed catalysts in catalytic reactions, for example OCM, are also provided. Furthermore, the present disclosure also provides for the preparation of downstream products of ethylene, wherein the ethylene has been prepared via a reaction employing a catalyst disclosed herein.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE SEVERAL VIEWS OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION OF THE INVENTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As discussed above, heterogeneous catalysis takes place between several phases. Generally, the catalyst is a solid, the reactants are gases or liquids and the products are gases or liquids. Thus, a heterogeneous catalyst provides a surface that has multiple active sites for adsorption of one more gas or liquid reactants. Once adsorbed, certain bonds within the reactant molecules are weakened and dissociate, creating reactive fragments of the reactants, e.g., in free radical forms. One or more products are generated as new bonds between the resulting reactive fragments form, in part, due to their proximity to each other on the catalytic surface.

Figure 1:
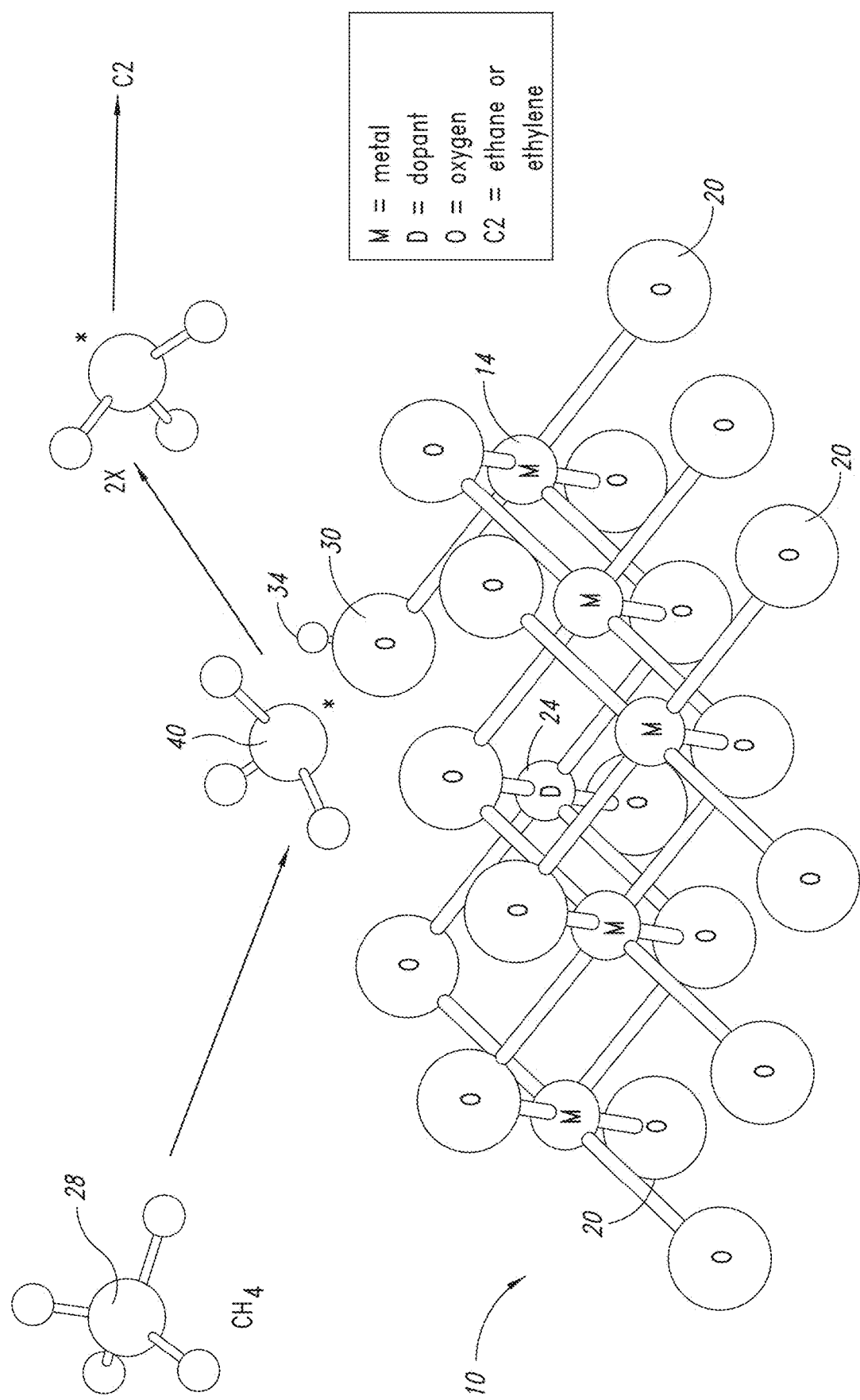
FIG. 1 schematically depicts a first part of an OCM reaction at the surface of a metal oxide catalyst.

As an example, FIG. 1 shows schematically the first part of an OCM reaction that takes place on the surface of a metal oxide catalyst 10 which is followed by methyl radical coupling in the gas phase. A crystal lattice structure of metal atoms 14 and oxygen atoms 20 are shown, with an optional dopant 24 incorporated into the lattice structure. In this reaction, a methane molecule 28 comes into contact with an active site (e.g., surface oxygen 30) and becomes activated when a hydrogen atom 34 dissociates from the methane molecule 28. As a result, a methyl radical 40 is generated on or near the catalytic surface. Two methyl radicals thus generated can couple in the gas phase to create ethane and/or ethylene, which are collectively referred to as the "C2" coupling products.

It is generally recognized that the catalytic properties of a catalyst strongly correlate to its surface morphology. Typically, the surface morphology can be defined by geometric parameters such as: (1) the number of surface atoms (e.g., the surface oxygen of FIG. 1) that coordinate to the reactant; and (2) the degree of coordinative unsaturation of the surface atoms, which is the coordination number of the surface atoms with their neighboring atoms. For example, the reactivity of a surface atom decreases with decreasing coordinative unsaturation. For example, for the dense surfaces of a face-centered crystal, a surface atom with 9 surface atom neighbors will have a different reactivity than one with 8 neighbors. Additional surface characteristics that may contribute to the catalytic properties include, for example, crystal dimensions, lattice distortion, surface reconstructions, defects, grain boundaries, and the like. See, e.g., Van Santen R. A. et al *New Trends in Materials Chemistry* 345-363 (1997).

Advantageously, the catalysts disclosed herein and methods of producing the same have general applicability to a wide variety of heterogeneous catalyses, including without limitation: oxidative coupling of methane (e.g., FIG. 1), oxidative dehydrogenation of alkanes to their corresponding alkenes, selective oxidation of alkanes to alkenes and alkynes, oxidation of carbon monoxide, dry reforming of methane, selective oxidation of aromatics, Fischer-Tropsch reaction, hydrocarbon cracking, combustions of hydrocarbons and the like.

Figure 2:
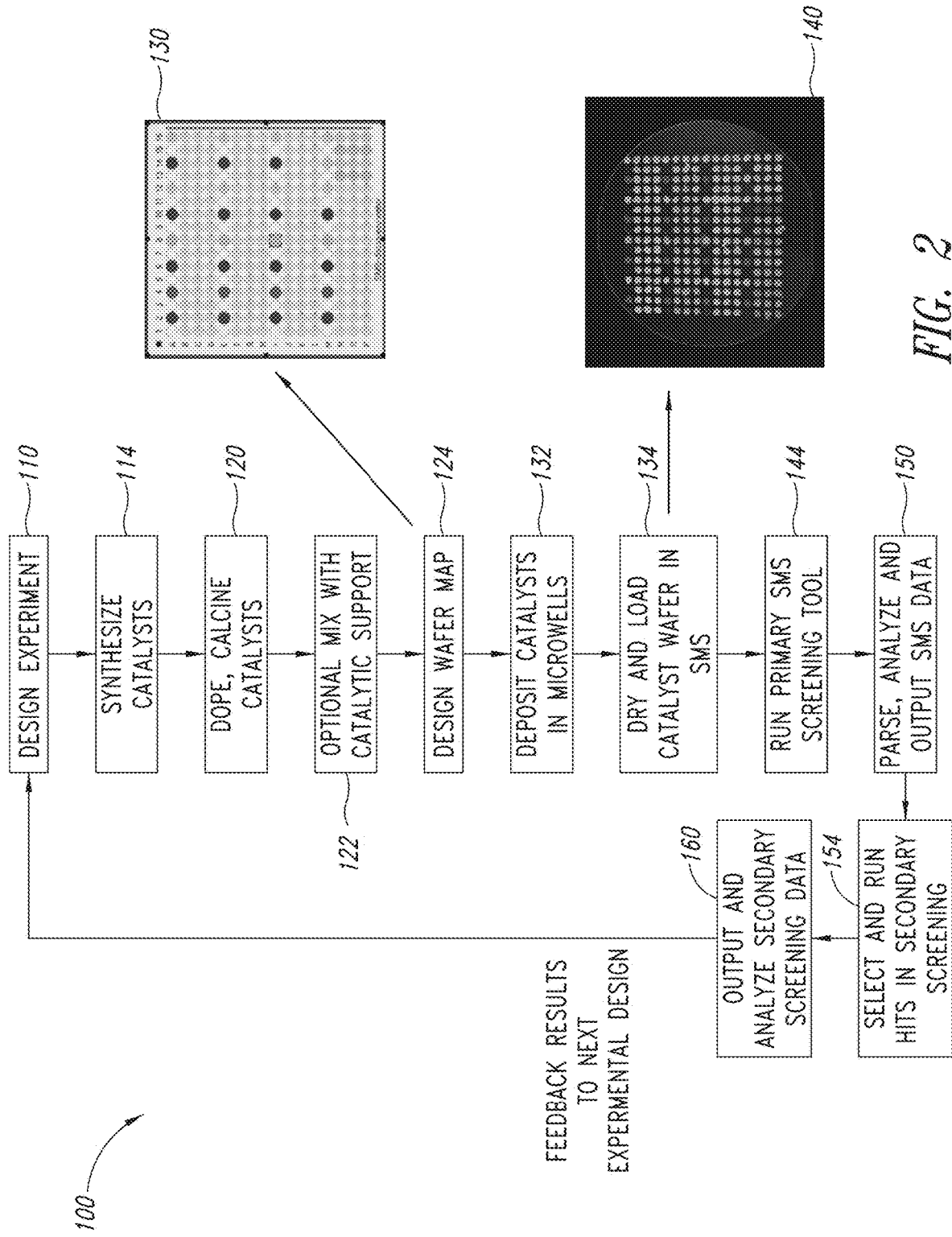
FIG. 2 shows a method for catalyst screening.

FIG. 2 schematically shows a high throughput work flow for generating libraries of diverse catalysts and screening for their catalytic properties. An initial phase of the work flow involves a primary screening, which is designed to broadly and efficiently screen a large and diverse set of catalysts that logically could perform the desired catalytic transformation. For example, certain doped metal oxides (e.g., Mn, Mg, W, etc.) are known catalysts for the OCM reaction. Therefore, catalysts of various metal oxide compositions comprising various dopants can be prepared and evaluated for their catalytic performances in an OCM reaction.

More specifically, the work flow 100 begins with designing synthetic experiments for making various metal oxide compositions (block 110). The synthesis, subsequent treatments and screenings can be manual or automated. As will be discussed in more detail herein, by varying the synthetic conditions, catalysts can be prepared with various surface morphologies and/or compositions in respective microwells (block 114). The catalysts are subsequently calcined and then optionally doped (block 120). Optionally, the doped and calcined catalysts are further mixed with a catalyst support (block 122). Beyond the optional support step, all subsequent steps are carried out in a "wafer" format, in which catalysts are deposited in a quartz wafer that has been etched to create an ordered array of microwells. Each microwell is a self-contained reactor, in which independently variable processing conditions can be designed to include, without limitation, respective choices of elemental compositions, catalyst support, reaction precursors, templates, reaction durations, pH values, temperatures, ratio between reactants, gas flows, and calcining conditions (block 124). Due to design constraints of some wafers, in some embodiments calcining and other temperature variables are identical in all microwells. A wafer map 130 can be created to correlate the processing conditions to the catalyst in each microwell. A library of diverse catalysts can be generated in which each library member corresponds to a particular set of processing conditions and corresponding compositional and/or morphological characteristics.

Catalysts obtained under various synthetic conditions and doping compositions are thereafter deposited in respective microwells of a wafer (140) for evaluating their respective catalytic properties in a given reaction (blocks 132 and 134). The catalytic performance of each library member can be screened serially by several known primary screening technologies, including scanning mass spectroscopy (SMS) (Symyx Technologies Inc., Santa Clara, Calif.). The screening process is fully automated, and the SMS tool can determine if a catalyst is catalytically active or not, as well as its relative strength as a catalyst at a particular temperature. Typically, the wafer is placed on a motion control stage capable of positioning a single well below a probe that flows the feed of the starting material over the catalyst surface and removes reaction products to a mass spectrometer and/or other detector technologies (blocks 134 and 140). The individual catalyst is heated to a preset reaction temperature, e.g., using a $CO_2$ IR laser from the backside of the quartz wafer and an IR camera to monitor temperature and a preset mixture of reactant gases. The SMS tool collects data with regard to the consumption of the reactant(s) and the generation of the product(s) of the catalytic reaction in each well (block 144), and at each temperature and flow rate.

The SMS data obtained as described above provide information on relative catalytic properties among all the library members (block 150). In order to obtain more quantitative data on the catalytic properties of the catalysts, possible hits that meet certain criteria are subjected to a secondary screening (block 154). Typically, secondary screening technologies include a single, or alternatively multiple channel fixed-bed or fluidized bed reactors (as described in more detail herein). In parallel reactor systems or multi-channel fixed-bed reactor system, a single feed system supplies reactants to a set of flow restrictors. The flow restrictors divide the flows evenly among parallel reactors. Care is taken to achieve uniform reaction temperature between the reactors such that the various catalysts can be differentiated solely based on their catalytic performances. The secondary screening allows for accurate determination of catalytic properties such as selectivity, yield and conversion (block 160). These results serve as a feedback for designing further catalyst libraries.

Figure 4:
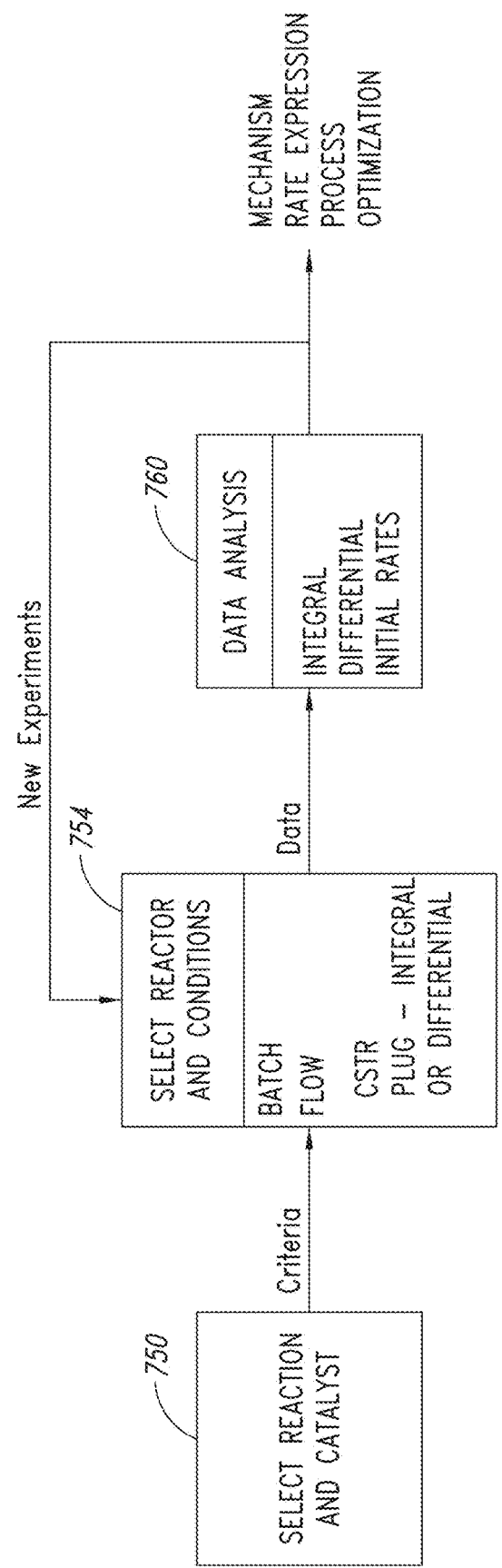
FIG. 4 is a flow chart for data collection and processing in evaluating catalytic performance.

Secondary screening is also schematically depicted in FIG. 4, which depicts a flow chart for data collection and processing in evaluating catalytic performance of catalysts according to the invention. Additional description of SMS tools in a combinatorial approach for discovering catalysts can be found in, e.g., Bergh, S. et al. *Topics in Catalysts* 23:1-4, 2003.

Thus, in accordance with various embodiments described herein, compositional and morphologically diverse catalysts can be rationally synthesized to meet catalytic performance criteria. These and other aspects of the present disclosure are described in more detail below.

Definitions

As used herein, and unless the context dictates otherwise, the following terms have the meanings as specified below.

"Catalyst" means a substance which alters the rate of a chemical reaction. A catalyst may either increase the chemical reaction rate (i.e. a "positive catalyst") or decrease the reaction rate (i.e. a "negative catalyst"). Catalysts participate in a reaction in a cyclic fashion such that the catalyst is cyclically regenerated. "Catalytic" means having the properties of a catalyst.

"Salt" means a compound comprising negative and positive ions. Salts are generally comprised of metallic cations and non-metallic counter ions. As used herein, a metal salt is typically a source of the metal element in a metal oxide catalyst.

"Crystal domain" means a continuous region over which a substance is crystalline.

"Turnover number" is a measure of the number of reactant molecules a catalyst can convert to product molecules per unit time.

"Active" or "catalytically active" refers to a catalyst which has substantial activity in the reaction of interest. For example, in some embodiments a catalyst which is OCM active (i.e., has activity in the OCM reaction) has a C2 selectivity of 5% or more and/or a methane conversion of 5% or more when the catalyst is employed as a heterogenous catalyst in the oxidative coupling of methane at a temperature of 750° C. or less.

"Inactive" or "catalytically inactive" refers to a catalyst which does not have substantial activity in the reaction of interest. For example, in some embodiments a catalyst which is OCM inactive has a C2 selectivity of less than 5% and/or a methane conversion of less than 5% when the catalyst is employed as a heterogenous catalyst in the oxidative coupling of methane at a temperature of 750° C. or less.

"Activation temperature" refers to the temperature at which a catalyst becomes catalytically active.

"OCM activity" refers to the ability of a catalyst to catalyse the OCM reaction.

A catalyst having "high OCM activity" refers to a catalyst having a C2 selectivity of 50% or more and/or a methane conversion of 20% or more when the catalyst is employed as a heterogenous catalyst in the oxidative coupling of methane at a specific temperature, for example 750° C. or less.

A catalyst having "moderate OCM activity" refers to a catalyst having a C2 selectivity of about 20-50% and/or a methane conversion of about 10-20% or more when the catalyst is employed as a heterogenous catalyst in the oxidative coupling of methane at a temperature of 750° C. or less.

A catalyst having "low OCM activity" refers to a catalyst having a C2 selectivity of about 5-20% and/or a methane conversion of about 5-10% or more when the catalyst is employed as a heterogenous catalyst in the oxidative coupling of methane at a temperature of 750° C. or less.

"Base material" refers to the major component of a catalyst. For example a mixed oxide of manganese and magnesium which is doped with lithium and/or boron comprises a manganese/magnesium oxide base material.

"Dopant" or "doping agent" or "doping element" is chemical compound which is added to or incorporated within a catalyst base material to optimize catalytic performance (e.g. increase or decrease catalytic activity). As compared to the undoped catalyst, a doped catalyst may increase or decrease the selectivity, conversion, and/or yield of a reaction catalyzed by the catalyst. Dopants which increase catalystic activity are referred to as "promoters" while dopants which decrease catalytic activity are referred to as "poisons". The dopant may be present in the catalyst in any form and may be derived from any suitable source of the element (e.g., chlorides, bromides, iodides, nitrates, oxynitrates, oxyhalides, acetates, formates, hydroxides, carbonates, phosphates, sulfates, alkoxides, and the like.)

"Atomic percent" (at % or at/at) or "atomic ratio" when used in the context of catalyst dopants refers to the ratio of the total number of dopant atoms to the total number of non-oxygen atoms in the base material. For example, the atomic percent of dopant in a lithium doped $Mg_6MnO_8$ catalyst is determined by calculating the total number of lithium atoms and dividing by the sum of the total number of magnesium and manganese atoms and multiplying by 100 (i.e., atomic percent of dopant=[Li atoms/(Mg atoms+Mn atoms)]×100).

"Weight percent" (wt/wt)" when used in the context of catalyst dopants refers to the ratio of the total weight of dopant to the total combined weight of the dopant and the catalyst. For example, the weight percent of dopant in a lithium doped $Mg_6MnO_8$ catalyst is determined by calculating the total weight of lithium and dividing by the sum of the total combined weight of lithium and $Mg_6MnO_8$ and multiplying by 100 (i.e., weight percent of dopant=[Li weight/(Li weight+$Mg_6MnO_8$ weight)]×100).

"Group 1" elements include lithium (Li), sodium (Na), potassium (K), rubidium (Rb), cesium (Cs), and francium (Fr).

"Group 2" elements include beryllium (Be), magnesium (Mg), calcium (Ca), strontium (Sr), barium (Ba), and radium (Ra).

"Group 3" elements include scandium (Sc) and yttrium (Y).

"Group 4" elements include titanium (Ti), zirconium (Zr), hafnium (Hf), and rutherfordium (Rf).

"Group 5" elements include vanadium (V), niobium (Nb), tantalum (Ta), and dubnium (Db).

"Group 6" elements include chromium (Cr), molybdenum (Mo), tungsten (W), and seaborgium (Sg).

"Group 7" elements include manganese (Mn), technetium (Tc), rhenium (Re), and bohrium (Bh).

"Group 8" elements include iron (Fe), ruthenium (Ru), osmium (Os), and hassium (Hs).

"Group 9" elements include cobalt (Co), rhodium (Rh), iridium (Ir), and meitnerium (Mt).

"Group 10" elements include nickel (Ni), palladium (Pd), platinum (Pt) and darmstadium (Ds).

"Group 11" elements include copper (Cu), silver (Ag), gold (Au), and roentgenium (Rg).

"Group 12" elements include zinc (Zn), cadmium (Cd), mercury (Hg), and copernicium (Cn).

"Group 16" elements include oxygen (O), sulfur (S), selenium (Se), tellurium (Te) and polonium (Po).

"Lanthanides" include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

"Actinides" include actinium (Ac), thorium (Th), protactinium (Pa), uranium (U), neptunium (Np), plutonium (Pu), americium (Am), curium (Cm), berkelium (Bk), californium (Cf), einsteinium (Es), fermium (Fm), mendelevium (Md), nobelium (No), and lawrencium (Lr).

"Rare earth elements" include the lanthanides, actinides and Group 3.

"Metal element" or "metal" is any element, except hydrogen, selected from Groups 1 through 12, lanthanides, actinides, aluminum (Al), gallium (Ga), indium (In), tin (Sn), thallium (Tl), lead (Pb), and bismuth (Bi). Metal elements include metal elements in their elemental form as well as metal elements in an oxidized or reduced state, for example, when a metal element is combined with other elements in the form of compounds comprising metal elements. For example, metal elements can be in the form of hydrates, salts, oxides, as well as various polymorphs thereof, and the like.

"Semi-metal element" refers to an element selected from boron (B), silicon (Si), germanium (Ge), arsenic (As), antimony (Sb), tellurium (Te), and polonium (Po).

"Non-metal element" refers to an element selected from carbon (C), nitrogen (N), oxygen (O), fluorine (F), phosphorus (P), sulfur (S), chlorine (Cl), selenium (Se), bromine (Br), iodine (I), and astatine (At).

"Conversion" means the mole fraction (i.e., percent) of a reactant converted to a product or products.

"Selectivity" refers to the percent of converted reactant that went to a specified product, e.g., C2 selectivity is the % of converted methane that formed ethane and ethylene, C3 selectivity is the % of converted methane that formed propane and propylene, CO selectivity is the % of converted methane that formed CO.

"Yield" is a measure of (e.g. percent) of product obtained relative to the theoretical maximum product obtainable. Yield is calculated by dividing the amount of the obtained product in moles by the theoretical yield in moles. Percent yield is calculated by multiplying this value by 100. C2 yield is defined as the sum of the ethane and ethylene molar flow at the reactor outlet multiplied by two and divided by the inlet methane molar flow. C3 yield is defined as the sum of propane and propylene molar flow at the reactor outlet multiplied by three and divided by the inlet methane molar flow. C2+ yield is the sum of the C2 yield and C3 yield. Yield is also calculable by multiplying the methane conversion by the relevant selectivity, e.g. C2 yield is equal to the methane conversion times the C2 selectivity.

"C2" yield is the total combined yield of ethane and ethylene.

"C2" selectivity is the combined selectivity for ethane and ethylene.

"Bulk catalyst" or "bulk material" means a catalyst prepared by traditional techniques, for example by milling or grinding large catalyst particles to obtain smaller/higher surface area catalyst particles.

"Nanostructured catalyst" means a catalyst having at least one dimension on the order of nanometers (e.g. between about 1 and 100 nanometers). Non-limiting examples of nanostructured catalysts include nanoparticle catalysts and nanowire catalysts.

"Nanoparticle" means a particle having at least one diameter on the order of nanometers (e.g. between about 1 and 100 nanometers).

"Nanowire" means a nanowire structure having at least one diameter on the order of nanometers (e.g. between about 1 and 100 nanometers) and an aspect ratio greater than 10:1. The "aspect ratio" of a nanowire is the ratio of the actual length (L) of the nanowire to the diameter (D) of the nanowire. Aspect ratio is expressed as L:D. Exemplary nanowires are known in the art and described in more detail in co-pending U.S. application Ser. No. 13/115,082 (U.S. Pub. No. 2012/0041246); U.S. Provisional Application Nos. 61/564,834 and 61/564,836; and U.S. Provisional application entitled "Nanowire Catalysts", filed May 24, 2012, the full disclosures of which are hereby incorporated by reference in their entirety for all purposes.

An "extrudate" refers to a material (e.g., catalytic material) prepared by forcing a semisolid material comprising a catalyst through a die or opening of appropriate shape. Extrudates can be prepared in a variety of shapes and structures by common means known in the art.

A "pellet" or "pressed pellet" refers to a material (e.g., catalytic material) prepared by applying pressure to (i.e., compressing) a material comprising a catalyst into a desired shape. Pellets having various dimensions and shapes can be prepared according to common techniques in the art.

"Monolith" or "monolith support" is generally a structure formed from a single structural unit preferably having passages disposed through it in either an irregular or regular pattern with porous or non-porous walls separating adjacent passages. Examples of such monolithic supports include, e.g., ceramic or metal foam-like or porous structures. The single structural unit may be used in place of or in addition to conventional particulate or granular catalysts (e.g., pellets or extrudates). Examples of such irregular patterned monolith substrates include filters used for molten metals. Monoliths generally have a porous fraction ranging from about 60% to 90% and a flow resistance substantially less than the flow resistance of a packed bed of similar volume (e.g., about 10% to 30% of the flow resistance of a packed bed of similar volume). Examples of regular patterned substrates include monolith honeycomb supports used for purifying exhausts from motor vehicles and used in various chemical processes and ceramic foam structures having irregular passages. Many types of monolith support structures made from conventional refractory or ceramic materials such as alumina, zirconia, yttria, silicon carbide, and mixtures thereof, are well known and commercially available from, among others, Corning, lac.; Vesuvius Hi-Tech Ceramics, Inc.; and Porvair Advanced Materials, Inc. and SiCAT (Sicatalyst.com). Monoliths include foams, honeycombs, foils, mesh, gauze and the like.

"Alkane" means a straight chain or branched, noncyclic or cyclic, saturated aliphatic hydrocarbon. Alkanes include linear, branched and cyclic structures. Representative straight chain alkanes include methane, ethane, n-propane, n-butane, n-pentane, n-hexane, and the like; while branched alkanes include isopropane, sec-butane, isobutane, tert-butane, isopentane, and the like. Representative cyclic alkanes include cyclopropane, cyclobutane, cyclopentane, cyclohexane, and the like. "Alkene" means a straight chain or branched, noncyclic or cyclic, unsaturated aliphatic hydrocarbon having at least one carbon-carbon double bond. Alkenes include linear, branched and cyclic structures. Representative straight chain and branched alkenes include ethylene, propylene, 1-butene, 2-butene, isobutene, 1-pentene, 2-pentene, 3-methyl-1-butene, 2-methyl-2-butene, 2,3-dimethyl-2-butene, and the like. Cyclic alkenes include cyclohexene and cyclopentene and the like. "Alkyne" means a straight chain or branched, noncyclic or cyclic, unsaturated aliphatic hydrocarbon having at least one carbon-carbon triple bond. Alkynes include linear, branched and cyclic structures. Representative straight chain and branched alkynes include acetylene, propyne, 1-butyne, 2-butyne, 1-pentyne, 2-pentyne, 3-methyl-1-butyne, and the like. Representative cyclic alkynes include cycloheptyne and the like.

"Aromatic" means a carbocyclic moiety having a cyclic system of conjugated p orbitals. Representative examples of aromatics include benzene, naphthalene and toluene.

"Carbon-containing compounds" are compounds which comprise carbon. Non-limiting examples of carbon-containing compounds include hydrocarbons, CO and $CO_2$.

"Oxide" refers to a metal compound comprising oxygen. Examples of oxides include, but are not limited to, metal oxides ($M_xO_y$), metal oxyhalide ($M_xO_yX_z$), metal oxynitrates ($M_xO_y(NO_3)_x$), metal phosphates ($M_x(PO_4)_y$), and the like, wherein x, y and z are numbers from 1 to 100.

"Mixed oxide" or "mixed metal oxide" refers to a compound comprising two or more oxidized metals and oxygen (i.e., $M1_xM2_yO_z$, wherein M1 and M2 are the same or different metal elements, O is oxygen and x, y and z are numbers from 1 to 100). A mixed oxide may comprise metal elements in various oxidation states and may comprise more than one type of metal element. For example, a mixed oxide of manganese and magnesium comprises oxidized forms of magnesium and manganese. Each individual manganese and magnesium atom may or may not have the same oxidation state. Mixed oxides comprising 2, 3, 4, 5, 6 or more metal elements can be represented in an analogous manner. Mixed oxides also include oxy-hydroxides (e.g., $M_xO_yOH_z$, wherein M is a metal element, O is oxygen, x, y and z are numbers from 1 to 100 and OH is hydroxy). Mixed oxides may be represented herein as M1-M2, wherein M1 and M2 are each independently a metal element.

"Rare earth oxide" refers to an oxide of an element from group 3, lanthanides or actinides. Rare earth oxides include mixed oxide containing a rare earth element. Examples of rare earth oxides include, but are not limited to, $La_2O_3$, $Nd_2O_3$, $Yb_2O_3$, $Eu_2O_3$, $Sm_2O_3$, $Y_2O_3$, $Ce_2O_3$, $Pr_2O_3$, $Ln1_{4-x}Ln2_xO_6$, $La_{4-x}Ln1_xO_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La and Ce—La.

Catalysts

1. Molecular Composition of the Catalysts

As noted above, disclosed herein are catalysts useful in various catalytic reactions. In some embodiments, the catalysts are bulk catalysts (i.e., not nanowire or other nanostructured catalysts). In some embodiments, the catalysts comprise one or more metal elements for example, the catalysts may be mono-metallic, bi-metallic, tri-metallic, etc (i.e. contain one, two, three, etc. metal elements). In some embodiments, the metal elements are present in the catalysts in elemental form while in other embodiments the metal elements are present in oxidized form. In other embodiments the metal elements are present in the catalysts in the form of a compound comprising a metal element. The metal element or compound comprising the metal element may be in the form of oxides (e.g., mixed oxides), hydroxides, carbonates, oxy-hydroxides, oxycarbonates, salts, hydrates, and the like. The metal element or compound comprising the metal element may also be in the form of any of a number of different polymorphs or crystal structures.

In other embodiments, the catalysts may comprise one or more element from group 2 and one or more element from group 7 which may be in the form of an oxide. For example, the catalyst may comprise magnesium and manganese. The magnesium and manganese may be in oxidized form, for example in the form of a mixed metal oxide.

Catalysts comprising mixed oxides of Mn and Mg are well suited for incorporation of dopants because magnesium atoms can be easily substituted by other atoms as long as their size is comparable with magnesium. A family of "doped" $Mg_6MnO_8$ compounds with the composition $M_{(x)}Mg_{(6-x)}MnO_8$, wherein each M is independently a dopant as defined herein and x is 0 to 6, can thus be created. The oxidation state of Mn can be tuned by selecting different amounts (i.e., different values of x) of M with different oxidation states, for example $Li_{(x)}Mg_{(6-x)}MnO$ would contain a mixture of Mn(IV) and Mn(V) with x<1 and a mixture that may include Mn(V), Mn(VI), Mn(VII) with x>1. The maximum value of x depends on the ability of a particular atom M to be incorporated in the $Mg_6MnO_8$ crystal structure and therefore varies depending on M. It is believed that the ability to tune the manganese oxidation state as described above could have advantageous effect on the catalytic activity (e.g., selectivity, yield, conversion, etc.) of the disclosed catalysts in various reactions, including the OCM reaction. Accordingly, in some embodiments, the present disclosure provides a mixed oxide of manganese and magnesium which has been doped with lithium and boron. In further embodiments, the catalyst comprises a $C_2$ selectivity of greater than 50% and a methane conversion of greater than 20% when the catalyst is employed as a heterogenous catalyst in the oxidative coupling of methane at a temperature of 750° C. or less.

Suprisingly, it has been found that addition of further dopants to the above described catalyst increases the catalytic activity of the catalyst in the OCM and other reactions. For example, a catalyst comprising a mixed oxide of manganese and magnesium which further comprises lithium and boron and at least one doping element from any of groups 1-13 are effective catalysts for use in the OCM reaction. In some specific examples, the at least one doping element is from groups 4, 9, 12 or 13, and in further embodiments, the catalyst comprises a $C_2$ selectivity of greater than 50% and a methane conversion of greater than 20% when the catalyst is employed as a heterogenous catalyst in the oxidative coupling of methane at a temperature of 750° C. or less. In some examples, the doping element is rhodium. In other examples, the doping element is cobalt. In yet other embodiments, the doping element is zirconium, while in other embodiments, the doping element is zinc. Other embodiments include a gallium doping element or a sodium doping element.

In addition, Applicants have discovered that further doping of the manganese/magnesium mixed oxide catalyst can further improve the catalytic activity of the catalyst. For example, although sodium itself is not a promoting dopant, it has been found that addition of sodium, together with a cobalt or gallium dopant to the above catalyst results in an effective OCM catalyst. Thus in one embodiment of the foregoing, the present disclosure provides a mixed oxide of manganese and magnesium which further includes lithium, boron, cobalt and sodium as dopants. In other examples, the catalyst comprises a mixed oxide of manganese and magnesium which further includes lithium, boron, gallium and sodium as dopants.

Inclusion of even further dopants within the above noted catalysts can improve the activity thereof. For example, in some embodiments the catalyst comprises a mixed oxide of manganese and magnesium and further comprises lithium and boron dopants and at least one doping element from groups 4, 9, 12, 13 or combinations thereof, and further comprises at least one additional doping element from group 2. For example, a catalyst comprising a mixed oxide of manganese and magnesium which further includes lithium, boron, cobalt and sodium can be further doped with beryllium, barium, aluminum, hafnium or combinations thereof. In other embodiments, the mixed oxide of manganese and magnesium is further doped with beryllium. In other embodiments, the mixed oxide of manganese and magnesium is further doped with barium. In other embodiments, the mixed oxide of manganese and magnesium is further doped with aluminum. In other embodiments, the mixed oxide of manganese and magnesium is further doped with hafnium.

Similarly, a catalyst comprising a mixed oxide of manganese and magnesium which further includes lithium, boron, gallium and sodium can be further doped with beryllium, barium, aluminum, hafnium or combinations thereof. In other embodiments of the foregoing catalyst, the mixed oxide of manganese and magnesium is further doped with beryllium. In other embodiments, the mixed oxide of manganese and magnesium is further doped with barium. In other embodiments, the mixed oxide of manganese and magnesium is further doped with aluminum. In other embodiments, the mixed oxide of manganese and magnesium is further doped with hafnium.

Mixed oxides comprising manganese, tungsten and sodium (Na/Mn/W/O) is a promising OCM catalyst. The Na/Mn/W/O system is attractive due to its high C2 selectivity and yield. Unfortunately, good catalytic activity is only achievable at temperatures greater than 800° C. and although the exact active portion of the catalyst is still subject to debate, it is thought that sodium plays an important role in the catalytic cycle. In addition, the Na/Mn/W/O catalyst surface area is relatively low <2 m²/g. However, applicants have discovered that addition of certain dopants to the Na/Mn/W/O catalyst system can increase the catalytic activity thereof. In addition, certain catalyst supports as described below, with or without dopants, can increase the catalytic activity of the Na/Mn/W/O catalyst, for example in the OCM reaction. In some embodiments, the Na/Mn/W/O catalyst comprises a $C_2$ selectivity of greater than 50% and a methane conversion of greater than 20% when the catalyst is employed as a heterogenous catalyst in the oxidative coupling of methane at a temperature of 750° C. or less.

Doping elements which have been found to increase the catalytic activity of a Na/Mn/W/O catalyst include elements from groups 2, 16 or combinations thereof. Accordingly, in some embodiments the Na/Mn/W/O catalyst is doped with at least one doping element from group 2, 16 or combinations thereof. For example, some embodiments include beryllium, barium, aluminum, hafnium or combinations thereof as dopants. In other embodiments, the doping element is beryllium. In some other embodiments, the doping element is barium. In yet other embodiments, the doping element is aluminum, while in other embodiments, the doping element is hafnium. The Na/Mn/W/O catalyst (doped or undoped) has also been found to benefit from various catalyst supports, including those described below. For example, in some embodiments the catalyst support is $SiO_2$. In other embodiments, the catalyst support is $SiO_2$, $ZrO_2$, $HfO_2$, $InO_2$ or combinations thereof.

Catalysts comprising rare earth oxides (i.e., lanthanides, actinides and Group 3) doped with various elements are also effective catalysts in the OCM reaction. In some embodiments the rare earth oxide is a rare earth mixed oxide (i.e., an oxide of two or more rare earth elements). The rare earth oxide may comprise any rare earth element, and in certain embodiments the rare earth element is La, Nd, Eu, Sm, Yb, Gd or Y. In some embodiments, the rare earth element is La. In other embodiments, the rare earth element is Nd. In other embodiments, the rare earth element is Eu. In other embodiments, the rare earth element is Sm. In other embodiments, the rare earth element is Yb. In other embodiments, the rare earth element is Gd. In other embodiments, the rare earth element is Y.

In certain embodiments of the catalysts comprising rare earth oxides, the catalyst may further comprise a dopant selected from alkaline earth (Group 2) elements. For example, in some embodiments the dopant is selected from Be, Mg, Ca, Sr and Ba. In other embodiments, the dopant is Be. In other embodiments, the dopant is Ca. In other embodiments, the dopant is Sr. In other embodiments, the dopant is Ba.

In some specific embodiments, the rare earth oxide is a mixed rare earth oxide such as $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$ or combinations thereof and the like.

The degree of effectiveness of a particular dopant is a function of the rare earth used and the concentration of the dopant. In addition to Alkali earth elements, further embodiments of the rare earth oxide catalysts include embodiments wherein the catalysts comprise alkali elements as dopants which further promote the selectivity of the OCM catalytic activity of the doped material. In yet other embodiments of the foregoing, the catalysts comprise both an alkali element and alkali earth element as dopant.

In still further embodiments, the catalyst comprises a rare earth oxide (e.g., rare earth mixed oxides) and at least one dopant is selected from groups 1-16, lanthanides actinides or combinations thereof. In certain embodiments, such catalysts comprises a $C_2$ selectivity of greater than 50% and a methane conversion of greater than 20% when the catalyst is employed as a heterogenous catalyst in the oxidative coupling of methane at a temperature of 750° C. or less. In some embodiments, the at least one doping element is selected from groups 1-4, 8, 13, 14, lactinides, actinides and combinations thereof. In some other embodiments, the at least one doping element is selected from groups 1-6, 8, 11, 13-15, lactinides, actinides and combinations thereof.

In some further embodiments of the foregoing, the at least one doping element is a rare earth element. In some embodiments, the at least one doping element is Na, Mg, Ca, Sr, Ga, Sc, Y, Zr, In, Nd, Eu, Sm, Ce, Gd, Hf, Ho, Tm, W, La, K, Dy, Cs, S, Zn, Rb, Ba, Yb, Ni, Lu, Ta, P, Pt, Bi, Sn, Nb, Sb, Ge, Ag, Au, Pb, Re, Fe, Al, Tl, Pr, Co, Rh, Ti, V, Cr, Mn, Ir, As, Li, Tb, Er, Te or Mo.

In other embodiments, the at least one doping element is sodium. In other embodiments, the at least one doping element is magnesium. In other embodiments, the at least one doping element is calcium. In other embodiments, the at least one doping element is strontium. In other embodiments, the at least one doping element is gallium. In other embodiments, the at least one doping element is Scandium. In other embodiments, the at least one doping element is yttrium. In other embodiments, the at least one doping element is zirconium. In other embodiments, the at least one doping element is indium. In other embodiments, the at least one doping element is neodymium. In other embodiments, the at least one doping element is europium. In other embodiments, the at least one doping element is cerium. In other embodiments, the at least one doping element is gadolinium. In other embodiments, the at least one doping element is hafnium. In other embodiments, the at least one doping element is holmium. In other embodiments, the at least one doping element is thulium. In other embodiments, the at least one doping element is tungsten. In other embodiments, the at least one doping element is lanthanum. In other embodiments, the at least one doping element is potassium. In other embodiments, the at least one doping element is dysprosium. In other embodiments, the at least one doping element is caesium. In other embodiments, the at least one doping element is sulfur. In other embodiments, the at least one doping element is zinc. In other embodiments, the at least one doping element is rubidium. In other embodiments, the at least one doping element is barium. In other embodiments, the at least one doping element is ytterbium. In other embodiments, the at least one doping element is nickel. In other embodiments, the at least one doping element is lutetium. In other embodiments, the at least one doping element is tantalum. In other embodiments, the at least one doping element is phosphorous. In other embodiments, the at least one doping element is platinum. In other embodiments, the at least one doping element is bismuth. In other embodiments, the at least one doping element is tin. In other embodiments, the at least one doping element is niobium. In other embodiments, the at least one doping element is antimony. In other embodiments, the at least one doping element is germanium. In other embodiments, the at least one doping element is silver. In other embodiments, the at least one doping element is gold. In other embodiments, the at least one doping element is lead. In other embodiments, the at least one doping element is rhenium. In other embodiments, the at least one doping element is iron. In other embodiments, the at least one doping element is aluminum. In other embodiments, the at least one doping element is thallium. In other embodiments, the at least one doping element is praseodymium. In other embodiments, the at least one doping element is cobalt. In other embodiments, the at least one doping element is rhodium. In other embodiments, the at least one doping element is titanium. In other embodiments, the at least one doping element is vanadium. In other embodiments, the at least one doping element is chromium. In other embodiments, the at least one doping element is manganese. In other embodiments, the at least one doping element is iridium. In other embodiments, the at least one doping element is arsenic. In other embodiments, the at least one doping element is lithium. In other embodiments, the at least one doping element is terbium. In other embodiments, the at least one doping element is erbium. In other embodiments, the at least one doping element is tellurium. In other embodiments, the at least one doping element is molybdenum.

In some embodiments, the catalyst comprises a rare earth oxide and a combination of at least two different doping elements. For example, in some embodiments the two different doping elements are selected from Na, Mg, Ca, Sr, Ga, Sc, Y, Zr, In, Nd, Eu, Sm, Ce, Gd, Hf, Ho, Tm, W, La, K, Dy, In, Cs, S, Zn, Rb, Ba, Yb, Ni, Lu, Ta, P, Pt, Bi, Sn, Nb, Sb, Ge, Ag, Au, Pb, Re, Fe, Al, Tl, Pr, Co, Rh, Ti, V, Cr, Mn, Ir, As, Li, Tb, Er, Te and Mo. In other embodiments, the combination of at least two doping elements is Eu/Na, Sr/Na, Mg/Na, Sr/W, K/La, K/Na, Li/Cs, Li/Na, Zn/K, Li/K, Rb/Hf, Ca/Cs, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Zr/Cs, Ca/Ce, Li/Sr, Cs/Zn, Dy/K, La/Mg, In/Sr, Sr/Cs, Ga/Cs, Lu/Fe, Sr/Tm, La/Dy, Mg/K, Zr/K, Li/Cs, Sm/Cs, In/K, Lu/Tl, Pr/Zn, Lu/Nb, Na/Pt, Na/Ce, Ba/Ta, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Ca/Sr, Sr/Pb or Sr/Hf.

In other embodiments, the combination of at least two different doping elements is La/Nd, La/Sm, La/Ce, La/Sr, Eu/Na, Eu/Gd, Ca/Na, Eu/Sm, Eu/Sr, Mg/Sr, Ce/Mg, Gd/Sm, Sr/W, Sr/Ta, Au/Re, Au/Pb, Bi/Hf, Sr/Sn, Mg/N, Ca/S, Rb/S, Sr/Nd, Eu/Y, Mg/Nd, Sr/Na, Nd/Mg, La/Mg, Yb/S, Mg/Na, Sr/W, K/La, K/Na, Li/Cs, Li/Na, Zn/K, Li/K, Rb/Hf, Ca/Cs, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Zr/Cs, Ca/Ce, Li/Sr, Cs/Zn, Dy/K, La/Mg, In/Sr, Sr/Cs, Ga/Cs, Lu/Fe, Sr/Tm, La/Dy, Mg/K, Zr/K, Li/Cs, Sm/Cs, In/K, Lu/Tl, Pr/Zn, Lu/Nb, Na/Pt, Na/Ce, Ba/Ta, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Ca/Sr, Sr/Pb or Sr/Hf.

In other embodiments, the combination of two doping elements is La/Nd. In other embodiments, the combination of two doping elements is La/Sm. In other embodiments, the combination of two doping elements is La/Ce. In other embodiments, the combination of two doping elements is La/Sr. In other embodiments, the combination of two doping elements is Eu/Na. In other embodiments, the combination of two doping elements is Eu/Gd. In other embodiments, the combination of two doping elements is Ca/Na. In other embodiments, the combination of two doping elements is Eu/Sm. In other embodiments, the combination of two doping elements is Eu/Sr. In other embodiments, the combination of two doping elements is Mg/Sr. In other embodiments, the combination of two doping elements is Ce/Mg. In other embodiments, the combination of two doping elements is Gd/Sm. In other embodiments, the combination of two doping elements is Sr/W. In other embodiments, the combination of two doping elements is Sr/Ta. In other embodiments, the combination of two doping elements is Au/Re. In other embodiments, the combination of two doping elements is Au/Pb. In other embodiments, the combination of two doping elements is Bi/Hf. In other embodiments, the combination of two doping elements is Sr/Sn. In other embodiments, the combination of two doping elements is Mg/N. In other embodiments, the combination of two doping elements is Ca/S. In other embodiments, the combination of two doping elements is Rb/S. In other embodiments, the combination of two doping elements is Sr/Nd. In other embodiments, the combination of two doping elements is Eu/Y. In other embodiments, the combination of two doping elements is Mg/Nd. In other embodiments, the combination of two doping elements is Sr/Na. In other embodiments, the combination of two doping elements is Nd/Mg. In other embodiments, the combination of two doping elements is La/Mg. In other embodiments, the combination of two doping elements is Yb/S. In other embodiments, the combination of two doping elements is Mg/Na. In other embodiments, the combination of two doping elements is Sr/W. In other embodiments, the combination of two doping elements is K/La. In other embodiments, the combination of two doping elements is K/Na. In other embodiments, the combination of two doping elements is Li/Cs. In other embodiments, the combination of two doping elements is Li/Na. In other embodiments, the combination of two doping elements is Zn/K. In other embodiments, the combination of two doping elements is Li/K. In other embodiments, the combination of two doping elements is Rb/Hf. In other embodiments, the combination of two doping elements is Ca/Cs. In other embodiments, the combination of two doping elements is Hf/Bi. In other embodiments, the combination of two doping elements is Sr/Sn. In other embodiments, the combination of two doping elements is Sr/W. In other embodiments, the combination of two doping elements is Sr/Nb. In other embodiments, the combination of two doping elements is Zr/W. In other embodiments, the combination of two doping elements is Y/W. In other embodiments, the combination of two doping elements is Na/W. In other embodiments, the combination of two doping elements is Bi/W. In other embodiments, the combination of two doping elements is Bi/Cs. In other embodiments, the combination of two doping elements is Bi/Ca. In other embodiments, the combination of two doping elements is Bi/Sn. In other embodiments, the combination of two doping elements is Bi/Sb. In other embodiments, the combination of two doping elements is Ge/Hf. In other embodiments, the combination of two doping elements is Hf/Sm. In other embodiments, the combination of two doping elements is Sb/Ag. In other embodiments, the combination of two doping elements is Sb/Bi. In other embodiments, the combination of two doping elements is Sb/Au. In other embodiments, the combination of two doping elements is Sb/Sm. In other embodiments, the combination of two doping elements is Sb/Sr. In other embodiments, the combination of two doping elements is Sb/W. In other embodiments, the combination of two doping elements is Sb/Hf. In other embodiments, the combination of two doping elements is Sb/Yb. In other embodiments, the combination of two doping elements is Sb/Sn. In other embodiments, the combination of two doping elements is Yb/Au. In other embodiments, the combination of two doping elements is Yb/Ta. In other embodiments, the combination of two doping elements is Yb/W. In other embodiments, the combination of two doping elements is Yb/Sr. In other embodiments, the combination of two doping elements is Yb/Pb. In other embodiments, the combination of two doping elements is Yb/W. In other embodiments, the combination of two doping elements is Yb/Ag. In other embodiments, the combination of two doping elements is Au/Sr. In other embodiments, the combination of two doping elements is W/Ge. In other embodiments, the combination of two doping elements is Ta/Hf. In other embodiments, the combination of two doping elements is W/Au. In other embodiments, the combination of two doping elements is Ca/W. In other embodiments, the combination of two doping elements is Au/Re. In other embodiments, the combination of two doping elements is Sm/Li. In other embodiments, the combination of two doping elements is La/K. In other embodiments, the combination of two doping elements is Zn/Cs. In other embodiments, the combination of two doping elements is Zr/Cs. In other embodiments, the combination of two doping elements is Ca/Ce. In other embodiments, the combination of two doping elements is Li/Sr. In other embodiments, the combination of two doping elements is Cs/Zn. In other embodiments, the combination of two doping elements is Dy/K. In other embodiments, the combination of two doping elements is La/Mg. In other embodiments, the combination of two doping elements is In/Sr. In other embodiments, the combination of two doping elements is Sr/Cs. In other embodiments, the combination of two doping elements is Ga/Cs. In other embodiments, the combination of two doping elements is Lu/Fe. In other embodiments, the combination of two doping elements is Sr/Tm. In other embodiments, the combination of two doping elements is La/Dy. In other embodiments, the combination of two doping elements is Mg/K. In other embodiments, the combination of two doping elements is Zr/K. In other embodiments, the combination of two doping elements is Li/Cs. In other embodiments, the combination of two doping elements is Sm/Cs. In other embodiments, the combination of two doping elements is In/K. In other embodiments, the combination of two doping elements is Lu/Tl. In other embodiments, the combination of two doping elements is Pr/Zn. In other embodiments, the combination of two doping elements is Lu/Nb. In other embodiments, the combination of two doping elements is Na/Pt. In other embodiments, the combination of two doping elements is Na/Ce. In other embodiments, the combination of two doping elements is Ba/Ta. In other embodiments, the combination of two doping elements is Cu/Sn. In other embodiments, the combination of two doping elements is Ag/Au. In other embodiments, the combination of two doping elements is Al/Bi. In other embodiments, the combination of two doping elements is Al/Mo. In other embodiments, the combination of two doping elements is Al/Nb. In other embodiments, the combination of two doping elements is Au/Pt. In other embodiments, the combination of two doping elements is Ga/Bi. In other embodiments, the combination of two doping elements is Mg/W. In other embodiments, the combination of two doping elements is Pb/Au. In other embodiments, the combination of two doping elements is Sn/Mg. In other embodiments, the combination of two doping elements is Zn/Bi. In other embodiments, the combination of two doping elements is Gd/Ho. In other embodiments, the combination of two doping elements is Zr/Bi. In other embodiments, the combination of two doping elements is Ho/Sr. In other embodiments, the combination of two doping elements is Ca/Sr. In other embodiments, the combination of two doping elements is Sr/Pb. In other embodiments, the combination of two doping elements is Sr/Hf.

In some other embodiments, the oxide of a rare earth element comprises a combination of at least three different doping elements. In certain examples, the three different doping elements are selected from Na, Mg, Ca, Sr, Ga, Sc, Y, Zr, In, Nd, Eu, Sm, Ce, Gd, Hf, Ho, Tm, W, La, K, Dy, In, Cs, S, Zn, Rb, Ba, Yb, Ni, Lu, Ta, P, Pt, Bi, Sn, Nb, Sb, Ge, Ag, Au, Pb, Re, Fe, Al, Tl, Pr, Co, Rh, Ti, V, Cr, Mn, Ir, As, Li, Tb, Er, Te and Mo. In certain other embodiments, the combination of at least three different doping elements is Mg/La/K, Na/Dy/K, Na/La/Dy, Na/La/Eu, Na/La/K, K/La/S, Li/Cs/La, Li/Sr/Cs, Li/Ga/Cs, Li/Na/Sr, Li/Sm/Cs, Cs/K/La, Sr/Cs/La, Sr/Ho/Tm, La/Nd/S, Li/Rb/Ca, Rb/Sr/Lu, Na/Eu/Hf, Dy/Rb/Gd, Na/Pt/Bi, Ca/Mg/Na, Na/K/Mg, Na/Li/Cs, La/Dy/K, Sm/Li/Sr, Li/Rb/Ga, Li/Cs/Tm, Li/K/La, Ce/Zr/La, Ca/Al/La, Sr/Zn/La, Cs/La/Na, La/S/Sr, Rb/Sr/La, Na/Sr/Lu, Sr/Eu/Dy, La/Dy/Gd, Gd/Li/K, Rb/K/Lu, Na/Ce/Co, Ba/Rh/Ta, Na/Al/Bi, Cs/Eu/S, Sm/Tm/Yb, Hf/Zr/Ta, Na/Ca/Lu, Gd/Ho/Sr, Ca/Sr/W, Na/Zr/Eu/Tm, Sr/W/Li, Ca/Sr/W or Mg/Nd/Fe.

In still other embodiments, the combination of at least three different doping elements is Nd/Sr/CaO, La/Nd/Sr, La/Bi/Sr, Mg/Nd/Fe, Mg/La/K, Na/Dy/K, Na/La/Dy, Na/La/Eu, Na/La/K, K/La/S, Li/Cs/La, Li/Sr/Cs, Li/Ga/Cs, Li/Na/Sr, Li/Sm/Cs, Cs/K/La, Sr/Cs/La, Sr/Ho/Tm, La/Nd/S, Li/Rb/Ca, Rb/Sr/Lu, Na/Eu/Hf, Dy/Rb/Gd, Na/Pt/Bi, Ca/Mg/Na, Na/K/Mg, Na/Li/Cs, La/Dy/K, Sm/Li/Sr, Li/Rb/Ga, Li/Cs/Tm, Li/K/La, Ce/Zr/La, Ca/Al/La, Sr/Zn/La, Cs/La/Na, La/S/Sr, Rb/Sr/La, Na/Sr/Lu, Sr/Eu/Dy, La/Dy/Gd, Gd/Li/K, Rb/K/Lu, Na/Ce/Co, Ba/Rh/Ta, Na/Al/Bi, Cs/Eu/S, Sm/Tm/Yb, Hf/Zr/Ta, Na/Ca/Lu, Gd/Ho/Sr, Ca/Sr/W, Na/Zr/Eu/Tm, Sr/W/Li or Ca/Sr/W.

In other embodiments, the combination of at least three different doping elements is Nd/Sr/CaO. In other embodiments, the combination of at least three different doping elements is La/Nd/Sr. In other embodiments, the combination of at least three different doping elements is La/Bi/Sr. In other embodiments, the combination of at least three different doping elements is Mg/Nd/Fe. In other embodiments, the combination of at least three different doping elements is Mg/La/K. In other embodiments, the combination of at least three different doping elements is Na/Dy/K. In other embodiments, the combination of at least three different doping elements is Na/La/Dy. In other embodiments, the combination of at least three different doping elements is Na/La/Eu. In other embodiments, the combination of at least three different doping elements is Na/La/K. In other embodiments, the combination of at least three different doping elements is K/La/S. In other embodiments, the combination of at least three different doping elements is Li/Cs/La. In other embodiments, the combination of at least three different doping elements is Li/Sr/Cs. In other embodiments, the combination of at least three different doping elements is Li/Ga/Cs. In other embodiments, the combination of at least three different doping elements is Li/Na/Sr. In other embodiments, the combination of at least three different doping elements is Li/Sm/Cs. In other embodiments, the combination of at least three different doping elements is Cs/K/La. In other embodiments, the combination of at least three different doping elements is Sr/Cs/La. In other embodiments, the combination of at least three different doping elements is Sr/Ho/Tm. In other embodiments, the combination of at least three different doping elements is La/Nd/S. In other embodiments, the combination of at least three different doping elements is Li/Rb/Ca. In other embodiments, the combination of at least three different doping elements is Rb/Sr/Lu. In other embodiments, the combination of at least three different doping elements is Na/Eu/Hf. In other embodiments, the combination of at least three different doping elements is Dy/Rb/Gd. In other embodiments, the combination of at least three different doping elements is Na/Pt/Bi. In other embodiments, the combination of at least three different doping elements is Ca/Mg/Na. In other embodiments, the combination of at least three different doping elements is Na/K/Mg. In other embodiments, the combination of at least three different doping elements is Na/Li/Cs. In other embodiments, the combination of at least three different doping elements is La/Dy/K. In other embodiments, the combination of at least three different doping elements is Sm/Li/Sr. In other embodiments, the combination of at least three different doping elements is Li/Rb/Ga. In other embodiments, the combination of at least three different doping elements is Li/Cs/Tm. In other embodiments, the combination of at least three different doping elements is Li/K/La. In other embodiments, the combination of at least three different doping elements is Ce/Zr/La. In other embodiments, the combination of at least three different doping elements is Ca/Al/La. In other embodiments, the combination of at least three different doping elements is Sr/Zn/La. In other embodiments, the combination of at least three different doping elements is Cs/La/Na. In other embodiments, the combination of at least three different doping elements is La/S/Sr. In other embodiments, the combination of at least three different doping elements is Rb/Sr/La. In other embodiments, the combination of at least three different doping elements is Na/Sr/Lu. In other embodiments, the combination of at least three different doping elements is Sr/Eu/Dy. In other embodiments, the combination of at least three different doping elements is La/Dy/Gd. In other embodiments, the combination of at least three different doping elements is Gd/Li/K. In other embodiments, the combination of at least three different doping elements is Rb/K/Lu. In other embodiments, the combination of at least three different doping elements is Na/Ce/Co. In other embodiments, the combination of at least three different doping elements is Ba/Rh/Ta. In other embodiments, the combination of at least three different doping elements is Na/Al/Bi. In other embodiments, the combination of at least three different doping elements is Cs/Eu/S. In other embodiments, the combination of at least three different doping elements is Sm/Tm/Yb. In other embodiments, the combination of at least three different doping elements is Hf/Zr/Ta. In other embodiments, the combination of at least three different doping elements is Na/Ca/Lu. In other embodiments, the combination of at least three different doping elements is Gd/Ho/Sr. In other embodiments, the combination of at least three different doping elements is Ca/Sr/W. In other embodiments, the combination of at least three different doping elements is Na/Zr/Eu/Tm. In other embodiments, the combination of at least three different doping elements is Sr/W/Li. In other embodiments, the combination of at least three different doping elements is Ca/Sr/W.

In yet other embodiments, the oxide of a rare earth element comprises a combination of at least four different doping elements. In some examples, the four different doping elements are selected from Na, Mg, Ca, Sr, Ga, Sc, Y, Zr, In, Nd, Eu, Sm, Ce, Gd, Hf, Ho, Tm, W, La, K, Dy, In, Cs, S, Zn, Rb, Ba, Yb, Ni, Lu, Ta, P, Pt, Bi, Sn, Nb, Sb, Ge, Ag, Au, Pb, Re, Fe, Al, Tl, Pr, Co, Rh, Ti, V, Cr, Mn, Ir, As, Li, Tb, Er, Te and Mo. More specific examples include catalysts wherein the combination of at least four different doping elements is Sr/Sm/Ho/Tm, Na/K/Mg/Tm, Na/La/Eu/In, Na/La/Li/Cs, Li/Cs/La/Tm, Li/Cs/Sr/Tm, Li/Sr/Zn/K, Li/Ga/Cs, Li/K/Sr/La, Li/Na/Rb/Ga, Li/Na/Sr/La, Ba/Sm/Yb/S, Ba/Tm/K/La, Ba/Tm/Zn/K, Cs/La/Tm/Na, Cs/Li/K/La, Sm/Li/Sr/Cs, Sr/Tm/Li/Cs, Zr/Cs/K/La, Rb/Ca/In/Ni, Tm/Lu/Ta/P, Rb/Ca/Dy/P, Mg/La/Yb/Zn, Na/Sr/Lu/Nb, Na/Nd/In/K, K/La/Zr/Ag, Ho/Cs/Li/La, K/La/Zr/Ag, Na/Sr/Eu/Ca, K/Cs/Sr/La, Na/Mg/Tl/P, Sr/La/Dy/S, Na/Ga/Gd/Al, Sm/Tm/Yb/Fe, Rb/Gd/Li/K, Gd/Ho/Al/P, Na/Zr/Eu/T, Sr/Ho/Tm/Na, Na/Zr/Eu/Ca, Rb/Ga/Tm/Cs or La/Bi/Ce/Nd/Sr.

In other embodiments, the combination of at least four different doping elements is Sr/Sm/Ho/Tm. In other embodiments, the combination of at least four different doping elements is Na/K/Mg/Tm. In other embodiments, the combination of at least four different doping elements is Na/La/Eu/In. In other embodiments, the combination of at least four different doping elements is Na/La/Li/Cs. In other embodiments, the combination of at least four different doping elements is Li/Cs/La/Tm. In other embodiments, the combination of at least four different doping elements is Li/Cs/Sr/Tm. In other embodiments, the combination of at least four different doping elements is Li/Sr/Zn/K. In other embodiments, the combination of at least four different doping elements is Li/Ga/Cs. In other embodiments, the combination of at least four different doping elements is Li/K/Sr/La. In other embodiments, the combination of at least four different doping elements is Li/Na/Rb/Ga. In other embodiments, the combination of at least four different doping elements is Li/Na/Sr/La. In other embodiments, the combination of at least four different doping elements is Ba/Sm/Yb/S. In other embodiments, the combination of at least four different doping elements is Ba/Tm/K/La. In other embodiments, the combination of at least four different doping elements is Ba/Tm/Zn/K. In other embodiments, the combination of at least four different doping elements is Cs/La/Tm/Na. In other embodiments, the combination of at least four different doping elements is Cs/Li/K/La. In other embodiments, the combination of at least four different doping elements is Sm/Li/Sr/Cs. In other embodiments, the combination of at least four different doping elements is Sr/Tm/Li/Cs. In other embodiments, the combination of at least four different doping elements is Zr/Cs/K/La. In other embodiments, the combination of at least four different doping elements is Rb/Ca/In/Ni. In other embodiments, the combination of at least four different doping elements is Tm/Lu/Ta/P. In other embodiments, the combination of at least four different doping elements is Rb/Ca/Dy/P. In other embodiments, the combination of at least four different doping elements is Mg/La/Yb/Zn. In other embodiments, the combination of at least four different doping elements is Na/Sr/Lu/Nb. In other embodiments, the combination of at least four different doping elements is Na/Nd/In/K. In other embodiments, the combination of at least four different doping elements is K/La/Zr/Ag. In other embodiments, the combination of at least four different doping elements is Ho/Cs/Li/La. In other embodiments, the combination of at least four different doping elements is K/La/Zr/Ag. In other embodiments, the combination of at least four different doping elements is Na/Sr/Eu/Ca. In other embodiments, the combination of at least four different doping elements is K/Cs/Sr/La. In other embodiments, the combination of at least four different doping elements is Na/Mg/Tl/P. In other embodiments, the combination of at least four different doping elements is Sr/La/Dy/S. In other embodiments, the combination of at least four different doping elements is Na/Ga/Gd/Al. In other embodiments, the combination of at least four different doping elements is Sm/Tm/Yb/Fe. In other embodiments, the combination of at least four different doping elements is Rb/Gd/Li/K. In other embodiments, the combination of at least four different doping elements is Gd/Ho/Al/P. In other embodiments, the combination of at least four different doping elements is Na/Zr/Eu/T. In other embodiments, the combination of at least four different doping elements is Sr/Ho/Tm/Na. In other embodiments, the combination of at least four different doping elements is Na/Zr/Eu/Ca. In other embodiments, the combination of at least four different doping elements is Rb/Ga/Tm/Cs. In other embodiments, the combination of at least four different doping elements is La/Bi/Ce/Nd/Sr.

In some embodiments, the oxide of a rare earth element is a mixed oxide.

In other embodiments, the oxide of a rare earth element comprises a lanthanum oxide, a neodymium oxide, a ytterbium oxide, a europium oxide, a samarium oxide, a yttrium oxide, a cerium oxide or a praseodymium oxide.

In yet other embodiments, the oxide of a rare earth element comprises $Ln1_{4-x}Ln2_xO_6$, wherein Ln1 and Ln2 are each independently a lanthanide element, wherein Ln1 and Ln2 are not the same and x is a number ranging from greater than 0 to less than 4. For example, in some embodiments the rare earth oxide comprises $La_{4-x}Nd_xO_6$, wherein x is a number ranging from greater than 0 to less than 4. In even further embodiments, the rare earth oxide comprises $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$ or combinations thereof.

In yet other embodiments, the oxide of a rare earth element comprises a mixed oxide. For example, in some embodiments the mixed oxide comprises Y—La, Zr—La, Pr—La, Ce—La or combinations thereof.

In some embodiments, the rare earth oxide catalyst comprises a $C_2$ selectivity of greater than 50% and a methane conversion of greater than 20% when the catalyst is employed as a heterogenous catalyst in the oxidative coupling of methane at a temperature of 750° C. or less.

In other embodiments, the catalysts comprise $La_2O_3$ or $LaO_y(OH)_x$, wherein x and y are each independently an integer from 1 to 10 doped with Na, Mg, Ca, Sr, Ga, Sc, Y, Zr, In, Nd, Eu, Sm, Ce, Gd or combinations thereof. In yet further embodiments, the $La_2O_3$ or $LaO_y(OH)_x$ catalysts are doped with binary dopant combinations of Eu/Na; Eu/Gd; Ca/Na; Eu/Sm; Eu/Sr; Mg/Sr; Ce/Mg; Gd/Sm, Mg/Na, Mg/Y, Ga/Sr or Nd/Mg.

In other embodiments, the catalysts comprise $Nd_2O_3$ or $NdO_y(OH)_x$, wherein x and y are each independently an integer from 1 to 10, doped with Sr, Ca, Rb, Li, Na or combinations thereof. In certain other embodiments, the $Nd_2O_3$ or $NdO_y(OH)_x$ catalysts are doped with binary dopant combinations of Ca/Sr or Rb/Sr.

In still other examples of the doped catalysts, the catalysts comprise $Yb_2O_3$ or $YbO_y(OH)_x$, wherein x and y are each independently an integer from 1 to 10, doped with Sr, Ca, Ba, Nd or combinations thereof. In certain other embodiments, the $Yb_2O_3$ or $YbO_y(OH)_x$ OCM catalysts are doped with a binary combination of Sr/Nd.

Still other examples of doped catalysts, the catalysts comprise $Eu_2O_3$ or $EuO_y(OH)_x$, wherein x and y are each independently an integer from 1 to 10, doped with Sr, Ba, Sm or combinations thereof or a binary dopant combination of Sr/Na.

Examples of dopants for $Sm_2O_3$ or $SmO_y(OH)_x$ catalysts, wherein x and y are each independently an integer from 1 to 10, include Sr, and examples of dopants for $Y_2O_3$ or $YO_y(OH)_x$ catalysts wherein x and y are each independently an integer from 1 to 10, comprise Ga, La, Nd or combinations thereof. In certain other embodiments, the $Y_2O_3$ or $YO_y(OH)_x$ catalysts comprise a binary dopant combination of Sr/Nd, Eu/Y or Mg/Nd or a tertiary dopant combination of Mg/Nd/Fe.

Rare earth mixed oxide catalysts which without doping have low OCM selectivity can be greatly improved by doping to reduce their combustion activity. In particular, catalysts comprising $CeO_2$ and $Pr_2O_3$ tend to have strong total oxidation activity for methane, however doping with additional rare earth elements can significantly moderate the combustion activity and improve the overall utility of the catalyst. Examples of dopants which improve the selectivity of the catalysts, for example the $Pr_2O_3$ or $PrO_y(OH)_x$ catalysts, wherein x and y are each independently an integer from 1 to 10, comprise binary dopants of Nd/Mg, La/Mg or Yb/Sr.

In yet other embodiments of the rare earth oxide, the rare earth element may be in the form of a metal oxyhalide, a metal oxynitrate or a metal phosphate.

In still other embodiments, the present disclosure provides a catalyst comprising a mixed oxide of manganese and tungsten, wherein the catalyst further comprises a sodium dopant and at least one doping element from groups 2, 4-6, 8-15, lanthanides or combinations thereof. The catalyst may comprise a $C_2$ selectivity of greater than 50% and a methane conversion of greater than 20% when the catalyst is employed as a heterogenous catalyst in the oxidative coupling of methane at a temperature of 750° C. or less.

In further embodiments of the foregoing, the at least one doping element is Fe, Co, Ce, Cu, Ni, Sr, Ga, Zr, Pb, Zn, Cr, Pt, Al, Nb, La, Ba, Bi, Sn, In, Ru, P or combinations thereof. In this regard, all binary and ternary combinations of the foregoing dopants are contemplated. The at least one doping element may be Fe. The at least one doping element may be Co. The at least one doping element may be Ce. The at least one doping element may be Cu. The at least one doping element may be Ni. The at least one doping element may be Sr. The at least one doping element may be Ga. The at least one doping element may be Zr. The at least one doping element may be Pb. The at least one doping element may be Zn. The at least one doping element may be Cr. The at least one doping element may be Pt. The at least one doping element may be Al. The at least one doping element may be Nb. The at least one doping element may be La. The at least one doping element may be Ba. The at least one doping element may be Bi. The at least one doping element may be Sn. The at least one doping element may be In. The at least one doping element may be Ru. The at least one doping element may be P.

Applicants have also found that mixed oxides of lanthanides and tungsten are effective catalysts, for example in the OCM reaction. Accordingly, in one embodiment the disclosure provides a catalyst comprising a mixed oxide of a lanthanide and tungsten, wherein the catalyst further comprises a sodium dopant and at least one doping element from groups 2, 4-15, lanthanides or combinations thereof. In further embodiments, the catalyst comprises a $C_2$ selectivity of greater than 50% and a methane conversion of greater than 20% when the catalyst is employed as a heterogenous catalyst in the oxidative coupling of methane at a temperature of 750° C. or less.

In other embodiments of the foregoing, the lanthanide is Ce, Pr, Nd, La, Eu, Sm or Y. In other embodiments, the at least one doping element is Fe, Co, Mn, Cu, Ni, Sr, Ga, Zr, Pb, Zn, Cr, Pt, Al, Nb, La, Ba, Bi, Sn, In, Ru, P or combinations thereof. Binary and ternary combinations of the foregoing dopants are also contemplated. The at least one doping element may be Fe. The at least one doping element may be Co. The at least one doping element may be Mn. The at least one doping element may be Cu. The at least one doping element may be Ni. The at least one doping element may be Sr. The at least one doping element may be Ga. The at least one doping element may be Zr. The at least one doping element may be Pb. The at least one doping element may be Zn. The at least one doping element may be Cr. The at least one doping element may be Pt. The at least one doping element may be Al. The at least one doping element may be Nb. The at least one doping element may be La. The at least one doping element may be Ba. The at least one doping element may be Bi. The at least one doping element may be Sn. The at least one doping element may be In. The at least one doping element may be Ru. The at least one doping element may be P.

In addition to the above compositions, the present inventors have determined that certain rare earth compositions are useful as catalysts in a number of reactions, for example the OCM reaction. In some embodiments, these lanthanide compositions comprise $La_2O_3$, $Nd_2O_3$, $Yb_2O_3$, $Eu_2O_3$, $Sm_2O_3$, $Ln1_{4-x}Ln2_xO_6$, $La_{4-x}Ln1O_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, or combinations thereof. Certain lanthanide mixed oxides such as Y—La, Zr—La, Pr—La or Ce—La are also useful as catalysts in the OCM reaction. Further, Applicants have discovered that certain doping combinations, when combined with the above lanthanide compositions, serve to enhance the catalytic activity of the catalysts in certain catalytic reactions, for example OCM. The dopants may be present in various levels (e.g., w/w or at/at), and the catalysts may be prepared by any number of methods. Various aspects of the above lanthanide catalysts are provided in the following paragraphs and in Tables 1-4.

As noted above, certain combinations of dopants have been found useful when combined with certain catalysts. In one embodiment, the catalyst comprises a rare earth oxide and two or more dopants, wherein the dopants are selected from Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ca/Cs, Ca/Mg/Na, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Gd/Ho/Sr, Ca/Sr, Ca/Sr/W, Na/Zr/Eu/Tm, Sr/Ho/Tm/Na, Sr/Pb, Sr/W/Li, Ca/Sr/W and Sr/Hf.

In other embodiments of the foregoing rare earth oxide, the dopant is selected from Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Gd/Ho/Sr, Ca/Sr, Ca/Sr/W, Na/Zr/Eu/Tm, Sr/Ho/Tm/Na, Sr/Pb, Ca, Sr/W/Li, Ca/Sr/W, Sr/Hf, Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga and Li/Na/Sr.

In still other embodiments of the rare earth oxide, the dopant is selected from Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Cs/Eu/S, Sm/Tm/Yb/Fe, Sm/Tm/Yb, Hf/Zr/Ta, Rb/Gd/Li/K, Gd/Ho/Al/P and Na/Ca/Lu.

In still other embodiments of the foregoing rare earth oxide, the dopant is selected from Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ca/Cs, Ca/Mg/Na, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr and W/Ge.

In various embodiments of the foregoing rare earth oxides, the catalysts comprise $La_2O_3$, $Nd_2O_3$, $Yb_2O_3$, $Eu_2O_3$, $Y_2O_3$, $Ce_2O_3$, $Pr_2O_3$ $Sm_2O_3$, $Ln1_{4-x}Ln2_xO_6$, $La_{4-x}Ln1_xO_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.50}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La or combinations thereof. In other various embodiments, the rare earth oxide catalyst comprises a $C_2$ selectivity of greater than 50% and a methane conversion of greater than 20% when the rare earth oxide catalyst is employed as a heterogenous catalyst in the oxidative coupling of methane at a temperature of 750° C. or less.

In other embodiments, the catalysts comprise $La_2O_3$, $Yb_2O_3$, $Nd_2O_3$, $Eu_2O_3$, $Sm_2O_3$, $Y_2O_3$, $Ln1_{4-x}Ln2_xO_6$, $La_{4-x}Ln1O_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La doped with Sr/Ta, for example in some embodiments the catalysts comprise Sr/Ta/$La_2O_3$, Sr/Ta/$Yb_2O_3$, Sr/Ta/$Nd_2O_3$, Sr/Ta/$Eu_2O_3$, Sr/Ta/$Sm_2O_3$, Sr/Ta/$Ln1_{4-x}Ln2_xO_6$, Sr/Ta/$La_{4-x}Ln1_xO_6$, Sr/Ta/$La_{4-x}Nd_xO_6$, Sr/Ta/$La_3NdO_6$, Sr/Ta/$LaNd_3O_6$, Sr/Ta/$La_{1.5}Nd_{2.5}O_6$, Sr/Ta/$La_{2.5}Nd_{1.5}O_6$, Sr/Ta/$La_{3.2}Nd_{0.8}O_6$, Sr/Ta/$La_{3.5}Nd_{0.5}O_6$, Sr/Ta/$La_{3.8}Nd_{0.2}O_6$, Sr/Ta/Y—La, Sr/Ta/Zr—La, Sr/Ta/Pr—La or Sr/Ta/Ce—La or combinations thereof. In other embodiments, the catalysts comprise $Ln1_{4-x}Ln2_xO_6$, $La_{4-x}Ln1_xO_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La doped with Na, Sr, Ca, Yb, Cs, Sb, or combinations thereof, for example the catalysts may comprise $Na/Ln1_{4-x}Ln2_xO_6$, $Sr/Ln1_{4-x}Ln2_xO_6$, $Ca/Ln1_{4-x}Ln2_xO_6$, $Yb/Ln1_{4-x}Ln2_xO_6$, $Cs/Ln1_{4-x}Ln2_xO_6$, $Sb/Ln1_{4-x}Ln2_xO_6$, $Na/La_{4-x}Ln1_xO_6$, $Na/La_3NdO_6$, $Sr/La_{4-x}Ln1_xO_6$, $Ca/La_{4-x}Ln1_xO_6$, $Yb/La_{4-x}Ln1_xO_6$, $Cs/La_{4-x}Ln1_xO_6$, $Sb/La_{4-x}Ln1_xO_6$, $Na/La_{4-x}Nd_xO_6$, $Sr/La_{4-x}Nd_xO_6$, $Ca/La_{4-x}Nd_xO_6$, $Yb/La_{4-x}Nd_xO_6$, Cs $La_{4-x}Nd_xO_6$, $Sb/La_{4-x}Nd_xO_6$, $Na/La_3NdO_6$, $Na/LaNd_3O_6$, $Na/La_{1.5}Nd_{2.5}O_6$, $Na/La_{2.5}Nd_{1.5}O_6$, $Na/La_{3.2}Nd_{0.8}O_6$, $Na/La_{3.5}Nd_{0.5}O_6$, $Na/La_{3.8}Nd_{0.2}O_6$, Na/Y—La, Na/Zr—La, Na/Pr—La, Na/Ce—La, $Sr/La_3NdO_6$, $Sr/LaNd_3O_6$, $Sr/La_{1.5}Nd_{2.5}O_6$, $Sr/La_{2.5}Nd_{1.5}O_6$, $Sr/La_{3.2}Nd_{0.8}O_6$, $Sr/La_{3.5}Nd_{0.5}O_6$, $Sr/La_{3.8}Nd_{0.2}O_6$, Sr/Y—La, Sr/Zr—La, Sr/Pr—La, Sr/Ce—La, $Ca/La_3NdO_6$, $Ca/LaNd_3O_6$, $Ca/La_{1.5}Nd_{2.5}O_6$, $Ca/La_{2.5}Nd_{1.5}O_6$, $Ca/La_{3.2}Nd_{0.8}O_6$, $Ca/La_{3.5}Nd_{0.5}O_6$, $Ca/La_{3.8}Nd_{0.2}O_6$, Ca/Y—La, Ca/Zr—La, Ca/Pr—La, Ca/Ce—La, $Yb/La_3NdO_6$, $Yb/LaNd_3O_6$, $Yb/La_{1.5}Nd_{2.5}O_6$, $Yb/La_{2.5}Nd_{1.5}O_6$, $Yb/La_{3.2}Nd_{0.8}O_6$, $Yb/La_{3.5}Nd_{0.5}O_6$, $Yb/La_{3.8}Nd_{0.2}O_6$, Yb/Y—La, Yb/Zr—La, Yb/Pr—La, Yb/Ce—La, $Cs/La_3NdO_6$ $LaNd_3O_6$, $Cs/La_{1.5}Nd_{2.5}O_6$, $Cs/La_{2.5}Nd_{1.5}O_6$, $Cs/La_{3.2}Nd_{0.8}O_6$, $Cs/La_{3.5}Nd_{0.5}O_6$, $Cs/La_{3.8}Nd_{0.2}O_6$, Cs/Y—La, Cs/Zr—La, Cs/Pr—La, Cs/Ce—La, $Sb/La_3NdO_6$, $Sb/LaNd_3O_6$, $Sb/La_{1.5}Nd_{2.5}O_6$, $Sb/La_{2.5}Nd_{1.5}O_6$, $Sb/La_{3.2}Nd_{0.8}O_6$, $Sb/La_{3.5}Nd_{0.5}O_6$, $Sb/La_{3.8}Nd_{0.2}O_6$, Sb/Y—La, Sb/Zr—La, Sb/Pr—La, Sb/Ce—La or combinations thereof.

In other embodiments, the catalysts comprise a mixed oxide selected from a Y—La mixed oxide doped with Na. (Y ranges from 5 to 20% of La at/at); a Zr—La mixed oxide doped with Na (Zr ranges from 1 to 5% of La at/at); a Pr—La mixed oxide doped with a group 1 element (Pr ranges from 2 to 6% of La at/at); and a Ce—La mixed oxide doped with a group 1 element (Ce ranges from 5 to 20% of La at/at). As used herein, the notation "M1-M2", wherein M1 and M2 are each independently metals refers to a mixed metal oxide comprising the two metals. M1 and M2 may be present in equal or different amounts (at/at).

In still other embodiments, the catalysts comprise a mixed oxide of a rare earth element and a Group 13 element, wherein the catalyst further comprises one or more Group 2 elements. In certain embodiments of the foregoing, the Group 13 element is B, Al, Ga or In. In other embodiments, the Group 2 element is Ca or Sr. In still other embodiments, the rare earth element is La, Y, Nd, Yb, Sm, Pr, Ce or Eu.

Specific examples of the foregoing include, but are not limited to $CaLnBO_x$, $CaLnAlO_x$, $CaLnGaO_x$, $CaLnInO_x$, $CaLnAlSrO_x$ and $CaLnAlSrO_x$, wherein Ln is a lanthanide or yttrium and x is number such that all charges are balanced. For example, in some embodiments the catalyst comprises $CaLaBO_4$, $CaLaAlO_4$, $CaLaGaO_4$, $CaLaInO_4$, $CaLaAlSrO_5$, $CaLaAlSrO_5$, $CaNdBO_4$, $CaNdAlO_4$, $CaNdGaO_4$, $CaNdInO_4$, $CaNdAlSrO_4$, $CaNdAlSrO_4$, $CaYbBO_4$, $CaYbAlO_4$, $CaYbGaO_4$, $CaYbInO_4$, $CaYbAlSrO_5$, $CaYbAlSrO_5$, $CaEuBO_4$, $CaEuAlO_4$, $CaEuGaO_4$, $CaEuInO_4$, $CaEuAlSrO_5$, $CaEuAlSrO_5$, $CaSmBO_4$, $CaSmAlO_4$, $CaSmGaO_4$, $CaSmInO_4$, $CaSmAlSrO_5$, $CaSmAlSrO_5$, $CaYBO_4$, $CaYAlO_4$, $CaYGaO_4$, $CaYInO_4$, $CaYAlSrOs_5$, $CaYAlSrOs_5$, $CaCeBO_4$, $CaCeAlO_4$, $CaCeGaO_4$, $CaCeInO_4$, $CaCeAlSrOs_5$, $CaCeAlSrOs_5$, $CaPrBO_4$, $CaPrAlO_4$, $CaPrGaO_4$, $CaPrInO_4$, $CaPrAlSrO_5$ or $CaPrAlSrOs$.

Furthermore, the present inventors have discovered that lanthanide oxides doped with alkali metals and/or alkaline earth metals and at least one other dopant selected from Groups 3-16 have desirable catalytic properties and are useful in a variety of catalytic reactions, such as OCM. Accordingly, in one embodiment the catalysts comprise a lanthanide oxide doped with an alkali metal, an alkaline earth metal or combinations thereof, and at least one other dopant from groups 3-16. In some embodiments, the catalyst comprises a lanthanide oxide, an alkali metal dopant and at least one other dopant selected from Groups 3-16. In other embodiments, the catalyst comprises a lanthanide oxide, an alkaline earth metal dopant and at least one other dopant selected from Groups 3-16.

In some more specific embodiments of the foregoing, the catalyst comprises a lanthanide oxide, a lithium dopant and at least one other dopant selected from Groups 3-16. In still other embodiments, the catalyst comprises a lanthanide oxide, a sodium dopant and at least one other dopant selected from Groups 3-16. In other embodiments, the catalyst comprises a lanthanide oxide, a potassium dopant and at least one other dopant selected from Groups 3-16. In other embodiments, the catalyst comprises a lanthanide oxide, a rubidium dopant and at least one other dopant selected from Groups 3-16. In more embodiments, the catalyst comprises a lanthanide oxide, a caesium dopant and at least one other dopant selected from Groups 3-16.

In still other embodiments of the foregoing, the catalyst comprises a lanthanide oxide, a beryllium dopant and at least one other dopant selected from Groups 3-16. In other embodiments, the catalyst comprises a lanthanide oxide, a magnesium dopant and at least one other dopant selected from Groups 3-16. In still other embodiments, the catalyst comprises a lanthanide oxide, a calcium dopant and at least one other dopant selected from Groups 3-16. In more embodiments, the catalyst comprises a lanthanide oxide, a strontium dopant and at least one other dopant selected from Groups 3-16. In more embodiments, the catalyst comprises a lanthanide oxide, a barium dopant and at least one other dopant selected from Groups 3-16.

In some embodiments of the foregoing lanthanide oxide catalysts, the catalysts comprise $La_2O_3$, $Nd_2O_3$, $Yb_2O_3$, $Eu_2O_3$, $Sm_2O_3$, $Ln1_{4-x}Ln2_xO_6$, $La_{4-x}Ln1_xO_6$, $La_{4-x}Nd_xO_6$, wherein Ln1 and Ln2 are each independently a lanthanide element, wherein Ln1 and Ln2 are not the same and x is a number ranging from greater than 0 to less than 4, $La_3NdO_6$, $LaNd_3O_6$, $La_{1.5}Nd_{2.5}O_6$, $La_{2.5}Nd_{1.5}O_6$, $La_{3.2}Nd_{0.8}O_6$, $La_{3.5}Nd_{0.5}O_6$, $La_{3.8}Nd_{0.2}O_6$, Y—La, Zr—La, Pr—La or Ce—La or combinations thereof. In other various embodiments, the lanthanide oxide catalyst comprises a $C_2$ selectivity of greater than 50% and a methane conversion of greater than 20% when the lanthanide oxide catalyst is employed as a heterogenous catalyst in the oxidative coupling of methane at a temperature of 750° C. or less.

In various embodiments, of any of the above catalysts, the catalyst comprises a $C_2$ selectivity of greater than 50% and a methane conversion of greater than 20% when the catalyst is employed as a heterogenous catalyst in the oxidative coupling of methane at a temperature of 750° C. or less, 700° C. or less, 650° C. or less or even 600° C. or less.

In more embodiments, of any of the above catalysts, the catalyst comprises a $C_2$ selectivity of greater than 50%, greater than 55%, greater than 60%, greater than 65%, greater than 70%, or even greater than 75%, and a methane conversion of greater than 20% when the catalyst is employed as a heterogenous catalyst in the oxidative coupling of methane at a temperature of 750° C. or less.

In other embodiments, of any of the above catalysts, the catalyst comprises a $C_2$ selectivity of greater than 50%, and a methane conversion of greater than 20%, greater than 25%, greater than 30%, greater than 35%, greater than 40%, greater than 45%, or even greater than 50% when the catalyst is employed as a heterogenous catalyst in the oxidative coupling of methane at a temperature of 750° C. or less. In some embodiments of the foregoing, the methan conversion and C2 selectivity are calculated based on a single pass basis (i.e., the percent of methane converted or C2 selectivity upon a single pass over the catalyst or catalytic bed, etc.)

The metal oxides disclosed herein can be in the form of oxides, oxyhydroxides, hydroxides, oxycarbonates or combination thereof after being exposed to moisture, carbon dioxide, undergoing incomplete calcination or combination thereof.

The foregoing doped catalysts comprise 1, 2, 3, 4 or more doping elements. In this regard, each dopant may be present in the catalysts (for example any of the catalysts described above and/or disclosed in Tables 1-4) in up to 75% by weight of the catalyst. For example, in one embodiment the concentration of a first doping element ranges from 0.01% to 1% w/w, 1%-5% w/w, 5%-10% w/w. 10%-20% ww, 20%-30% w/w, 30%-40% w/w or 40%-50% w/w, for example about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w. about 14% w/w, about 15% w/w, about 16% w/w, about 17% w/w, about 18% w/w, about 19% w/w or about 20% w/w.

In other embodiments, the concentration of a second doping element (when present) ranges from 0.01% to 1% w/w, 1%-5% w/w, 5%-10% w/w. 10%-20% ww, 20%-30% w/w, 30%-40% w/w or 40%-50% w/w, for example about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w. about 14% w/w, about 15% w/w, about 16% w/w, about 17% w/w, about 18% w/w, about 19% w/w or about 20% w/w.

In other embodiments, the concentration of a third doping element (when present) ranges from 0.01% to 1% w/w, 1%-5% w/w, 5%-10% w/w. 10%-20% ww, 20%-30% w/w, 30%-40% w/w or 40%-50% w/w, for example about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w. about 14% w/w, about 15% w/w, about 16% w/w, about 17% w/w, about 18% w/w, about 19% w/w or about 20% w/w.

In other embodiments, the concentration of a fourth doping element (when present) ranges from 0.01% to 1% w/w, 1%-5% w/w, 5%-10% w/w. 10%-20% ww, 20%-30% w/w, 30%-40% w/w or 40%-50% w/w, for example about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w. about 14% w/w, about 15% w/w, about 16% w/w, about 17% w/w, about 18% w/w, about 19% w/w or about 20% w/w.

In other embodiments, the concentration of the dopant is measured in terms of atomic percent (at/at). In some of these embodiments, each dopant may be present in the catalysts (for example any of the catalysts described above and/or disclosed in Tables 1-4) in up to 75% at/at. For example, in one embodiment the concentration of a first doping element ranges from 0.01% to 1% at/at, 1%-5% at/at, 5%-10% at/at. 10%-20% at/at, 20%-30% at/at, 30%-40% at/at or 40%-50% at/at, for example about 1% at/at, about 2% at/at, about 3% at/at, about 4% at/at, about 5% at/at, about 6% at/at, about 7% at/at, about 8% at/at, about 9% at/at, about 10% at/at, about 11% at/at, about 12% at/at, about 13% at/at. about 14% at/at, about 15% at/at, about 16% at/at, about 17% at/at, about 18% at/at, about 19% at/at or about 20% at/at.

In other embodiments, the concentration of a second doping element (when present) ranges from 0.01% to 1% at/at, 1%-5% at/at, 5%-10% at/at. 10%-20% ww, 20%-30% at/at, 30%-40% at/at or 40%-50% at/at, for example about 1% at/at, about 2% at/at, about 3% at/at, about 4% at/at, about 5% at/at, about 6% at/at, about 7% at/at, about 8% at/at, about 9% at/at, about 10% at/at, about 11% at/at, about 12% at/at, about 13% at/at. about 14% at/at, about 15% at/at, about 16% at/at, about 17% at/at, about 18% at/at, about 19% at/at or about 20% at/at.

In other embodiments, the concentration of a third doping element (when present) ranges from 0.01% to 1% at/at, 1%-5% at/at, 5%-10% at/at. 10%-20% ww, 20%-30% at/at, 30%-40% at/at or 40%-50% at/at, for example about 1% at/at, about 2% at/at, about 3% at/at, about 4% at/at, about 5% at/at, about 6% at/at, about 7% at/at, about 8% at/at, about 9% at/at, about 10% at/at, about 11% at/at, about 12% at/at, about 13% at/at. about 14% at/at, about 15% at/at, about 16% at/at, about 17% at/at, about 18% at/at, about 19% at/at or about 20% at/at.

In other embodiments, the concentration of a fourth doping element (when present) ranges from 0.01% to 1% at/at, 1%-5% at/at, 5%-10% at/at. 10%-20% ww, 20%-30% at/at, 30%-40% at/at or 40%-50% at/at, for example about 1% at/at, about 2% at/at, about 3% at/at, about 4% at/at, about 5% at/at, about 6% at/at, about 7% at/at, about 8% at/at, about 9% at/at, about 10% at/at, about 11% at/at, about 12% at/at, about 13% at/at. about 14% at/at, about 15% at/at, about 16% at/at, about 17% at/at, about 18% at/at, about 19% at/at or about 20% at/at.

Accordingly, any of the doped catalysts described above or in Tables 1-4, may comprise any of the foregoing doping concentrations.

Furthermore, different catalytic characteristics of the above doped catalysts can be varied or "tuned" based on the method used to prepare them. Such methods are described in more detail herein and other methods are known in the art. In addition, the above dopants may be incorporated either before or after (or combinations thereof) an optional calcination step as described herein.

Tables 1-4 below show exemplary doped catalysts in accordance with various specific embodiments. Dopants are shown in the vertical columns and base catalyst in the horizontal rows. The resulting doped catalysts are shown in the intersecting cells.

TABLE 1

| CATALYSTS (CAT) DOPED WITH SPECIFIC DOPANTS (DOP) | | | | | | |
|---|---|---|---|---|---|---|
| Dop\Cat | $La_2O_3$ | $Nd_2O_3$ | $Yb_2O_3$ | $Eu_2O_3$ | $Sm_2O_3$ | $La_3NdO_6$ |
| Eu/Na | Eu/Na/ $La_2O_3$ | Eu/Na/ $Nd_2O_3$ | Eu/Na/ $Yb_2O_3$ | Eu/Na/ $Eu_2O_3$ | Eu/Na/ $Sm_2O_3$ | Eu/Na/ $La_3NdO_6$ |

TABLE 1-continued

CATALYSTS (CAT) DOPED WITH SPECIFIC DOPANTS (DOP)

| Dop\Cat | $La_2O_3$ | $Nd_2O_3$ | $Yb_2O_3$ | $Eu_2O_3$ | $Sm_2O_3$ | $La_3NdO_6$ |
|---|---|---|---|---|---|---|
| Sr/Na | Sr/Na/$La_2O_3$ | Sr/Na/$Nd_2O_3$ | Sr/Na/$Yb_2O_3$ | Sr/Na/$Eu_2O_3$ | Sr/Na/$Sm_2O_3$ | Sr/Na/$La_3NdO_6$ |
| Na/Zr/Eu/Ca | Na/Zr/Eu/Ca/$La_2O_3$ | Na/Zr/Eu/Ca/$Nd_2O_3$ | Na/Zr/Eu/Ca/$Yb_2O_3$ | Na/Zr/Eu/Ca/$Eu_2O_3$ | Na/Zr/Eu/Ca/$Sm_2O_3$ | Na/Zr/Eu/Ca/$La_3NdO_6$ |
| Mg/Na | Mg/Na/$La_2O_3$ | Mg/Na/$Nd_2O_3$ | Mg/Na/$Yb_2O_3$ | Mg/Na/$Eu_2O_3$ | Mg/Na/$Sm_2O_3$ | Mg/Na/$La_3NdO_6$ |
| Sr/Sm/Ho/Tm | Sr/Sm/Ho/Tm/$La_2O_3$ | Sr/Sm/Ho/Tm/$Nd_2O_3$ | Sr/Sm/Ho/Tm/$Yb_2O_3$ | Sr/Sm/Ho/Tm/$Eu_2O_3$ | Sr/Sm/Ho/Tm/$Sm_2O_3$ | Sr/Sm/Ho/Tm/$La_3NdO_6$ |
| Sr/W | Sr/W/$La_2O_3$ | Sr/W/$Nd_2O_3$ | Sr/W/$Yb_2O_3$ | Sr/W/$Eu_2O_3$ | Sr/W/$Sm_2O_3$ | Sr/W/$La_3NdO_6$ |
| Mg/La/K | Mg/La/K/$La_2O_3$ | Mg/La/K/$Nd_2O_3$ | Mg/La/K/$Yb_2O_3$ | Mg/La/K/$Eu_2O_3$ | Mg/La/K/$Sm_2O_3$ | Mg/La/K/$La_3NdO_6$ |
| Na/K/Mg/Tm | Na/K/Mg/Tm/$La_2O_3$ | Na/K/Mg/Tm/$Nd_2O_3$ | Na/K/Mg/Tm/$Yb_2O_3$ | Na/K/Mg/Tm/$Eu_2O_3$ | Na/K/Mg/Tm/$Sm_2O_3$ | Na/K/Mg/Tm/$La_3NdO_6$ |
| Na/Dy/K | Na/Dy/K/$La_2O_3$ | Na/Dy/K/$Nd_2O_3$ | Na/Dy/K/$Yb_2O_3$ | Na/Dy/K/$Eu_2O_3$ | Na/Dy/K/$Sm_2O_3$ | Na/Dy/K/$La_3NdO_6$ |
| Na/La/Dy | Na/La/Dy/$La_2O_3$ | Na/La/Dy/$Nd_2O_3$ | Na/La/Dy/$Yb_2O_3$ | Na/La/Dy/$Eu_2O_3$ | Na/La/Dy/$Sm_2O_3$ | Na/La/Dy/$La_3NdO_6$ |
| Na/La/Eu | Na/La/Eu/$La_2O_3$ | Na/La/Eu/$Nd_2O_3$ | Na/La/Eu/$Yb_2O_3$ | Na/La/Eu/$Eu_2O_3$ | Na/La/Eu/$Sm_2O_3$ | Na/La/Eu/$La_3NdO_6$ |
| Na/La/Eu/In | Na/La/Eu/In/$La_2O_3$ | Na/La/Eu/In/$Nd_2O_3$ | Na/La/Eu/In/$Yb_2O_3$ | Na/La/Eu/In/$Eu_2O_3$ | Na/La/Eu/In/$Sm_2O_3$ | Na/La/Eu/In/$La_3NdO_6$ |
| Na/La/K | Na/La/K/$La_2O_3$ | Na/La/K/$Nd_2O_3$ | Na/La/K/$Yb_2O_3$ | Na/La/K/$Eu_2O_3$ | Na/La/K/$Sm_2O_3$ | Na/La/K/$La_3NdO_6$ |
| Na/La/Li/Cs | Na/La/Li/Cs/$La_2O_3$ | Na/La/Li/Cs/$Nd_2O_3$ | Na/La/Li/Cs/$Yb_2O_3$ | Na/La/Li/Cs/$Eu_2O_3$ | Na/La/Li/Cs/$Sm_2O_3$ | Na/La/Li/Cs/$La_3NdO_6$ |
| K/La | K/La/$La_2O_3$ | K/La/$Nd_2O_3$ | K/La/$Yb_2O_3$ | K/La/$Eu_2O_3$ | K/La/$Sm_2O_3$ | K/La/$La_3NdO_6$ |
| K/La/S | K/La/S/$La_2O_3$ | K/La/S/$Nd_2O_3$ | K/La/S/$Yb_2O_3$ | K/La/S/$Eu_2O_3$ | K/La/S/$Sm_2O_3$ | K/La/S/$La_3NdO_6$ |
| K/Na | K/Na/$La_2O_3$ | K/Na/$Nd_2O_3$ | K/Na/$Yb_2O_3$ | K/Na/$Eu_2O_3$ | K/Na/$Sm_2O_3$ | K/Na/$La_3NdO_6$ |
| Li/Cs | Li/Cs/$La_2O_3$ | Li/Cs/$Nd_2O_3$ | Li/Cs/$Yb_2O_3$ | Li/Cs/$Eu_2O_3$ | Li/Cs/$Sm_2O_3$ | Li/Cs/$La_3NdO_6$ |
| Li/Cs/La | Li/Cs/La/$La_2O_3$ | Li/Cs/La/$Nd_2O_3$ | Li/Cs/La/$Yb_2O_3$ | Li/Cs/La/$Eu_2O_3$ | Li/Cs/La/$Sm_2O_3$ | Li/Cs/La/$La_3NdO_6$ |
| Li/Cs/La/Tm | Li/Cs/La/Tm/$La_2O_3$ | Li/Cs/La/Tm/$Nd_2O_3$ | Li/Cs/La/Tm/$Yb_2O_3$ | Li/Cs/La/Tm/$Eu_2O_3$ | Li/Cs/La/Tm/$Sm_2O_3$ | Li/Cs/La/Tm/$La_3NdO_6$ |
| Li/Cs/Sr/Tm | Li/Cs/Sr/Tm/$La_2O_3$ | Li/Cs/Sr/Tm/$Nd_2O_3$ | Li/Cs/Sr/Tm/$Yb_2O_3$ | Li/Cs/Sr/Tm/$Eu_2O_3$ | Li/Cs/Sr/Tm/$Sm_2O_3$ | Li/Cs/Sr/Tm/$La_3NdO_6$ |
| Li/Sr/Cs | Li/Sr/Cs/$La_2O_3$ | Li/Sr/Cs/$Nd_2O_3$ | Li/Sr/Cs/$Yb_2O_3$ | Li/Sr/Cs/$Eu_2O_3$ | Li/Sr/Cs/$Sm_2O_3$ | Li/Sr/Cs/$La_3NdO_6$ |
| Li/Sr/Zn/K | Li/Sr/Zn/K/$La_2O_3$ | Li/Sr/Zn/K/$Nd_2O_3$ | Li/Sr/Zn/K/$Yb_2O_3$ | Li/Sr/Zn/K/$Eu_2O_3$ | Li/Sr/Zn/K/$Sm_2O_3$ | Li/Sr/Zn/K/$La_3NdO_6$ |
| Li/Ga/Cs | Li/Ga/Cs/$La_2O_3$ | Li/Ga/Cs/$Nd_2O_3$ | Li/Ga/Cs/$Yb_2O_3$ | Li/Ga/Cs/$Eu_2O_3$ | Li/Ga/Cs/$Sm_2O_3$ | Li/Ga/Cs/$La_3NdO_6$ |
| Li/K/Sr/La | Li/K/Sr/La/$La_2O_3$ | Li/K/Sr/La/$Nd_2O_3$ | Li/K/Sr/La/$Yb_2O_3$ | Li/K/Sr/La/$Eu_2O_3$ | Li/K/Sr/La/$Sm_2O_3$ | Li/K/Sr/La/$La_3NdO_6$ |
| Li/Na | Li/Na/$La_2O_3$ | Li/Na/$Nd_2O_3$ | Li/Na/$Yb_2O_3$ | Li/Na/$Eu_2O_3$ | Li/Na/$Sm_2O_3$ | Li/Na/$La_3NdO_6$ |
| Li/Na/Rb/Ga | Li/Na/Rb/Ga/$La_2O_3$ | Li/Na/Rb/Ga/$Nd_2O_3$ | Li/Na/Rb/Ga/$Yb_2O_3$ | Li/Na/Rb/Ga/$Eu_2O_3$ | Li/Na/Rb/Ga/$Sm_2O_3$ | Li/Na/Rb/Ga/$La_3NdO_6$ |
| Li/Na/Sr | Li/Na/Sr/$La_2O_3$ | Li/Na/Sr/$Nd_2O_3$ | Li/Na/Sr/$Yb_2O_3$ | Li/Na/Sr/$Eu_2O_3$ | Li/Na/Sr/$Sm_2O_3$ | Li/Na/Sr/$La_3NdO_6$ |
| Li/Na/Sr/La | Li/Na/Sr/La/$La_2O_3$ | Li/Na/Sr/La/$Nd_2O_3$ | Li/Na/Sr/La/$Yb_2O_3$ | Li/Na/Sr/La/$Eu_2O_3$ | Li/Na/Sr/La/$Sm_2O_3$ | Li/Na/Sr/La/$La_3NdO_6$ |
| Li/Sm/Cs | Li/Sm/Cs/$La_2O_3$ | Li/Sm/Cs/$Nd_2O_3$ | Li/Sm/Cs/$Yb_2O_3$ | Li/Sm/Cs/$Eu_2O_3$ | Li/Sm/Cs/$Sm_2O_3$ | Li/Sm/Cs/$La_3NdO_6$ |
| Ba/Sm/Yb/S | Ba/Sm/Yb/S/$La_2O_3$ | Ba/Sm/Yb/S/$Nd_2O_3$ | Ba/Sm/Yb/S/$Yb_2O_3$ | Ba/Sm/Yb/S/$Eu_2O_3$ | Ba/Sm/Yb/S/$Sm_2O_3$ | Ba/Sm/Yb/S/$La_3NdO_6$ |
| Ba/Tm/K/La | Ba/Tm/K/La/$La_2O_3$ | Ba/Tm/K/La/$Nd_2O_3$ | Ba/Tm/K/La/$Yb_2O_3$ | Ba/Tm/K/La/$Eu_2O_3$ | Ba/Tm/K/La/$Sm_2O_3$ | Ba/Tm/K/La/$La_3NdO_6$ |
| Ba/Tm/Zn/K | Ba/Tm/Zn/K/La2O3 | Ba/Tm/Zn/K/$Nd_2O_3$ | Ba/Tm/Zn/K/$Yb_2O_3$ | Ba/Tm/Zn/K/$Eu_2O_3$ | Ba/Tm/Zn/K/$Sm_2O_3$ | Ba/Tm/Zn/K/$La_3NdO_6$ |
| Cs/K/La | Cs/K/La/$La_2O_3$ | Cs/K/La/$Nd_2O_3$ | Cs/K/La/$Yb_2O_3$ | Cs/K/La/$Eu_2O_3$ | Cs/K/La/$Sm_2O_3$ | Cs/K/La/$La_3NdO_6$ |
| Cs/La/Tm/Na | Cs/La/Tm/Na/$La_2O_3$ | Cs/La/Tm/Na/$Nd_2O_3$ | Cs/La/Tm/Na/$Yb_2O_3$ | Cs/La/Tm/Na/$Eu_2O_3$ | Cs/La/Tm/Na/$Sm_2O_3$ | Cs/La/Tm/Na/$La_3NdO_6$ |
| Cs/Li/K/La | Cs/Li/K/La/$La_2O_3$ | Cs/Li/K/La/$Nd_2O_3$ | Cs/Li/K/La/$Yb_2O_3$ | Cs/Li/K/La/$Eu_2O_3$ | Cs/Li/K/La/$Sm_2O_3$ | Cs/Li/K/La/$La_3NdO_6$ |
| Sm/Li/Sr/Cs | Sm/Li/Sr/Cs/$La_2O_3$ | Sm/Li/Sr/Cs/$Nd_2O_3$ | Sm/Li/Sr/Cs/$Yb_2O_3$ | Sm/Li/Sr/Cs/$Eu_2O_3$ | Sm/Li/Sr/Cs/$Sm_2O_3$ | Sm/Li/Sr/Cs/$La_3NdO_6$ |
| Sr/Cs/La | Sr/Cs/La/$La_2O_3$ | Sr/Cs/La/$Nd_2O_3$ | Sr/Cs/La/$Yb_2O_3$ | Sr/Cs/La/$Eu_2O_3$ | Sr/Cs/La/$Sm_2O_3$ | Sr/Cs/La/$La_3NdO_6$ |
| Sr/Tm/Li/Cs | Sr/Tm/Li/Cs/$La_2O_3$ | Sr/Tm/Li/Cs/$Nd_2O_3$ | Sr/Tm/Li/Cs/$Yb_2O_3$ | Sr/Tm/Li/Cs/$Eu_2O_3$ | Sr/Tm/Li/Cs/$Sm_2O_3$ | Sr/Tm/Li/Cs/$La_3NdO_6$ |

TABLE 1-continued

CATALYSTS (CAT) DOPED WITH SPECIFIC DOPANTS (DOP)

| Dop\Cat | $La_2O_3$ | $Nd_2O_3$ | $Yb_2O_3$ | $Eu_2O_3$ | $Sm_2O_3$ | $La_3NdO_6$ |
|---|---|---|---|---|---|---|
| Zn/K | Zn/K/$La_2O_3$ | Zn/K/$Nd_2O_3$ | Zn/K/$Yb_2O_3$ | Zn/K/$Eu_2O_3$ | Zn/K/$Sm_2O_3$ | Zn/K/$La_3NdO_6$ |
| Zr/Cs/K/La | Zr/Cs/K/La/$La_2O_3$ | Zr/Cs/K/La/$Nd_2O_3$ | Zr/Cs/K/La/$Yb_2O_3$ | Zr/Cs/K/La/$Eu_2O_3$ | Zr/Cs/K/La/$Sm_2O_3$ | Zr/Cs/K/La/$La_3NdO_6$ |
| Rb/Ca/In/Ni | Rb/Ca/In/Ni/$La_2O_3$ | Rb/Ca/In/Ni/$Nd_2O_3$ | Rb/Ca/In/Ni/$Yb_2O_3$ | Rb/Ca/In/Ni/$Eu_2O_3$ | Rb/Ca/In/Ni/$Sm_2O_3$ | Rb/Ca/In/Ni/$La_3NdO_6$ |
| Sr/Ho/Tm | Sr/Ho/Tm/$La_2O_3$ | Sr/Ho/Tm/$Nd_2O_3$ | Sr/Ho/Tm/$Yb_2O_3$ | Sr/Ho/Tm/$Eu_2O_3$ | Sr/Ho/Tm/$Sm_2O_3$ | Sr/Ho/Tm/$La_3NdO_6$ |
| La/Nd/S | La/Nd/S/$La_2O_3$ | La/Nd/S/$Nd_2O_3$ | La/Nd/S/$Yb_2O_3$ | La/Nd/S/$Eu_2O_3$ | La/Nd/S/$Sm_2O_3$ | La/Nd/S/$La_3NdO_6$ |
| Li/Rb/Ca | Li/Rb/Ca/$La_2O_3$ | Li/Rb/Ca/$Nd_2O_3$ | Li/Rb/Ca/$Yb_2O_3$ | Li/Rb/Ca/$Eu_2O_3$ | Li/Rb/Ca/$Sm_2O_3$ | Li/Rb/Ca/$La_3NdO_6$ |
| Li/K | Li/K/$La_2O_3$ | Li/K/$Nd_2O_3$ | Li/K/$Yb_2O_3$ | Li/K/$Eu_2O_3$ | Li/K/$Sm_2O_3$ | Li/K/$La_3NdO_6$ |
| Tm/Lu/Ta/P | Tm/Lu/Ta/P/$La_2O_3$ | Tm/Lu/Ta/P/$Nd_2O_3$ | Tm/Lu/Ta/P/$Yb_2O_3$ | Tm/Lu/Ta/P/$Eu_2O_3$ | Tm/Lu/Ta/P/$Sm_2O_3$ | Tm/Lu/Ta/P/$La_3NdO_6$ |
| Rb/Ca/Dy/P | Rb/Ca/Dy/P/$La_2O_3$ | Rb/Ca/Dy/P/$Nd_2O_3$ | Rb/Ca/Dy/P/$Yb_2O_3$ | Rb/Ca/Dy/P/$Eu_2O_3$ | Rb/Ca/Dy/P/$Sm_2O_3$ | Rb/Ca/Dy/P/$La_3NdO_6$ |
| Mg/La/Yb/Zn | Mg/La/Yb/Zn/$La_2O_3$ | Mg/La/Yb/Zn/$Nd_2O_3$ | Mg/La/Yb/Zn/$Yb_2O_3$ | Mg/La/Yb/Zn/$Eu_2O_3$ | Mg/La/Yb/Zn/$Sm_2O_3$ | Mg/La/Yb/Zn/$La_3NdO_6$ |
| Rb/Sr/Lu | Rb/Sr/Lu/$La_2O_3$ | Rb/Sr/Lu/$Nd_2O_3$ | Rb/Sr/Lu/$Yb_2O_3$ | Rb/Sr/Lu/$Eu_2O_3$ | Rb/Sr/Lu/$Sm_2O_3$ | Rb/Sr/Lu/$La_3NdO_6$ |
| Na/Sr/Lu/Nb | Na/Sr/Lu/Nb/$La_2O_3$ | Na/Sr/Lu/Nb/$Nd_2O_3$ | Na/Sr/Lu/Nb/$Yb_2O_3$ | Na/Sr/Lu/Nb/$Eu_2O_3$ | Na/Sr/Lu/Nb/$Sm_2O_3$ | Na/Sr/Lu/Nb/$La_3NdO_6$ |
| Na/Eu/Hf | Na/Eu/Hf/$La_2O_3$ | Na/Eu/Hf/$Nd_2O_3$ | Na/Eu/Hf/$Yb_2O_3$ | Na/Eu/Hf/$Eu_2O_3$ | Na/Eu/Hf/$Sm_2O_3$ | Na/Eu/Hf/$La_3NdO_6$ |
| Dy/Rb/Gd | Dy/Rb/Gd/$La_2O_3$ | Dy/Rb/Gd/$Nd_2O_3$ | Dy/Rb/Gd/$Yb_2O_3$ | Dy/Rb/Gd/$Eu_2O_3$ | Dy/Rb/Gd/$Sm_2O_3$ | Dy/Rb/Gd/$La_3NdO_6$ |
| Na/Pt/Bi | Na/Pt/Bi/$La_2O_3$ | Na/Pt/Bi/$Nd_2O_3$ | Na/Pt/Bi/$Yb_2O_3$ | Na/Pt/Bi/$Eu_2O_3$ | Na/Pt/Bi/$Sm_2O_3$ | Na/Pt/Bi/$La_3NdO_6$ |
| Rb/Hf | Rb/Hf/$La_2O_3$ | Rb/Hf/$Nd_2O_3$ | Rb/Hf/$Yb_2O_3$ | Rb/Hf/$Eu_2O_3$ | Rb/Hf/$Sm_2O_3$ | Rb/Hf/$La_3NdO_6$ |
| Ca/Cs | Ca/Cs/$La_2O_3$ | Ca/Cs/$Nd_2O_3$ | Ca/Cs/$Yb_2O_3$ | Ca/Cs/$Eu_2O_3$ | Ca/Cs/$Sm_2O_3$ | Ca/Cs/$La_3NdO_6$ |
| Ca/Mg/Na | Ca/Mg/Na/$La_2O_3$ | Ca/Mg/Na/$Nd_2O_3$ | Ca/Mg/Na/$Yb_2O_3$ | Ca/Mg/Na/$Eu_2O_3$ | Ca/Mg/Na/$Sm_2O_3$ | Ca/Mg/Na/$La_3NdO_6$ |
| Hf/Bi | Hf/Bi/$La_2O_3$ | Hf/Bi/$Nd_2O_3$ | Hf/Bi/$Yb_2O_3$ | Hf/Bi/$Eu_2O_3$ | Hf/Bi/$Sm_2O_3$ | Hf/Bi/$La_3NdO_6$ |
| Sr/Sn | Sr/Sn/$La_2O_3$ | Sr/Sn/$Nd_2O_3$ | Sr/Sn/$Yb_2O_3$ | Sr/Sn/$Eu_2O_3$ | Sr/Sn/$Sm_2O_3$ | Sr/Sn/$La_3NdO_6$ |
| Sr/W | Sr/W/$La_2O_3$ | Sr/W/$Nd_2O_3$ | Sr/W/$Yb_2O_3$ | Sr/W/$Eu_2O_3$ | Sr/W/$Sm_2O_3$ | Sr/W/$La_3NdO_6$ |
| Sr/Nb | Sr/Nb/$La_2O_3$ | Sr/Nb/$Nd_2O_3$ | Sr/Nb/$Yb_2O_3$ | Sr/Nb/$Eu_2O_3$ | Sr/Nb/$Sm_2O_3$ | Sr/Nb/$La_3NdO_6$ |
| Zr/W | Zr/W/$La_2O_3$ | Zr/W/$Nd_2O_3$ | Zr/W/$Yb_2O_3$ | Zr/W/$Eu_2O_3$ | Zr/W/$Sm_2O_3$ | Zr/W/$La_3NdO_6$ |
| Y/W | Y/W/$La_2O_3$ | Y/W/$Nd_2O_3$ | Y/W/$Yb_2O_3$ | Y/W/$Eu_2O_3$ | Y/W/$Sm_2O_3$ | Y/W/$La_3NdO_6$ |
| Na/W | Na/W/$La_2O_3$ | Na/W/$Nd_2O_3$ | Na/W/$Yb_2O_3$ | Na/W/$Eu_2O_3$ | Na/W/$Sm_2O_3$ | Na/W/$La_3NdO_6$ |
| Bi/W | Bi/W/$La_2O_3$ | Bi/W/$Nd_2O_3$ | Bi/W/$Yb_2O_3$ | Bi/W/$Eu_2O_3$ | Bi/W/$Sm_2O_3$ | Bi/W/$La_3NdO_6$ |
| Bi/Cs | Bi/Cs/$La_2O_3$ | Bi/Cs/$Nd_2O_3$ | Bi/Cs/$Yb_2O_3$ | Bi/Cs/$Eu_2O_3$ | Bi/Cs/$Sm_2O_3$ | Bi/Cs/$La_3NdO_6$ |
| Bi/Ca | Bi/Ca/$La_2O_3$ | Bi/Ca/$Nd_2O_3$ | Bi/Ca/$Yb_2O_3$ | Bi/Ca/$Eu_2O_3$ | Bi/Ca/$Sm_2O_3$ | Bi/Ca/$La_3NdO_6$ |
| Bi/Sn | Bi/Sn/$La_2O_3$ | Bi/Sn/$Nd_2O_3$ | Bi/Sn/$Yb_2O_3$ | Bi/Sn/$Eu_2O_3$ | Bi/Sn/$Sm_2O_3$ | Bi/Sn/$La_3NdO_6$ |
| Bi/Sb | Bi/Sb/$La_2O_3$ | Bi/Sb/$Nd_2O_3$ | Bi/Sb/$Yb_2O_3$ | Bi/Sb/$Eu_2O_3$ | Bi/Sb/$Sm_2O_3$ | Bi/Sb/$La_3NdO_6$ |
| Ge/Hf | Ge/Hf/$La_2O_3$ | Ge/Hf/$Nd_2O_3$ | Ge/Hf/$Yb_2O_3$ | Ge/Hf/$Eu_2O_3$ | Ge/Hf/$Sm_2O_3$ | Ge/Hf/$La_3NdO_6$ |
| Hf/Sm | Hf/Sm/$La_2O_3$ | Hf/Sm/$Nd_2O_3$ | Hf/Sm/$Yb_2O_3$ | Hf/Sm/$Eu_2O_3$ | Hf/Sm/$Sm_2O_3$ | Hf/Sm/$La_3NdO_6$ |
| Sb/Ag | Sb/Ag/$La_2O_3$ | Sb/Ag/$Nd_2O_3$ | Sb/Ag/$Yb_2O_3$ | Sb/Ag/$Eu_2O_3$ | Sb/Ag/$Sm_2O_3$ | Sb/Ag/$La_3NdO_6$ |
| Sb/Bi | Sb/Bi/$La_2O_3$ | Sb/Bi/$Nd_2O_3$ | Sb/Bi/$Yb_2O_3$ | Sb/Bi/$Eu_2O_3$ | Sb/Bi/$Sm_2O_3$ | Sb/Bi/$La_3NdO_6$ |
| Sb/Au | Sb/Au/$La_2O_3$ | Sb/Au/$Nd_2O_3$ | Sb/Au/$Yb_2O_3$ | Sb/Au/$Eu_2O_3$ | Sb/Au/$Sm_2O_3$ | Sb/Au/$La_3NdO_6$ |
| Sb/Sm | Sb/Sm/$La_2O_3$ | Sb/Sm/$Nd_2O_3$ | Sb/Sm/$Yb_2O_3$ | Sb/Sm/$Eu_2O_3$ | Sb/Sm/$Sm_2O_3$ | Sb/Sm/$La_3NdO_6$ |
| Sb/Sr | Sb/Sr/$La_2O_3$ | Sb/Sr/$Nd_2O_3$ | Sb/Sr/$Yb_2O_3$ | Sb/Sr/$Eu_2O_3$ | Sb/Sr/$Sm_2O_3$ | Sb/Sr/$La_3NdO_6$ |
| Sb/W | Sb/W/$La_2O_3$ | Sb/W/$Nd_2O_3$ | Sb/W/$Yb_2O_3$ | Sb/W/$Eu_2O_3$ | Sb/W/$Sm_2O_3$ | Sb/W/$La_3NdO_6$ |

TABLE 1-continued

CATALYSTS (CAT) DOPED WITH SPECIFIC DOPANTS (DOP)

| Dop\Cat | La$_2$O$_3$ | Nd$_2$O$_3$ | Yb$_2$O$_3$ | Eu$_2$O$_3$ | Sm$_2$O$_3$ | La$_3$NdO$_6$ |
|---|---|---|---|---|---|---|
| Sb/Hf | Sb/Hf/La$_2$O$_3$ | Sb/Hf/Nd$_2$O$_3$ | Sb/Hf/Yb$_2$O$_3$ | Sb/Hf/Eu$_2$O$_3$ | Sb/Hf/Sm$_2$O$_3$ | Sb/Hf/La$_3$NdO$_6$ |
| Sb/Yb | Sb/Yb/La$_2$O$_3$ | Sb/Yb/Nd$_2$O$_3$ | Sb/Yb/Yb$_2$O$_3$ | Sb/Yb/Eu$_2$O$_3$ | Sb/Yb/Sm$_2$O$_3$ | Sb/Yb/La$_3$NdO$_6$ |
| Sb/Sn | Sb/Sn/La$_2$O$_3$ | Sb/Sn/Nd$_2$O$_3$ | Sb/Sn/Yb$_2$O$_3$ | Sb/Sn/Eu$_2$O$_3$ | Sb/Sn/Sm$_2$O$_3$ | Sb/Sn/La$_3$NdO$_6$ |
| Yb/Au | Yb/Au/La$_2$O$_3$ | Yb/Au/Nd$_2$O$_3$ | Yb/Au/Yb$_2$O$_3$ | Yb/Au/Eu$_2$O$_3$ | Yb/Au/Sm$_2$O$_3$ | Yb/Au/La$_3$NdO$_6$ |
| Yb/Ta | Yb/Ta/La$_2$O$_3$ | Yb/Ta/Nd$_2$O$_3$ | Yb/Ta/Yb$_2$O$_3$ | Yb/Ta/Eu$_2$O$_3$ | Yb/Ta/Sm$_2$O$_3$ | Yb/Ta/La$_3$NdO$_6$ |
| Yb/W | Yb/W/La$_2$O$_3$ | Yb/W/Nd$_2$O$_3$ | Yb/W/Yb$_2$O$_3$ | Yb/W/Eu$_2$O$_3$ | Yb/W/Sm$_2$O$_3$ | Yb/W/La$_3$NdO$_6$ |
| Yb/Sr | Yb/Sr/La$_2$O$_3$ | Yb/Sr/Nd$_2$O$_3$ | Yb/Sr/Yb$_2$O$_3$ | Yb/Sr/Eu$_2$O$_3$ | Yb/Sr/Sm$_2$O$_3$ | Yb/Sr/La$_3$NdO$_6$ |
| Yb/Pb | Yb/Pb/La$_2$O$_3$ | Yb/Pb/Nd$_2$O$_3$ | Yb/Pb/Yb$_2$O$_3$ | Yb/Pb/Eu$_2$O$_3$ | Yb/Pb/Sm$_2$O$_3$ | Yb/Pb/La$_3$NdO$_6$ |
| Yb/Ag | Yb/Ag/La$_2$O$_3$ | Yb/Ag/Nd$_2$O$_3$ | Yb/Ag/Yb$_2$O$_3$ | Yb/Ag/Eu$_2$O$_3$ | Yb/Ag/Sm$_2$O$_3$ | Yb/Ag/La$_3$NdO$_6$ |
| Au/Sr | Au/Sr/La$_2$O$_3$ | Au/Sr/Nd$_2$O$_3$ | Au/Sr/Yb$_2$O$_3$ | Au/Sr/Eu$_2$O$_3$ | Au/Sr/Sm$_2$O$_3$ | Au/Sr/La$_3$NdO$_6$ |
| W/Ge | W/Ge/La$_2$O$_3$ | W/Ge/Nd$_2$O$_3$ | W/Ge/Yb$_2$O$_3$ | W/Ge/Eu$_2$O$_3$ | W/Ge/Sm$_2$O$_3$ | W/Ge/La$_3$NdO$_6$ |
| Ta/Sr | Ta/Sr/La$_2$O$_3$ | Ta/Sr/Nd$_2$O$_3$ | Ta/Sr/Yb$_2$O$_3$ | Ta/Sr/Eu$_2$O$_3$ | Ta/Sr/Sm$_2$O$_3$ | Ta/Sr/La$_3$NdO$_6$ |
| Ta/Hf | Ta/Hf/La$_2$O$_3$ | Ta/Hf/Nd$_2$O$_3$ | Ta/Hf/Yb$_2$O$_3$ | Ta/Hf/Eu$_2$O$_3$ | Ta/Hf/Sm$_2$O$_3$ | Ta/Hf/La$_3$NdO$_6$ |
| W/Au | W/Au/La$_2$O$_3$ | W/Au/Nd$_2$O$_3$ | W/Au/Yb$_2$O$_3$ | W/Au/Eu$_2$O$_3$ | W/Au/Sm$_2$O$_3$ | W/Au/La$_3$NdO$_6$ |
| Ca/W | Ca/W/La$_2$O$_3$ | Ca/W/Nd$_2$O$_3$ | Ca/W/Yb$_2$O$_3$ | Ca/W/Eu$_2$O$_3$ | Ca/W/Sm$_2$O$_3$ | Ca/W/La$_3$NdO$_6$ |
| Au/Re | Au/Re/La$_2$O$_3$ | Au/Re/Nd$_2$O$_3$ | Au/Re/Yb$_2$O$_3$ | Au/Re/Eu$_2$O$_3$ | Au/Re/Sm$_2$O$_3$ | Au/Re/La$_3$NdO$_6$ |
| Sm/Li | Sm/Li/La$_2$O$_3$ | Sm/Li/Nd$_2$O$_3$ | Sm/Li/Yb$_2$O$_3$ | Sm/Li/Eu$_2$O$_3$ | Sm/Li/Sm$_2$O$_3$ | Sm/Li/La$_3$NdO$_6$ |
| La/K | La/K/La$_2$O$_3$ | La/K/Nd$_2$O$_3$ | La/K/Yb$_2$O$_3$ | La/K/Eu$_2$O$_3$ | La/K/Sm$_2$O$_3$ | La/K/La$_3$NdO$_6$ |
| Zn/Cs | Zn/Cs/La$_2$O$_3$ | Zn/Cs/Nd$_2$O$_3$ | Zn/Cs/Yb$_2$O$_3$ | Zn/Cs/Eu$_2$O$_3$ | Zn/Cs/Sm$_2$O$_3$ | Zn/Cs/La$_3$NdO$_6$ |
| Na/K/Mg | Na/K/Mg/La$_2$O$_3$ | Na/K/Mg/Nd$_2$O$_3$ | Na/K/Mg/Yb$_2$O$_3$ | Na/K/Mg/Eu$_2$O$_3$ | Na/K/Mg/Sm$_2$O$_3$ | Na/K/Mg/La$_3$NdO$_6$ |
| Zr/Cs | Zr/Cs/La$_2$O$_3$ | Zr/Cs/Nd$_2$O$_3$ | Zr/Cs/Yb$_2$O$_3$ | Zr/Cs/Eu$_2$O$_3$ | Zr/Cs/Sm$_2$O$_3$ | Zr/Cs/La$_3$NdO$_6$ |
| Ca/Ce | Ca/Ce/La$_2$O$_3$ | Ca/Ce/Nd$_2$O$_3$ | Ca/Ce/Yb$_2$O$_3$ | Ca/Ce/Eu$_2$O$_3$ | Ca/Ce/Sm$_2$O$_3$ | Ca/Ce/La$_3$NdO$_6$ |
| Na/Li/Cs | Na/Li/Cs/La$_2$O$_3$ | Na/Li/Cs/Nd$_2$O$_3$ | Na/Li/Cs/Yb$_2$O$_3$ | Na/Li/Cs/Eu$_2$O$_3$ | Na/Li/Cs/Sm$_2$O$_3$ | Na/Li/Cs/La$_3$NdO$_6$ |
| Li/Sr | Li/Sr/La$_2$O$_3$ | Li/Sr/Nd$_2$O$_3$ | Li/Sr/Yb$_2$O$_3$ | Li/Sr/Eu$_2$O$_3$ | Li/Sr/Sm$_2$O$_3$ | Li/Sr/La$_3$NdO$_6$ |
| La/Dy/K | La/Dy/K/La$_2$O$_3$ | La/Dy/K/Nd$_2$O$_3$ | La/Dy/K/Yb$_2$O$_3$ | La/Dy/K/Eu$_2$O$_3$ | La/Dy/K/Sm$_2$O$_3$ | La/Dy/K/La$_3$NdO$_6$ |
| Dy/K | Dy/K/La$_2$O$_3$ | Dy/K/Nd$_2$O$_3$ | Dy/K/Yb$_2$O$_3$ | Dy/K/Eu$_2$O$_3$ | Dy/K/Sm$_2$O$_3$ | Dy/K/La$_3$NdO$_6$ |
| La/Mg | La/Mg/La$_2$O$_3$ | La/Mg/Nd$_2$O$_3$ | La/Mg/Yb$_2$O$_3$ | La/Mg/Eu$_2$O$_3$ | La/Mg/Sm$_2$O$_3$ | La/Mg/La$_3$NdO$_6$ |
| Na/Nd/In/K | Na/Nd/In/K/La$_2$O$_3$ | Na/Nd/In/K/Nd$_2$O$_3$ | Na/Nd/In/K/Yb$_2$O$_3$ | Na/Nd/In/K/Eu$_2$O$_3$ | Na/Nd/In/K/Sm$_2$O$_3$ | Na/Nd/In/K/La$_3$NdO$_6$ |
| In/Sr | In/Sr/La$_2$O$_3$ | In/Sr/Nd$_2$O$_3$ | In/Sr/Yb$_2$O$_3$ | In/Sr/Eu$_2$O$_3$ | In/Sr/Sm$_2$O$_3$ | In/Sr/La$_3$NdO$_6$ |
| Sr/Cs | Sr/Cs/La$_2$O$_3$ | Sr/Cs/Nd$_2$O$_3$ | Sr/Cs/Yb$_2$O$_3$ | Sr/Cs/Eu$_2$O$_3$ | Sr/Cs/Sm$_2$O$_3$ | Sr/Cs/La$_3$NdO$_6$ |
| Rb/Ga/Tm/Cs | Rb/Ga/Tm/Cs/La$_2$O$_3$ | Rb/Ga/Tm/Cs/Nd$_2$O$_3$ | Rb/Ga/Tm/Cs/Yb$_2$O$_3$ | Rb/Ga/Tm/Cs/Eu$_2$O$_3$ | Rb/Ga/Tm/Cs/Sm$_2$O$_3$ | Rb/Ga/Tm/Cs/La$_3$NdO$_6$ |
| Ga/Cs | Ga/Cs/La$_2$O$_3$ | Ga/Cs/Nd$_2$O$_3$ | Ga/Cs/Yb$_2$O$_3$ | Ga/Cs/Eu$_2$O$_3$ | Ga/Cs/Sm$_2$O$_3$ | Ga/Cs/La$_3$NdO$_6$ |
| K/La/Zr/Ag | K/La/Zr/Ag/La$_2$O$_3$ | K/La/Zr/Ag/Nd$_2$O$_3$ | K/La/Zr/Ag/Yb$_2$O$_3$ | K/La/Zr/Ag/Eu$_2$O$_3$ | K/La/Zr/Ag/Sm$_2$O$_3$ | K/La/Zr/Ag/La$_3$NdO$_6$ |
| Lu/Fe | Lu/Fe/La$_2$O$_3$ | Lu/Fe/Nd$_2$O$_3$ | Lu/Fe/Yb$_2$O$_3$ | Lu/Fe/Eu$_2$O$_3$ | Lu/Fe/Sm$_2$O$_3$ | Lu/Fe/La$_3$NdO$_6$ |
| Sr/Tm | Sr/Tm/La$_2$O$_3$ | Sr/Tm/Nd$_2$O$_3$ | Sr/Tm/Yb$_2$O$_3$ | Sr/Tm/Eu$_2$O$_3$ | Sr/Tm/Sm$_2$O$_3$ | Sr/Tm/La$_3$NdO$_6$ |
| La/Dy | La/Dy/La$_2$O$_3$ | La/Dy/Nd$_2$O$_3$ | La/Dy/Yb$_2$O$_3$ | La/Dy/Eu$_2$O$_3$ | La/Dy/Sm$_2$O$_3$ | La/Dy/La$_3$NdO$_6$ |
| Sm/Li/Sr | Sm/Li/Sr/La$_2$O$_3$ | Sm/Li/Sr/Nd$_2$O$_3$ | Sm/Li/Sr/Yb$_2$O$_3$ | Sm/Li/Sr/Eu$_2$O$_3$ | Sm/Li/Sr/Sm$_2$O$_3$ | Sm/Li/Sr/La$_3$NdO$_6$ |
| Mg/K | Mg/K/La$_2$O$_3$ | Mg/K/Nd$_2$O$_3$ | Mg/K/Yb$_2$O$_3$ | Mg/K/Eu$_2$O$_3$ | Mg/K/Sm$_2$O$_3$ | Mg/K/La$_3$NdO$_6$ |

TABLE 1-continued

CATALYSTS (CAT) DOPED WITH SPECIFIC DOPANTS (DOP)

| Dop\Cat | La$_2$O$_3$ | Nd$_2$O$_3$ | Yb$_2$O$_3$ | Eu$_2$O$_3$ | Sm$_2$O$_3$ | La$_3$NdO$_6$ |
|---|---|---|---|---|---|---|
| Li/Rb/Ga | Li/Rb/Ga/La$_2$O$_3$ | Li/Rb/Ga/Nd$_2$O$_3$ | Li/Rb/Ga/Yb$_2$O$_3$ | Li/Rb/Ga/Eu$_2$O$_3$ | Li/Rb/Ga/Sm$_2$O$_3$ | Li/Rb/Ga/La$_3$NdO$_6$ |
| Li/Cs/Tm | Li/Cs/Tm/La$_2$O$_3$ | Li/Cs/Tm/Nd$_2$O$_3$ | Li/Cs/Tm/Yb$_2$O$_3$ | Li/Cs/Tm/Eu$_2$O$_3$ | Li/Cs/Tm/Sm$_2$O$_3$ | Li/Cs/Tm/La$_3$NdO$_6$ |
| Zr/K | Zr/K/La$_2$O$_3$ | Zr/K/Nd$_2$O$_3$ | Zr/K/Yb$_2$O$_3$ | Zr/K/Eu$_2$O$_3$ | Zr/K/Sm$_2$O$_3$ | Zr/K/La$_3$NdO$_6$ |
| Li/Cs | Li/Cs/La$_2$O$_3$ | Li/Cs/Nd$_2$O$_3$ | Li/Cs/Yb$_2$O$_3$ | Li/Cs/Eu$_2$O$_3$ | Li/Cs/Sm$_2$O$_3$ | Li/Cs/La$_3$NdO$_6$ |
| Li/K/La | Li/K/La/La$_2$O$_3$ | Li/K/La/Nd$_2$O$_3$ | Li/K/La/Yb$_2$O$_3$ | Li/K/La/Eu$_2$O$_3$ | Li/K/La/Sm$_2$O$_3$ | Li/K/La/La$_3$NdO$_6$ |
| Ce/Zr/La | Ce/Zr/La/La$_2$O$_3$ | Ce/Zr/La/Nd$_2$O$_3$ | Ce/Zr/La/Yb$_2$O$_3$ | Ce/Zr/La/Eu$_2$O$_3$ | Ce/Zr/La/Sm$_2$O$_3$ | Ce/Zr/La/La$_3$NdO$_6$ |
| Ca/Al/La | Ca/Al/La/La$_2$O$_3$ | Ca/Al/La/Nd$_2$O$_3$ | Ca/Al/La/Yb$_2$O$_3$ | Ca/Al/La/Eu$_2$O$_3$ | Ca/Al/La/Sm$_2$O$_3$ | Ca/Al/La/La$_3$NdO$_6$ |
| Sr/Zn/La | Sr/Zn/La/La$_2$O$_3$ | Sr/Zn/La/Nd$_2$O$_3$ | Sr/Zn/La/Yb$_2$O$_3$ | Sr/Zn/La/Eu$_2$O$_3$ | Sr/Zn/La/Sm$_2$O$_3$ | Sr/Zn/La/La$_3$NdO$_6$ |
| Sr/Cs/Zn | Sr/Cs/Zn/La$_2$O$_3$ | Sr/Cs/Zn/Nd$_2$O$_3$ | Sr/Cs/Zn/Yb$_2$O$_3$ | Sr/Cs/Zn/Eu$_2$O$_3$ | Sr/Cs/Zn/Sm$_2$O$_3$ | Sr/Cs/Zn/La$_3$NdO$_6$ |
| Sm/Cs | Sm/Cs/La$_2$O$_3$ | Sm/Cs/Nd$_2$O$_3$ | Sm/Cs/Yb$_2$O$_3$ | Sm/Cs/Eu$_2$O$_3$ | Sm/Cs/Sm$_2$O$_3$ | Sm/Cs/La$_3$NdO$_6$ |
| In/K | In/K/La$_2$O$_3$ | In/K/Nd$_2$O$_3$ | In/K/Yb$_2$O$_3$ | In/K/Eu$_2$O$_3$ | In/K/Sm$_2$O$_3$ | In/K/La$_3$NdO$_6$ |
| Ho/Cs/Li/La | Ho/Cs/Li/La/La$_2$O$_3$ | Ho/Cs/Li/La/Nd$_2$O$_3$ | Ho/Cs/Li/La/Yb$_2$O$_3$ | Ho/Cs/Li/La/Eu$_2$O$_3$ | Ho/Cs/Li/La/Sm$_2$O$_3$ | Ho/Cs/Li/La/La$_3$NdO$_6$ |
| Cs/La/Na | Cs/La/Na/La$_2$O$_3$ | Cs/La/Na/Nd$_2$O$_3$ | Cs/La/Na/Yb$_2$O$_3$ | Cs/La/Na/Eu$_2$O$_3$ | Cs/La/Na/Sm$_2$O$_3$ | Cs/La/Na/La$_3$NdO$_6$ |
| La/S/Sr | La/S/Sr/La$_2$O$_3$ | La/S/Sr/Nd$_2$O$_3$ | La/S/Sr/Yb$_2$O$_3$ | La/S/Sr/Eu$_2$O$_3$ | La/S/Sr/Sm$_2$O$_3$ | La/S/Sr/La$_3$NdO$_6$ |
| K/La/Zr/Ag | K/La/Zr/Ag/La$_2$O$_3$ | K/La/Zr/Ag/Nd$_2$O$_3$ | K/La/Zr/Ag/Yb$_2$O$_3$ | K/La/Zr/Ag/Eu$_2$O$_3$ | K/La/Zr/Ag/Sm$_2$O$_3$ | K/La/Zr/Ag/La$_3$NdO$_6$ |
| Lu/Tl | Lu/Tl/La$_2$O$_3$ | Lu/Tl/Nd$_2$O$_3$ | Lu/Tl/Yb$_2$O$_3$ | Lu/Tl/Eu$_2$O$_3$ | Lu/Tl/Sm$_2$O$_3$ | Lu/Tl/La$_3$NdO$_6$ |
| Pr/Zn | Pr/Zn/La$_2$O$_3$ | Pr/Zn/Nd$_2$O$_3$ | Pr/Zn/Yb$_2$O$_3$ | Pr/Zn/Eu$_2$O$_3$ | Pr/Zn/Sm$_2$O$_3$ | Pr/Zn/La$_3$NdO$_6$ |
| Rb/Sr/La | Rb/Sr/La/La$_2$O$_3$ | Rb/Sr/La/Nd$_2$O$_3$ | Rb/Sr/La/Yb$_2$O$_3$ | Rb/Sr/La/Eu$_2$O$_3$ | Rb/Sr/La/Sm$_2$O$_3$ | Rb/Sr/La/La$_3$NdO$_6$ |
| Na/Sr/Eu/Ca | Na/Sr/Eu/Ca/La$_2$O$_3$ | Na/Sr/Eu/Ca/Nd$_2$O$_3$ | Na/Sr/Eu/Ca/Yb$_2$O$_3$ | Na/Sr/Eu/Ca/Eu$_2$O$_3$ | Na/Sr/Eu/Ca/Sm$_2$O$_3$ | Na/Sr/Eu/Ca/La$_3$NdO$_6$ |
| K/Cs/Sr/La | K/Cs/Sr/La/La$_2$O$_3$ | K/Cs/Sr/La/Nd$_2$O$_3$ | K/Cs/Sr/La/Yb$_2$O$_3$ | K/Cs/Sr/La/Eu$_2$O$_3$ | K/Cs/Sr/La/Sm$_2$O$_3$ | K/Cs/Sr/La/La$_3$NdO$_6$ |
| Na/Sr/Lu | Na/Sr/Lu/La$_2$O$_3$ | Na/Sr/Lu/Nd$_2$O$_3$ | Na/Sr/Lu/Yb$_2$O$_3$ | Na/Sr/Lu/Eu$_2$O$_3$ | Na/Sr/Lu/Sm$_2$O$_3$ | Na/Sr/Lu/La$_3$NdO$_6$ |
| Sr/Eu/Dy | Sr/Eu/Dy/La$_2$O$_3$ | Sr/Eu/Dy/Nd$_2$O$_3$ | Sr/Eu/Dy/Yb$_2$O$_3$ | Sr/Eu/Dy/Eu$_2$O$_3$ | Sr/Eu/Dy/Sm$_2$O$_3$ | Sr/Eu/Dy/La$_3$NdO$_6$ |
| Lu/Nb | Lu/Nb/La$_2$O$_3$ | Lu/Nb/Nd$_2$O$_3$ | Lu/Nb/Yb$_2$O$_3$ | Lu/Nb/Eu$_2$O$_3$ | Lu/Nb/Sm$_2$O$_3$ | Lu/Nb/La$_3$NdO$_6$ |
| La/Dy/Gd | La/Dy/Gd/La$_2$O$_3$ | La/Dy/Gd/Nd$_2$O$_3$ | La/Dy/Gd/Yb$_2$O$_3$ | La/Dy/Gd/Eu$_2$O$_3$ | La/Dy/Gd/Sm$_2$O$_3$ | La/Dy/Gd/La$_3$NdO$_6$ |
| Na/Mg/Tl/P | Na/Mg/Tl/P/La$_2$O$_3$ | Na/Mg/Tl/P/Nd$_2$O$_3$ | Na/Mg/Tl/P/Yb$_2$O$_3$ | Na/Mg/Tl/P/Eu$_2$O$_3$ | Na/Mg/Tl/P/Sm$_2$O$_3$ | Na/Mg/Tl/P/La$_3$NdO$_6$ |
| Na/Pt | Na/Pt/La$_2$O$_3$ | Na/Pt/Nd$_2$O$_3$ | Na/Pt/Yb$_2$O$_3$ | Na/Pt/Eu$_2$O$_3$ | Na/Pt/Sm$_2$O$_3$ | Na/Pt/La$_3$NdO$_6$ |
| Gd/Li/K | Gd/Li/K/La$_2$O$_3$ | Gd/Li/K/Nd$_2$O$_3$ | Gd/Li/K/Yb$_2$O$_3$ | Gd/Li/K/Eu$_2$O$_3$ | Gd/Li/K/Sm$_2$O$_3$ | Gd/Li/K/La$_3$NdO$_6$ |
| Rb/K/Lu | Rb/K/Lu/La$_2$O$_3$ | Rb/K/Lu/Nd$_2$O$_3$ | Rb/K/Lu/Yb$_2$O$_3$ | Rb/K/Lu/Eu$_2$O$_3$ | Rb/K/Lu/Sm$_2$O$_3$ | Rb/K/Lu/La$_3$NdO$_6$ |
| Sr/La/Dy/S | Sr/La/Dy/S/La$_2$O$_3$ | Sr/La/Dy/S/Nd$_2$O$_3$ | Sr/La/Dy/S/Yb$_2$O$_3$ | Sr/La/Dy/S/Eu$_2$O$_3$ | Sr/La/Dy/S/Sm$_2$O$_3$ | Sr/La/Dy/S/La$_3$NdO$_6$ |
| Na/Ce/Co | Na/Ce/Co/La$_2$O$_3$ | Na/Ce/Co/Nd$_2$O$_3$ | Na/Ce/Co/Yb$_2$O$_3$ | Na/Ce/Co/Eu$_2$O$_3$ | Na/Ce/Co/Sm$_2$O$_3$ | Na/Ce/Co/La$_3$NdO$_6$ |
| Na/Ce | Na/Ce/La$_2$O$_3$ | Na/Ce/Nd$_2$O$_3$ | Na/Ce/Yb$_2$O$_3$ | Na/Ce/Eu$_2$O$_3$ | Na/Ce/Sm$_2$O$_3$ | Na/Ce/La$_3$NdO$_6$ |
| Na/Ga/Gd/Al | Na/Ga/Gd/Al/La$_2$O$_3$ | Na/Ga/Gd/Al/Nd$_2$O$_3$ | Na/Ga/Gd/Al/Yb$_2$O$_3$ | Na/Ga/Gd/Al/Eu$_2$O$_3$ | Na/Ga/Gd/Al/Sm$_2$O$_3$ | Na/Ga/Gd/Al/La$_3$NdO$_6$ |
| Ba/Rh/Ta | Ba/Rh/Ta/La$_2$O$_3$ | Ba/Rh/Ta/Nd$_2$O$_3$ | Ba/Rh/Ta/Yb$_2$O$_3$ | Ba/Rh/Ta/Eu$_2$O$_3$ | Ba/Rh/Ta/Sm$_2$O$_3$ | Ba/Rh/Ta/La$_3$NdO$_6$ |
| Ba/Ta | Ba/Ta/La$_2$O$_3$ | Ba/Ta/Nd$_2$O$_3$ | Ba/Ta/Yb$_2$O$_3$ | Ba/Ta/Eu$_2$O$_3$ | Ba/Ta/Sm$_2$O$_3$ | Ba/Ta/La$_3$NdO$_6$ |
| Na/Al/Bi | Na/Al/Bi/La$_2$O$_3$ | Na/Al/Bi/Nd$_2$O$_3$ | Na/Al/Bi/Yb$_2$O$_3$ | Na/Al/Bi/Eu$_2$O$_3$ | Na/Al/Bi/Sm$_2$O$_3$ | Na/Al/Bi/La$_3$NdO$_6$ |
| Cs/Eu/S | Cs/Eu/S/La$_2$O$_3$ | Cs/Eu/S/Nd$_2$O$_3$ | Cs/Eu/S/Yb$_2$O$_3$ | Cs/Eu/S/Eu$_2$O$_3$ | Cs/Eu/S/Sm$_2$O$_3$ | Cs/Eu/S/La$_3$NdO$_6$ |
| Sm/Tm/Yb/Fe | Sm/Tm/Yb/Fe/La$_2$O$_3$ | Sm/Tm/Yb/Fe/Nd$_2$O$_3$ | Sm/Tm/Yb/Fe/Yb$_2$O$_3$ | Sm/Tm/Yb/Fe/Eu$_2$O$_3$ | Sm/Tm/Yb/Fe/Sm$_2$O$_3$ | Sm/Tm/Yb/Fe/La$_3$NdO$_6$ |
| Sm/Tm/Yb | Sm/Tm/Yb/La$_2$O$_3$ | Sm/Tm/Yb/Nd$_2$O$_3$ | Sm/Tm/Yb/Yb$_2$O$_3$ | Sm/Tm/Yb/Eu$_2$O$_3$ | Sm/Tm/Yb/Sm$_2$O$_3$ | Sm/Tm/Yb/La$_3$NdO$_6$ |

TABLE 1-continued

CATALYSTS (CAT) DOPED WITH SPECIFIC DOPANTS (DOP)

| Dop\Cat | La$_2$O$_3$ | Nd$_2$O$_3$ | Yb$_2$O$_3$ | Eu$_2$O$_3$ | Sm$_2$O$_3$ | La$_3$NdO$_6$ |
|---|---|---|---|---|---|---|
| Hf/Zr/Ta | Hf/Zr/Ta/La$_2$O$_3$ | Hf/Zr/Ta/Nd$_2$O$_3$ | Hf/Zr/Ta/Yb$_2$O$_3$ | Hf/Zr/Ta/Eu$_2$O$_3$ | Hf/Zr/Ta/Sm$_2$O$_3$ | Hf/Zr/Ta/La$_3$NdO$_6$ |
| Rb/Gd/Li/K | Rb/Gd/Li/K/La$_2$O$_3$ | Rb/Gd/Li/K/Nd$_2$O$_3$ | Rb/Gd/Li/K/Yb$_2$O$_3$ | Rb/Gd/Li/K/Eu$_2$O$_3$ | Rb/Gd/Li/K/Sm$_2$O$_3$ | Rb/Gd/Li/K/La$_3$NdO$_6$ |
| Gd/Ho/Al/P | Gd/Ho/Al/P/La$_2$O$_3$ | Gd/Ho/Al/P/Nd$_2$O$_3$ | Gd/Ho/Al/P/Yb$_2$O$_3$ | Gd/Ho/Al/P/Eu$_2$O$_3$ | Gd/Ho/Al/P/Sm$_2$O$_3$ | Gd/Ho/Al/P/La$_3$NdO$_6$ |
| Na/Ca/Lu | Na/Ca/Lu/La$_2$O$_3$ | Na/Ca/Lu/Nd$_2$O$_3$ | Na/Ca/Lu/Yb$_2$O$_3$ | Na/Ca/Lu/Eu$_2$O$_3$ | Na/Ca/Lu/Sm$_2$O$_3$ | Na/Ca/Lu/La$_3$NdO$_6$ |
| Cu/Sn | Cu/Sn/La$_2$O$_3$ | Cu/Sn/Nd$_2$O$_3$ | Cu/Sn/Yb$_2$O$_3$ | Cu/Sn/Eu$_2$O$_3$ | Cu/Sn/Sm$_2$O$_3$ | Cu/Sn/La$_3$NdO$_6$ |
| Ag/Au | Ag/Au/La$_2$O$_3$ | Ag/Au/Nd$_2$O$_3$ | Ag/Au/Yb$_2$O$_3$ | Ag/Au/Eu$_2$O$_3$ | Ag/Au/Sm$_2$O$_3$ | Ag/Au/La$_3$NdO$_6$ |
| Al/Bi | Al/Bi/La$_2$O$_3$ | Al/Bi/Nd$_2$O$_3$ | Al/Bi/Yb$_2$O$_3$ | Al/Bi/Eu$_2$O$_3$ | Al/Bi/Sm$_2$O$_3$ | Al/Bi/La$_3$NdO$_6$ |
| Al/Mo | Al/Mo/La$_2$O$_3$ | Al/Mo/Nd$_2$O$_3$ | Al/Mo/Yb$_2$O$_3$ | Al/Mo/Eu$_2$O$_3$ | Al/Mo/Sm$_2$O$_3$ | Al/Mo/La$_3$NdO$_6$ |
| Al/Nb | Al/Nb/La$_2$O$_3$ | Al/Nb/Nd$_2$O$_3$ | Al/Nb/Yb$_2$O$_3$ | Al/Nb/Eu$_2$O$_3$ | Al/Nb/Sm$_2$O$_3$ | Al/Nb/La$_3$NdO$_6$ |
| Au/Pt | Au/Pt/La$_2$O$_3$ | Au/Pt/Nd$_2$O$_3$ | Au/Pt/Yb$_2$O$_3$ | Au/Pt/Eu$_2$O$_3$ | Au/Pt/Sm$_2$O$_3$ | Au/Pt/La$_3$NdO$_6$ |
| Ga/Bi | Ga/Bi/La$_2$O$_3$ | Ga/Bi/Nd$_2$O$_3$ | Ga/Bi/Yb$_2$O$_3$ | Ga/Bi/Eu$_2$O$_3$ | Ga/Bi/Sm$_2$O$_3$ | Ga/Bi/La$_3$NdO$_6$ |
| Mg/W | Mg/W/La$_2$O$_3$ | Mg/W/Nd$_2$O$_3$ | Mg/W/Yb$_2$O$_3$ | Mg/W/Eu$_2$O$_3$ | Mg/W/Sm$_2$O$_3$ | Mg/W/La$_3$NdO$_6$ |
| Pb/Au | Pb/Au/La$_2$O$_3$ | Pb/Au/Nd$_2$O$_3$ | Pb/Au/Yb$_2$O$_3$ | Pb/Au/Eu$_2$O$_3$ | Pb/Au/Sm$_2$O$_3$ | Pb/Au/La$_3$NdO$_6$ |
| Sn/Mg | Sn/Mg/La$_2$O$_3$ | Sn/Mg/Nd$_2$O$_3$ | Sn/Mg/Yb$_2$O$_3$ | Sn/Mg/Eu$_2$O$_3$ | Sn/Mg/Sm$_2$O$_3$ | Sn/Mg/La$_3$NdO$_6$ |
| Zn/Bi | Zn/Bi/La$_2$O$_3$ | Zn/Bi/Nd$_2$O$_3$ | Zn/Bi/Yb$_2$O$_3$ | Zn/Bi/Eu$_2$O$_3$ | Zn/Bi/Sm$_2$O$_3$ | Zn/Bi/La$_3$NdO$_6$ |
| Sr/Ta | Sr/Ta/La$_2$O$_3$ | Sr/Ta/Nd$_2$O$_3$ | Sr/Ta/Yb$_2$O$_3$ | Sr/Ta/Eu$_2$O$_3$ | Sr/Ta/Sm$_2$O$_3$ | Sr/Ta/La$_3$NdO$_6$ |
| Na | Na/La$_2$O$_3$ | Na/Nd$_2$O$_3$ | Na/Yb$_2$O$_3$ | Na/Eu$_2$O$_3$ | Na/Sm$_2$O$_3$ | Na/La$_3$NdO$_6$ |
| Sr | Sr/La$_2$O$_3$ | Sr/Nd$_2$O$_3$ | Sr/Yb$_2$O$_3$ | Sr/Eu$_2$O$_3$ | Sr/Sm$_2$O$_3$ | Sr/La$_3$NdO$_6$ |
| Ca | Ca/La$_2$O$_3$ | Ca/Nd$_2$O$_3$ | Ca/Yb$_2$O$_3$ | Ca/Eu$_2$O$_3$ | Ca/Sm$_2$O$_3$ | Ca/La$_3$NdO$_6$ |
| Yb | Yb/La$_2$O$_3$ | Yb/Nd$_2$O$_3$ | Yb/Yb$_2$O$_3$ | Yb/Eu$_2$O$_3$ | Yb/Sm$_2$O$_3$ | Yb/La$_3$NdO$_6$ |
| Cs | Cs/La$_2$O$_3$ | Cs/Nd$_2$O$_3$ | Cs/Yb$_2$O$_3$ | Cs/Eu$_2$O$_3$ | Cs/Sm$_2$O$_3$ | Cs/La$_3$NdO$_6$ |
| Sb | Sb/La$_2$O$_3$ | Sb/Nd$_2$O$_3$ | Sb/Yb$_2$O$_3$ | Sb/Eu$_2$O$_3$ | Sb/Sm$_2$O$_3$ | Sb/La$_3$NdO$_6$ |
| Gd/Ho | Gd/Ho/La$_2$O$_3$ | Gd/Ho/Nd$_2$O$_3$ | Gd/Ho/Yb$_2$O$_3$ | Gd/Ho/Eu$_2$O$_3$ | Gd/Ho/Sm$_2$O$_3$ | Gd/Ho/La$_3$NdO$_6$ |
| Zr/Bi | Zr/Bi/La$_2$O$_3$ | Zr/Bi/Nd$_2$O$_3$ | Zr/Bi/Yb$_2$O$_3$ | Zr/Bi/Eu$_2$O$_3$ | Zr/Bi/Sm$_2$O$_3$ | Zr/Bi/La$_3$NdO$_6$ |
| Ho/Sr | Ho/Sr/La$_2$O$_3$ | Ho/Sr/Nd$_2$O$_3$ | Ho/Sr/Yb$_2$O$_3$ | Ho/Sr/Eu$_2$O$_3$ | Ho/Sr/Sm$_2$O$_3$ | Ho/Sr/La$_3$NdO$_6$ |
| Gd/Ho/Sr | Gd/Ho/Sr/La$_2$O$_3$ | Gd/Ho/Sr/Nd$_2$O$_3$ | Gd/Ho/Sr/Yb$_2$O$_3$ | Gd/Ho/Sr/Eu$_2$O$_3$ | Gd/Ho/Sr/Sm$_2$O$_3$ | Gd/Ho/Sr/La$_3$NdO$_6$ |
| Ca/Sr | Ca/Sr/La$_2$O$_3$ | Ca/Sr/Nd$_2$O$_3$ | Ca/Sr/Yb$_2$O$_3$ | Ca/Sr/Eu$_2$O$_3$ | Ca/Sr/Sm$_2$O$_3$ | Ca/Sr/La$_3$NdO$_6$ |
| Ca/Sr/W | Ca/Sr/W/La$_2$O$_3$ | Ca/Sr/W/Nd$_2$O$_3$ | Ca/Sr/W/Yb$_2$O$_3$ | Ca/Sr/W/Eu$_2$O$_3$ | Ca/Sr/W/Sm$_2$O$_3$ | Ca/Sr/W/La$_3$NdO$_6$ |
| Na/Zr/Eu/Tm | Na/Zr/Eu/Tm/La$_2$O$_3$ | Na/Zr/Eu/Tm/Nd$_2$O$_3$ | Na/Zr/Eu/Tm/Yb$_2$O$_3$ | Na/Zr/Eu/Tm/Eu$_2$O$_3$ | Na/Zr/Eu/Tm/Sm$_2$O$_3$ | Na/Zr/Eu/Tm/La$_3$NdO$_6$ |
| Sr/Ho/Tm/Na | Sr/Ho/Tm/Na/La$_2$O$_3$ | Sr/Ho/Tm/Na/Nd$_2$O$_3$ | Sr/Ho/Tm/Na/Yb$_2$O$_3$ | Sr/Ho/Tm/Na/Eu$_2$O$_3$ | Sr/Ho/Tm/Na/Sm$_2$O$_3$ | Sr/Ho/Tm/Na/La$_3$NdO$_6$ |
| Sr/Pb | Sr/Pb/La$_2$O$_3$ | Sr/Pb/Nd$_2$O$_3$ | Sr/Pb/Yb$_2$O$_3$ | Sr/Pb/Eu$_2$O$_3$ | Sr/Pb/Sm$_2$O$_3$ | Sr/Pb/La$_3$NdO$_6$ |
| Sr/W/Li | Sr/W/Li/La$_2$O$_3$ | Sr/W/Li/Nd$_2$O$_3$ | Sr/W/Li/Yb$_2$O$_3$ | Sr/W/Li/Eu$_2$O$_3$ | Sr/W/Li/Sm$_2$O$_3$ | Sr/W/Li/La$_3$NdO$_6$ |
| Ca/Sr/W | Ca/Sr/W/La$_2$O$_3$ | Ca/Sr/W/Nd$_2$O$_3$ | Ca/Sr/W/Yb$_2$O$_3$ | Ca/Sr/W/Eu$_2$O$_3$ | Ca/Sr/W/Sm$_2$O$_3$ | Ca/Sr/W/La$_3$NdO$_6$ |
| Sr/Hf | Sr/Hf/La$_2$O$_3$ | Sr/Hf/Nd$_2$O$_3$ | Sr/Hf/Yb$_2$O$_3$ | Sr/Hf/Eu$_2$O$_3$ | Sr/Hf/Sm$_2$O$_3$ | Sr/Hf/La$_3$NdO$_6$ |
| Au/Re | Au/Re/La$_2$O$_3$ | Au/Re/Nd$_2$O$_3$ | Au/Re/Yb$_2$O$_3$ | Au/Re/Eu$_2$O$_3$ | Au/Re/Sm$_2$O$_3$ | Au/Re/La$_3$NdO$_6$ |
| Sr/W | Sr/W/La$_2$O$_3$ | Sr/W/Nd$_2$O$_3$ | Sr/W/Yb$_2$O$_3$ | Sr/W/Eu$_2$O$_3$ | Sr/W/Sm$_2$O$_3$ | Sr/W/La$_3$NdO$_6$ |
| La/Nd | La/Nd/La$_2$O$_3$ | La/Nd/Nd$_2$O$_3$ | La/Nd/Yb$_2$O$_3$ | La/Nd/Eu$_2$O$_3$ | La/Nd/Sm$_2$O$_3$ | La/Nd/La$_3$NdO$_6$ |
| La/Sm | La/Sm/La$_2$O$_3$ | La/Sm/Nd$_2$O$_3$ | La/Sm/Yb$_2$O$_3$ | La/Sm/Eu$_2$O$_3$ | La/Sm/Sm$_2$O$_3$ | La/Sm/La$_3$NdO$_6$ |

TABLE 1-continued

CATALYSTS (CAT) DOPED WITH SPECIFIC DOPANTS (DOP)

| Dop\Cat | $La_2O_3$ | $Nd_2O_3$ | $Yb_2O_3$ | $Eu_2O_3$ | $Sm_2O_3$ | $La_3NdO_6$ |
|---|---|---|---|---|---|---|
| La/Ce | La/Ce/ $La_2O_3$ | La/Ce/ $Nd_2O_3$ | La/Ce/ $Yb_2O_3$ | La/Ce/ $Eu_2O_3$ | La/Ce/ $Sm_2O_3$ | La/Ce/ $La_3NdO_6$ |
| La/Sr | La/Sr/ $La_2O_3$ | La/Sr/ $Nd_2O_3$ | La/Sr/ $Yb_2O_3$ | La/Sr/ $Eu_2O_3$ | La/Sr/ $Sm_2O_3$ | La/Sr/ $La_3NdO_6$ |
| La/Nd/Sr | La/Nd/Sr/ $La_2O_3$ | La/Nd/Sr/ $Nd_2O_3$ | La/Nd/Sr/ $Yb_2O_3$ | La/Nd/Sr/ $Eu_2O_3$ | La/Nd/Sr/ $Sm_2O_3$ | La/Nd/Sr/ $La_3NdO_6$ |
| La/Bi/Sr | La/Bi/Sr/ $La_2O_3$ | La/Bi/Sr/ $Nd_2O_3$ | La/Bi/Sr/ $Yb_2O_3$ | La/Bi/Sr/ $Eu_2O_3$ | La/Bi/Sr/ $Sm_2O_3$ | La/Bi/Sr/ $La_3NdO_6$ |
| La/Ce/Nd/Sr | La/Ce/Nd/Sr/ $La_2O_3$ | La/Ce/Nd/Sr/ $Nd_2O_3$ | La/Ce/Nd/Sr/ $Yb_2O_3$ | La/Ce/Nd/Sr/ $Eu_2O_3$ | La/Ce/Nd/Sr/ $Sm_2O_3$ | La/Ce/Nd/Sr/ $La_3NdO_6$ |
| La/Bi/Ce/Nd/Sr | La/Bi/Ce/Nd/Sr/ $La_2O_3$ | La/Bi/Ce/Nd/Sr/ $Nd_2O_3$ | La/Bi/Ce/Nd/Sr/ $Yb_2O_3$ | La/Bi/Ce/Nd/Sr/ $Eu_2O_3$ | La/Bi/Ce/Nd/Sr/ $Sm_2O_3$ | La/Bi/Ce/Nd/Sr/ $La_3NdO_6$ |
| Eu/Gd | Eu/Gd/ $La_2O_3$ | Eu/Gd/ $Nd_2O_3$ | Eu/Gd/ $Yb_2O_3$ | Eu/Gd/ $Eu_2O_3$ | Eu/Gd/ $Sm_2O_3$ | Eu/Gd/ $La_3NdO_6$ |
| Ca/Na | Ca/Na/ $La_2O_3$ | Ca/Na/ $Nd_2O_3$ | Ca/Na/ $Yb_2O_3$ | Ca/Na/ $Eu_2O_3$ | Ca/Na/ $Sm_2O_3$ | Ca/Na/ $La_3NdO_6$ |
| Eu/Sm | Eu/Sm/ $La_2O_3$ | Eu/Sm/ $Nd_2O_3$ | Eu/Sm/ $Yb_2O_3$ | Eu/Sm/ $Eu_2O_3$ | Eu/Sm/ $Sm_2O_3$ | Eu/Sm/ $La_3NdO_6$ |
| Eu/Sr | Eu/Sr/ $La_2O_3$ | Eu/Sr/ $Nd_2O_3$ | Eu/Sr/ $Yb_2O_3$ | Eu/Sr/ $Eu_2O_3$ | Eu/Sr/ $Sm_2O_3$ | Eu/Sr/ $La_3NdO_6$ |
| Mg/Sr | Mg/Sr/ $La_2O_3$ | Mg/Sr/ $Nd_2O_3$ | Mg/Sr/ $Yb_2O_3$ | Mg/Sr/ $Eu_2O_3$ | Mg/Sr/ $Sm_2O_3$ | Mg/Sr/ $La_3NdO_6$ |
| Ce/Mg | Ce/Mg/ $La_2O_3$ | Ce/Mg/ $Nd_2O_3$ | Ce/Mg/ $Yb_2O_3$ | Ce/Mg/ $Eu_2O_3$ | Ce/Mg/ $Sm_2O_3$ | Ce/Mg/ $La_3NdO_6$ |
| Gd/Sm | Gd/Sm/ $La_2O_3$ | Gd/Sm/ $Nd_2O_3$ | Gd/Sm/ $Yb_2O_3$ | Gd/Sm/ $Eu_2O_3$ | Gd/Sm/ $Sm_2O_3$ | Gd/Sm/ $La_3NdO_6$ |
| Au/Pb | Au/Pb/ $La_2O_3$ | Au/Pb/ $Nd_2O_3$ | Au/Pb/ $Yb_2O_3$ | Au/Pb/ $Eu_2O_3$ | Au/Pb/ $Sm_2O_3$ | Au/Pb/ $La_3NdO_6$ |
| Bi/Hf | Bi/Hf/ $La_2O_3$ | Bi/Hf/ $Nd_2O_3$ | Bi/Hf/ $Yb_2O_3$ | Bi/Hf/ $Eu_2O_3$ | Bi/Hf/ $Sm_2O_3$ | Bi/Hf/ $La_3NdO_6$ |
| Rb/S | Rb/S/ $La_2O_3$ | Rb/S/ $Nd_2O_3$ | Rb/S/ $Yb_2O_3$ | Rb/S/ $Eu_2O_3$ | Rb/S/ $Sm_2O_3$ | Rb/S/ $La_3NdO_6$ |
| Sr/Nd | Sr/Nd/ $La_2O_3$ | Sr/Nd/ $Nd_2O_3$ | Sr/Nd/ $Yb_2O_3$ | Sr/Nd/ $Eu_2O_3$ | Sr/Nd/ $Sm_2O_3$ | Sr/Nd/ $La_3NdO_6$ |
| Eu/Y | Eu/Y/ $La_2O_3$ | Eu/Y/ $Nd_2O_3$ | Eu/Y/ $Yb_2O_3$ | Eu/Y/ $Eu_2O_3$ | Eu/Y/ $Sm_2O_3$ | Eu/Y/ $La_3NdO_6$ |
| Mg/Nd | Mg/Nd/ $La_2O_3$ | Mg/Nd/ $Nd_2O_3$ | Mg/Nd/ $Yb_2O_3$ | Mg/Nd/ $Eu_2O_3$ | Mg/Nd/ $Sm_2O_3$ | Mg/Nd/ $La_3NdO_6$ |
| La/Mg | La/Mg/ $La_2O_3$ | La/Mg/ $Nd_2O_3$ | La/Mg/ $Yb_2O_3$ | La/Mg/ $Eu_2O_3$ | La/Mg/ $Sm_2O_3$ | La/Mg/ $La_3NdO_6$ |
| Mg/Nd/Fe | Mg/Nd/Fe/ $La_2O_3$ | Mg/Nd/Fe/ $Nd_2O_3$ | Mg/Nd/Fe/ $Yb_2O_3$ | Mg/Nd/Fe/ $Eu_2O_3$ | Mg/Nd/Fe/ $Sm_2O_3$ | Mg/Nd/Fe/ $La_3NdO_6$ |
| Rb/Sr | Rb/Sr/ $La_2O_3$ | Rb/Sr/ $Nd_2O_3$ | Rb/Sr/ $Yb_2O_3$ | Rb/Sr/ $Eu_2O_3$ | Rb/Sr/ $Sm_2O_3$ | Rb/Sr/ $La_3NdO_6$ |

TABLE 2

CATALYSTS (CAT) DOPED WITH SPECIFIC DOPANTS (DOP)

| Dop\Cat | $La_{4-x}Nd_xO6$ | $LaNd_3O6$ | $La_{1.5}Nd_{2.5}O6$ | $La_{2.5}Nd_{1.5}O6$ | $La_{3.2}Nd_{0.8}O6$ | $La_{3.5}Nd_{0.5}O6$ |
|---|---|---|---|---|---|---|
| Eu/Na | Eu/Na/ $La_{4-x}Nd_xO6$ | Eu/Na/ $LaNd_3O6$ | Eu/Na/ $La_{1.5}Nd_{2.5}O6$ | Eu/Na/ $La_{2.5}Nd_{1.5}O6$ | Eu/Na/ $La_{3.2}Nd_{0.8}O6$ | Eu/Na/ $La_{3.5}Nd_{0.5}O6$ |
| Sr/Na | Sr/Na/ $La_{4-x}Nd_xO6$ | Sr/Na/ $LaNd_3O6$ | Sr/Na/ $La_{1.5}Nd_{2.5}O6$ | Sr/Na/ $La_{2.5}Nd_{1.5}O6$ | Sr/Na/ $La_{3.2}Nd_{0.8}O6$ | Sr/Na/ $La_{3.5}Nd_{0.5}O6$ |
| Na/Zr/Eu/Ca | Na/Zr/Eu/Ca/ $La_{4-x}Nd_xO6$ | Na/Zr/Eu/Ca/ $LaNd_3O6$ | Na/Zr/Eu/Ca/ $La_{1.5}Nd_{2.5}O6$ | Na/Zr/Eu/Ca/ $La_{2.5}Nd_{1.5}O6$ | Na/Zr/Eu/Ca/ $La_{3.2}Nd_{0.8}O6$ | Na/Zr/Eu/Ca/ $La_{3.5}Nd_{0.5}O6$ |
| Mg/Na | Mg/Na/ $La_{4-x}Nd_xO6$ | Mg/Na/ $LaNd_3O6$ | Mg/Na/ $La_{1.5}Nd_{2.5}O6$ | Mg/Na/ $La_{2.5}Nd_{1.5}O6$ | Mg/Na/ $La_{3.2}Nd_{0.8}O6$ | Mg/Na/ $La_{3.5}Nd_{0.5}O6$ |
| Sr/Sm/Ho/Tm | Sr/Sm/Ho/Tm/ $La_{4-x}Nd_xO6$ | Sr/Sm/Ho/Tm/ $LaNd_3O6$ | Sr/Sm/Ho/Tm/ $La_{1.5}Nd_{2.5}O6$ | Sr/Sm/Ho/Tm/ $La_{2.5}Nd_{1.5}O6$ | Sr/Sm/Ho/Tm/ $La_{3.2}Nd_{0.8}O6$ | Sr/Sm/Ho/Tm/ $La_{3.5}Nd_{0.5}O6$ |
| Sr/W | Sr/W/ $La_{4-x}Nd_xO6$ | Sr/W/ $LaNd_3O6$ | Sr/W/ $La_{1.5}Nd_{2.5}O6$ | Sr/W/ $La_{2.5}Nd_{1.5}O6$ | Sr/W/ $La_{3.2}Nd_{0.8}O6$ | Sr/W/ $La_{3.5}Nd_{0.5}O6$ |
| Mg/La/K | Mg/La/K/ $La_{4-x}Nd_xO6$ | Mg/La/K/ $LaNd_3O6$ | Mg/La/K/ $La_{1.5}Nd_{2.5}O6$ | Mg/La/K/ $La_{2.5}Nd_{1.5}O6$ | Mg/La/K/ $La_{3.2}Nd_{0.8}O6$ | Mg/La/K/ $La_{3.5}Nd_{0.5}O6$ |
| Na/K/Mg/Tm | Na/K/Mg/Tm/ $La_{4-x}Nd_xO6$ | Na/K/Mg/Tm/ $LaNd_3O6$ | Na/K/Mg/Tm/ $La_{1.5}Nd_{2.5}O6$ | Na/K/Mg/Tm/ $La_{2.5}Nd_{1.5}O6$ | Na/K/Mg/Tm/ $La_{3.2}Nd_{0.8}O6$ | Na/K/Mg/Tm/ $La_{3.5}Nd_{0.5}O6$ |
| Na/Dy/K | Na/Dy/K/ $La_{4-x}Nd_xO6$ | Na/Dy/K/ $LaNd_3O6$ | Na/Dy/K/ $La_{1.5}Nd_{2.5}O6$ | Na/Dy/K/ $La_{2.5}Nd_{1.5}O6$ | Na/Dy/K/ $La_{3.2}Nd_{0.8}O6$ | Na/Dy/K/ $La_{3.5}Nd_{0.5}O6$ |
| Na/La/Dy | Na/La/Dy/ $La_{4-x}Nd_xO6$ | Na/La/Dy/ $LaNd_3O6$ | Na/La/Dy/ $La_{1.5}Nd_{2.5}O6$ | Na/La/Dy/ $La_{2.5}Nd_{1.5}O6$ | Na/La/Dy/ $La_{3.2}Nd_{0.8}O6$ | Na/La/Dy/ $La_{3.5}Nd_{0.5}O6$ |
| Na/La/Eu | Na/La/Eu/ $La_{4-x}Nd_xO6$ | Na/La/Eu/ $LaNd_3O6$ | Na/La/Eu/ $La_{1.5}Nd_{2.5}O6$ | Na/La/Eu/ $La_{2.5}Nd_{1.5}O6$ | Na/La/Eu/ $La_{3.2}Nd_{0.8}O6$ | Na/La/Eu/ $La_{3.5}Nd_{0.5}O6$ |

TABLE 2-continued

CATALYSTS (CAT) DOPED WITH SPECIFIC DOPANTS (DOP)

| Dop\Cat | $La_{4-x}Nd_xO6$ | $LaNd_3O6$ | $La_{1.5}Nd_{2.5}O6$ | $La_{2.5}Nd_{1.5}O6$ | $La_{3.2}Nd_{0.8}O6$ | $La_{3.5}Nd_{0.5}O6$ |
|---|---|---|---|---|---|---|
| Na/La/Eu/In | Na/La/Eu/In/ $La_{4-x}Nd_xO6$ | Na/La/Eu/In/ $LaNd_3O6$ | Na/La/Eu/In/ $La_{1.5}Nd_{2.5}O6$ | Na/La/Eu/In/ $La_{2.5}Nd_{1.5}O6$ | Na/La/Eu/In/ $La_{3.2}Nd_{0.8}O6$ | Na/La/Eu/In/ $La_{3.5}Nd_{0.5}O6$ |
| Na/La/K | Na/La/K/ $La_{4-x}Nd_xO6$ | Na/La/K/ $LaNd_3O6$ | Na/La/K/ $La_{1.5}Nd_{2.5}O6$ | Na/La/K/ $La_{2.5}Nd_{1.5}O6$ | Na/La/K/ $La_{3.2}Nd_{0.8}O6$ | Na/La/K/ $La_{3.5}Nd_{0.5}O6$ |
| Na/La/Li/Cs | Na/La/Li/Cs/ $La_{4-x}Nd_xO6$ | Na/La/Li/Cs/ $LaNd_3O6$ | Na/La/Li/Cs/ $La_{1.5}Nd_{2.5}O6$ | Na/La/Li/Cs/ $La_{2.5}Nd_{1.5}O6$ | Na/La/Li/Cs/ $La_{3.2}Nd_{0.8}O6$ | Na/La/Li/Cs/ $La_{3.5}Nd_{0.5}O6$ |
| K/La | K/La/ $La_{4-x}Nd_xO6$ | K/La/ $LaNd_3O6$ | K/La/ $La_{1.5}Nd_{2.5}O6$ | K/La/ $La_{2.5}Nd_{1.5}O6$ | K/La/ $La_{3.2}Nd_{0.8}O6$ | K/La/ $La_{3.5}Nd_{0.5}O6$ |
| K/La/S | K/La/S/ $La_{4-x}Nd_xO6$ | K/La/S/ $LaNd_3O6$ | K/La/S/ $La_{1.5}Nd_{2.5}O6$ | K/La/S/ $La_{2.5}Nd_{1.5}O6$ | K/La/S/ $La_{3.2}Nd_{0.8}O6$ | K/La/S/ $La_{3.5}Nd_{0.5}O6$ |
| K/Na | K/Na/ $La_{4-x}Nd_xO6$ | K/Na/ $LaNd_3O6$ | K/Na/ $La_{1.5}Nd_{2.5}O6$ | K/Na/ $La_{2.5}Nd_{1.5}O6$ | K/Na/ $La_{3.2}Nd_{0.8}O6$ | K/Na/ $La_{3.5}Nd_{0.5}O6$ |
| Li/Cs | Li/Cs/ $La_{4-x}Nd_xO6$ | Li/Cs/ $LaNd_3O6$ | Li/Cs/ $La_{1.5}Nd_{2.5}O6$ | Li/Cs/ $La_{2.5}Nd_{1.5}O6$ | Li/Cs/ $La_{3.2}Nd_{0.8}O6$ | Li/Cs/ $La_{3.5}Nd_{0.5}O6$ |
| Li/Cs/La | Li/Cs/La/ $La_{4-x}Nd_xO6$ | Li/Cs/La/ $LaNd_3O6$ | Li/Cs/La/ $La_{1.5}Nd_{2.5}O6$ | Li/Cs/La/ $La_{2.5}Nd_{1.5}O6$ | Li/Cs/La/ $La_{3.2}Nd_{0.8}O6$ | Li/Cs/La/ $La_{3.5}Nd_{0.5}O6$ |
| Li/Cs/La/Tm | Li/Cs/La/Tm/ $La_{4-x}Nd_xO6$ | Li/Cs/La/Tm/ $LaNd_3O6$ | Li/Cs/La/Tm/ $La_{1.5}Nd_{2.5}O6$ | Li/Cs/La/Tm/ $La_{2.5}Nd_{1.5}O6$ | Li/Cs/La/Tm/ $La_{3.2}Nd_{0.8}O6$ | Li/Cs/La/Tm/ $La_{3.5}Nd_{0.5}O6$ |
| Li/Cs/Sr/Tm | Li/Cs/Sr/Tm/ $La_{4-x}Nd_xO6$ | Li/Cs/Sr/Tm/ $LaNd_3O6$ | Li/Cs/Sr/Tm/ $La_{1.5}Nd_{2.5}O6$ | Li/Cs/Sr/Tm/ $La_{2.5}Nd_{1.5}O6$ | Li/Cs/Sr/Tm/ $La_{3.2}Nd_{0.8}O6$ | Li/Cs/Sr/Tm/ $La_{3.5}Nd_{0.5}O6$ |
| Li/Sr/Cs | Li/Sr/Cs/ $La_{4-x}Nd_xO6$ | Li/Sr/Cs/ $LaNd_3O6$ | Li/Sr/Cs/ $La_{1.5}Nd_{2.5}O6$ | Li/Sr/Cs/ $La_{2.5}Nd_{1.5}O6$ | Li/Sr/Cs/ $La_{3.2}Nd_{0.8}O6$ | Li/Sr/Cs/ $La_{3.5}Nd_{0.5}O6$ |
| Li/Sr/Zn/K | Li/Sr/Zn/K/ $La_{4-x}Nd_xO6$ | Li/Sr/Zn/K/ $LaNd_3O6$ | Li/Sr/Zn/K/ $La_{1.5}Nd_{2.5}O6$ | Li/Sr/Zn/K/ $La_{2.5}Nd_{1.5}O6$ | Li/Sr/Zn/K/ $La_{3.2}Nd_{0.8}O6$ | Li/Sr/Zn/K/ $La_{3.5}Nd_{0.5}O6$ |
| Li/Ga/Cs | Li/Ga/Cs/ $La_{4-x}Nd_xO6$ | Li/Ga/Cs/ $LaNd_3O6$ | Li/Ga/Cs/ $La_{1.5}Nd_{2.5}O6$ | Li/Ga/Cs/ $La_{2.5}Nd_{1.5}O6$ | Li/Ga/Cs/ $La_{3.2}Nd_{0.8}O6$ | Li/Ga/Cs/ $La_{3.5}Nd_{0.5}O6$ |
| Li/K/Sr/La | Li/K/Sr/La/ $La_{4-x}Nd_xO6$ | Li/K/Sr/La/ $LaNd_3O6$ | Li/K/Sr/La/ $La_{1.5}Nd_{2.5}O6$ | Li/K/Sr/La/ $La_{2.5}Nd_{1.5}O6$ | Li/K/Sr/La/ $La_{3.2}Nd_{0.8}O6$ | Li/K/Sr/La/ $La_{3.5}Nd_{0.5}O6$ |
| Li/Na | Li/Na/ $La_{4-x}Nd_xO6$ | Li/Na/ $LaNd_3O6$ | Li/Na/ $La_{1.5}Nd_{2.5}O6$ | Li/Na/ $La_{2.5}Nd_{1.5}O6$ | Li/Na/ $La_{3.2}Nd_{0.8}O6$ | Li/Na/ $La_{3.5}Nd_{0.5}O6$ |
| Li/Na/Rb/Ga | Li/Na/Rb/Ga/ $La_{4-x}Nd_xO6$ | Li/Na/Rb/Ga/ $LaNd_3O6$ | Li/Na/Rb/Ga/ $La_{1.5}Nd_{2.5}O6$ | Li/Na/Rb/Ga/ $La_{2.5}Nd_{1.5}O6$ | Li/Na/Rb/Ga/ $La_{3.2}Nd_{0.8}O6$ | Li/Na/Rb/Ga/ $La_{3.5}Nd_{0.5}O6$ |
| Li/Na/Sr | Li/Na/Sr/ $La_{4-x}Nd_xO6$ | Li/Na/Sr/ $LaNd_3O6$ | Li/Na/Sr/ $La_{1.5}Nd_{2.5}O6$ | Li/Na/Sr/ $La_{2.5}Nd_{1.5}O6$ | Li/Na/Sr/ $La_{3.2}Nd_{0.8}O6$ | Li/Na/Sr/ $La_{3.5}Nd_{0.5}O6$ |
| Li/Na/Sr/La | Li/Na/Sr/La/ $La_{4-x}Nd_xO6$ | Li/Na/Sr/La/ $LaNd_3O6$ | Li/Na/Sr/La/ $La_{1.5}Nd_{2.5}O6$ | Li/Na/Sr/La/ $La_{2.5}Nd_{1.5}O6$ | Li/Na/Sr/La/ $La_{3.2}Nd_{0.8}O6$ | Li/Na/Sr/La/ $La_{3.5}Nd_{0.5}O6$ |
| Li/Sm/Cs | Li/Sm/Cs/ $La_{4-x}Nd_xO6$ | Li/Sm/Cs/ $LaNd_3O6$ | Li/Sm/Cs/ $La_{1.5}Nd_{2.5}O6$ | Li/Sm/Cs/ $La_{2.5}Nd_{1.5}O6$ | Li/Sm/Cs/ $La_{3.2}Nd_{0.8}O6$ | Li/Sm/Cs/ $La_{3.5}Nd_{0.5}O6$ |
| Ba/Sm/Yb/S | Ba/Sm/Yb/S/ $La_{4-x}Nd_xO6$ | Ba/Sm/Yb/S/ $LaNd_3O6$ | Ba/Sm/Yb/S/ $La_{1.5}Nd_{2.5}O6$ | Ba/Sm/Yb/S/ $La_{2.5}Nd_{1.5}O6$ | Ba/Sm/Yb/S/ $La_{3.2}Nd_{0.8}O6$ | Ba/Sm/Yb/S/ $La_{3.5}Nd_{0.5}O6$ |
| Ba/Tm/K/La | Ba/Tm/K/La/ $La_{4-x}Nd_xO6$ | Ba/Tm/K/La/ $LaNd_3O6$ | Ba/Tm/K/La/ $La_{1.5}Nd_{2.5}O6$ | Ba/Tm/K/La/ $La_{2.5}Nd_{1.5}O6$ | Ba/Tm/K/La/ $La_{3.2}Nd_{0.8}O6$ | Ba/Tm/K/La/ $La_{3.5}Nd_{0.5}O6$ |
| Ba/Tm/Zn/K | Ba/Tm/Zn/K/ $La_{4-x}Nd_xO6$ | Ba/Tm/Zn/K/ $LaNd_3O6$ | Ba/Tm/Zn/K/ $La_{1.5}Nd_{2.5}O6$ | Ba/Tm/Zn/K/ $La_{2.5}Nd_{1.5}O6$ | Ba/Tm/Zn/K/ $La_{3.2}Nd_{0.8}O6$ | Ba/Tm/Zn/K/ $La_{3.5}Nd_{0.5}O6$ |
| Cs/K/La | Cs/K/La/ $La_{4-x}Nd_xO6$ | Cs/K/La/ $LaNd_3O6$ | Cs/K/La/ $La_{1.5}Nd_{2.5}O6$ | Cs/K/La/ $La_{2.5}Nd_{1.5}O6$ | Cs/K/La/ $La_{3.2}Nd_{0.8}O6$ | Cs/K/La/ $La_{3.5}Nd_{0.5}O6$ |
| Cs/La/Tm/Na | Cs/La/Tm/Na/ $La_{4-x}Nd_xO6$ | Cs/La/Tm/Na/ $LaNd_3O6$ | Cs/La/Tm/Na/ $La_{1.5}Nd_{2.5}O6$ | Cs/La/Tm/Na/ $La_{2.5}Nd_{1.5}O6$ | Cs/La/Tm/Na/ $La_{3.2}Nd_{0.8}O6$ | Cs/La/Tm/Na/ $La_{3.5}Nd_{0.5}O6$ |
| Cs/Li/K/La | Cs/Li/K/La/ $La_{4-x}Nd_xO6$ | Cs/Li/K/La/ $LaNd_3O6$ | Cs/Li/K/La/ $La_{1.5}Nd_{2.5}O6$ | Cs/Li/K/La/ $La_{2.5}Nd_{1.5}O6$ | Cs/Li/K/La/ $La_{3.2}Nd_{0.8}O6$ | Cs/Li/K/La/ $La_{3.5}Nd_{0.5}O6$ |
| Sm/Li/Sr/Cs | Sm/Li/Sr/Cs/ $La_{4-x}Nd_xO6$ | Sm/Li/Sr/Cs/ $LaNd_3O6$ | Sm/Li/Sr/Cs/ $La_{1.5}Nd_{2.5}O6$ | Sm/Li/Sr/Cs/ $La_{2.5}Nd_{1.5}O6$ | Sm/Li/Sr/Cs/ $La_{3.2}Nd_{0.8}O6$ | Sm/Li/Sr/Cs/ $La_{3.5}Nd_{0.5}O6$ |
| Sr/Cs/La | Sr/Cs/La/ $La_{4-x}Nd_xO6$ | Sr/Cs/La/ $LaNd_3O6$ | Sr/Cs/La/ $La_{1.5}Nd_{2.5}O6$ | Sr/Cs/La/ $La_{2.5}Nd_{1.5}O6$ | Sr/Cs/La/ $La_{3.2}Nd_{0.8}O6$ | Sr/Cs/La/ $La_{3.5}Nd_{0.5}O6$ |
| Sr/Tm/Li/Cs | Sr/Tm/Li/Cs/ $La_{4-x}Nd_xO6$ | Sr/Tm/Li/Cs/ $LaNd_3O6$ | Sr/Tm/Li/Cs/ $La_{1.5}Nd_{2.5}O6$ | Sr/Tm/Li/Cs/ $La_{2.5}Nd_{1.5}O6$ | Sr/Tm/Li/Cs/ $La_{3.2}Nd_{0.8}O6$ | Sr/Tm/Li/Cs/ $La_{3.5}Nd_{0.5}O6$ |
| Zn/K | Zn/K/ $La_{4-x}Nd_xO6$ | Zn/K/ $LaNd_3O6$ | Zn/K/ $La_{1.5}Nd_{2.5}O6$ | Zn/K/ $La_{2.5}Nd_{1.5}O6$ | Zn/K/ $La_{3.2}Nd_{0.8}O6$ | Zn/K/ $La_{3.5}Nd_{0.5}O6$ |
| Zr/Cs/K/La | Zr/Cs/K/La/ $La_{4-x}Nd_xO6$ | Zr/Cs/K/La/ $LaNd_3O6$ | Zr/Cs/K/La/ $La_{1.5}Nd_{2.5}O6$ | Zr/Cs/K/La/ $La_{2.5}Nd_{1.5}O6$ | Zr/Cs/K/La/ $La_{3.2}Nd_{0.8}O6$ | Zr/Cs/K/La/ $La_{3.5}Nd_{0.5}O6$ |
| Rb/Ca/In/Ni | Rb/Ca/In/Ni/ $La_{4-x}Nd_xO6$ | Rb/Ca/In/Ni/ $LaNd_3O6$ | Rb/Ca/In/Ni/ $La_{1.5}Nd_{2.5}O6$ | Rb/Ca/In/Ni/ $La_{2.5}Nd_{1.5}O6$ | Rb/Ca/In/Ni/ $La_{3.2}Nd_{0.8}O6$ | Rb/Ca/In/Ni/ $La_{3.5}Nd_{0.5}O6$ |
| Sr/Ho/Tm | Sr/Ho/Tm/ $La_{4-x}Nd_xO6$ | Sr/Ho/Tm/ $LaNd_3O6$ | Sr/Ho/Tm/ $La_{1.5}Nd_{2.5}O6$ | Sr/Ho/Tm/ $La_{2.5}Nd_{1.5}O6$ | Sr/Ho/Tm/ $La_{3.2}Nd_{0.8}O6$ | Sr/Ho/Tm/ $La_{3.5}Nd_{0.5}O6$ |
| La/Nd/S | La/Nd/S/ $La_{4-x}Nd_xO6$ | La/Nd/S/ $LaNd_3O6$ | La/Nd/S/ $La_{1.5}Nd_{2.5}O6$ | La/Nd/S/ $La_{2.5}Nd_{1.5}O6$ | La/Nd/S/ $La_{3.2}Nd_{0.8}O6$ | La/Nd/S/ $La_{3.5}Nd_{0.5}O6$ |
| Li/Rb/Ca | Li/Rb/Ca/ $La_{4-x}Nd_xO6$ | Li/Rb/Ca/ $LaNd_3O6$ | Li/Rb/Ca/ $La_{1.5}Nd_{2.5}O6$ | Li/Rb/Ca/ $La_{2.5}Nd_{1.5}O6$ | Li/Rb/Ca/ $La_{3.2}Nd_{0.8}O6$ | Li/Rb/Ca/ $La_{3.5}Nd_{0.5}O6$ |
| Li/K | Li/K/ $La_{4-x}Nd_xO6$ | Li/K/ $LaNd_3O6$ | Li/K/ $La_{1.5}Nd_{2.5}O6$ | Li/K/ $La_{2.5}Nd_{1.5}O6$ | Li/K/ $La_{3.2}Nd_{0.8}O6$ | Li/K/ $La_{3.5}Nd_{0.5}O6$ |
| Tm/Lu/Ta/P | Tm/Lu/Ta/P/ $La_{4-x}Nd_xO6$ | Tm/Lu/Ta/P/ $LaNd_3O6$ | Tm/Lu/Ta/P/ $La_{1.5}Nd_{2.5}O6$ | Tm/Lu/Ta/P/ $La_{2.5}Nd_{1.5}O6$ | Tm/Lu/Ta/P/ $La_{3.2}Nd_{0.8}O6$ | Tm/Lu/Ta/P/ $La_{3.5}Nd_{0.5}O6$ |
| Rb/Ca/Dy/P | Rb/Ca/Dy/P/ $La_{4-x}Nd_xO6$ | Rb/Ca/Dy/P/ $LaNd_3O6$ | Rb/Ca/Dy/P/ $La_{1.5}Nd_{2.5}O6$ | Rb/Ca/Dy/P/ $La_{2.5}Nd_{1.5}O6$ | Rb/Ca/Dy/P/ $La_{3.2}Nd_{0.8}O6$ | Rb/Ca/Dy/P/ $La_{3.5}Nd_{0.5}O6$ |
| Mg/La/Yb/Zn | Mg/La/Yb/Zn/ $La_{4-x}Nd_xO6$ | Mg/La/Yb/Zn/ $LaNd_3O6$ | Mg/La/Yb/Zn/ $La_{1.5}Nd_{2.5}O6$ | Mg/La/Yb/Zn/ $La_{2.5}Nd_{1.5}O6$ | Mg/La/Yb/Zn/ $La_{3.2}Nd_{0.8}O6$ | Mg/La/Yb/Zn/ $La_{3.5}Nd_{0.5}O6$ |

TABLE 2-continued

CATALYSTS (CAT) DOPED WITH SPECIFIC DOPANTS (DOP)

| Dop\Cat | $La_{4-x}Nd_xO6$ | $LaNd_3O6$ | $La_{1.5}Nd_{2.5}O6$ | $La_{2.5}Nd_{1.5}O6$ | $La_{3.2}Nd_{0.8}O6$ | $La_{3.5}Nd_{0.5}O6$ |
|---|---|---|---|---|---|---|
| Rb/Sr/Lu | Rb/Sr/Lu/ $La_{4-x}Nd_xO6$ | Rb/Sr/Lu/ $LaNd_3O6$ | Rb/Sr/Lu/ $La_{1.5}Nd_{2.5}O6$ | Rb/Sr/Lu/ $La_{2.5}Nd_{1.5}O6$ | Rb/Sr/Lu/ $La_{3.2}Nd_{0.8}O6$ | Rb/Sr/Lu/ $La_{3.5}Nd_{0.5}O6$ |
| Na/Sr/Lu/Nb | Na/Sr/Lu/Nb/ $La_{4-x}Nd_xO6$ | Na/Sr/Lu/Nb/ $LaNd_3O6$ | Na/Sr/Lu/Nb/ $La_{1.5}Nd_{2.5}O6$ | Na/Sr/Lu/Nb/ $La_{2.5}Nd_{1.5}O6$ | Na/Sr/Lu/Nb/ $La_{3.2}Nd_{0.8}O6$ | Na/Sr/Lu/Nb/ $La_{3.5}Nd_{0.5}O6$ |
| Na/Eu/Hf | Na/Eu/Hf/ $La_{4-x}Nd_xO6$ | Na/Eu/Hf/ $LaNd_3O6$ | Na/Eu/Hf/ $La_{1.5}Nd_{2.5}O6$ | Na/Eu/Hf/ $La_{2.5}Nd_{1.5}O6$ | Na/Eu/Hf/ $La_{3.2}Nd_{0.8}O6$ | Na/Eu/Hf/ $La_{3.5}Nd_{0.5}O6$ |
| Dy/Rb/Gd | Dy/Rb/Gd/ $La_{4-x}Nd_xO6$ | Dy/Rb/Gd/ $LaNd_3O6$ | Dy/Rb/Gd/ $La_{1.5}Nd_{2.5}O6$ | Dy/Rb/Gd/ $La_{2.5}Nd_{1.5}O6$ | Dy/Rb/Gd/ $La_{3.2}Nd_{0.8}O6$ | Dy/Rb/Gd/ $La_{3.5}Nd_{0.5}O6$ |
| Na/Pt/Bi | Na/Pt/Bi/ $La_{4-x}Nd_xO6$ | Na/Pt/Bi/ $LaNd_3O6$ | Na/Pt/Bi/ $La_{1.5}Nd_{2.5}O6$ | Na/Pt/Bi/ $La_{2.5}Nd_{1.5}O6$ | Na/Pt/Bi/ $La_{3.2}Nd_{0.8}O6$ | Na/Pt/Bi/ $La_{3.5}Nd_{0.5}O6$ |
| Rb/Hf | Rb/Hf/ $La_{4-x}Nd_xO6$ | Rb/Hf/ $LaNd_3O6$ | Rb/Hf/ $La_{1.5}Nd_{2.5}O6$ | Rb/Hf/ $La_{2.5}Nd_{1.5}O6$ | Rb/Hf/ $La_{3.2}Nd_{0.8}O6$ | Rb/Hf/ $La_{3.5}Nd_{0.5}O6$ |
| Ca/Cs | Ca/Cs/ $La_{4-x}Nd_xO6$ | Ca/Cs/ $LaNd_3O6$ | Ca/Cs/ $La_{1.5}Nd_{2.5}O6$ | Ca/Cs/ $La_{2.5}Nd_{1.5}O6$ | Ca/Cs/ $La_{3.2}Nd_{0.8}O6$ | Ca/Cs/ $La_{3.5}Nd_{0.5}O6$ |
| Ca/Mg/Na | Ca/Mg/Na/ $La_{4-x}Nd_xO6$ | Ca/Mg/Na/ $LaNd_3O6$ | Ca/Mg/Na/ $La_{1.5}Nd_{2.5}O6$ | Ca/Mg/Na/ $La_{2.5}Nd_{1.5}O6$ | Ca/Mg/Na/ $La_{3.2}Nd_{0.8}O6$ | Ca/Mg/Na/ $La_{3.5}Nd_{0.5}O6$ |
| Hf/Bi | Hf/Bi/ $La_{4-x}Nd_xO6$ | Hf/Bi/ $LaNd_3O6$ | Hf/Bi/ $La_{1.5}Nd_{2.5}O6$ | Hf/Bi/ $La_{2.5}Nd_{1.5}O6$ | Hf/Bi/ $La_{3.2}Nd_{0.8}O6$ | Hf/Bi/ $La_{3.5}Nd_{0.5}O6$ |
| Sr/Sn | Sr/Sn/ $La_{4-x}Nd_xO6$ | Sr/Sn/ $LaNd_3O6$ | Sr/Sn/ $La_{1.5}Nd_{2.5}O6$ | Sr/Sn/ $La_{2.5}Nd_{1.5}O6$ | Sr/Sn/ $La_{3.2}Nd_{0.8}O6$ | Sr/Sn/ $La_{3.5}Nd_{0.5}O6$ |
| Sr/W | Sr/W/ $La_{4-x}Nd_xO6$ | Sr/W/ $LaNd_3O6$ | Sr/W/ $La_{1.5}Nd_{2.5}O6$ | Sr/W/ $La_{2.5}Nd_{1.5}O6$ | Sr/W/ $La_{3.2}Nd_{0.8}O6$ | Sr/W/ $La_{3.5}Nd_{0.5}O6$ |
| Sr/Nb | Sr/Nb/ $La_{4-x}Nd_xO6$ | Sr/Nb/ $LaNd_3O6$ | Sr/Nb/ $La_{1.5}Nd_{2.5}O6$ | Sr/Nb/ $La_{2.5}Nd_{1.5}O6$ | Sr/Nb/ $La_{3.2}Nd_{0.8}O6$ | Sr/Nb/ $La_{3.5}Nd_{0.5}O6$ |
| Zr/W | Zr/W/ $La_{4-x}Nd_xO6$ | Zr/W/ $LaNd_3O6$ | Zr/W/ $La_{1.5}Nd_{2.5}O6$ | Zr/W/ $La_{2.5}Nd_{1.5}O6$ | Zr/W/ $La_{3.2}Nd_{0.8}O6$ | Zr/W/ $La_{3.5}Nd_{0.5}O6$ |
| Y/W | Y/W/ $La_{4-x}Nd_xO6$ | Y/W/ $LaNd_3O6$ | Y/W/ $La_{1.5}Nd_{2.5}O6$ | Y/W/ $La_{2.5}Nd_{1.5}O6$ | Y/W/ $La_{3.2}Nd_{0.8}O6$ | Y/W/ $La_{3.5}Nd_{0.5}O6$ |
| Na/W | Na/W/ $La_{4-x}Nd_xO6$ | Na/W/ $LaNd_3O6$ | Na/W/ $La_{1.5}Nd_{2.5}O6$ | Na/W/ $La_{2.5}Nd_{1.5}O6$ | Na/W/ $La_{3.2}Nd_{0.8}O6$ | Na/W/ $La_{3.5}Nd_{0.5}O6$ |
| Bi/W | Bi/W/ $La_{4-x}Nd_xO6$ | Bi/W/ $LaNd_3O6$ | Bi/W/ $La_{1.5}Nd_{2.5}O6$ | Bi/W/ $La_{2.5}Nd_{1.5}O6$ | Bi/W/ $La_{3.2}Nd_{0.8}O6$ | Bi/W/ $La_{3.5}Nd_{0.5}O6$ |
| Bi/Cs | Bi/Cs/ $La_{4-x}Nd_xO6$ | Bi/Cs/ $LaNd_3O6$ | Bi/Cs/ $La_{1.5}Nd_{2.5}O6$ | Bi/Cs/ $La_{2.5}Nd_{1.5}O6$ | Bi/Cs/ $La_{3.2}Nd_{0.8}O6$ | Bi/Cs/ $La_{3.5}Nd_{0.5}O6$ |
| Bi/Ca | Bi/Ca/ $La_{4-x}Nd_xO6$ | Bi/Ca/ $LaNd_3O6$ | Bi/Ca/ $La_{1.5}Nd_{2.5}O6$ | Bi/Ca/ $La_{2.5}Nd_{1.5}O6$ | Bi/Ca/ $La_{3.2}Nd_{0.8}O6$ | Bi/Ca/ $La_{3.5}Nd_{0.5}O6$ |
| Bi/Sn | Bi/Sn/ $La_{4-x}Nd_xO6$ | Bi/Sn/ $LaNd_3O6$ | Bi/Sn/ $La_{1.5}Nd_{2.5}O6$ | Bi/Sn/ $La_{2.5}Nd_{1.5}O6$ | Bi/Sn/ $La_{3.2}Nd_{0.8}O6$ | Bi/Sn/ $La_{3.5}Nd_{0.5}O6$ |
| Bi/Sb | Bi/Sb/ $La_{4-x}Nd_xO6$ | Bi/Sb/ $LaNd_3O6$ | Bi/Sb/ $La_{1.5}Nd_{2.5}O6$ | Bi/Sb/ $La_{2.5}Nd_{1.5}O6$ | Bi/Sb/ $La_{3.2}Nd_{0.8}O6$ | Bi/Sb/ $La_{3.5}Nd_{0.5}O6$ |
| Ge/Hf | Ge/Hf/ $La_{4-x}Nd_xO6$ | Ge/Hf/ $LaNd_3O6$ | Ge/Hf/ $La_{1.5}Nd_{2.5}O6$ | Ge/Hf/ $La_{2.5}Nd_{1.5}O6$ | Ge/Hf/ $La_{3.2}Nd_{0.8}O6$ | Ge/Hf/ $La_{3.5}Nd_{0.5}O6$ |
| Hf/Sm | Hf/Sm/ $La_{4-x}Nd_xO6$ | Hf/Sm/ $LaNd_3O6$ | Hf/Sm/ $La_{1.5}Nd_{2.5}O6$ | Hf/Sm/ $La_{2.5}Nd_{1.5}O6$ | Hf/Sm/ $La_{3.2}Nd_{0.8}O6$ | Hf/Sm/ $La_{3.5}Nd_{0.5}O6$ |
| Sb/Ag | Sb/Ag/ $La_{4-x}Nd_xO6$ | Sb/Ag/ $LaNd_3O6$ | Sb/Ag/ $La_{1.5}Nd_{2.5}O6$ | Sb/Ag/ $La_{2.5}Nd_{1.5}O6$ | Sb/Ag/ $La_{3.2}Nd_{0.8}O6$ | Sb/Ag/ $La_{3.5}Nd_{0.5}O6$ |
| Sb/Bi | Sb/Bi/ $La_{4-x}Nd_xO6$ | Sb/Bi/ $LaNd_3O6$ | Sb/Bi/ $La_{1.5}Nd_{2.5}O6$ | Sb/Bi/ $La_{2.5}Nd_{1.5}O6$ | Sb/Bi/ $La_{3.2}Nd_{0.8}O6$ | Sb/Bi/ $La_{3.5}Nd_{0.5}O6$ |
| Sb/Au | Sb/Au/ $La_{4-x}Nd_xO6$ | Sb/Au/ $LaNd_3O6$ | Sb/Au/ $La_{1.5}Nd_{2.5}O6$ | Sb/Au/ $La_{2.5}Nd_{1.5}O6$ | Sb/Au/ $La_{3.2}Nd_{0.8}O6$ | Sb/Au/ $La_{3.5}Nd_{0.5}O6$ |
| Sb/Sm | Sb/Sm/ $La_{4-x}Nd_xO6$ | Sb/Sm/ $LaNd_3O6$ | Sb/Sm/ $La_{1.5}Nd_{2.5}O6$ | Sb/Sm/ $La_{2.5}Nd_{1.5}O6$ | Sb/Sm/ $La_{3.2}Nd_{0.8}O6$ | Sb/Sm/ $La_{3.5}Nd_{0.5}O6$ |
| Sb/Sr | Sb/Sr/ $La_{4-x}Nd_xO6$ | Sb/Sr/ $LaNd_3O6$ | Sb/Sr/ $La_{1.5}Nd_{2.5}O6$ | Sb/Sr/ $La_{2.5}Nd_{1.5}O6$ | Sb/Sr/ $La_{3.2}Nd_{0.8}O6$ | Sb/Sr/ $La_{3.5}Nd_{0.5}O6$ |
| Sb/W | Sb/W/ $La_{4-x}Nd_xO6$ | Sb/W/ $LaNd_3O6$ | Sb/W/ $La_{1.5}Nd_{2.5}O6$ | Sb/W/ $La_{2.5}Nd_{1.5}O6$ | Sb/W/ $La_{3.2}Nd_{0.8}O6$ | Sb/W/ $La_{3.5}Nd_{0.5}O6$ |
| Sb/Hf | Sb/Hf/ $La_{4-x}Nd_xO6$ | Sb/Hf/ $LaNd_3O6$ | Sb/Hf/ $La_{1.5}Nd_{2.5}O6$ | Sb/Hf/ $La_{2.5}Nd_{1.5}O6$ | Sb/Hf/ $La_{3.2}Nd_{0.8}O6$ | Sb/Hf/ $La_{3.5}Nd_{0.5}O6$ |
| Sb/Yb | Sb/Yb/ $La_{4-x}Nd_xO6$ | Sb/Yb/ $LaNd_3O6$ | Sb/Yb/ $La_{1.5}Nd_{2.5}O6$ | Sb/Yb/ $La_{2.5}Nd_{1.5}O6$ | Sb/Yb/ $La_{3.2}Nd_{0.8}O6$ | Sb/Yb/ $La_{3.5}Nd_{0.5}O6$ |
| Sb/Sn | Sb/Sn/ $La_{4-x}Nd_xO6$ | Sb/Sn/ $LaNd_3O6$ | Sb/Sn/ $La_{1.5}Nd_{2.5}O6$ | Sb/Sn/ $La_{2.5}Nd_{1.5}O6$ | Sb/Sn/ $La_{3.2}Nd_{0.8}O6$ | Sb/Sn/ $La_{3.5}Nd_{0.5}O6$ |
| Yb/Au | Yb/Au/ $La_{4-x}Nd_xO6$ | Yb/Au/ $LaNd_3O6$ | Yb/Au/ $La_{1.5}Nd_{2.5}O6$ | Yb/Au/ $La_{2.5}Nd_{1.5}O6$ | Yb/Au/ $La_{3.2}Nd_{0.8}O6$ | Yb/Au/ $La_{3.5}Nd_{0.5}O6$ |
| Yb/Ta | Yb/Ta/ $La_{4-x}Nd_xO6$ | Yb/Ta/ $LaNd_3O6$ | Yb/Ta/ $La_{1.5}Nd_{2.5}O6$ | Yb/Ta/ $La_{2.5}Nd_{1.5}O6$ | Yb/Ta/ $La_{3.2}Nd_{0.8}O6$ | Yb/Ta/ $La_{3.5}Nd_{0.5}O6$ |
| Yb/W | Yb/W/ $La_{4-x}Nd_xO6$ | Yb/W/ $LaNd_3O6$ | Yb/W/ $La_{1.5}Nd_{2.5}O6$ | Yb/W/ $La_{2.5}Nd_{1.5}O6$ | Yb/W/ $La_{3.2}Nd_{0.8}O6$ | Yb/W/ $La_{3.5}Nd_{0.5}O6$ |
| Yb/Sr | Yb/Sr/ $La_{4-x}Nd_xO6$ | Yb/Sr/ $LaNd_3O6$ | Yb/Sr/ $La_{1.5}Nd_{2.5}O6$ | Yb/Sr/ $La_{2.5}Nd_{1.5}O6$ | Yb/Sr/ $La_{3.2}Nd_{0.8}O6$ | Yb/Sr/ $La_{3.5}Nd_{0.5}O6$ |
| Yb/Pb | Yb/Pb/ $La_{4-x}Nd_xO6$ | Yb/Pb/ $LaNd_3O6$ | Yb/Pb/ $La_{1.5}Nd_{2.5}O6$ | Yb/Pb/ $La_{2.5}Nd_{1.5}O6$ | Yb/Pb/ $La_{3.2}Nd_{0.8}O6$ | Yb/Pb/ $La_{3.5}Nd_{0.5}O6$ |
| Yb/W | Yb/W/ $La_{4-x}Nd_xO6$ | Yb/W/ $LaNd_3O6$ | Yb/W/ $La_{1.5}Nd_{2.5}O6$ | Yb/W/ $La_{2.5}Nd_{1.5}O6$ | Yb/W/ $La_{3.2}Nd_{0.8}O6$ | Yb/W/ $La_{3.5}Nd_{0.5}O6$ |
| Yb/Ag | Yb/Ag/ $La_{4-x}Nd_xO6$ | Yb/Ag/ $LaNd_3O6$ | Yb/Ag/ $La_{1.5}Nd_{2.5}O6$ | Yb/Ag/ $La_{2.5}Nd_{1.5}O6$ | Yb/Ag/ $La_{3.2}Nd_{0.8}O6$ | Yb/Ag/ $La_{3.5}Nd_{0.5}O6$ |

TABLE 2-continued

CATALYSTS (CAT) DOPED WITH SPECIFIC DOPANTS (DOP)

| Dop\Cat | $La_{4-x}Nd_xO6$ | $LaNd_3O6$ | $La_{1.5}Nd_{2.5}O6$ | $La_{2.5}Nd_{1.5}O6$ | $La_{3.2}Nd_{0.8}O6$ | $La_{3.5}Nd_{0.5}O6$ |
|---|---|---|---|---|---|---|
| Au/Sr | Au/Sr/ $La_{4-x}Nd_xO6$ | Au/Sr/ $LaNd_3O6$ | Au/Sr/ $La_{1.5}Nd_{2.5}O6$ | Au/Sr/ $La_{2.5}Nd_{1.5}O6$ | Au/Sr/ $La_{3.2}Nd_{0.8}O6$ | Au/Sr/ $La_{3.5}Nd_{0.5}O6$ |
| W/Ge | W/Ge/ $La_{4-x}Nd_xO6$ | W/Ge/ $LaNd_3O6$ | W/Ge/ $La_{1.5}Nd_{2.5}O6$ | W/Ge/ $La_{2.5}Nd_{1.5}O6$ | W/Ge/ $La_{3.2}Nd_{0.8}O6$ | W/Ge/ $La_{3.5}Nd_{0.5}O6$ |
| Ta/Sr | Ta/Sr/ $La_{4-x}Nd_xO6$ | Ta/Sr/ $LaNd_3O6$ | Ta/Sr/ $La_{1.5}Nd_{2.5}O6$ | Ta/Sr/ $La_{2.5}Nd_{1.5}O6$ | Ta/Sr/ $La_{3.2}Nd_{0.8}O6$ | Ta/Sr/ $La_{3.5}Nd_{0.5}O6$ |
| Ta/Hf | Ta/Hf/ $La_{4-x}Nd_xO6$ | Ta/Hf/ $LaNd_3O6$ | Ta/Hf/ $La_{1.5}Nd_{2.5}O6$ | Ta/Hf/ $La_{2.5}Nd_{1.5}O6$ | Ta/Hf/ $La_{3.2}Nd_{0.8}O6$ | Ta/Hf/ $La_{3.5}Nd_{0.5}O6$ |
| W/Au | W/Au/ $La_{4-x}Nd_xO6$ | W/Au/ $LaNd_3O6$ | W/Au/ $La_{1.5}Nd_{2.5}O6$ | W/Au/ $La_{2.5}Nd_{1.5}O6$ | W/Au/ $La_{3.2}Nd_{0.8}O6$ | W/Au/ $La_{3.5}Nd_{0.5}O6$ |
| Ca/W | Ca/W/ $La_{4-x}Nd_xO6$ | Ca/W/ $LaNd_3O6$ | Ca/W/ $La_{1.5}Nd_{2.5}O6$ | Ca/W/ $La_{2.5}Nd_{1.5}O6$ | Ca/W/ $La_{3.2}Nd_{0.8}O6$ | Ca/W/ $La_{3.5}Nd_{0.5}O6$ |
| Au/Re | Au/Re/ $La_{4-x}Nd_xO6$ | Au/Re/ $LaNd_3O6$ | Au/Re/ $La_{1.5}Nd_{2.5}O6$ | Au/Re/ $La_{2.5}Nd_{1.5}O6$ | Au/Re/ $La_{3.2}Nd_{0.8}O6$ | Au/Re/ $La_{3.5}Nd_{0.5}O6$ |
| Sm/Li | Sm/Li/ $La_{4-x}Nd_xO6$ | Sm/Li/ $LaNd_3O6$ | Sm/Li/ $La_{1.5}Nd_{2.5}O6$ | Sm/Li/ $La_{2.5}Nd_{1.5}O6$ | Sm/Li/ $La_{3.2}Nd_{0.8}O6$ | Sm/Li/ $La_{3.5}Nd_{0.5}O6$ |
| La/K | La/K/ $La_{4-x}Nd_xO6$ | La/K/ $LaNd_3O6$ | La/K/ $La_{1.5}Nd_{2.5}O6$ | La/K/ $La_{2.5}Nd_{1.5}O6$ | La/K/ $La_{3.2}Nd_{0.8}O6$ | La/K/ $La_{3.5}Nd_{0.5}O6$ |
| Zn/Cs | Zn/Cs/ $La_{4-x}Nd_xO6$ | Zn/Cs/ $LaNd_3O6$ | Zn/Cs/ $La_{1.5}Nd_{2.5}O6$ | Zn/Cs/ $La_{2.5}Nd_{1.5}O6$ | Zn/Cs/ $La_{3.2}Nd_{0.8}O6$ | Zn/Cs/ $La_{3.5}Nd_{0.5}O6$ |
| Na/K/Mg | Na/K/Mg/ $La_{4-x}Nd_xO6$ | Na/K/Mg/ $LaNd_3O6$ | Na/K/Mg/ $La_{1.5}Nd_{2.5}O6$ | Na/K/Mg/ $La_{2.5}Nd_{1.5}O6$ | Na/K/Mg/ $La_{3.2}Nd_{0.8}O6$ | Na/K/Mg/ $La_{3.5}Nd_{0.5}O6$ |
| Zr/Cs | Zr/Cs/ $La_{4-x}Nd_xO6$ | Zr/Cs/ $LaNd_3O6$ | Zr/Cs/ $La_{1.5}Nd_{2.5}O6$ | Zr/Cs/ $La_{2.5}Nd_{1.5}O6$ | Zr/Cs/ $La_{3.2}Nd_{0.8}O6$ | Zr/Cs/ $La_{3.5}Nd_{0.5}O6$ |
| Ca/Ce | Ca/Ce/ $La_{4-x}Nd_xO6$ | Ca/Ce/ $LaNd_3O6$ | Ca/Ce/ $La_{1.5}Nd_{2.5}O6$ | Ca/Ce/ $La_{2.5}Nd_{1.5}O6$ | Ca/Ce/ $La_{3.2}Nd_{0.8}O6$ | Ca/Ce/ $La_{3.5}Nd_{0.5}O6$ |
| Na/Li/Cs | Na/Li/Cs/ $La_{4-x}Nd_xO6$ | Na/Li/Cs/ $LaNd_3O6$ | Na/Li/Cs/ $La_{1.5}Nd_{2.5}O6$ | Na/Li/Cs/ $La_{2.5}Nd_{1.5}O6$ | Na/Li/Cs/ $La_{3.2}Nd_{0.8}O6$ | Na/Li/Cs/ $La_{3.5}Nd_{0.5}O6$ |
| Li/Sr | Li/Sr/ $La_{4-x}Nd_xO6$ | Li/Sr/ $LaNd_3O6$ | Li/Sr/ $La_{1.5}Nd_{2.5}O6$ | Li/Sr/ $La_{2.5}Nd_{1.5}O6$ | Li/Sr/ $La_{3.2}Nd_{0.8}O6$ | Li/Sr/ $La_{3.5}Nd_{0.5}O6$ |
| La/Dy/K | La/Dy/K/ $La_{4-x}Nd_xO6$ | La/Dy/K/ $LaNd_3O6$ | La/Dy/K/ $La_{1.5}Nd_{2.5}O6$ | La/Dy/K/ $La_{2.5}Nd_{1.5}O6$ | La/Dy/K/ $La_{3.2}Nd_{0.8}O6$ | La/Dy/K/ $La_{3.5}Nd_{0.5}O6$ |
| Dy/K | Dy/K/ $La_{4-x}Nd_xO6$ | Dy/K/ $LaNd_3O6$ | Dy/K/ $La_{1.5}Nd_{2.5}O6$ | Dy/K/ $La_{2.5}Nd_{1.5}O6$ | Dy/K/ $La_{3.2}Nd_{0.8}O6$ | Dy/K/ $La_{3.5}Nd_{0.5}O6$ |
| La/Mg | La/Mg/ $La_{4-x}Nd_xO6$ | La/Mg/ $LaNd_3O6$ | La/Mg/ $La_{1.5}Nd_{2.5}O6$ | La/Mg/ $La_{2.5}Nd_{1.5}O6$ | La/Mg/ $La_{3.2}Nd_{0.8}O6$ | La/Mg/ $La_{3.5}Nd_{0.5}O6$ |
| Na/Nd/In/K | Na/Nd/In/K/ $La_{4-x}Nd_xO6$ | Na/Nd/In/K/ $LaNd_3O6$ | Na/Nd/In/K/ $La_{1.5}Nd_{2.5}O6$ | Na/Nd/In/K/ $La_{2.5}Nd_{1.5}O6$ | Na/Nd/In/K/ $La_{3.2}Nd_{0.8}O6$ | Na/Nd/In/K/ $La_{3.5}Nd_{0.5}O6$ |
| In/Sr | In/Sr/ $La_{4-x}Nd_xO6$ | In/Sr/ $LaNd_3O6$ | In/Sr/ $La_{1.5}Nd_{2.5}O6$ | In/Sr/ $La_{2.5}Nd_{1.5}O6$ | In/Sr/ $La_{3.2}Nd_{0.8}O6$ | In/Sr/ $La_{3.5}Nd_{0.5}O6$ |
| Sr/Cs | Sr/Cs/ $La_{4-x}Nd_xO6$ | Sr/Cs/ $LaNd_3O6$ | Sr/Cs/ $La_{1.5}Nd_{2.5}O6$ | Sr/Cs/ $La_{2.5}Nd_{1.5}O6$ | Sr/Cs/ $La_{3.2}Nd_{0.8}O6$ | Sr/Cs/ $La_{3.5}Nd_{0.5}O6$ |
| Rb/Ga/Tm/Cs | Rb/Ga/Tm/Cs/ $La_{4-x}Nd_xO6$ | Rb/Ga/Tm/Cs/ $LaNd_3O6$ | Rb/Ga/Tm/Cs/ $La_{1.5}Nd_{2.5}O6$ | Rb/Ga/Tm/Cs/ $La_{2.5}Nd_{1.5}O6$ | Rb/Ga/Tm/Cs/ $La_{3.2}Nd_{0.8}O6$ | Rb/Ga/Tm/Cs/ $La_{3.5}Nd_{0.5}O6$ |
| Ga/Cs | Ga/Cs/ $La_{4-x}Nd_xO6$ | Ga/Cs/ $LaNd_3O6$ | Ga/Cs/ $La_{1.5}Nd_{2.5}O6$ | Ga/Cs/ $La_{2.5}Nd_{1.5}O6$ | Ga/Cs/ $La_{3.2}Nd_{0.8}O6$ | Ga/Cs/ $La_{3.5}Nd_{0.5}O6$ |
| K/La/Zr/Ag | K/La/Zr/Ag/ $La_{4-x}Nd_xO6$ | K/La/Zr/Ag/ $LaNd_3O6$ | K/La/Zr/Ag/ $La_{1.5}Nd_{2.5}O6$ | K/La/Zr/Ag/ $La_{2.5}Nd_{1.5}O6$ | K/La/Zr/Ag/ $La_{3.2}Nd_{0.8}O6$ | K/La/Zr/Ag/ $La_{3.5}Nd_{0.5}O6$ |
| Lu/Fe | Lu/Fe/ $La_{4-x}Nd_xO6$ | Lu/Fe/ $LaNd_3O6$ | Lu/Fe/ $La_{1.5}Nd_{2.5}O6$ | Lu/Fe/ $La_{2.5}Nd_{1.5}O6$ | Lu/Fe/ $La_{3.2}Nd_{0.8}O6$ | Lu/Fe/ $La_{3.5}Nd_{0.5}O6$ |
| Sr/Tm | Sr/Tm/ $La_{4-x}Nd_xO6$ | Sr/Tm/ $LaNd_3O6$ | Sr/Tm/ $La_{1.5}Nd_{2.5}O6$ | Sr/Tm/ $La_{2.5}Nd_{1.5}O6$ | Sr/Tm/ $La_{3.2}Nd_{0.8}O6$ | Sr/Tm/ $La_{3.5}Nd_{0.5}O6$ |
| La/Dy | La/Dy/ $La_{4-x}Nd_xO6$ | La/Dy/ $LaNd_3O6$ | La/Dy/ $La_{1.5}Nd_{2.5}O6$ | La/Dy/ $La_{2.5}Nd_{1.5}O6$ | La/Dy/ $La_{3.2}Nd_{0.8}O6$ | La/Dy/ $La_{3.5}Nd_{0.5}O6$ |
| Sm/Li/Sr | Sm/Li/Sr/ $La_{4-x}Nd_xO6$ | Sm/Li/Sr/ $LaNd_3O6$ | Sm/Li/Sr/ $La_{1.5}Nd_{2.5}O6$ | Sm/Li/Sr/ $La_{2.5}Nd_{1.5}O6$ | Sm/Li/Sr/ $La_{3.2}Nd_{0.8}O6$ | Sm/Li/Sr/ $La_{3.5}Nd_{0.5}O6$ |
| Mg/K | Mg/K/ $La_{4-x}Nd_xO6$ | Mg/K/ $LaNd_3O6$ | Mg/K/ $La_{1.5}Nd_{2.5}O6$ | Mg/K/ $La_{2.5}Nd_{1.5}O6$ | Mg/K/ $La_{3.2}Nd_{0.8}O6$ | Mg/K/ $La_{3.5}Nd_{0.5}O6$ |
| Li/Rb/Ga | Li/Rb/Ga/ $La_{4-x}Nd_xO6$ | Li/Rb/Ga/ $LaNd_3O6$ | Li/Rb/Ga/ $La_{1.5}Nd_{2.5}O6$ | Li/Rb/Ga/ $La_{2.5}Nd_{1.5}O6$ | Li/Rb/Ga/ $La_{3.2}Nd_{0.8}O6$ | Li/Rb/Ga/ $La_{3.5}Nd_{0.5}O6$ |
| Li/Cs/Tm | Li/Cs/Tm/ $La_{4-x}Nd_xO6$ | Li/Cs/Tm/ $LaNd_3O6$ | Li/Cs/Tm/ $La_{1.5}Nd_{2.5}O6$ | Li/Cs/Tm/ $La_{2.5}Nd_{1.5}O6$ | Li/Cs/Tm/ $La_{3.2}Nd_{0.8}O6$ | Li/Cs/Tm/ $La_{3.5}Nd_{0.5}O6$ |
| Zr/K | Zr/K/ $La_{4-x}Nd_xO6$ | Zr/K/ $LaNd_3O6$ | Zr/K/ $La_{1.5}Nd_{2.5}O6$ | Zr/K/ $La_{2.5}Nd_{1.5}O6$ | Zr/K/ $La_{3.2}Nd_{0.8}O6$ | Zr/K/ $La_{3.5}Nd_{0.5}O6$ |
| Li/Cs | Li/Cs/ $La_{4-x}Nd_xO6$ | Li/Cs/ $LaNd_3O6$ | Li/Cs/ $La_{1.5}Nd_{2.5}O6$ | Li/Cs/ $La_{2.5}Nd_{1.5}O6$ | Li/Cs/ $La_{3.2}Nd_{0.8}O6$ | Li/Cs/ $La_{3.5}Nd_{0.5}O6$ |
| Li/K/La | Li/K/La/ $La_{4-x}Nd_xO6$ | Li/K/La/ $LaNd_3O6$ | Li/K/La/ $La_{1.5}Nd_{2.5}O6$ | Li/K/La/ $La_{2.5}Nd_{1.5}O6$ | Li/K/La/ $La_{3.2}Nd_{0.8}O6$ | Li/K/La/ $La_{3.5}Nd_{0.5}O6$ |
| Ce/Zr/La | Ce/Zr/La/ $La_{4-x}Nd_xO6$ | Ce/Zr/La/ $LaNd_3O6$ | Ce/Zr/La/ $La_{1.5}Nd_{2.5}O6$ | Ce/Zr/La/ $La_{2.5}Nd_{1.5}O6$ | Ce/Zr/La/ $La_{3.2}Nd_{0.8}O6$ | Ce/Zr/La/ $La_{3.5}Nd_{0.5}O6$ |
| Ca/Al/La | Ca/Al/La/ $La_{4-x}Nd_xO6$ | Ca/Al/La/ $LaNd_3O6$ | Ca/Al/La/ $La_{1.5}Nd_{2.5}O6$ | Ca/Al/La/ $La_{2.5}Nd_{1.5}O6$ | Ca/Al/La/ $La_{3.2}Nd_{0.8}O6$ | Ca/Al/La/ $La_{3.5}Nd_{0.5}O6$ |
| Sr/Zn/La | Sr/Zn/La/ $La_{4-x}Nd_xO6$ | Sr/Zn/La/ $LaNd_3O6$ | Sr/Zn/La/ $La_{1.5}Nd_{2.5}O6$ | Sr/Zn/La/ $La_{2.5}Nd_{1.5}O6$ | Sr/Zn/La/ $La_{3.2}Nd_{0.8}O6$ | Sr/Zn/La/ $La_{3.5}Nd_{0.5}O6$ |
| Sr/Cs/Zn | Sr/Cs/Zn/ $La_{4-x}Nd_xO6$ | Sr/Cs/Zn/ $LaNd_3O6$ | Sr/Cs/Zn/ $La_{1.5}Nd_{2.5}O6$ | Sr/Cs/Zn/ $La_{2.5}Nd_{1.5}O6$ | Sr/Cs/Zn/ $La_{3.2}Nd_{0.8}O6$ | Sr/Cs/Zn/ $La_{3.5}Nd_{0.5}O6$ |

TABLE 2-continued

CATALYSTS (CAT) DOPED WITH SPECIFIC DOPANTS (DOP)

| Dop\Cat | $La_{4-x}Nd_xO6$ | $LaNd_3O6$ | $La_{1.5}Nd_{2.5}O6$ | $La_{2.5}Nd_{1.5}O6$ | $La_{3.2}Nd_{0.8}O6$ | $La_{3.5}Nd_{0.5}O6$ |
|---|---|---|---|---|---|---|
| Sm/Cs | Sm/Cs/ $La_{4-x}Nd_xO6$ | Sm/Cs/ $LaNd_3O6$ | Sm/Cs/ $La_{1.5}Nd_{2.5}O6$ | Sm/Cs/ $La_{2.5}Nd_{1.5}O6$ | Sm/Cs/ $La_{3.2}Nd_{0.8}O6$ | Sm/Cs/ $La_{3.5}Nd_{0.5}O6$ |
| In/K | In/K/ $La_{4-x}Nd_xO6$ | In/K/ $LaNd_3O6$ | In/K/ $La_{1.5}Nd_{2.5}O6$ | In/K/ $La_{2.5}Nd_{1.5}O6$ | In/K/ $La_{3.2}Nd_{0.8}O6$ | In/K/ $La_{3.5}Nd_{0.5}O6$ |
| Ho/Cs/Li/La | Ho/Cs/Li/La/ $La_{4-x}Nd_xO6$ | Ho/Cs/Li/La/ $LaNd_3O6$ | Ho/Cs/Li/La/ $La_{1.5}Nd_{2.5}O6$ | Ho/Cs/Li/La/ $La_{2.5}Nd_{1.5}O6$ | Ho/Cs/Li/La/ $La_{3.2}Nd_{0.8}O6$ | Ho/Cs/Li/La/ $La_{3.5}Nd_{0.5}O6$ |
| Cs/La/Na | Cs/La/Na/ $La_{4-x}Nd_xO6$ | Cs/La/Na/ $LaNd_3O6$ | Cs/La/Na/ $La_{1.5}Nd_{2.5}O6$ | Cs/La/Na/ $La_{2.5}Nd_{1.5}O6$ | Cs/La/Na/ $La_{3.2}Nd_{0.8}O6$ | Cs/La/Na/ $La_{3.5}Nd_{0.5}O6$ |
| La/S/Sr | La/S/Sr/ $La_{4-x}Nd_xO6$ | La/S/Sr/ $LaNd_3O6$ | La/S/Sr/ $La_{1.5}Nd_{2.5}O6$ | La/S/Sr/ $La_{2.5}Nd_{1.5}O6$ | La/S/Sr/ $La_{3.2}Nd_{0.8}O6$ | La/S/Sr/ $La_{3.5}Nd_{0.5}O6$ |
| K/La/Zr/Ag | K/La/Zr/Ag/ $La_{4-x}Nd_xO6$ | K/La/Zr/Ag/ $LaNd_3O6$ | K/La/Zr/Ag/ $La_{1.5}Nd_{2.5}O6$ | K/La/Zr/Ag/ $La_{2.5}Nd_{1.5}O6$ | K/La/Zr/Ag/ $La_{3.2}Nd_{0.8}O6$ | K/La/Zr/Ag/ $La_{3.5}Nd_{0.5}O6$ |
| Lu/Tl | Lu/Tl/ $La_{4-x}Nd_xO6$ | Lu/Tl/ $LaNd_3O6$ | Lu/Tl/ $La_{1.5}Nd_{2.5}O6$ | Lu/Tl/ $La_{2.5}Nd_{1.5}O6$ | Lu/Tl/ $La_{3.2}Nd_{0.8}O6$ | Lu/Tl/ $La_{3.5}Nd_{0.5}O6$ |
| Pr/Zn | Pr/Zn/ $La_{4-x}Nd_xO6$ | Pr/Zn/ $LaNd_3O6$ | Pr/Zn/ $La_{1.5}Nd_{2.5}O6$ | Pr/Zn/ $La_{2.5}Nd_{1.5}O6$ | Pr/Zn/ $La_{3.2}Nd_{0.8}O6$ | Pr/Zn/ $La_{3.5}Nd_{0.5}O6$ |
| Rb/Sr/La | Rb/Sr/La/ $La_{4-x}Nd_xO6$ | Rb/Sr/La/ $LaNd_3O6$ | Rb/Sr/La/ $La_{1.5}Nd_{2.5}O6$ | Rb/Sr/La/ $La_{2.5}Nd_{1.5}O6$ | Rb/Sr/La/ $La_{3.2}Nd_{0.8}O6$ | Rb/Sr/La/ $La_{3.5}Nd_{0.5}O6$ |
| Na/Sr/Eu/Ca | Na/Sr/Eu/Ca/ $La_{4-x}Nd_xO6$ | Na/Sr/Eu/Ca/ $LaNd_3O6$ | Na/Sr/Eu/Ca/ $La_{1.5}Nd_{2.5}O6$ | Na/Sr/Eu/Ca/ $La_{2.5}Nd_{1.5}O6$ | Na/Sr/Eu/Ca/ $La_{3.2}Nd_{0.8}O6$ | Na/Sr/Eu/Ca/ $La_{3.5}Nd_{0.5}O6$ |
| K/Cs/Sr/La | K/Cs/Sr/La/ $La_{4-x}Nd_xO6$ | K/Cs/Sr/La/ $LaNd_3O6$ | K/Cs/Sr/La/ $La_{1.5}Nd_{2.5}O6$ | K/Cs/Sr/La/ $La_{2.5}Nd_{1.5}O6$ | K/Cs/Sr/La/ $La_{3.2}Nd_{0.8}O6$ | K/Cs/Sr/La/ $La_{3.5}Nd_{0.5}O6$ |
| Na/Sr/Lu | Na/Sr/Lu/ $La_{4-x}Nd_xO6$ | Na/Sr/Lu/ $LaNd_3O6$ | Na/Sr/Lu/ $La_{1.5}Nd_{2.5}O6$ | Na/Sr/Lu/ $La_{2.5}Nd_{1.5}O6$ | Na/Sr/Lu/ $La_{3.2}Nd_{0.8}O6$ | Na/Sr/Lu/ $La_{3.5}Nd_{0.5}O6$ |
| Sr/Eu/Dy | Sr/Eu/Dy/ $La_{4-x}Nd_xO6$ | Sr/Eu/Dy/ $LaNd_3O6$ | Sr/Eu/Dy/ $La_{1.5}Nd_{2.5}O6$ | Sr/Eu/Dy/ $La_{2.5}Nd_{1.5}O6$ | Sr/Eu/Dy/ $La_{3.2}Nd_{0.8}O6$ | Sr/Eu/Dy/ $La_{3.5}Nd_{0.5}O6$ |
| Lu/Nb | Lu/Nb/ $La_{4-x}Nd_xO6$ | Lu/Nb/ $LaNd_3O6$ | Lu/Nb/ $La_{1.5}Nd_{2.5}O6$ | Lu/Nb/ $La_{2.5}Nd_{1.5}O6$ | Lu/Nb/ $La_{3.2}Nd_{0.8}O6$ | Lu/Nb/ $La_{3.5}Nd_{0.5}O6$ |
| La/Dy/Gd | La/Dy/Gd/ $La_{4-x}Nd_xO6$ | La/Dy/Gd/ $LaNd_3O6$ | La/Dy/Gd/ $La_{1.5}Nd_{2.5}O6$ | La/Dy/Gd/ $La_{2.5}Nd_{1.5}O6$ | La/Dy/Gd/ $La_{3.2}Nd_{0.8}O6$ | La/Dy/Gd/ $La_{3.5}Nd_{0.5}O6$ |
| Na/Mg/Tl/P | Na/Mg/Tl/P/ $La_{4-x}Nd_xO6$ | Na/Mg/Tl/P/ $LaNd_3O6$ | Na/Mg/Tl/P/ $La_{1.5}Nd_{2.5}O6$ | Na/Mg/Tl/P/ $La_{2.5}Nd_{1.5}O6$ | Na/Mg/Tl/P/ $La_{3.2}Nd_{0.8}O6$ | Na/Mg/Tl/P/ $La_{3.5}Nd_{0.5}O6$ |
| Na/Pt | Na/Pt/ $La_{4-x}Nd_xO6$ | Na/Pt/ $LaNd_3O6$ | Na/Pt/ $La_{1.5}Nd_{2.5}O6$ | Na/Pt/ $La_{2.5}Nd_{1.5}O6$ | Na/Pt/ $La_{3.2}Nd_{0.8}O6$ | Na/Pt/ $La_{3.5}Nd_{0.5}O6$ |
| Gd/Li/K | Gd/Li/K/ $La_{4-x}Nd_xO6$ | Gd/Li/K/ $LaNd_3O6$ | Gd/Li/K/ $La_{1.5}Nd_{2.5}O6$ | Gd/Li/K/ $La_{2.5}Nd_{1.5}O6$ | Gd/Li/K/ $La_{3.2}Nd_{0.8}O6$ | Gd/Li/K/ $La_{3.5}Nd_{0.5}O6$ |
| Rb/K/Lu | Rb/K/Lu/ $La_{4-x}Nd_xO6$ | Rb/K/Lu/ $LaNd_3O6$ | Rb/K/Lu/ $La_{1.5}Nd_{2.5}O6$ | Rb/K/Lu/ $La_{2.5}Nd_{1.5}O6$ | Rb/K/Lu/ $La_{3.2}Nd_{0.8}O6$ | Rb/K/Lu/ $La_{3.5}Nd_{0.5}O6$ |
| Sr/La/Dy/S | Sr/La/Dy/S/ $La_{4-x}Nd_xO6$ | Sr/La/Dy/S/ $LaNd_3O6$ | Sr/La/Dy/S/ $La_{1.5}Nd_{2.5}O6$ | Sr/La/Dy/S/ $La_{2.5}Nd_{1.5}O6$ | Sr/La/Dy/S/ $La_{3.2}Nd_{0.8}O6$ | Sr/La/Dy/S/ $La_{3.5}Nd_{0.5}O6$ |
| Na/Ce/Co | Na/Ce/Co/ $La_{4-x}Nd_xO6$ | Na/Ce/Co/ $LaNd_3O6$ | Na/Ce/Co/ $La_{1.5}Nd_{2.5}O6$ | Na/Ce/Co/ $La_{2.5}Nd_{1.5}O6$ | Na/Ce/Co/ $La_{3.2}Nd_{0.8}O6$ | Na/Ce/Co/ $La_{3.5}Nd_{0.5}O6$ |
| Na/Ce | Na/Ce/ $La_{4-x}Nd_xO6$ | Na/Ce/ $LaNd_3O6$ | Na/Ce/ $La_{1.5}Nd_{2.5}O6$ | Na/Ce/ $La_{2.5}Nd_{1.5}O6$ | Na/Ce/ $La_{3.2}Nd_{0.8}O6$ | Na/Ce/ $La_{3.5}Nd_{0.5}O6$ |
| Na/Ga/Gd/Al | Na/Ga/Gd/Al/ $La_{4-x}Nd_xO6$ | Na/Ga/Gd/Al/ $LaNd_3O6$ | Na/Ga/Gd/Al/ $La_{1.5}Nd_{2.5}O6$ | Na/Ga/Gd/Al/ $La_{2.5}Nd_{1.5}O6$ | Na/Ga/Gd/Al/ $La_{3.2}Nd_{0.8}O6$ | Na/Ga/Gd/Al/ $La_{3.5}Nd_{0.5}O6$ |
| Ba/Rh/Ta | Ba/Rh/Ta/ $La_{4-x}Nd_xO6$ | Ba/Rh/Ta/ $LaNd_3O6$ | Ba/Rh/Ta/ $La_{1.5}Nd_{2.5}O6$ | Ba/Rh/Ta/ $La_{2.5}Nd_{1.5}O6$ | Ba/Rh/Ta/ $La_{3.2}Nd_{0.8}O6$ | Ba/Rh/Ta/ $La_{3.5}Nd_{0.5}O6$ |
| Ba/Ta | Ba/Ta/ $La_{4-x}Nd_xO6$ | Ba/Ta/ $LaNd_3O6$ | Ba/Ta/ $La_{1.5}Nd_{2.5}O6$ | Ba/Ta/ $La_{2.5}Nd_{1.5}O6$ | Ba/Ta/ $La_{3.2}Nd_{0.8}O6$ | Ba/Ta/ $La_{3.5}Nd_{0.5}O6$ |
| Na/Al/Bi | Na/Al/Bi/ $La_{4-x}Nd_xO6$ | Na/Al/Bi/ $LaNd_3O6$ | Na/Al/Bi/ $La_{1.5}Nd_{2.5}O6$ | Na/Al/Bi/ $La_{2.5}Nd_{1.5}O6$ | Na/Al/Bi/ $La_{3.2}Nd_{0.8}O6$ | Na/Al/Bi/ $La_{3.5}Nd_{0.5}O6$ |
| Cs/Eu/S | Cs/Eu/S/ $La_{4-x}Nd_xO6$ | Cs/Eu/S/ $LaNd_3O6$ | Cs/Eu/S/ $La_{1.5}Nd_{2.5}O6$ | Cs/Eu/S/ $La_{2.5}Nd_{1.5}O6$ | Cs/Eu/S/ $La_{3.2}Nd_{0.8}O6$ | Cs/Eu/S/ $La_{3.5}Nd_{0.5}O6$ |
| Sm/Tm/Yb/Fe | Sm/Tm/Yb/Fe/ $La_{4-x}Nd_xO6$ | Sm/Tm/Yb/Fe/ $LaNd_3O6$ | Sm/Tm/Yb/Fe/ $La_{1.5}Nd_{2.5}O6$ | Sm/Tm/Yb/Fe/ $La_{2.5}Nd_{1.5}O6$ | Sm/Tm/Yb/Fe/ $La_{3.2}Nd_{0.8}O6$ | Sm/Tm/Yb/Fe/ $La_{3.5}Nd_{0.5}O6$ |
| Sm/Tm/Yb | Sm/Tm/Yb/ $La_{4-x}Nd_xO6$ | Sm/Tm/Yb/ $LaNd_3O6$ | Sm/Tm/Yb/ $La_{1.5}Nd_{2.5}O6$ | Sm/Tm/Yb/ $La_{2.5}Nd_{1.5}O6$ | Sm/Tm/Yb/ $La_{3.2}Nd_{0.8}O6$ | Sm/Tm/Yb/ $La_{3.5}Nd_{0.5}O6$ |
| Hf/Zr/Ta | Hf/Zr/Ta/ $La_{4-x}Nd_xO6$ | Hf/Zr/Ta/ $LaNd_3O6$ | Hf/Zr/Ta/ $La_{1.5}Nd_{2.5}O6$ | Hf/Zr/Ta/ $La_{2.5}Nd_{1.5}O6$ | Hf/Zr/Ta/ $La_{3.2}Nd_{0.8}O6$ | Hf/Zr/Ta/ $La_{3.5}Nd_{0.5}O6$ |
| Rb/Gd/Li/K | Rb/Gd/Li/K/ $La_{4-x}Nd_xO6$ | Rb/Gd/Li/K/ $LaNd_3O6$ | Rb/Gd/Li/K/ $La_{1.5}Nd_{2.5}O6$ | Rb/Gd/Li/K/ $La_{2.5}Nd_{1.5}O6$ | Rb/Gd/Li/K/ $La_{3.2}Nd_{0.8}O6$ | Rb/Gd/Li/K/ $La_{3.5}Nd_{0.5}O6$ |
| Gd/Ho/Al/P | Gd/Ho/Al/P/ $La_{4-x}Nd_xO6$ | Gd/Ho/Al/P/ $LaNd_3O6$ | Gd/Ho/Al/P/ $La_{1.5}Nd_{2.5}O6$ | Gd/Ho/Al/P/ $La_{2.5}Nd_{1.5}O6$ | Gd/Ho/Al/P/ $La_{3.2}Nd_{0.8}O6$ | Gd/Ho/Al/P/ $La_{3.5}Nd_{0.5}O6$ |
| Na/Ca/Lu | Na/Ca/Lu/ $La_{4-x}Nd_xO6$ | Na/Ca/Lu/ $LaNd_3O6$ | Na/Ca/Lu/ $La_{1.5}Nd_{2.5}O6$ | Na/Ca/Lu/ $La_{2.5}Nd_{1.5}O6$ | Na/Ca/Lu/ $La_{3.2}Nd_{0.8}O6$ | Na/Ca/Lu/ $La_{3.5}Nd_{0.5}O6$ |
| Cu/Sn | Cu/Sn/ $La_{4-x}Nd_xO6$ | Cu/Sn/ $LaNd_3O6$ | Cu/Sn/ $La_{1.5}Nd_{2.5}O6$ | Cu/Sn/ $La_{2.5}Nd_{1.5}O6$ | Cu/Sn/ $La_{3.2}Nd_{0.8}O6$ | Cu/Sn/ $La_{3.5}Nd_{0.5}O6$ |
| Ag/Au | Ag/Au/ $La_{4-x}Nd_xO6$ | Ag/Au/ $LaNd_3O6$ | Ag/Au/ $La_{1.5}Nd_{2.5}O6$ | Ag/Au/ $La_{2.5}Nd_{1.5}O6$ | Ag/Au/ $La_{3.2}Nd_{0.8}O6$ | Ag/Au/ $La_{3.5}Nd_{0.5}O6$ |
| Al/Bi | Al/Bi/ $La_{4-x}Nd_xO6$ | Al/Bi/ $LaNd_3O6$ | Al/Bi/ $La_{1.5}Nd_{2.5}O6$ | Al/Bi/ $La_{2.5}Nd_{1.5}O6$ | Al/Bi/ $La_{3.2}Nd_{0.8}O6$ | Al/Bi/ $La_{3.5}Nd_{0.5}O6$ |
| Al/Mo | Al/Mo/ $La_{4-x}Nd_xO6$ | Al/Mo/ $LaNd_3O6$ | Al/Mo/ $La_{1.5}Nd_{2.5}O6$ | Al/Mo/ $La_{2.5}Nd_{1.5}O6$ | Al/Mo/ $La_{3.2}Nd_{0.8}O6$ | Al/Mo/ $La_{3.5}Nd_{0.5}O6$ |
| Al/Nb | Al/Nb/ $La_{4-x}Nd_xO6$ | Al/Nb/ $LaNd_3O6$ | Al/Nb/ $La_{1.5}Nd_{2.5}O6$ | Al/Nb/ $La_{2.5}Nd_{1.5}O6$ | Al/Nb/ $La_{3.2}Nd_{0.8}O6$ | Al/Nb/ $La_{3.5}Nd_{0.5}O6$ |

TABLE 2-continued

CATALYSTS (CAT) DOPED WITH SPECIFIC DOPANTS (DOP)

| Dop\Cat | $La_{4-x}Nd_xO6$ | $LaNd_3O6$ | $La_{1.5}Nd_{2.5}O6$ | $La_{2.5}Nd_{1.5}O6$ | $La_{3.2}Nd_{0.8}O6$ | $La_{3.5}Nd_{0.5}O6$ |
|---|---|---|---|---|---|---|
| Au/Pt | Au/Pt/$La_{4-x}Nd_xO6$ | Au/Pt/$LaNd_3O6$ | Au/Pt/$La_{1.5}Nd_{2.5}O6$ | Au/Pt/$La_{2.5}Nd_{1.5}O6$ | Au/Pt/$La_{3.2}Nd_{0.8}O6$ | Au/Pt/$La_{3.5}Nd_{0.5}O6$ |
| Ga/Bi | Ga/Bi/$La_{4-x}Nd_xO6$ | Ga/Bi/$LaNd_3O6$ | Ga/Bi/$La_{1.5}Nd_{2.5}O6$ | Ga/Bi/$La_{2.5}Nd_{1.5}O6$ | Ga/Bi/$La_{3.2}Nd_{0.8}O6$ | Ga/Bi/$La_{3.5}Nd_{0.5}O6$ |
| Mg/W | Mg/W/$La_{4-x}Nd_xO6$ | Mg/W/$LaNd_3O6$ | Mg/W/$La_{1.5}Nd_{2.5}O6$ | Mg/W/$La_{2.5}Nd_{1.5}O6$ | Mg/W/$La_{3.2}Nd_{0.8}O6$ | Mg/W/$La_{3.5}Nd_{0.5}O6$ |
| Pb/Au | Pb/Au/$La_{4-x}Nd_xO6$ | Pb/Au/$LaNd_3O6$ | Pb/Au/$La_{1.5}Nd_{2.5}O6$ | Pb/Au/$La_{2.5}Nd_{1.5}O6$ | Pb/Au/$La_{3.2}Nd_{0.8}O6$ | Pb/Au/$La_{3.5}Nd_{0.5}O6$ |
| Sn/Mg | Sn/Mg/$La_{4-x}Nd_xO6$ | Sn/Mg/$LaNd_3O6$ | Sn/Mg/$La_{1.5}Nd_{2.5}O6$ | Sn/Mg/$La_{2.5}Nd_{1.5}O6$ | Sn/Mg/$La_{3.2}Nd_{0.8}O6$ | Sn/Mg/$La_{3.5}Nd_{0.5}O6$ |
| Zn/Bi | Zn/Bi/$La_{4-x}Nd_xO6$ | Zn/Bi/$LaNd_3O6$ | Zn/Bi/$La_{1.5}Nd_{2.5}O6$ | Zn/Bi/$La_{2.5}Nd_{1.5}O6$ | Zn/Bi/$La_{3.2}Nd_{0.8}O6$ | Zn/Bi/$La_{3.5}Nd_{0.5}O6$ |
| Sr/Ta | Sr/Ta/$La_{4-x}Nd_xO6$ | Sr/Ta/$LaNd_3O6$ | Sr/Ta/$La_{1.5}Nd_{2.5}O6$ | Sr/Ta/$La_{2.5}Nd_{1.5}O6$ | Sr/Ta/$La_{3.2}Nd_{0.8}O6$ | Sr/Ta/$La_{3.5}Nd_{0.5}O6$ |
| Na | Na/$La_{4-x}Nd_xO6$ | Na/$LaNd_3O6$ | Na/$La_{1.5}Nd_{2.5}O6$ | Na/$La_{2.5}Nd_{1.5}O6$ | Na/$La_{3.2}Nd_{0.8}O6$ | Na/$La_{3.5}Nd_{0.5}O6$ |
| Sr | Sr/$La_{4-x}Nd_xO6$ | Sr/$LaNd_3O6$ | Sr/$La_{1.5}Nd_{2.5}O6$ | Sr/$La_{2.5}Nd_{1.5}O6$ | Sr/$La_{3.2}Nd_{0.8}O6$ | Sr/$La_{3.5}Nd_{0.5}O6$ |
| Ca | Ca/$La_{4-x}Nd_xO6$ | Ca/$LaNd_3O6$ | Ca/$La_{1.5}Nd_{2.5}O6$ | Ca/$La_{2.5}Nd_{1.5}O6$ | Ca/$La_{3.2}Nd_{0.8}O6$ | Ca/$La_{3.5}Nd_{0.5}O6$ |
| Yb | Yb/$La_{4-x}Nd_xO6$ | Yb/$LaNd_3O6$ | Yb/$La_{1.5}Nd_{2.5}O6$ | Yb/$La_{2.5}Nd_{1.5}O6$ | Yb/$La_{3.2}Nd_{0.8}O6$ | Yb/$La_{3.5}Nd_{0.5}O6$ |
| Cs | Cs/$La_{4-x}Nd_xO6$ | Cs/$LaNd_3O6$ | Cs/$La_{1.5}Nd_{2.5}O6$ | Cs/$La_{2.5}Nd_{1.5}O6$ | Cs/$La_{3.2}Nd_{0.8}O6$ | Cs/$La_{3.5}Nd_{0.5}O6$ |
| Sb | Sb/$La_{4-x}Nd_xO6$ | Sb/$LaNd_3O6$ | Sb/$La_{1.5}Nd_{2.5}O6$ | Sb/$La_{2.5}Nd_{1.5}O6$ | Sb/$La_{3.2}Nd_{0.8}O6$ | Sb/$La_{3.5}Nd_{0.5}O6$ |
| Gd/Ho | Gd/Ho/$La_{4-x}Nd_xO6$ | Gd/Ho/$LaNd_3O6$ | Gd/Ho/$La_{1.5}Nd_{2.5}O6$ | Gd/Ho/$La_{2.5}Nd_{1.5}O6$ | Gd/Ho/$La_{3.2}Nd_{0.8}O6$ | Gd/Ho/$La_{3.5}Nd_{0.5}O6$ |
| Zr/Bi | Zr/Bi/$La_{4-x}Nd_xO6$ | Zr/Bi/$LaNd_3O6$ | Zr/Bi/$La_{1.5}Nd_{2.5}O6$ | Zr/Bi/$La_{2.5}Nd_{1.5}O6$ | Zr/Bi/$La_{3.2}Nd_{0.8}O6$ | Zr/Bi/$La_{3.5}Nd_{0.5}O6$ |
| Ho/Sr | Ho/Sr/$La_{4-x}Nd_xO6$ | Ho/Sr/$LaNd_3O6$ | Ho/Sr/$La_{1.5}Nd_{2.5}O6$ | Ho/Sr/$La_{2.5}Nd_{1.5}O6$ | Ho/Sr/$La_{3.2}Nd_{0.8}O6$ | Ho/Sr/$La_{3.5}Nd_{0.5}O6$ |
| Gd/Ho/Sr | Gd/Ho/Sr/$La_{4-x}Nd_xO6$ | Gd/Ho/Sr/$LaNd_3O6$ | Gd/Ho/Sr/$La_{1.5}Nd_{2.5}O6$ | Gd/Ho/Sr/$La_{2.5}Nd_{1.5}O6$ | Gd/Ho/Sr/$La_{3.2}Nd_{0.8}O6$ | Gd/Ho/Sr/$La_{3.5}Nd_{0.5}O6$ |
| Ca/Sr | Ca/Sr/$La_{4-x}Nd_xO6$ | Ca/Sr/$LaNd_3O6$ | Ca/Sr/$La_{1.5}Nd_{2.5}O6$ | Ca/Sr/$La_{2.5}Nd_{1.5}O6$ | Ca/Sr/$La_{3.2}Nd_{0.8}O6$ | Ca/Sr/$La_{3.5}Nd_{0.5}O6$ |
| Ca/Sr/W | Ca/Sr/W/$La_{4-x}Nd_xO6$ | Ca/Sr/W/$LaNd_3O6$ | Ca/Sr/W/$La_{1.5}Nd_{2.5}O6$ | Ca/Sr/W/$La_{2.5}Nd_{1.5}O6$ | Ca/Sr/W/$La_{3.2}Nd_{0.8}O6$ | Ca/Sr/W/$La_{3.5}Nd_{0.5}O6$ |
| Na/Zr/Eu/Tm | Na/Zr/Eu/Tm/$La_{4-x}Nd_xO6$ | Na/Zr/Eu/Tm/$LaNd_3O6$ | Na/Zr/Eu/Tm/$La_{1.5}Nd_{2.5}O6$ | Na/Zr/Eu/Tm/$La_{2.5}Nd_{1.5}O6$ | Na/Zr/Eu/Tm/$La_{3.2}Nd_{0.8}O6$ | Na/Zr/Eu/Tm/$La_{3.5}Nd_{0.5}O6$ |
| Sr/Ho/Tm/Na | Sr/Ho/Tm/Na/$La_{4-x}Nd_xO6$ | Sr/Ho/Tm/Na/$LaNd_3O6$ | Sr/Ho/Tm/Na/$La_{1.5}Nd_{2.5}O6$ | Sr/Ho/Tm/Na/$La_{2.5}Nd_{1.5}O6$ | Sr/Ho/Tm/Na/$La_{3.2}Nd_{0.8}O6$ | Sr/Ho/Tm/Na/$La_{3.5}Nd_{0.5}O6$ |
| Sr/Pb | Sr/Pb/$La_{4-x}Nd_xO6$ | Sr/Pb/$LaNd_3O6$ | Sr/Pb/$La_{1.5}Nd_{2.5}O6$ | Sr/Pb/$La_{2.5}Nd_{1.5}O6$ | Sr/Pb/$La_{3.2}Nd_{0.8}O6$ | Sr/Pb/$La_{3.5}Nd_{0.5}O6$ |
| Sr/W/Li | Sr/W/Li/$La_{4-x}Nd_xO6$ | Sr/W/Li/$LaNd_3O6$ | Sr/W/Li/$La_{1.5}Nd_{2.5}O6$ | Sr/W/Li/$La_{2.5}Nd_{1.5}O6$ | Sr/W/Li/$La_{3.2}Nd_{0.8}O6$ | Sr/W/Li/$La_{3.5}Nd_{0.5}O6$ |
| Ca/Sr/W | Ca/Sr/W/$La_{4-x}Nd_xO6$ | Ca/Sr/W/$LaNd_3O6$ | Ca/Sr/W/$La_{1.5}Nd_{2.5}O6$ | Ca/Sr/W/$La_{2.5}Nd_{1.5}O6$ | Ca/Sr/W/$La_{3.2}Nd_{0.8}O6$ | Ca/Sr/W/$La_{3.5}Nd_{0.5}O6$ |
| Sr/Hf | Sr/Hf/$La_{4-x}Nd_xO6$ | Sr/Hf/$LaNd_3O6$ | Sr/Hf/$La_{1.5}Nd_{2.5}O6$ | Sr/Hf/$La_{2.5}Nd_{1.5}O6$ | Sr/Hf/$La_{3.2}Nd_{0.8}O6$ | Sr/Hf/$La_{3.5}Nd_{0.5}O6$ |
| Au/Re | Au/Re/$La_{4-x}Nd_xO6$ | Au/Re/$LaNd_3O6$ | Au/Re/$La_{1.5}Nd_{2.5}O6$ | Au/Re/$La_{2.5}Nd_{1.5}O6$ | Au/Re/$La_{3.2}Nd_{0.8}O6$ | Au/Re/$La_{3.5}Nd_{0.5}O6$ |
| Sr/W | Sr/W/$La_{4-x}Nd_xO6$ | Sr/W/$LaNd_3O6$ | Sr/W/$La_{1.5}Nd_{2.5}O6$ | Sr/W/$La_{2.5}Nd_{1.5}O6$ | Sr/W/$La_{3.2}Nd_{0.8}O6$ | Sr/W/$La_{3.5}Nd_{0.5}O6$ |
| La/Nd | La/Nd/$La_{4-x}Nd_xO_6$ | La/Nd/$LaNd_3O_6$ | La/Nd/$La_{1.5}Nd_{2.5}O_6$ | La/Nd/$La_{2.5}Nd_{1.5}O_6$ | La/Nd/$La_{3.2}Nd_{0.8}O_6$ | La/Nd/$La_{3.5}Nd_{0.5}O_6$ |
| La/Sm | La/Sm/$La_{4-x}Nd_xO_6$ | La/Sm/$LaNd_3O_6$ | La/Sm/$La_{1.5}Nd_{2.5}O_6$ | La/Sm/$La_{2.5}Nd_{1.5}O_6$ | La/Sm/$La_{3.2}Nd_{0.8}O_6$ | La/Sm/$La_{3.5}Nd_{0.5}O_6$ |
| La/Ce | La/Ce/$La_{4-x}Nd_xO_6$ | La/Ce/$LaNd_3O_6$ | La/Ce/$La_{1.5}Nd_{2.5}O_6$ | La/Ce/$La_{2.5}Nd_{1.5}O_6$ | La/Ce/$La_{3.2}Nd_{0.8}O_6$ | La/Ce/$La_{3.5}Nd_{0.5}O_6$ |
| La/Sr | La/Sr/$La_{4-x}Nd_xO_6$ | La/Sr/$LaNd_3O_6$ | La/Sr/$La_{1.5}Nd_{2.5}O_6$ | La/Sr/$La_{2.5}Nd_{1.5}O_6$ | La/Sr/$La_{3.2}Nd_{0.8}O_6$ | La/Sr/$La_{3.5}Nd_{0.5}O_6$ |
| La/Nd/Sr | La/Nd/Sr/$La_{4-x}Nd_xO_6$ | La/Nd/Sr/$LaNd_3O_6$ | La/Nd/Sr/$La_{1.5}Nd_{2.5}O_6$ | La/Nd/Sr/$La_{2.5}Nd_{1.5}O_6$ | La/Nd/Sr/$La_{3.2}Nd_{0.8}O_6$ | La/Nd/Sr/$La_{3.5}Nd_{0.5}O_6$ |
| La/Bi/Sr | La/Bi/Sr/$La_{4-x}Nd_xO_6$ | La/Bi/Sr/$LaNd_3O_6$ | La/Bi/Sr/$La_{1.5}Nd_{2.5}O_6$ | La/Bi/Sr/$La_{2.5}Nd_{1.5}O_6$ | La/Bi/Sr/$La_{3.2}Nd_{0.8}O_6$ | La/Bi/Sr/$La_{3.5}Nd_{0.5}O_6$ |
| La/Ce/Nd/Sr | La/Ce/Nd/Sr/$La_{4-x}Nd_xO_6$ | La/Ce/Nd/Sr/$LaNd_3O_6$ | La/Ce/Nd/Sr/$La_{1.5}Nd_{2.5}O_6$ | La/Ce/Nd/Sr/$La_{2.5}Nd_{1.5}O_6$ | La/Ce/Nd/Sr/$La_{3.2}Nd_{0.8}O_6$ | La/Ce/Nd/Sr/$La_{3.5}Nd_{0.5}O_6$ |
| La/Bi/Ce/Nd/Sr | La/Bi/Ce/Nd/Sr/$La_{4-x}Nd_xO_6$ | La/Bi/Ce/Nd/Sr/$LaNd_3O_6$ | La/Bi/Ce/Nd/Sr/$La_{1.5}Nd_{2.5}O_6$ | La/Bi/Ce/Nd/Sr/$La_{2.5}Nd_{1.5}O_6$ | La/Bi/Ce/Nd/Sr/$La_{3.2}Nd_{0.8}O_6$ | La/Bi/Ce/Nd/Sr/$La_{3.5}Nd_{0.5}O_6$ |
| Eu/Gd | Eu/Gd/$La_{4-x}Nd_xO_6$ | Eu/Gd/$LaNd_3O_6$ | Eu/Gd/$La_{1.5}Nd_{2.5}O_6$ | Eu/Gd/$La_{2.5}Nd_{1.5}O_6$ | Eu/Gd/$La_{3.2}Nd_{0.8}O_6$ | Eu/Gd/$La_{3.5}Nd_{0.5}O_6$ |
| Ca/Na | Ca/Na/$La_{4-x}Nd_xO_6$ | Ca/Na/$LaNd_3O_6$ | Ca/Na/$La_{1.5}Nd_{2.5}O_6$ | Ca/Na/$La_{2.5}Nd_{1.5}O_6$ | Ca/Na/$La_{3.2}Nd_{0.8}O_6$ | Ca/Na/$La_{3.5}Nd_{0.5}O_6$ |
| Eu/Sm | Eu/Sm/$La_{4-x}Nd_xO_6$ | Eu/Sm/$LaNd_3O_6$ | Eu/Sm/$La_{1.5}Nd_{2.5}O_6$ | Eu/Sm/$La_{2.5}Nd_{1.5}O_6$ | Eu/Sm/$La_{3.2}Nd_{0.8}O_6$ | Eu/Sm/$La_{3.5}Nd_{0.5}O_6$ |

TABLE 2-continued

CATALYSTS (CAT) DOPED WITH SPECIFIC DOPANTS (DOP)

| Dop\Cat | $La_{4-x}Nd_xO6$ | $LaNd_3O_6$ | $La_{1.5}Nd_{2.5}O_6$ | $La_{2.5}Nd_{1.5}O_6$ | $La_{3.2}Nd_{0.8}O_6$ | $La_{3.5}Nd_{0.5}O_6$ |
|---|---|---|---|---|---|---|
| Eu/Sr | Eu/Sr/ $La_{4-x}Nd_xO_6$ | Eu/Sr/ $LaNd_3O_6$ | Eu/Sr/ $La_{1.5}Nd_{2.5}O_6$ | Eu/Sr/ $La_{2.5}Nd_{1.5}O_6$ | Eu/Sr/ $La_{3.2}Nd_{0.8}O_6$ | Eu/Sr/ $La_{3.5}Nd_{0.5}O_6$ |
| Mg/Sr | Mg/Sr/ $La_{4-x}Nd_xO_6$ | Mg/Sr/ $LaNd_3O_6$ | Mg/Sr/ $La_{1.5}Nd_{2.5}O_6$ | Mg/Sr/ $La_{2.5}Nd_{1.5}O_6$ | Mg/Sr/ $La_{3.2}Nd_{0.8}O_6$ | Mg/Sr/ $La_{3.5}Nd_{0.5}O_6$ |
| Ce/Mg | Ce/Mg/ $La_{4-x}Nd_xO_6$ | Ce/Mg/ $LaNd_3O_6$ | Ce/Mg/ $La_{1.5}Nd_{2.5}O_6$ | Ce/Mg/ $La_{2.5}Nd_{1.5}O_6$ | Ce/Mg/ $La_{3.2}Nd_{0.8}O_6$ | Ce/Mg/ $La_{3.5}Nd_{0.5}O_6$ |
| Gd/Sm | Gd/Sm/ $La_{4-x}Nd_xO_6$ | Gd/Sm/ $LaNd_3O_6$ | Gd/Sm/ $La_{1.5}Nd_{2.5}O_6$ | Gd/Sm/ $La_{2.5}Nd_{1.5}O_6$ | Gd/Sm/ $La_{3.2}Nd_{0.8}O_6$ | Gd/Sm/ $La_{3.5}Nd_{0.5}O_6$ |
| Au/Pb | Au/Pb/ $La_{4-x}Nd_xO_6$ | Au/Pb/ $LaNd_3O_6$ | Au/Pb/ $La_{1.5}Nd_{2.5}O_6$ | Au/Pb/ $La_{2.5}Nd_{1.5}O_6$ | Au/Pb/ $La_{3.2}Nd_{0.8}O_6$ | Au/Pb/ $La_{3.5}Nd_{0.5}O_6$ |
| Bi/Hf | Bi/Hf/ $La_{4-x}Nd_xO_6$ | Bi/Hf/ $LaNd_3O_6$ | Bi/Hf/ $La_{1.5}Nd_{2.5}O_6$ | Bi/Hf/ $La_{2.5}Nd_{1.5}O_6$ | Bi/Hf/ $La_{3.2}Nd_{0.8}O_6$ | Bi/Hf/ $La_{3.5}Nd_{0.5}O_6$ |
| Rb/S | Rb/S/ $La_{4-x}Nd_xO_6$ | Rb/S/ $LaNd_3O_6$ | Rb/S/ $La_{1.5}Nd_{2.5}O_6$ | Rb/S/ $La_{2.5}Nd_{1.5}O_6$ | Rb/S/ $La_{3.2}Nd_{0.8}O_6$ | Rb/S/ $La_{3.5}Nd_{0.5}O_6$ |
| Sr/Nd | Sr/Nd/ $La_{4-x}Nd_xO_6$ | Sr/Nd/ $LaNd_3O_6$ | Sr/Nd/ $La_{1.5}Nd_{2.5}O_6$ | Sr/Nd/ $La_{2.5}Nd_{1.5}O_6$ | Sr/Nd/ $La_{3.2}Nd_{0.8}O_6$ | Sr/Nd/ $La_{3.5}Nd_{0.5}O_6$ |
| Eu/Y | Eu/Y/ $La_{4-x}Nd_xO_6$ | Eu/Y/ $LaNd_3O_6$ | Eu/Y/ $La_{1.5}Nd_{2.5}O_6$ | Eu/Y/ $La_{2.5}Nd_{1.5}O_6$ | Eu/Y/ $La_{3.2}Nd_{0.8}O_6$ | Eu/Y/ $La_{3.5}Nd_{0.5}O_6$ |
| Mg/Nd | Mg/Nd/ $La_{4-x}Nd_xO_6$ | Mg/Nd/ $LaNd_3O_6$ | Mg/Nd/ $La_{1.5}Nd_{2.5}O_6$ | Mg/Nd/ $La_{2.5}Nd_{1.5}O_6$ | Mg/Nd/ $La_{3.2}Nd_{0.8}O_6$ | Mg/Nd/ $La_{3.5}Nd_{0.5}O_6$ |
| La/Mg | La/Mg/ $La_{4-x}Nd_xO_6$ | La/Mg/ $LaNd_3O_6$ | La/Mg/ $La_{1.5}Nd_{2.5}O_6$ | La/Mg/ $La_{2.5}Nd_{1.5}O_6$ | La/Mg/ $La_{3.2}Nd_{0.8}O_6$ | La/Mg/ $La_{3.5}Nd_{0.5}O_6$ |
| Mg/Nd/Fe | Mg/Nd/Fe/ $La_{4-x}Nd_xO_6$ | Mg/Nd/Fe/ $LaNd_3O_6$ | Mg/Nd/Fe/ $La_{1.5}Nd_{2.5}O_6$ | Mg/Nd/Fe/ $La_{2.5}Nd_{1.5}O_6$ | Mg/Nd/Fe/ $La_{3.2}Nd_{0.8}O_6$ | Mg/Nd/Fe/ $La_{3.5}Nd_{0.5}O_6$ |
| Rb/Sr | Rb/Sr/ $La_{4-x}Nd_xO_6$ | Rb/Sr/ $LaNd_3O_6$ | Rb/Sr/ $La_{1.5}Nd_{2.5}O_6$ | Rb/Sr/ $La_{2.5}Nd_{1.5}O_6$ | Rb/Sr/ $La_{3.2}Nd_{0.8}O_6$ | Rb/Sr/ $La_{3.5}Nd_{0.5}O_6$ |

TABLE 3

CATALYSTS (CAT) DOPED WITH SPECIFIC DOPANTS (DOP)

| Dop\Cat | $La_{3.8}Nd_{0.2}O_6$ | Y—La | Zr—La | Pr—La | Ce—La |
|---|---|---|---|---|---|
| Eu/Na | Eu/Na/ $La_{3.8}Nd_{0.2}O_6$ | Eu/Na/ Y—La | Eu/Na/ Zr—La | Eu/Na/ Pr—La | Eu/Na/ Ce—La |
| Sr/Na | Sr/Na/ $La_{3.8}Nd_{0.2}O_6$ | Sr/Na/ Y—La | Sr/Na/ Zr—La | Sr/Na/ Pr—La | Sr/Na/ Ce—La |
| Na/Zr/Eu/Ca | Na/Zr/Eu/Ca/ $La_{3.8}Nd_{0.2}O_6$ | Na/Zr/Eu/Ca/ Y—La | Na/Zr/Eu/Ca/ Zr—La | Na/Zr/Eu/Ca/ Pr—Laa | Na/Zr/Eu/Ca/ Ce—La |
| Mg/Na | Mg/Na/ $La_{3.8}Nd_{0.2}O_6$ | Mg/Na/ Y—La | Mg/Na/ Zr—La | Mg/Na/ Pr—La | Mg/Na/ Ce—La |
| Sr/Sm/Ho/Tm | Sr/Sm/Ho/Tm/ $La_{3.8}Nd_{0.2}O_6$ | Sr/Sm/Ho/Tm/ Y—La | Sr/Sm/Ho/Tm/ Zr—La | Sr/Sm/Ho/Tm/ Pr—La | Sr/Sm/Ho/Tm/ Ce—La |
| Sr/W | Sr/W/ $La_{3.8}Nd_{0.2}O_6$ | Sr/W/ Y—La | Sr/W/ Zr—La | Sr/W/ Pr—La | Sr/W/ Ce—La |
| Mg/La/K | Mg/La/K/ $La_{3.8}Nd_{0.2}O_6$ | Mg/La/K/ Y—La | Mg/La/K/ Zr—La | Mg/La/K/ Pr—La | Mg/La/K/ Ce—La |
| Na/K/Mg/Tm | Na/K/Mg/Tm/ $La_{3.8}Nd_{0.2}O_6$ | Na/K/Mg/Tm/ Y—La | Na/K/Mg/Tm/ Zr—La | Na/K/Mg/Tm/ Pr—La | Na/K/Mg/Tm/ Ce—La |
| Na/Dy/K | Na/Dy/K/ $La_{3.8}Nd_{0.2}O_6$ | Na/Dy/K/ Y—La | Na/Dy/K/ Zr—La | Na/Dy/K/ Pr—La | Na/Dy/K/ Ce—La |
| Na/La/Dy | Na/La/Dy/ $La_{3.8}Nd_{0.2}O_6$ | Na/La/Dy/ Y—La | Na/La/Dy/ Zr—La | Na/La/Dy/ Pr—La | Na/La/Dy/ Ce—La |
| Na/La/Eu | Na/La/Eu/ $La_{3.8}Nd_{0.2}O_6$ | Na/La/Eu/ Y—La | Na/La/Eu/ Zr—La | Na/La/Eu/ Pr—La | Na/La/Eu/ Ce—La |
| Na/La/Eu/In | Na/La/Eu/In/ $La_{3.8}Nd_{0.2}O_6$ | Na/La/Eu/In/ Y—La | Na/La/Eu/In/ Zr—La | Na/La/Eu/In/ Pr—La | Na/La/Eu/In/ Ce—La |
| Na/La/K | Na/La/K/ $La_{3.8}Nd_{0.2}O_6$ | Na/La/K/ Y—La | Na/La/K/ Zr—La | Na/La/K/ Pr—La | Na/La/K/ Ce—La |
| Na/La/Li/Cs | Na/La/Li/Cs/ $La_{3.8}Nd_{0.2}O_6$ | Na/La/Li/Cs/ Y—La | Na/La/Li/Cs/ Zr—La | Na/La/Li/Cs/ Pr—La | Na/La/Li/Cs/ Ce—La |
| K/La | K/La/ $La_{3.8}Nd_{0.2}O_6$ | K/La/ Y—La | K/La/ Zr—La | K/La/ Pr—La | K/La/ Ce—La |
| K/La/S | K/La/S/ $La_{3.8}Nd_{0.2}O_6$ | K/La/S/ Y—La | K/La/S/ Zr—La | K/La/S/ Pr—La | K/La/S/ Ce—La |
| K/Na | K/Na/ $La_{3.8}Nd_{0.2}O_6$ | K/Na/ Y—La | K/Na/ Zr—La | K/Na/ Pr—La | K/Na/ Ce—La |
| Li/Cs | Li/Cs/ $La_{3.8}Nd_{0.2}O_6$ | Li/Cs/ Y—La | Li/Cs/ Zr—La | Li/Cs/ Pr—La | Li/Cs/ Ce—La |
| Li/Cs/La | Li/Cs/La/ $La_{3.8}Nd_{0.2}O_6$ | Li/Cs/La/ Y—La | Li/Cs/La/ Zr—La | Li/Cs/La/ Pr—La | Li/Cs/La/ Ce—La |
| Li/Cs/La/Tm | Li/Cs/La/Tm/ $La_{3.8}Nd_{0.2}O_6$ | Li/Cs/La/Tm/ Y—La | Li/Cs/La/Tm/ Zr—La | Li/Cs/La/Tm/ Pr—La | Li/Cs/La/Tm/ Ce—La |

TABLE 3-continued

CATALYSTS (CAT) DOPED WITH SPECIFIC DOPANTS (DOP)

| Dop\Cat | $La_{3.8}Nd_{0.2}O6$ | Y—La | Zr—La | Pr—La | Ce—La |
|---|---|---|---|---|---|
| Li/Cs/Sr/Tm | Li/Cs/Sr/Tm/$La_{3.8}Nd_{0.2}O6$ | Li/Cs/Sr/Tm/Y—La | Li/Cs/Sr/Tm/Zr—La | Li/Cs/Sr/Tm/Pr—La | Li/Cs/Sr/Tm/Ce—La |
| Li/Sr/Cs | Li/Sr/Cs/$La_{3.8}Nd_{0.2}O6$ | Li/Sr/Cs/Y—La | Li/Sr/Cs/Zr—La | Li/Sr/Cs/Pr—La | Li/Sr/Cs/Ce—La |
| Li/Sr/Zn/K | Li/Sr/Zn/K/$La_{3.8}Nd_{0.2}O6$ | Li/Sr/Zn/K/Y—La | Li/Sr/Zn/K/Zr—La | Li/Sr/Zn/K/Pr—La | Li/Sr/Zn/K/Ce—La |
| Li/Ga/Cs | Li/Ga/Cs/$La_{3.8}Nd_{0.2}O6$ | Li/Ga/Cs/Y—La | Li/Ga/Cs/Zr—La | Li/Ga/Cs/Pr—La | Li/Ga/Cs/Ce—La |
| Li/K/Sr/La | Li/K/Sr/La/$La_{3.8}Nd_{0.2}O6$ | Li/K/Sr/La/Y—La | Li/K/Sr/La/Zr—La | Li/K/Sr/La/Pr—La | Li/K/Sr/La/Ce—La |
| Li/Na | Li/Na/$La_{3.8}Nd_{0.2}O6$ | Li/Na/Y—La | Li/Na/Zr—La | Li/Na/Pr—La | Li/Na/Ce—La |
| Li/Na/Rb/Ga | Li/Na/Rb/Ga/$La_{3.8}Nd_{0.2}O6$ | Li/Na/Rb/Ga/Y—La | Li/Na/Rb/Ga/Zr—La | Li/Na/Rb/Ga/Pr—La | Li/Na/Rb/Ga/Ce—La |
| Li/Na/Sr | Li/Na/Sr/$La_{3.8}Nd_{0.2}O6$ | Li/Na/Sr/Y—La | Li/Na/Sr/Zr—La | Li/Na/Sr/Pr—La | Li/Na/Sr/Ce—La |
| Li/Na/Sr/La | Li/Na/Sr/La/$La_{3.8}Nd_{0.2}O6$ | Li/Na/Sr/La/Y—La | Li/Na/Sr/La/Zr—La | Li/Na/Sr/La/Pr—La | Li/Na/Sr/La/Ce—La |
| Li/Sm/Cs | Li/Sm/Cs/$La_{3.8}Nd_{0.2}O6$ | Li/Sm/Cs/Y—La | Li/Sm/Cs/Zr—La | Li/Sm/Cs/Pr—La | Li/Sm/Cs/Ce—La |
| Ba/Sm/Yb/S | Ba/Sm/Yb/S/$La_{3.8}Nd_{0.2}O6$ | Ba/Sm/Yb/S/Y—La | Ba/Sm/Yb/S/Zr—La | Ba/Sm/Yb/S/Pr—La | Ba/Sm/Yb/S/Ce—La |
| Ba/Tm/K/La | Ba/Tm/K/La/$La_{3.8}Nd_{0.2}O6$ | Ba/Tm/K/La/Y—La | Ba/Tm/K/La/Zr—La | Ba/Tm/K/La/Pr—La | Ba/Tm/K/La/Ce—La |
| Ba/Tm/Zn/K | Ba/Tm/Zn/K/$La_{3.8}Nd_{0.2}O6$ | Ba/Tm/Zn/K/Y—La | Ba/Tm/Zn/K/Zr—La | Ba/Tm/Zn/K/Pr—La | Ba/Tm/Zn/K/Ce—La |
| C + s/K/La | Cs/K/La/$La_{3.8}Nd_{0.2}O6$ | Cs/K/La/Y—La | Cs/K/La/Zr—La | Cs/K/La/Pr—La | Cs/K/La/Ce—La |
| Cs/La/Tm/Na | Cs/La/Tm/Na/$La_{3.8}Nd_{0.2}O6$ | Cs/La/Tm/Na/Y—La | Cs/La/Tm/Na/Zr—La | Cs/La/Tm/Na/Pr—La | Cs/La/Tm/Na/Ce—La |
| Cs/Li/K/La | Cs/Li/K/La/$La_{3.8}Nd_{0.2}O6$ | Cs/Li/K/La/Y—La | Cs/Li/K/La/Zr—La | Cs/Li/K/La/Pr—La | Cs/Li/K/La/Ce—La |
| Sm/Li/Sr/Cs | Sm/Li/Sr/Cs/$La_{3.8}Nd_{0.2}O6$ | Sm/Li/Sr/Cs/Y—La | Sm/Li/Sr/Cs/Zr—La | Sm/Li/Sr/Cs/Pr—La | Sm/Li/Sr/Cs/Ce—La |
| Sr/Cs/La | Sr/Cs/La/$La_{3.8}Nd_{0.2}O6$ | Sr/Cs/La/Y—La | Sr/Cs/La/Zr—La | Sr/Cs/La/Pr—La | Sr/Cs/La/Ce—La |
| Sr/Tm/Li/Cs | Sr/Tm/Li/Cs/$La_{3.8}Nd_{0.2}O6$ | Sr/Tm/Li/Cs/Y—La | Sr/Tm/Li/Cs/Zr—La | Sr/Tm/Li/Cs/Pr—La | Sr/Tm/Li/Cs/Ce—La |
| Zn/K | Zn/K/$La_{3.8}Nd_{0.2}O6$ | Zn/K/Y—La | Zn/K/Zr—La | Zn/K/Pr—La | Zn/K/Ce—La |
| Zr/Cs/K/La | Zr/Cs/K/La/$La_{3.8}Nd_{0.2}O6$ | Zr/Cs/K/La/Y—La | Zr/Cs/K/La/Zr—La | Zr/Cs/K/La/Pr—La | Zr/Cs/K/La/Ce—La |
| Rb/Ca/In/Ni | Rb/Ca/In/Ni/$La_{3.8}Nd_{0.2}O6$ | Rb/Ca/In/Ni/Y—La | Rb/Ca/In/Ni/Zr—La | Rb/Ca/In/Ni/Pr—La | Rb/Ca/In/Ni/Ce—La |
| Sr/Ho/Tm | Sr/Ho/Tm/$La_{3.8}Nd_{0.2}O6$ | Sr/Ho/Tm/Y—La | Sr/Ho/Tm/Zr—La | Sr/Ho/Tm/Pr—La | Sr/Ho/Tm/Ce—La |
| La/Nd/S | La/Nd/S/$La_{3.8}Nd_{0.2}O6$ | La/Nd/S/Y—La | La/Nd/S/Zr—La | La/Nd/S/Pr—La | La/Nd/S/Ce—La |
| Li/Rb/Ca | Li/Rb/Ca/$La_{3.8}Nd_{0.2}O6$ | Li/Rb/Ca/Y—La | Li/Rb/Ca/Zr—La | Li/Rb/Ca/Pr—La | Li/Rb/Ca/Ce—La |
| Li/K | Li/K/$La_{3.8}Nd_{0.2}O6$ | Li/K/Y—La | Li/K/Zr—La | Li/K/Pr—La | Li/K/Ce—La |
| Tm/Lu/Ta/P | Tm/Lu/Ta/P/$La_{3.8}Nd_{0.2}O6$ | Tm/Lu/Ta/P/Y—La | Tm/Lu/Ta/P/Zr—La | Tm/Lu/Ta/P/Pr—La | Tm/Lu/Ta/P/Ce—La |
| Rb/Ca/Dy/P | Rb/Ca/Dy/P/$La_{3.8}Nd_{0.2}O6$ | Rb/Ca/Dy/P/Y—La | Rb/Ca/Dy/P/Zr—La | Rb/Ca/Dy/P/Pr—La | Rb/Ca/Dy/P/Ce—La |
| Mg/La/Yb/Zn | Mg/La/Yb/Zn/$La_{3.8}Nd_{0.2}O6$ | Mg/La/Yb/Zn/Y—La | Mg/La/Yb/Zn/Zr—La | Mg/La/Yb/Zn/Pr—La | Mg/La/Yb/Zn/Ce—La |
| Rb/Sr/Lu | Rb/Sr/Lu/$La_{3.8}Nd_{0.2}O6$ | Rb/Sr/Lu/Y—La | Rb/Sr/Lu/Zr—La | Rb/Sr/Lu/Pr—La | Rb/Sr/Lu/Ce—La |
| Na/Sr/Lu/Nb | Na/Sr/Lu/Nb/$La_{3.8}Nd_{0.2}O6$ | Na/Sr/Lu/Nb/Y—La | Na/Sr/Lu/Nb/Zr—La | Na/Sr/Lu/Nb/Pr—La | Na/Sr/Lu/Nb/Ce—La |
| Na/Eu/Hf | Na/Eu/Hf/$La_{3.8}Nd_{0.2}O6$ | Na/Eu/Hf/Y—La | Na/Eu/Hf/Zr—La | Na/Eu/Hf/Pr—La | Na/Eu/Hf/Ce—La |
| Dy/Rb/Gd | Dy/Rb/Gd/$La_{3.8}Nd_{0.2}O6$ | Dy/Rb/Gd/Y—La | Dy/Rb/Gd/Zr—La | Dy/Rb/Gd/Pr—La | Dy/Rb/Gd/Ce—La |
| Na/Pt/Bi | Na/Pt/Bi/$La_{3.8}Nd_{0.2}O6$ | Na/Pt/Bi/Y—La | Na/Pt/Bi/Zr—La | Na/Pt/Bi/Pr—La | Na/Pt/Bi/Ce—La |
| Rb/Hf | Rb/Hf/$La_{3.8}Nd_{0.2}O6$ | Rb/Hf/Y—La | Rb/Hf/Zr—La | Rb/Hf/Pr—La | Rb/Hf/Ce—La |
| Ca/Cs | Ca/Cs/$La_{3.8}Nd_{0.2}O6$ | Ca/Cs/Y—La | Ca/Cs/Zr—La | Ca/Cs/Pr—La | Ca/Cs/Ce—La |
| Ca/Mg/Na | Ca/Mg/Na/$La_{3.8}Nd_{0.2}O6$ | Ca/Mg/Na/Y—La | Ca/Mg/Na/Zr—La | Ca/Mg/Na/Pr—La | Ca/Mg/Na/Ce—La |
| Hf/Bi | Hf/Bi/$La_{3.8}Nd_{0.2}O6$ | Hf/Bi/Y—La | Hf/Bi/Zr—La | Hf/Bi/Pr—La | Hf/Bi/Ce—La |

TABLE 3-continued

CATALYSTS (CAT) DOPED WITH SPECIFIC DOPANTS (DOP)

| Dop\Cat | $La_{3.8}Nd_{0.2}O6$ | Y—La | Zr—La | Pr—La | Ce—La |
|---|---|---|---|---|---|
| Sr/Sn | Sr/Sn/$La_{3.8}Nd_{0.2}O6$ | Sr/Sn/Y—La | Sr/Sn/Zr—La | Sr/Sn/Pr—La | Sr/Sn/Ce—La |
| Sr/W | Sr/W/$La_{3.8}Nd_{0.2}O6$ | Sr/W/Y—La | Sr/W/Zr—La | Sr/W/Pr—La | Sr/W/Ce—La |
| Sr/Nb | Sr/Nb/$La_{3.8}Nd_{0.2}O6$ | Sr/Nb/Y—La | Sr/Nb/Zr—La | Sr/Nb/Pr—La | Sr/Nb/Ce—La |
| Zr/W | Zr/W/$La_{3.8}Nd_{0.2}O6$ | Zr/W/Y—La | Zr/W/Zr—La | Zr/W/Pr—La | Zr/W/Ce—La |
| Y/W | Y/W/$La_{3.8}Nd_{0.2}O6$ | Y/W/Y—La | Y/W/Zr—La | Y/W/Pr—La | Y/W/Ce—La |
| Na/W | Na/W/$La_{3.8}Nd_{0.2}O6$ | Na/W/Y—La | Na/W/Zr—La | Na/W/Pr—La | Na/W/Ce—La |
| Bi/W | Bi/W/$La_{3.8}Nd_{0.2}O6$ | Bi/W/Y—La | Bi/W/Zr—La | Bi/W/Pr—La | Bi/W/Ce—La |
| Bi/Cs | Bi/Cs/$La_{3.8}Nd_{0.2}O6$ | Bi/Cs/Y—La | Bi/Cs/Zr—La | Bi/Cs/Pr—La | Bi/Cs/Ce—La |
| Bi/Ca | Bi/Ca/$La_{3.8}Nd_{0.2}O6$ | Bi/Ca/Y—La | Bi/Ca/Zr—La | Bi/Ca/Pr—La | Bi/Ca/Ce—La |
| Bi/Sn | Bi/Sn/$La_{3.8}Nd_{0.2}O6$ | Bi/Sn/Y—La | Bi/Sn/Zr—La | Bi/Sn/Pr—La | Bi/Sn/Ce—La |
| Bi/Sb | Bi/Sb/$La_{3.8}Nd_{0.2}O6$ | Bi/Sb/Y—La | Bi/Sb/Zr—La | Bi/Sb/Pr—La | Bi/Sb/Ce—La |
| Ge/Hf | Ge/Hf/$La_{3.8}Nd_{0.2}O6$ | Ge/Hf/Y—La | Ge/Hf/Zr—La | Ge/Hf/Pr—La | Ge/Hf/Ce—La |
| Hf/Sm | Hf/Sm/$La_{3.8}Nd_{0.2}O6$ | Hf/Sm/Y—La | Hf/Sm/Zr—La | Hf/Sm/Pr—La | Hf/Sm/Ce—La |
| Sb/Ag | Sb/Ag/$La_{3.8}Nd_{0.2}O6$ | Sb/Ag/Y—La | Sb/Ag/Zr—La | Sb/Ag/Pr—La | Sb/Ag/Ce—La |
| Sb/Bi | Sb/Bi/$La_{3.8}Nd_{0.2}O6$ | Sb/Bi/Y—La | Sb/Bi/Zr—La | Sb/Bi/Pr—La | Sb/Bi/Ce—La |
| Sb/Au | Sb/Au/$La_{3.8}Nd_{0.2}O6$ | Sb/Au/Y—La | Sb/Au/Zr—La | Sb/Au/Pr—La | Sb/Au/Ce—La |
| Sb/Sm | Sb/Sm/$La_{3.8}Nd_{0.2}O6$ | Sb/Sm/Y—La | Sb/Sm/Zr—La | Sb/Sm/Pr—La | Sb/Sm/Ce—La |
| Sb/Sr | Sb/Sr/$La_{3.8}Nd_{0.2}O6$ | Sb/Sr/Y—La | Sb/Sr/Zr—La | Sb/Sr/Pr—La | Sb/Sr/Ce—La |
| Sb/W | Sb/W/$La_{3.8}Nd_{0.2}O6$ | Sb/W/Y—La | Sb/W/Zr—La | Sb/W/Pr—La | Sb/W/Ce—La |
| Sb/Hf | Sb/Hf/$La_{3.8}Nd_{0.2}O6$ | Sb/Hf/Y—La | Sb/Hf/Zr—La | Sb/Hf/Pr—La | Sb/Hf/Ce—La |
| Sb/Yb | Sb/Yb/$La_{3.8}Nd_{0.2}O6$ | Sb/Yb/Y—La | Sb/Yb/Zr—La | Sb/Yb/Pr—La | Sb/Yb/Ce—La |
| Sb/Sn | Sb/Sn/$La_{3.8}Nd_{0.2}O6$ | Sb/Sn/Y—La | Sb/Sn/Zr—La | Sb/Sn/Pr—La | Sb/Sn/Ce—La |
| Yb/Au | Yb/Au/$La_{3.8}Nd_{0.2}O6$ | Yb/Au/Y—La | Yb/Au/Zr—La | Yb/Au/Pr—La | Yb/Au/Ce—La |
| Yb/Ta | Yb/Ta/$La_{3.8}Nd_{0.2}O6$ | Yb/Ta/Y—La | Yb/Ta/Zr—La | Yb/Ta/Pr—La | Yb/Ta/Ce—La |
| Yb/W | Yb/W/$La_{3.8}Nd_{0.2}O6$ | Yb/W/Y—La | Yb/W/Zr—La | Yb/W/Pr—La | Yb/W/Ce—La |
| Yb/Sr | Yb/Sr/$La_{3.8}Nd_{0.2}O6$ | Yb/Sr/Y—La | Yb/Sr/Zr—La | Yb/Sr/Pr—La | Yb/Sr/Ce—La |
| Yb/Pb | Yb/Pb/$La_{3.8}Nd_{0.2}O6$ | Yb/Pb/Y—La | Yb/Pb/Zr—La | Yb/Pb/Pr—La | Yb/Pb/Ce—La |
| Yb/W | Yb/W/$La_{3.8}Nd_{0.2}O6$ | Yb/W/Y—La | Yb/W/Zr—La | Yb/W/Pr—La | Yb/W/Ce—La |
| Yb/Ag | Yb/Ag/$La_{3.8}Nd_{0.2}O6$ | Yb/Ag/Y—La | Yb/Ag/Zr—La | Yb/Ag/Pr—La | Yb/Ag/Ce—La |
| Au/Sr | Au/Sr/$La_{3.8}Nd_{0.2}O6$ | Au/Sr/Y—La | Au/Sr/Zr—La | Au/Sr/Pr—La | Au/Sr/Ce—La |
| W/Ge | W/Ge/$La_{3.8}Nd_{0.2}O6$ | W/Ge/Y—La | W/Ge/Zr—La | W/Ge/Pr—La | W/Ge/Ce—La |
| Ta/Sr | Ta/Sr/$La_{3.8}Nd_{0.2}O6$ | Ta/Sr/Y—La | Ta/Sr/Zr—La | Ta/Sr/Pr—La | Ta/Sr/Ce—La |
| Ta/Hf | Ta/Hf/$La_{3.8}Nd_{0.2}O6$ | Ta/Hf/Y—La | Ta/Hf/Zr—La | Ta/Hf/Pr—La | Ta/Hf/Ce—La |
| W/Au | W/Au/$La_{3.8}Nd_{0.2}O6$ | W/Au/Y—La | W/Au/Zr—La | W/Au/Pr—La | W/Au/Ce—La |
| Ca/W | Ca/W/$La_{3.8}Nd_{0.2}O6$ | Ca/W/Y—La | Ca/W/Zr—La | Ca/W/Pr—La | Ca/W/Ce—La |
| Au/Re | Au/Re/$La_{3.8}Nd_{0.2}O6$ | Au/Re/Y—La | Au/Re/Zr—La | Au/Re/Pr—La | Au/Re/Ce—La |
| Sm/Li | Sm/Li/$La_{3.8}Nd_{0.2}O6$ | Sm/Li/Y—La | Sm/Li/Zr—La | Sm/Li/Pr—La | Sm/Li/Ce—La |
| La/K | La/K/$La_{3.8}Nd_{0.2}O6$ | La/K/Y—La | La/K/Zr—La | La/K/Pr—La | La/K/Ce—La |

TABLE 3-continued

CATALYSTS (CAT) DOPED WITH SPECIFIC DOPANTS (DOP)

| Dop\Cat | La$_{3.8}$Nd$_{0.2}$O6 | Y—La | Zr—La | Pr—La | Ce—La |
|---|---|---|---|---|---|
| Zn/Cs | Zn/Cs/La$_{3.8}$Nd$_{0.2}$O6 | Zn/Cs/Y—La | Zn/Cs/Zr—La | Zn/Cs/Pr—La | Zn/Cs/Ce—La |
| Na/K/Mg | Na/K/Mg/La$_{3.8}$Nd$_{0.2}$O6 | Na/K/Mg/Y—La | Na/K/Mg/Zr—La | Na/K/Mg/Pr—La | Na/K/Mg/Ce—La |
| Zr/Cs | Zr/Cs/La$_{3.8}$Nd$_{0.2}$O6 | Zr/Cs/Y—La | Zr/Cs/Zr—La | Zr/Cs/Pr—La | Zr/Cs/Ce—La |
| Ca/Ce | Ca/Ce/La$_{3.8}$Nd$_{0.2}$O6 | Ca/Ce/Y—La | Ca/Ce/Zr—La | Ca/Ce/Pr—La | Ca/Ce/Ce—La |
| Na/Li/Cs | Na/Li/Cs/La$_{3.8}$Nd$_{0.2}$O6 | Na/Li/Cs/Y—La | Na/Li/Cs/Zr—La | Na/Li/Cs/Pr—La | Na/Li/Cs/Ce—La |
| Li/Sr | Li/Sr/La$_{3.8}$Nd$_{0.2}$O6 | Li/Sr/Y—La | Li/Sr/Zr—La | Li/Sr/Pr—La | Li/Sr/Ce—La |
| La/Dy/K | La/Dy/K/La$_{3.8}$Nd$_{0.2}$O6 | La/Dy/K/Y—La | La/Dy/K/Zr—La | La/Dy/K/Pr—La | La/Dy/K/Ce—La |
| Dy/K | Dy/K/La$_{3.8}$Nd$_{0.2}$O6 | Dy/K/Y—La | Dy/K/Zr—La | Dy/K/Pr—La | Dy/K/Ce—La |
| La/Mg | La/Mg/La$_{3.8}$Nd$_{0.2}$O6 | La/Mg/Y—La | La/Mg/Zr—La | La/Mg/Pr—La | La/Mg/Ce—La |
| Na/Nd/In/K | Na/Nd/In/K/La$_{3.8}$Nd$_{0.2}$O6 | Na/Nd/In/K/Y—La | Na/Nd/In/K/Zr—La | Na/Nd/In/K/Pr—La | Na/Nd/In/K/Ce—La |
| In/Sr | In/Sr/La$_{3.8}$Nd$_{0.2}$O6 | In/Sr/Y—La | In/Sr/Zr—La | In/Sr/Pr—La | In/Sr/Ce—La |
| Sr/Cs | Sr/Cs/La$_{3.8}$Nd$_{0.2}$O6 | Sr/Cs/Y—La | Sr/Cs/Zr—La | Sr/Cs/Pr—La | Sr/Cs/Ce—La |
| Rb/Ga/Tm/Cs | Rb/Ga/Tm/Cs/La$_{3.8}$Nd$_{0.2}$O6 | Rb/Ga/Tm/Cs/Y—La | Rb/Ga/Tm/Cs/Zr—La | Rb/Ga/Tm/Cs/Pr—La | Rb/Ga/Tm/Cs/Ce—La |
| Ga/Cs | Ga/Cs/La$_{3.8}$Nd$_{0.2}$O6 | Ga/Cs/Y—La | Ga/Cs/Zr—La | Ga/Cs/Pr—La | Ga/Cs/Ce—La |
| K/La/Zr/Ag | K/La/Zr/Ag/La$_{3.8}$Nd$_{0.2}$O6 | K/La/Zr/Ag/Y—La | K/La/Zr/Ag/Zr—La | K/La/Zr/Ag/Pr—La | K/La/Zr/Ag/Ce—La |
| Lu/Fe | Lu/Fe/La$_{3.8}$Nd$_{0.2}$O6 | Lu/Fe/Y—La | Lu/Fe/Zr—La | Lu/Fe/Pr—La | Lu/Fe/Ce—La |
| Sr/Tm | Sr/Tm/La$_{3.8}$Nd$_{0.2}$O6 | Sr/Tm/Y—La | Sr/Tm/Zr—La | Sr/Tm/Pr—La | Sr/Tm/Ce—La |
| La/Dy | La/Dy/La$_{3.8}$Nd$_{0.2}$O6 | La/Dy/Y—La | La/Dy/Zr—La | La/Dy/Pr—La | La/Dy/Ce—La |
| Sm/Li/Sr | Sm/Li/Sr/La$_{3.8}$Nd$_{0.2}$O6 | Sm/Li/Sr/Y—La | Sm/Li/Sr/Zr—La | Sm/Li/Sr/Pr—La | Sm/Li/Sr/Ce—La |
| Mg/K | Mg/K/La$_{3.8}$Nd$_{0.2}$O6 | Mg/K/Y—La | Mg/K/Zr—La | Mg/K/Pr—La | Mg/K/Ce—La |
| Li/Rb/Ga | Li/Rb/Ga/La$_{3.8}$Nd$_{0.2}$O6 | Li/Rb/Ga/Y—La | Li/Rb/Ga/Zr—La | Li/Rb/Ga/Pr—La | Li/Rb/Ga/Ce—La |
| Li/Cs/Tm | Li/Cs/Tm/La$_{3.8}$Nd$_{0.2}$O6 | Li/Cs/Tm/Y—La | Li/Cs/Tm/Zr—La | Li/Cs/Tm/Pr—La | Li/Cs/Tm/Ce—La |
| Zr/K | Zr/K/La$_{3.8}$Nd$_{0.2}$O6 | Zr/K/Y—La | Zr/K/Zr—La | Zr/K/Pr—La | Zr/K/Ce—La |
| Li/Cs | Li/Cs/La$_{3.8}$Nd$_{0.2}$O6 | Li/Cs/Y—La | Li/Cs/Zr—La | Li/Cs/Pr—La | Li/Cs/Ce—La |
| Li/K/La | Li/K/La/La$_{3.8}$Nd$_{0.2}$O6 | Li/K/La/Y—La | Li/K/La/Zr—La | Li/K/La/Pr—La | Li/K/La/Ce—La |
| Ce/Zr/La | Ce/Zr/La/La$_{3.8}$Nd$_{0.2}$O6 | Ce/Zr/La/Y—La | Ce/Zr/La/Zr—La | Ce/Zr/La/Pr—La | Ce/Zr/La/Ce—La |
| Ca/Al/La | Ca/Al/La/La$_{3.8}$Nd$_{0.2}$O6 | Ca/Al/La/Y—La | Ca/Al/La/Zr—La | Ca/Al/La/Pr—La | Ca/Al/La/Ce—La |
| Sr/Zn/La | Sr/Zn/La/La$_{3.8}$Nd$_{0.2}$O6 | Sr/Zn/La/Y—La | Sr/Zn/La/Zr—La | Sr/Zn/La/Pr—La | Sr/Zn/La/Ce—La |
| Sr/Cs/Zn | Sr/Cs/Zn/La$_{3.8}$Nd$_{0.2}$O6 | Sr/Cs/Zn/Y—La | Sr/Cs/Zn/Zr—La | Sr/Cs/Zn/Pr—La | Sr/Cs/Zn/Ce—La |
| Sm/Cs | Sm/Cs/La$_{3.8}$Nd$_{0.2}$O6 | Sm/Cs/Y—La | Sm/Cs/Zr—La | Sm/Cs/Pr—La | Sm/Cs/Ce—La |
| In/K | In/K/La$_{3.8}$Nd$_{0.2}$O6 | In/K/Y—La | In/K/Zr—La | In/K/Pr—La | In/K/Ce—La |
| Ho/Cs/Li/La | Ho/Cs/Li/La/La$_{3.8}$Nd$_{0.2}$O6 | Ho/Cs/Li/La/Y—La | Ho/Cs/Li/La/Zr—La | Ho/Cs/Li/La/Pr—La | Ho/Cs/Li/La/Ce—La |
| Cs/La/Na | Cs/La/Na/La$_{3.8}$Nd$_{0.2}$O6 | Cs/La/Na/Y—La | Cs/La/Na/Zr—La | Cs/La/Na/Pr—La | Cs/La/Na/Ce—La |
| La/S/Sr | La/S/Sr/La$_{3.8}$Nd$_{0.2}$O6 | La/S/Sr/Y—La | La/S/Sr/Zr—La | La/S/Sr/Pr—La | La/S/Sr/Ce—La |
| K/La/Zr/Ag | K/La/Zr/Ag/La$_{3.8}$Nd$_{0.2}$O6 | K/La/Zr/Ag/Y—La | K/La/Zr/Ag/Zr—La | K/La/Zr/Ag/Pr—La | K/La/Zr/Ag/Ce—La |
| Lu/Tl | Lu/Tl/La$_{3.8}$Nd$_{0.2}$O6 | Lu/Tl/Y—La | Lu/Tl/Zr—La | Lu/Tl/Pr—La | Lu/Tl/Ce—La |
| Pr/Zn | Pr/Zn/La$_{3.8}$Nd$_{0.2}$O6 | Pr/Zn/Y—La | Pr/Zn/Zr—La | Pr/Zn/Pr—La | Pr/Zn/Ce—La |
| Rb/Sr/La | Rb/Sr/La/La$_{3.8}$Nd$_{0.2}$O6 | Rb/Sr/La/Y—La | Rb/Sr/La/Zr—La | Rb/Sr/La/Pr—La | Rb/Sr/La/Ce—La |

TABLE 3-continued

CATALYSTS (CAT) DOPED WITH SPECIFIC DOPANTS (DOP)

| Dop\Cat | $La_{3.8}Nd_{0.2}O6$ | Y—La | Zr—La | Pr—La | Ce—La |
|---|---|---|---|---|---|
| Na/Sr/Eu/Ca | Na/Sr/Eu/Ca/ $La_{3.8}Nd_{0.2}O6$ | Na/Sr/Eu/Ca/ Y—La | Na/Sr/Eu/Ca/ Zr—La | Na/Sr/Eu/Ca/ Pr—La | Na/Sr/Eu/Ca/ Ce—La |
| K/Cs/Sr/La | K/Cs/Sr/La/ $La_{3.8}Nd_{0.2}O6$ | K/Cs/Sr/La/ Y—La | K/Cs/Sr/La/ Zr—La | K/Cs/Sr/La/ Pr—La | K/Cs/Sr/La/ Ce—La |
| Na/Sr/Lu | Na/Sr/Lu/ $La_{3.8}Nd_{0.2}O6$ | Na/Sr/Lu/ Y—La | Na/Sr/Lu/ Zr—La | Na/Sr/Lu/ Pr—La | Na/Sr/Lu/ Ce—La |
| Sr/Eu/Dy | Sr/Eu/Dy/ $La_{3.8}Nd_{0.2}O6$ | Sr/Eu/Dy/ Y—La | Sr/Eu/Dy/ Zr—La | Sr/Eu/Dy/ Pr—La | Sr/Eu/Dy/ Ce—La |
| Lu/Nb | Lu/Nb/ $La_{3.8}Nd_{0.2}O6$ | Lu/Nb/ Y—La | Lu/Nb/ Zr—La | Lu/Nb/ Pr—La | Lu/Nb/ Ce—La |
| La/Dy/Gd | La/Dy/Gd/ $La_{3.8}Nd_{0.2}O6$ | La/Dy/Gd/ Y—La | La/Dy/Gd/ Zr—La | La/Dy/Gd/ Pr—La | La/Dy/Gd/ Ce—La |
| Na/Mg/Tl/P | Na/Mg/Tl/P/ $La_{3.8}Nd_{0.2}O6$ | Na/Mg/Tl/P/ Y—La | Na/Mg/Tl/P/ Zr—La | Na/Mg/Tl/P/ Pr—La | Na/Mg/Tl/P/ Ce—La |
| Na/Pt | Na/Pt/ $La_{3.8}Nd_{0.2}O6$ | Na/Pt/ Y—La | Na/Pt/ Zr—La | Na/Pt/ Pr—La | Na/Pt/ Ce—La |
| Gd/Li/K | Gd/Li/K/ $La_{3.8}Nd_{0.2}O6$ | Gd/Li/K/ Y—La | Gd/Li/K/ Zr—La | Gd/Li/K/ Pr—La | Gd/Li/K/ Ce—La |
| Rb/K/Lu | Rb/K/Lu/ $La_{3.8}Nd_{0.2}O6$ | Rb/K/Lu/ Y—La | Rb/K/Lu/ Zr—La | Rb/K/Lu/ Pr—La | Rb/K/Lu/ Ce—La |
| Sr/La/Dy/S | Sr/La/Dy/S/ $La_{3.8}Nd_{0.2}O6$ | Sr/La/Dy/S/ Y—La | Sr/La/Dy/S/ Zr—La | Sr/La/Dy/S/ Pr—La | Sr/La/Dy/S/ Ce—La |
| Na/Ce/Co | Na/Ce/Co/ $La_{3.8}Nd_{0.2}O6$ | Na/Ce/Co/ Y—La | Na/Ce/Co/ Zr—La | Na/Ce/Co/ Pr—La | Na/Ce/Co/ Ce—La |
| Na/Ce | Na/Ce/ $La_{3.8}Nd_{0.2}O6$ | Na/Ce/ Y—La | Na/Ce/ Zr—La | Na/Ce/ Pr—La | Na/Ce/ Ce—La |
| Na/Ga/Gd/Al | Na/Ga/Gd/Al/ $La_{3.8}Nd_{0.2}O6$ | Na/Ga/Gd/Al/ Y—La | Na/Ga/Gd/Al/ Zr—La | Na/Ga/Gd/Al/ Pr—La | Na/Ga/Gd/Al/ Ce—La |
| Ba/Rh/Ta | Ba/Rh/Ta/ $La_{3.8}Nd_{0.2}O6$ | Ba/Rh/Ta/ Y—La | Ba/Rh/Ta/ Zr—La | Ba/Rh/Ta/ Pr—La | Ba/Rh/Ta/ Ce—La |
| Ba/Ta | Ba/Ta/ $La_{3.8}Nd_{0.2}O6$ | Ba/Ta/ Y—La | Ba/Ta/ Zr—La | Ba/Ta/ Pr—La | Ba/Ta/ Ce—La |
| Na/Al/Bi | Na/Al/Bi/ $La_{3.8}Nd_{0.2}O6$ | Na/Al/Bi/ Y—La | Na/Al/Bi/ Zr—La | Na/Al/Bi/ Pr—La | Na/Al/Bi/ Ce—La |
| Cs/Eu/S | Cs/Eu/S/ $La_{3.8}Nd_{0.2}O6$ | Cs/Eu/S/ Y—La | Cs/Eu/S/ Zr—La | Cs/Eu/S/ Pr—La | Cs/Eu/S/ Ce—La |
| Sm/Tm/Yb/Fe | Sm/Tm/Yb/Fe/ $La_{3.8}Nd_{0.2}O6$ | Sm/Tm/Yb/Fe/ Y—La | Sm/Tm/Yb/Fe/ Zr—La | Sm/Tm/Yb/Fe/ Pr—La | Sm/Tm/Yb/Fe/ Ce—La |
| Sm/Tm/Yb | Sm/Tm/Yb/ $La_{3.8}Nd_{0.2}O6$ | Sm/Tm/Yb/ Y—La | Sm/Tm/Yb/ Zr—La | Sm/Tm/Yb/ Pr—La | Sm/Tm/Yb/ Ce—La |
| Hf/Zr/Ta | Hf/Zr/Ta/ $La_{3.8}Nd_{0.2}O6$ | Hf/Zr/Ta/ Y—La | Hf/Zr/Ta/ Zr—La | Hf/Zr/Ta/ Pr—La | Hf/Zr/Ta/ Ce—La |
| Rb/Gd/Li/K | Rb/Gd/Li/K/ $La_{3.8}Nd_{0.2}O6$ | Rb/Gd/Li/K/ Y—La | Rb/Gd/Li/K/ Zr—La | Rb/Gd/Li/K/ Pr—LAl/K | Rb/Gd/Li/K/ Ce—La |
| Gd/Ho/Al/P | Gd/Ho/Al/P/ $La_{3.8}Nd_{0.2}O6$ | Gd/Ho/Al/P/ Y—La | Gd/Ho/Al/P/ Zr—La | Gd/Ho/Al/P/ Pr—La | Gd/Ho/Al/P/ Ce—La |
| Na/Ca/Lu | Na/Ca/Lu/ $La_{3.8}Nd_{0.2}O6$ | Na/Ca/Lu/ Y—La | Na/Ca/Lu/ Zr—La | Na/Ca/Lu/ Pr—La | Na/Ca/Lu/ Ce—La |
| Cu/Sn | Cu/Sn/ $La_{3.8}Nd_{0.2}O6$ | Cu/Sn/ Y—La | Cu/Sn/ Zr—La | Cu/Sn/ Pr—La | Cu/Sn/ Ce—La |
| Ag/Au | Ag/Au/ $La_{3.8}Nd_{0.2}O6$ | Ag/Au/ Y—La | Ag/Au/ Zr—La | Ag/Au/ Pr—La | Ag/Au/ Ce—La |
| Al/Bi | Al/Bi/ $La_{3.8}Nd_{0.2}O6$ | Al/Bi/ Y—La | Al/Bi/ Zr—La | Al/Bi/ Pr—La | Al/Bi/ Ce—La |
| Al/Mo | Al/Mo/ $La_{3.8}Nd_{0.2}O6$ | Al/Mo/ Y—La | Al/Mo/ Zr—La | Al/Mo/ Pr—La | Al/Mo/ Ce—La |
| Al/Nb | Al/Nb/ $La_{3.8}Nd_{0.2}O6$ | Al/Nb/ Y—La | Al/Nb/ Zr—La | Al/Nb/ Pr—La | Al/Nb/ Ce—La |
| Au/Pt | Au/Pt/ $La_{3.8}Nd_{0.2}O6$ | Au/Pt/ Y—La | Au/Pt/ Zr—La | Au/Pt/ Pr—La | Au/Pt/ Ce—La |
| Ga/Bi | Ga/Bi/ $La_{3.8}Nd_{0.2}O6$ | Ga/Bi/ Y—La | Ga/Bi/ Zr—La | Ga/Bi/ Pr—La | Ga/Bi/ Ce—La |
| Mg/W | Mg/W/ $La_{3.8}Nd_{0.2}O6$ | Mg/W/ Y—La | Mg/W/ Zr—La | Mg/W/ Pr—La | Mg/W/ Ce—La |
| Pb/Au | Pb/Au/ $La_{3.8}Nd_{0.2}O6$ | Pb/Au/ Y—La | Pb/Au/ Zr—La | Pb/Au/ Pr—La | Pb/Au/ Ce—La |
| Sn/Mg | Sn/Mg/ $La_{3.8}Nd_{0.2}O6$ | Sn/Mg/ Y—La | Sn/Mg/ Zr—La | Sn/Mg/ Pr—La | Sn/Mg/ Ce—La |
| Zn/Bi | Zn/Bi/ $La_{3.8}Nd_{0.2}O6$ | Zn/Bi/ Y—La | Zn/Bi/ Zr—La | Zn/Bi/ Pr—La | Zn/Bi/ Ce—La |
| Sr/Ta | Sr/Ta/ $La_{3.8}Nd_{0.2}O6$ | Sr/Ta/ Y—La | Sr/Ta/ Zr—La | Sr/Ta/ Pr—La | Sr/Ta/ Ce—La |
| Na | Na/ $La_{3.8}Nd_{0.2}O6$ | Na/ Y—La | Na/ Zr—La | Na/ Pr—La | Na/ Ce—La |
| Sr | Sr/ $La_{3.8}Nd_{0.2}O6$ | Sr/ Y—La | Sr/ Zr—La | Sr/ Pr—La | Sr/ Ce—La |

TABLE 3-continued

CATALYSTS (CAT) DOPED WITH SPECIFIC DOPANTS (DOP)

| Dop\Cat | $La_{3.8}Nd_{0.2}O6$ | Y—La | Zr—La | Pr—La | Ce—La |
|---|---|---|---|---|---|
| Ca | Ca/ $La_{3.8}Nd_{0.2}O6$ | Ca/ Y—La | Ca/ Zr—La | Ca/ Pr—La | Ca/ Ce—La |
| Yb | Yb/ $La_{3.8}Nd_{0.2}O6$ | Yb/ Y—La | Yb/ Zr—La | Yb/ Pr—La | Yb/ Ce—La |
| Cs | Cs/ $La_{3.8}Nd_{0.2}O6$ | Cs/ Y—La | Cs/ Zr—La | Cs/ Pr—La | Cs/ Ce—La |
| Sb | Sb/ $La_{3.8}Nd_{0.2}O6$/ Zn/Bi | Sb/ Y—La/ Zn/Bi | Sb/ Zr—La/ Zn/Bi | Sb/ Pr—La/ Zn/Bi | Sb/ Ce—La/ Zn/Bi |
| Gd/Ho | Gd/Ho/ $La_{3.8}Nd_{0.2}O6$ | Gd/Ho/ Y—La | Gd/Ho/ Zr—La | Gd/Ho/ Pr—La | Gd/Ho/ Ce—La |
| Zr/Bi | Zr/Bi/ $La_{3.8}Nd_{0.2}O6$ | Zr/Bi/ Y—La | Zr/Bi/ Zr—La | Zr/Bi/ Pr—La | Zr/Bi/ Ce—La |
| Ho/Sr | Ho/Sr/ $La_{3.8}Nd_{0.2}O6$ | Ho/Sr/ Y—La | Ho/Sr/ Zr—La | Ho/Sr/ Pr—La | Ho/Sr/ Ce—La |
| Gd/Ho/Sr | Gd/Ho/Sr/ $La_{3.8}Nd_{0.2}O6$ | Gd/Ho/Sr/ Y—La | Gd/Ho/Sr/ Zr—La | Gd/Ho/Sr/ Pr—La | Gd/Ho/Sr/ Ce—La |
| Ca/Sr | Ca/Sr/ $La_{3.8}Nd_{0.2}O6$ | Ca/Sr/ Y—La | Ca/Sr/ Zr—La | Ca/Sr/ Pr—La | Ca/Sr/ Ce—La |
| Ca/Sr/W | Ca/Sr/W/ $La_{3.8}Nd_{0.2}O6$ | Ca/Sr/W/ Y—La | Ca/Sr/W/ Zr—La | Ca/Sr/W/ Pr—La | Ca/Sr/W/ Ce—La |
| Na/Zr/Eu/Tm | Na/Zr/Eu/Tm/ $La_{3.8}Nd_{0.2}O6$ | Na/Zr/Eu/Tm/ Y—La | Na/Zr/Eu/Tm/ Zr—La | Na/Zr/Eu/Tm/ Pr—La | Na/Zr/Eu/Tm/ Ce—La |
| Sr/Ho/Tm/Na | Sr/Ho/Tm/Na/ $La_{3.8}Nd_{0.2}O6$ | Sr/Ho/Tm/Na/ Y—La | Sr/Ho/Tm/Na/ Zr—La | Sr/Ho/Tm/Na/ Pr—La | Sr/Ho/Tm/Na/ Ce—La |
| Sr/Pb | Sr/Pb/ $La_{3.8}Nd_{0.2}O6$ | Sr/Pb/ Y—La | Sr/Pb/ Zr—La | Sr/Pb/ Pr—La | Sr/Pb/ Ce—La |
| Sr/W/Li | Sr/W/Li/ $La_{3.8}Nd_{0.2}O6$ | Sr/W/Li/ Y—La | Sr/W/Li/ Zr—La | Sr/W/Li/ Pr—La | Sr/W/Li/ Ce—La |
| Ca/Sr/W | Ca/Sr/W/ $La_{3.8}Nd_{0.2}O6$ | Ca/Sr/W/ Y—La | Ca/Sr/W/ Zr—La | Ca/Sr/W/ Pr—La | Ca/Sr/W/ Ce—La |
| Sr/Hf | Sr/Hf/ $La_{3.8}Nd_{0.2}O6$ | Sr/Hf/ Y—La | Sr/Hf/ Zr—La | Sr/Hf/ Pr—La | Sr/Hf/ Ce—La |
| Au/Re | Au/Re/ $La_{3.8}Nd_{0.2}O6$ | Au/Re/ Y—La | Au/Re/ Zr—La | Au/Re/ Pr—La | Au/Re/ Ce—La |
| Sr/W | Sr/W/ $La_{3.8}Nd_{0.2}O6$ | Sr/W/ Y—La | Sr/W/ Zr—La | Sr/W/ Pr—La | Sr/W/ Ce—La |
| La/Nd | La/Nd/ $La_{3.8}Nd_{0.2}O6$ | La/Nd/ Y—La | La/Nd/ Zr—La | La/Nd/ Pr—La | La/Nd/ Ce—La |
| La/Sm | La/Sm/ $La_{3.8}Nd_{0.2}O_6$ | La/Sm/ Y—La | La/Sm/ Zr—La | La/Sm/ Pr—La | La/Sm/ Ce—La |
| La/Ce | La/Ce/ $La_{3.8}Nd_{0.2}O_6$ | La/Ce/ Y—La | La/Ce/ Zr—La | La/Ce/ Pr—La | La/Ce/ Ce—La |
| La/Sr | La/Sr/ $La_{3.8}Nd_{0.2}O_6$ | La/Sr/ Y—La | La/Sr/ Zr—La | La/Sr/ Pr—La | La/Sr/ Ce—La |
| La/Nd/Sr | La/Nd/Sr/ $La_{3.8}Nd_{0.2}O_6$ | La/Nd/Sr/ Y—La | La/Nd/Sr/ Zr—La | La/Nd/Sr/ Pr—La | La/Nd/Sr/ Ce—La |
| La/Bi/Sr | La/Bi/Sr/ $La_{3.8}Nd_{0.2}O_6$ | La/Bi/Sr/ Y—La | La/Bi/Sr/ Zr—La | La/Bi/Sr/ Pr—La | La/Bi/Sr/ Ce—La |
| La/Ce/Nd/Sr | La/Ce/Nd/Sr/ $La_{3.8}Nd_{0.2}O_6$ | La/Ce/Nd/Sr/ Y—La | La/Ce/Nd/Sr/ Zr—La | La/Ce/Nd/Sr/ Pr—La | La/Ce/Nd/Sr/ Ce—La |
| La/Bi/Ce/Nd/Sr | La/Bi/Ce/Nd/Sr/ $La_{3.8}Nd_{0.2}O_6$ | La/Bi/Ce/Nd/Sr/ Y—La | La/Bi/Ce/Nd/Sr/ Zr—La | La/Bi/Ce/Nd/Sr/ Pr—La | La/Bi/Ce/Nd/Sr/ Ce—La |
| Eu/Gd | Eu/Gd/ $La_{3.8}Nd_{0.2}O_6$ | Eu/Gd/ Y—La | Eu/Gd/ Zr—La | Eu/Gd/ Pr—La | Eu/Gd/ Ce—La |
| Ca/Na | Ca/Na/ $La_{3.8}Nd_{0.2}O_6$ | Ca/Na/ Y—La | Ca/Na/ Zr—La | Ca/Na/ Pr—La | Ca/Na/ Ce—La |
| Eu/Sm | Eu/Sm/ $La_{3.8}Nd_{0.2}O_6$ | Eu/Sm/ Y—La | Eu/Sm/ Zr—La | Eu/Sm/ Pr—La | Eu/Sm/ Ce—La |
| Eu/Sr | Eu/Sr/ $La_{3.8}Nd_{0.2}O_6$ | Eu/Sr/ Y—La | Eu/Sr/ Zr—La | Eu/Sr/ Pr—La | Eu/Sr/ Ce—La |
| Mg/Sr | Mg/Sr/ $La_{3.8}Nd_{0.2}O_6$ | Mg/Sr/ Y—La | Mg/Sr/ Zr—La | Mg/Sr/ Pr—La | Mg/Sr/ Ce—La |
| Ce/Mg | Ce/Mg/ $La_{3.8}Nd_{0.2}O_6$ | Ce/Mg/ Y—La | Ce/Mg/ Zr—La | Ce/Mg/ Pr—La | Ce/Mg/ Ce—La |
| Gd/Sm | Gd/Sm/ $La_{3.8}Nd_{0.2}O_6$ | Gd/Sm/ Y—La | Gd/Sm/ Zr—La | Gd/Sm/ Pr—La | Gd/Sm/ Ce—La |
| Au/Pb | Au/Pb/ $La_{3.8}Nd_{0.2}O_6$ | Au/Pb/ Y—La | Au/Pb/ Zr—La | Au/Pb/ Pr—La | Au/Pb/ Ce—La |
| Bi/Hf | Bi/Hf/ $La_{3.8}Nd_{0.2}O_6$ | Bi/Hf/ Y—La | Bi/Hf/ Zr—La | Bi/Hf/ Pr—La | Bi/Hf/ Ce—La |
| Rb/S | Rb/S/ $La_{3.8}Nd_{0.2}O_6$ | Rb/S/ Y—La | Rb/S/ Zr—La | Rb/S/ Pr—La | Rb/S/ Ce—La |
| Sr/Nd | Sr/Nd/ $La_{3.8}Nd_{0.2}O_6$ | Sr/Nd/ Y—La | Sr/Nd/ Zr—La | Sr/Nd/ Pr—La | Sr/Nd/ Ce—La |

TABLE 3-continued

CATALYSTS (CAT) DOPED WITH SPECIFIC DOPANTS (DOP)

| Dop\Cat | $La_{3.8}Nd_{0.2}O_6$ | Y—La | Zr—La | Pr—La | Ce—La |
|---|---|---|---|---|---|
| Eu/Y | Eu/Y/ $La_{3.8}Nd_{0.2}O_6$ | Eu/Y/ Y—La | Eu/Y/ Zr—La | Eu/Y/ Pr—La | Eu/Y/ Ce—La |
| Mg/Nd | Mg/Nd/ $La_{3.8}Nd_{0.2}O_6$ | Mg/Nd/ Y—La | Mg/Nd/ Zr—La | Mg/Nd/ Pr—La | Mg/Nd/ Ce—La |
| La/Mg | La/Mg/ $La_{3.8}Nd_{0.2}O_6$ | La/Mg/ Y—La | La/Mg/ Zr—La | La/Mg/ Pr—La | La/Mg/ Ce—La |
| Mg/Nd/Fe | Mg/Nd/Fe/ $La_{3.8}Nd_{0.2}O_6$ | Mg/Nd/Fe/ Y—La | Mg/Nd/Fe/ Zr—La | Mg/Nd/Fe/ Pr—La | Mg/Nd/Fe/ Ce—La |
| Rb/Sr | Rb/Sr/ $La_{3.8}Nd_{0.2}O_6$ | Rb/Sr/ Y—La | Rb/Sr/ Zr—La | Rb/Sr/ Pr—La | Rb/Sr/ Ce—La |

TABLE 4

CATALYSTS (CAT) DOPED WITH SPECIFIC DOPANTS (DOP)

| Dop\Cat | $Ln1_{4-x}Ln2_xO_6$ | $La_{4-x}Ln1_xO_6$ | $Y_2O_3$ | MgO |
|---|---|---|---|---|
| Eu/Na | Eu/Na/ $Ln1_{4-x}Ln2_xO_6$ | Eu/Na/ $La_{4-x}Ln1_xO_6$ | Eu/Na/ $Y_2O_3$ | Eu/Na/ MgO |
| Sr/Na | Sr/Na/ $Ln1_{4-x}Ln2_xO_6$ | Sr/Na/ $La_{4-x}Ln1_xO_6$ | Sr/Na/ $Y_2O_3$ | Sr/Na/ MgO |
| Na/Zr/Eu/Ca | Na/Zr/Eu/Ca/ $Ln1_{4-x}Ln2_xO_6$ | Na/Zr/Eu/Ca/ $La_{4-x}Ln1_xO_6$ | Na/Zr/Eu/Ca/ $Y_2O_3$ | Na/Zr/Eu/Ca/ MgO |
| Mg/Na | Mg/Na/ $Ln1_{4-x}Ln2_xO_6$ | Mg/Na/ $La_{4-x}Ln1_xO_6$ | Mg/Na/ $Y_2O_3$ | Mg/Na/ MgO |
| Sr/Sm/Ho/Tm | Sr/Sm/Ho/Tm/ $Ln1_{4-x}Ln2_xO_6$ | Sr/Sm/Ho/Tm/ $La_{4-x}Ln1_xO_6$ | Sr/Sm/Ho/Tm/ $Y_2O_3$ | Sr/Sm/Ho/Tm/ MgO |
| Sr/W | Sr/W/ $Ln1_{4-x}Ln2_xO_6$ | Sr/W/ $La_{4-x}Ln1_xO_6$ | Sr/W/ $Y_2O_3$ | Sr/W/ MgO |
| Mg/La/K | Mg/La/K/ $Ln1_{4-x}Ln2_xO_6$ | Mg/La/K/ $La_{4-x}Ln1_xO_6$ | Mg/La/K/ $Y_2O_3$ | Mg/La/K/ MgO |
| Na/K/Mg/Tm | Na/K/Mg/Tm/ $Ln1_{4-x}Ln2_xO_6$ | Na/K/Mg/Tm/ $La_{4-x}Ln1_xO_6$ | Na/K/Mg/Tm/ $Y_2O_3$ | Na/K/Mg/Tm/ MgO |
| Na/Dy/K | Na/Dy/K/ $Ln1_{4-x}Ln2_xO_6$ | Na/Dy/K/ $La_{4-x}Ln1_xO_6$ | Na/Dy/K/ $Y_2O_3$ | Na/Dy/K/ MgO |
| Na/La/Dy | Na/La/Dy/ $Ln1_{4-x}Ln2_xO_6$ | Na/La/Dy/ $La_{4-x}Ln1_xO_6$ | Na/La/Dy/ $Y_2O_3$ | Na/La/Dy/ MgO |
| Na/La/Eu | Na/La/Eu/ $Ln1_{4-x}Ln2_xO_6$ | Na/La/Eu/ $La_{4-x}Ln1_xO_6$ | Na/La/Eu/ $Y_2O_3$ | Na/La/Eu/ MgO |
| Na/La/Eu/In | Na/La/Eu/In/ $Ln1_{4-x}Ln2_xO_6$ | Na/La/Eu/In/ $La_{4-x}Ln1_xO_6$ | Na/La/Eu/In/ $Y_2O_3$ | Na/La/Eu/In/ MgO |
| Na/La/K | Na/La/K/ $Ln1_{4-x}Ln2_xO_6$ | Na/La/K/ $La_{4-x}Ln1_xO_6$ | Na/La/K/ $Y_2O_3$ | Na/La/K/ MgO |
| Na/La/Li/Cs | Na/La/Li/Cs/ $Ln1_{4-x}Ln2_xO_6$ | Na/La/Li/Cs/ $La_{4-x}Ln1_xO_6$ | Na/La/Li/Cs/ $Y_2O_3$ | Na/La/Li/Cs/ MgO |
| K/La | K/La/ $Ln1_{4-x}Ln2_xO_6$ | K/La/ $La_{4-x}Ln1_xO_6$ | K/La/ $Y_2O_3$ | K/La/ MgO |
| K/La/S | K/La/S/ $Ln1_{4-x}Ln2_xO_6$ | K/La/S/ $La_{4-x}Ln1_xO_6$ | K/La/S/ $Y_2O_3$ | K/La/S/ MgO |
| K/Na | K/Na/ $Ln1_{4-x}Ln2_xO_6$ | K/Na/ $La_{4-x}Ln1_xO_6$ | K/Na/ $Y_2O_3$ | K/Na/ MgO |
| Li/Cs | Li/Cs/ $Ln1_{4-x}Ln2_xO_6$ | Li/Cs/ $La_{4-x}Ln1_xO_6$ | Li/Cs/ $Y_2O_3$ | Li/Cs/ MgO |
| Li/Cs/La | Li/Cs/La/ $Ln1_{4-x}Ln2_xO_6$ | Li/Cs/La/ $La_{4-x}Ln1_xO_6$ | Li/Cs/La/ $Y_2O_3$ | Li/Cs/La/ MgO |
| Li/Cs/La/Tm | Li/Cs/La/Tm/ $Ln1_{4-x}Ln2_xO_6$ | Li/Cs/La/Tm/ $La_{4-x}Ln1_xO_6$ | Li/Cs/La/Tm/ $Y_2O_3$ | Li/Cs/La/Tm/ MgO |
| Li/Cs/Sr/Tm | Li/Cs/Sr/Tm/ $Ln1_{4-x}Ln2_xO_6$ | Li/Cs/Sr/Tm/ $La_{4-x}Ln1_xO_6$ | Li/Cs/Sr/Tm/ $Y_2O_3$ | Li/Cs/Sr/Tm/ MgO |
| Li/Sr/Cs | Li/Sr/Cs/ $Ln1_{4-x}Ln2_xO_6$ | Li/Sr/Cs/ $La_{4-x}Ln1_xO_6$ | Li/Sr/Cs/ $Y_2O_3$ | Li/Sr/Cs/ MgO |
| Li/Sr/Zn/K | Li/Sr/Zn/K/ $Ln1_{4-x}Ln2_xO_6$ | Li/Sr/Zn/K/ $La_{4-x}Ln1_xO_6$ | Li/Sr/Zn/K/ $Y_2O_3$ | Li/Sr/Zn/K/ MgO |
| Li/Ga/Cs | Li/Ga/Cs/ $Ln1_{4-x}Ln2_xO_6$ | Li/Ga/Cs/ $La_{4-x}Ln1_xO_6$ | Li/Ga/Cs/ $Y_2O_3$ | Li/Ga/Cs/ MgO |
| Li/K/Sr/La | Li/K/Sr/La/ $Ln1_{4-x}Ln2_xO_6$ | Li/K/Sr/La/ $La_{4-x}Ln1_xO_6$ | Li/K/Sr/La/ $Y_2O_3$ | Li/K/Sr/La/ MgO |
| Li/Na | Li/Na/ $Ln1_{4-x}Ln2_xO_6$ | Li/Na/ $La_{4-x}Ln1_xO_6$ | Li/Na/ $Y_2O_3$ | Li/Na/ MgO |
| Li/Na/Rb/Ga | Li/Na/Rb/Ga/ $Ln1_{4-x}Ln2_xO_6$ | Li/Na/Rb/Ga/ $La_{4-x}Ln1_xO_6$ | Li/Na/Rb/Ga/ $Y_2O_3$ | Li/Na/Rb/Ga/ MgO |
| Li/Na/Sr | Li/Na/Sr/ $Ln1_{4-x}Ln2_xO_6$ | Li/Na/Sr/ $La_{4-x}Ln1_xO_6$ | Li/Na/Sr/ $Y_2O_3$ | Li/Na/Sr/ MgO |

TABLE 4-continued

CATALYSTS (CAT) DOPED WITH SPECIFIC DOPANTS (DOP)

| Dop\Cat | $Ln1_{4-x}Ln2_xO_6$ | $La_{4-x}Ln1_xO_6$ | $Y_2O_3$ | MgO |
|---|---|---|---|---|
| Li/Na/Sr/La | Li/Na/Sr/La/ $Ln1_{4-x}Ln2_xO_6$ | Li/Na/Sr/La/ $La_{4-x}Ln1_xO_6$ | Li/Na/Sr/La/ $Y_2O_3$ | Li/Na/Sr/La/ MgO |
| Li/Sm/Cs | Li/Sm/Cs/ $Ln1_{4-x}Ln2_xO_6$ | Li/Sm/Cs/ $La_{4-x}Ln1_xO_6$ | Li/Sm/Cs/ $Y_2O_3$ | Li/Sm/Cs/ MgO |
| Ba/Sm/Yb/S | Ba/Sm/Yb/S/ $Ln1_{4-x}Ln2_xO_6$ | Ba/Sm/Yb/S/ $La_{4-x}Ln1_xO_6$ | Ba/Sm/Yb/S/ $Y_2O_3$ | Ba/Sm/Yb/S/ MgO |
| Ba/Tm/K/La | Ba/Tm/K/La/ $Ln1_{4-x}Ln2_xO_6$ | Ba/Tm/K/La/ $La_{4-x}Ln1_xO_6$ | Ba/Tm/K/La/ $Y_2O_3$ | Ba/Tm/K/La/ MgO |
| Ba/Tm/Zn/K | Ba/Tm/Zn/K/ $Ln1_{4-x}Ln2_xO_6$ | Ba/Tm/Zn/K/ $La_{4-x}Ln1_xO_6$ | Ba/Tm/Zn/K/ $Y_2O_3$ | Ba/Tm/Zn/K/ MgO |
| Cs/K/La | Cs/K/La/ $Ln1_{4-x}Ln2_xO_6$ | Cs/K/La/ $La_{4-x}Ln1_xO_6$ | Cs/K/La/ $Y_2O_3$ | Cs/K/La/ MgO |
| Cs/La/Tm/Na | Cs/La/Tm/Na/ $Ln1_{4-x}Ln2_xO_6$ | Cs/La/Tm/Na/ $La_{4-x}Ln1_xO_6$ | Cs/La/Tm/Na/ $Y_2O_3$ | Cs/La/Tm/Na/ MgO |
| Cs/Li/K/La | Cs/Li/K/La/ $Ln1_{4-x}Ln2_xO_6$ | Cs/Li/K/La/ $La_{4-x}Ln1_xO_6$ | Cs/Li/K/La/ $Y_2O_3$ | Cs/Li/K/La/ MgO |
| Sm/Li/Sr/Cs | Sm/Li/Sr/Cs/ $Ln1_{4-x}Ln2_xO_6$ | Sm/Li/Sr/Cs/ $La_{4-x}Ln1_xO_6$ | Sm/Li/Sr/Cs/ $Y_2O_3$ | Sm/Li/Sr/Cs/ MgO |
| Sr/Cs/La | Sr/Cs/La/ $Ln1_{4-x}Ln2_xO_6$ | Sr/Cs/La/ $La_{4-x}Ln1_xO_6$ | Sr/Cs/La/ $Y_2O_3$ | Sr/Cs/La/ MgO |
| Sr/Tm/Li/Cs | Sr/Tm/Li/Cs/ $Ln1_{4-x}Ln2_xO_6$ | Sr/Tm/Li/Cs/ $La_{4-x}Ln1_xO_6$ | Sr/Tm/Li/Cs/ $Y_2O_3$ | Sr/Tm/Li/Cs/ MgO |
| Zn/K | Zn/K/ $Ln1_{4-x}Ln2_xO_6$ | Zn/K/ $La_{4-x}Ln1_xO_6$ | Zn/K/ $Y_2O_3$ | Zn/K/ MgO |
| Zr/Cs/K/La | Zr/Cs/K/La/ $Ln1_{4-x}Ln2_xO_6$ | Zr/Cs/K/La/ $La_{4-x}Ln1_xO_6$ | Zr/Cs/K/La/ $Y_2O_3$ | Zr/Cs/K/La/ MgO |
| Rb/Ca/In/Ni | Rb/Ca/In/Ni/ $Ln1_{4-x}Ln2_xO_6$ | Rb/Ca/In/Ni/ $La_{4-x}Ln1_xO_6$ | Rb/Ca/In/Ni/ $Y_2O_3$ | Rb/Ca/In/Ni/ MgO |
| Sr/Ho/Tm | Sr/Ho/Tm/ $Ln1_{4-x}Ln2_xO_6$ | Sr/Ho/Tm/ $La_{4-x}Ln1_xO_6$ | Sr/Ho/Tm/ $Y_2O_3$ | Sr/Ho/Tm/ MgO |
| La/Nd/S | La/Nd/S/ $Ln1_{4-x}Ln2_xO_6$ | La/Nd/S/ $La_{4-x}Ln1_xO_6$ | La/Nd/S/ $Y_2O_3$ | La/Nd/S/ MgO |
| Li/Rb/Ca | Li/Rb/Ca/ $Ln1_{4-x}Ln2_xO_6$ | Li/Rb/Ca/ $La_{4-x}Ln1_xO_6$ | Li/Rb/Ca/ $Y_2O_3$ | Li/Rb/Ca/ MgO |
| Li/K | Li/K/ $Ln1_{4-x}Ln2_xO_6$ | Li/K/ $La_{4-x}Ln1_xO_6$ | Li/K/ $Y_2O_3$ | Li/K/ MgO |
| Tm/Lu/Ta/P | Tm/Lu/Ta/P/ $Ln1_{4-x}Ln2_xO_6$ | Tm/Lu/Ta/P/ $La_{4-x}Ln1_xO_6$ | Tm/Lu/Ta/P/ $Y_2O_3$ | Tm/Lu/Ta/P/ MgO |
| Rb/Ca/Dy/P | Rb/Ca/Dy/P/ $Ln1_{4-x}Ln2_xO_6$ | Rb/Ca/Dy/P/ $La_{4-x}Ln1_xO_6$ | Rb/Ca/Dy/P/ $Y_2O_3$ | Rb/Ca/Dy/P/ MgO |
| Mg/La/Yb/Zn | Mg/La/Yb/Zn/ $Ln1_{4-x}Ln2_xO_6$ | Mg/La/Yb/Zn/ $La_{4-x}Ln1_xO_6$ | Mg/La/Yb/Zn/ $Y_2O_3$ | Mg/La/Yb/Zn/ MgO |
| Rb/Sr/Lu | Rb/Sr/Lu/ $Ln1_{4-x}Ln2_xO_6$ | Rb/Sr/Lu/ $La_{4-x}Ln1_xO_6$ | Rb/Sr/Lu/ $Y_2O_3$ | Rb/Sr/Lu/ MgO |
| Na/Sr/Lu/Nb | Na/Sr/Lu/Nb/ $Ln1_{4-x}Ln2_xO_6$ | Na/Sr/Lu/Nb/ $La_{4-x}Ln1_xO_6$ | Na/Sr/Lu/Nb/ $Y_2O_3$ | Na/Sr/Lu/Nb/ MgO |
| Na/Eu/Hf | Na/Eu/Hf/ $Ln1_{4-x}Ln2_xO_6$ | Na/Eu/Hf/ $La_{4-x}Ln1_xO_6$ | Na/Eu/Hf/ $Y_2O_3$ | Na/Eu/Hf/ MgO |
| Dy/Rb/Gd | Dy/Rb/Gd/ $Ln1_{4-x}Ln2_xO_6$ | Dy/Rb/Gd/ $La_{4-x}Ln1_xO_6$ | Dy/Rb/Gd/ $Y_2O_3$ | Dy/Rb/Gd/ MgO |
| Na/Pt/Bi | Na/Pt/Bi/ $Ln1_{4-x}Ln2_xO_6$ | Na/Pt/Bi/ $La_{4-x}Ln1_xO_6$ | Na/Pt/Bi/ $Y_2O_3$ | Na/Pt/Bi/ MgO |
| Rb/Hf | Rb/Hf/ $Ln1_{4-x}Ln2_xO_6$ | Rb/Hf/ $La_{4-x}Ln1_xO_6$ | Rb/Hf/ $Y_2O_3$ | Rb/Hf/ MgO |
| Ca/Cs | Ca/Cs/ $Ln1_{4-x}Ln2_xO_6$ | Ca/Cs/ $La_{4-x}Ln1_xO_6$ | Ca/Cs/ $Y_2O_3$ | Ca/Cs/ MgO |
| Ca/Mg/Na | Ca/Mg/Na/ $Ln1_{4-x}Ln2_xO_6$ | Ca/Mg/Na/ $La_{4-x}Ln1_xO_6$ | Ca/Mg/Na/ $Y_2O_3$ | Ca/Mg/Na/ MgO |
| Hf/Bi | Hf/Bi/ $Ln1_{4-x}Ln2_xO_6$ | Hf/Bi/ $La_{4-x}Ln1_xO_6$ | Hf/Bi/ $Y_2O_3$ | Hf/Bi/ MgO |
| Sr/Sn | Sr/Sn/ $Ln1_{4-x}Ln2_xO_6$ | Sr/Sn/ $La_{4-x}Ln1_xO_6$ | Sr/Sn/ $Y_2O_3$ | Sr/Sn/ MgO |
| Sr/W | Sr/W/ $Ln1_{4-x}Ln2_xO_6$ | Sr/W/ $La_{4-x}Ln1_xO_6$ | Sr/W/ $Y_2O_3$ | Sr/W/ MgO |
| Sr/Nb | Sr/Nb/ $Ln1_{4-x}Ln2_xO_6$ | Sr/Nb/ $La_{4-x}Ln1_xO_6$ | Sr/Nb/ $Y_2O_3$ | Sr/Nb/ MgO |
| Zr/W | Zr/W/ $Ln1_{4-x}Ln2_xO_6$ | Zr/W/ $La_{4-x}Ln1_xO_6$ | Zr/W/ $Y_2O_3$ | Zr/W/ MgO |
| Y/W | Y/W/ $Ln1_{4-x}Ln2_xO_6$ | Y/W/ $La_{4-x}Ln1_xO_6$ | Y/W/ $Y_2O_3$ | Y/W/ MgO |
| Na/W | Na/W/ $Ln1_{4-x}Ln2_xO_6$ | Na/W/ $La_{4-x}Ln1_xO_6$ | Na/W/ $Y_2O_3$ | Na/W/ MgO |
| Bi/W | Bi/W/ $Ln1_{4-x}Ln2_xO_6$ | Bi/W/ $La_{4-x}Ln1_xO_6$ | Bi/W/ $Y_2O_3$ | Bi/W/ MgO |
| Bi/Cs | Bi/Cs/ $Ln1_{4-x}Ln2_xO_6$ | Bi/Cs/ $La_{4-x}Ln1_xO_6$ | Bi/Cs/ $Y_2O_3$ | Bi/Cs/ MgO |

TABLE 4-continued

CATALYSTS (CAT) DOPED WITH SPECIFIC DOPANTS (DOP)

| Dop\Cat | $Ln1_{4-x}Ln2_xO_6$ | $La_{4-x}Ln1_xO_6$ | $Y_2O_3$ | MgO |
|---|---|---|---|---|
| Bi/Ca | Bi/Ca/ $Ln1_{4-x}Ln2_xO_6$ | Bi/Ca/ $La_{4-x}Ln1_xO_6$ | Bi/Ca/ $Y_2O_3$ | Bi/Ca/ MgO |
| Bi/Sn | Bi/Sn/ $Ln1_{4-x}Ln2_xO_6$ | Bi/Sn/ $La_{4-x}Ln1_xO_6$ | Bi/Sn/ $Y_2O_3$ | Bi/Sn/ MgO |
| Bi/Sb | Bi/Sb/ $Ln1_{4-x}Ln2_xO_6$ | Bi/Sb/ $La_{4-x}Ln1_xO_6$ | Bi/Sb/ $Y_2O_3$ | Bi/Sb/ MgO |
| Ge/Hf | Ge/Hf/ $Ln1_{4-x}Ln2_xO_6$ | Ge/Hf/ $La_{4-x}Ln1_xO_6$ | Ge/Hf/ $Y_2O_3$ | Ge/Hf/ MgO |
| Hf/Sm | Hf/Sm/ $Ln1_{4-x}Ln2_xO_6$ | Hf/Sm/ $La_{4-x}Ln1_xO_6$ | Hf/Sm/ $Y_2O_3$ | Hf/Sm/ MgO |
| Sb/Ag | Sb/Ag/ $Ln1_{4-x}Ln2_xO_6$ | Sb/Ag/ $La_{4-x}Ln1_xO_6$ | Sb/Ag/ $Y_2O_3$ | Sb/Ag/ MgO |
| Sb/Bi | Sb/Bi/ $Ln1_{4-x}Ln2_xO_6$ | Sb/Bi/ $La_{4-x}Ln1_xO_6$ | Sb/Bi/ $Y_2O_3$ | Sb/Bi/ MgO |
| Sb/Au | Sb/Au/ $Ln1_{4-x}Ln2_xO_6$ | Sb/Au/ $La_{4-x}Ln1_xO_6$ | Sb/Au/ $Y_2O_3$ | Sb/Au/ MgO |
| Sb/Sm | Sb/Sm/ $Ln1_{4-x}Ln2_xO_6$ | Sb/Sm/ $La_{4-x}Ln1_xO_6$ | Sb/Sm/ $Y_2O_3$ | Sb/Sm/ MgO |
| Sb/Sr | Sb/Sr/ $Ln1_{4-x}Ln2_xO_6$ | Sb/Sr/ $La_{4-x}Ln1_xO_6$ | Sb/Sr/ $Y_2O_3$ | Sb/Sr/ MgO |
| Sb/W | Sb/W/ $Ln1_{4-x}Ln2_xO_6$ | Sb/W/ $La_{4-x}Ln1_xO_6$ | Sb/W/ $Y_2O_3$ | Sb/W/ MgO |
| Sb/Hf | Sb/Hf/ $Ln1_{4-x}Ln2_xO_6$ | Sb/Hf/ $La_{4-x}Ln1_xO_6$ | Sb/Hf/ $Y_2O_3$ | Sb/Hf/ MgO |
| Sb/Yb | Sb/Yb/ $Ln1_{4-x}Ln2_xO_6$ | Sb/Yb/ $La_{4-x}Ln1_xO_6$ | Sb/Yb/ $Y_2O_3$ | Sb/Yb/ MgO |
| Sb/Sn | Sb/Sn/ $Ln1_{4-x}Ln2_xO_6$ | Sb/Sn/ $La_{4-x}Ln1_xO_6$ | Sb/Sn/ $Y_2O_3$ | Sb/Sn/ MgO |
| Yb/Au | Yb/Au/ $Ln1_{4-x}Ln2_xO_6$ | Yb/Au/ $La_{4-x}Ln1_xO_6$ | Yb/Au/ $Y_2O_3$ | Yb/Au/ MgO |
| Yb/Ta | Yb/Ta/ $Ln1_{4-x}Ln2_xO_6$ | Yb/Ta/ $La_{4-x}Ln1_xO_6$ | Yb/Ta/ $Y_2O_3$ | Yb/Ta/ MgO |
| Yb/W | Yb/W/ $Ln1_{4-x}Ln2_xO_6$ | Yb/W/ $La_{4-x}Ln1_xO_6$ | Yb/W/ $Y_2O_3$ | Yb/W/ MgO |
| Yb/Sr | Yb/Sr/ $Ln1_{4-x}Ln2_xO_6$ | Yb/Sr/ $La_{4-x}Ln1_xO_6$ | Yb/Sr/ $Y_2O_3$ | Yb/Sr/ MgO |
| Yb/Pb | Yb/Pb/ $Ln1_{4-x}Ln2_xO_6$ | Yb/Pb/ $La_{4-x}Ln1_xO_6$ | Yb/Pb/ $Y_2O_3$ | Yb/Pb/ MgO |
| Yb/W | Yb/W/ $Ln1_{4-x}Ln2_xO_6$ | Yb/W/ $La_{4-x}Ln1_xO_6$ | Yb/W/ $Y_2O_3$ | Yb/W/ MgO |
| Yb/Ag | Yb/Ag/ $Ln1_{4-x}Ln2_xO_6$ | Yb/Ag/ $La_{4-x}Ln1_xO_6$ | Yb/Ag/ $Y_2O_3$ | Yb/Ag/ MgO |
| Au/Sr | Au/Sr/ $Ln1_{4-x}Ln2_xO_6$ | Au/Sr/ $La_{4-x}Ln1_xO_6$ | Au/Sr/ $Y_2O_3$ | Au/Sr/ MgO |
| W/Ge | W/Ge/ $Ln1_{4-x}Ln2_xO_6$ | W/Ge/ $La_{4-x}Ln1_xO_6$ | W/Ge/ $Y_2O_3$ | W/Ge/ MgO |
| Ta/Sr | Ta/Sr/ $Ln1_{4-x}Ln2_xO_6$ | Ta/Sr/ $La_{4-x}Ln1_xO_6$ | Ta/Sr/ $Y_2O_3$ | Ta/Sr/ MgO |
| Ta/Hf | Ta/Hf/ $Ln1_{4-x}Ln2_xO_6$ | Ta/Hf/ $La_{4-x}Ln1_xO_6$ | Ta/Hf/ $Y_2O_3$ | Ta/Hf/ MgO |
| W/Au | W/Au/ $Ln1_{4-x}Ln2_xO_6$ | W/Au/ $La_{4-x}Ln1_xO_6$ | W/Au/ $Y_2O_3$ | W/Au/ MgO |
| Ca/W | Ca/W/ $Ln1_{4-x}Ln2_xO_6$ | Ca/W/ $La_{4-x}Ln1_xO_6$ | Ca/W/ $Y_2O_3$ | Ca/W/ MgO |
| Au/Re | Au/Re/ $Ln1_{4-x}Ln2_xO_6$ | Au/Re/ $La_{4-x}Ln1_xO_6$ | Au/Re/ $Y_2O_3$ | Au/Re/ MgO |
| Sm/Li | Sm/Li/ $Ln1_{4-x}Ln2_xO_6$ | Sm/Li/ $La_{4-x}Ln1_xO_6$ | Sm/Li/ $Y_2O_3$ | Sm/Li/ MgO |
| La/K | La/K/ $Ln1_{4-x}Ln2_xO_6$ | La/K/ $La_{4-x}Ln1_xO_6$ | La/K/ $Y_2O_3$ | La/K/ MgO |
| Zn/Cs | Zn/Cs/ $Ln1_{4-x}Ln2_xO_6$ | Zn/Cs/ $La_{4-x}Ln1_xO_6$ | Zn/Cs/ $Y_2O_3$ | Zn/Cs/ MgO |
| Na/K/Mg | Na/K/Mg/ $Ln1_{4-x}Ln2_xO_6$ | Na/K/Mg/ $La_{4-x}Ln1_xO_6$ | Na/K/Mg/ $Y_2O_3$ | Na/K/Mg/ MgO |
| Zr/Cs | Zr/Cs/ $Ln1_{4-x}Ln2_xO_6$ | Zr/Cs/ $La_{4-x}Ln1_xO_6$ | Zr/Cs/ $Y_2O_3$ | Zr/Cs/ MgO |
| Ca/Ce | Ca/Ce/ $Ln1_{4-x}Ln2_xO_6$ | Ca/Ce/ $La_{4-x}Ln1_xO_6$ | Ca/Ce/ $Y_2O_3$ | Ca/Ce/ MgO |
| Na/Li/Cs | Na/Li/Cs/ $Ln1_{4-x}Ln2_xO_6$ | Na/Li/Cs/ $La_{4-x}Ln1_xO_6$ | Na/Li/Cs/ $Y_2O_3$ | Na/Li/Cs/ MgO |
| Li/Sr | Li/Sr/ $Ln1_{4-x}Ln2_xO_6$ | Li/Sr/ $La_{4-x}Ln1_xO_6$ | Li/Sr/ $Y_2O_3$ | Li/Sr/ MgO |
| La/Dy/K | La/Dy/K/ $Ln1_{4-x}Ln2_xO_6$ | La/Dy/K/ $La_{4-x}Ln1_xO_6$ | La/Dy/K/ $Y_2O_3$ | La/Dy/K/ MgO |
| Dy/K | Dy/K/ $Ln1_{4-x}Ln2_xO_6$ | Dy/K/ $La_{4-x}Ln1_xO_6$ | Dy/K/ $Y_2O_3$ | Dy/K/ MgO |

TABLE 4-continued

CATALYSTS (CAT) DOPED WITH SPECIFIC DOPANTS (DOP)

| Dop\Cat | $Ln1_{4-x}Ln2_xO_6$ | $La_{4-x}Ln1_xO_6$ | $Y_2O_3$ | MgO |
|---|---|---|---|---|
| La/Mg | La/Mg/ $Ln1_{4-x}Ln2_xO_6$ | La/Mg/ $La_{4-x}Ln1_xO_6$ | La/Mg/ $Y_2O_3$ | La/Mg/ MgO |
| Na/Nd/In/K | Na/Nd/In/K/ $Ln1_{4-x}Ln2_xO_6$ | Na/Nd/In/K/ $La_{4-x}Ln1_xO_6$ | Na/Nd/In/K/ $Y_2O_3$ | Na/Nd/In/K/ MgO |
| In/Sr | In/Sr/ $Ln1_{4-x}Ln2_xO_6$ | In/Sr/ $La_{4-x}Ln1_xO_6$ | In/Sr/ $Y_2O_3$ | In/Sr/ MgO |
| Sr/Cs | Sr/Cs/ $Ln1_{4-x}Ln2_xO_6$ | Sr/Cs/ $La_{4-x}Ln1_xO_6$ | Sr/Cs/ $Y_2O_3$ | Sr/Cs/ MgO |
| Rb/Ga/Tm/Cs | Rb/Ga/Tm/Cs/ $Ln1_{4-x}Ln2_xO_6$ | Rb/Ga/Tm/Cs/ $La_{4-x}Ln1_xO_6$ | Rb/Ga/Tm/Cs/ $Y_2O_3$ | Rb/Ga/Tm/Cs/ MgO |
| Ga/Cs | Ga/Cs/ $Ln1_{4-x}Ln2_xO_6$ | Ga/Cs/ $La_{4-x}Ln1_xO_6$ | Ga/Cs/ $Y_2O_3$ | Ga/Cs/ MgO |
| K/La/Zr/Ag | K/La/Zr/Ag/ $Ln1_{4-x}Ln2_xO_6$ | K/La/Zr/Ag/ $La_{4-x}Ln1_xO_6$ | K/La/Zr/Ag/ $Y_2O_3$ | K/La/Zr/Ag/ MgO |
| Lu/Fe | Lu/Fe/ $Ln1_{4-x}Ln2_xO_6$ | Lu/Fe/ $La_{4-x}Ln1_xO_6$ | Lu/Fe/ $Y_2O_3$ | Lu/Fe/ MgO |
| Sr/Tm | Sr/Tm/ $Ln1_{4-x}Ln2_xO_6$ | Sr/Tm/ $La_{4-x}Ln1_xO_6$ | Sr/Tm/ $Y_2O_3$ | Sr/Tm/ MgO |
| La/Dy | La/Dy/ $Ln1_{4-x}Ln2_xO_6$ | La/Dy/ $La_{4-x}Ln1_xO_6$ | La/Dy/ $Y_2O_3$ | La/Dy/ MgO |
| Sm/Li/Sr | Sm/Li/Sr/ $Ln1_{4-x}Ln2_xO_6$ | Sm/Li/Sr/ $La_{4-x}Ln1_xO_6$ | Sm/Li/Sr/ $Y_2O_3$ | Sm/Li/Sr/ MgO |
| Mg/K | Mg/K/ $Ln1_{4-x}Ln2_xO_6$ | Mg/K/ $La_{4-x}Ln1_xO_6$ | Mg/K/ $Y_2O_3$ | Mg/K/ MgO |
| Li/Rb/Ga | Li/Rb/Ga/ $Ln1_{4-x}Ln2_xO_6$ | Li/Rb/Ga/ $La_{4-x}Ln1_xO_6$ | Li/Rb/Ga/ $Y_2O_3$ | Li/Rb/Ga/ MgO |
| Li/Cs/Tm | Li/Cs/Tm/ $Ln1_{4-x}Ln2_xO_6$ | Li/Cs/Tm/ $La_{4-x}Ln1_xO_6$ | Li/Cs/Tm/ $Y_2O_3$ | Li/Cs/Tm/ MgO |
| Zr/K | Zr/K/ $Ln1_{4-x}Ln2_xO_6$ | Zr/K/ $La_{4-x}Ln1_xO_6$ | Zr/K/ $Y_2O_3$ | Zr/K/ MgO |
| Li/Cs | Li/Cs/ $Ln1_{4-x}Ln2_xO_6$ | Li/Cs/ $La_{4-x}Ln1_xO_6$ | Li/Cs/ $Y_2O_3$ | Li/Cs/ MgO |
| Li/K/La | Li/K/La/ $Ln1_{4-x}Ln2_xO_6$ | Li/K/La/ $La_{4-x}Ln1_xO_6$ | Li/K/La/ $Y_2O_3$ | Li/K/La/ MgO |
| Ce/Zr/La | Ce/Zr/La/ $Ln1_{4-x}Ln2_xO_6$ | Ce/Zr/La/ $La_{4-x}Ln1_xO_6$ | Ce/Zr/La/ $Y_2O_3$ | Ce/Zr/La/ MgO |
| Ca/Al/La | Ca/Al/La/ $Ln1_{4-x}Ln2_xO_6$ | Ca/Al/La/ $La_{4-x}Ln1_xO_6$ | Ca/Al/La/ $Y_2O_3$ | Ca/Al/La/ MgO |
| Sr/Zn/La | Sr/Zn/La/ $Ln1_{4-x}Ln2_xO_6$ | Sr/Zn/La/ $La_{4-x}Ln1_xO_6$ | Sr/Zn/La/ $Y_2O_3$ | Sr/Zn/La/ MgO |
| Sr/Cs/Zn | Sr/Cs/Zn/ $Ln1_{4-x}Ln2_xO_6$ | Sr/Cs/Zn/ $La_{4-x}Ln1_xO_6$ | Sr/Cs/Zn/ $Y_2O_3$ | Sr/Cs/Zn/ MgO |
| Sm/Cs | Sm/Cs/ $Ln1_{4-x}Ln2_xO_6$ | Sm/Cs/ $La_{4-x}Ln1_xO_6$ | Sm/Cs/ $Y_2O_3$ | Sm/Cs/ MgO |
| In/K | In/K/ $Ln1_{4-x}Ln2_xO_6$ | In/K/ $La_{4-x}Ln1_xO_6$ | In/K/ $Y_2O_3$ | In/K/ MgO |
| Ho/Cs/Li/La | Ho/Cs/Li/La/ $Ln1_{4-x}Ln2_xO_6$ | Ho/Cs/Li/La/ $La_{4-x}Ln1_xO_6$ | Ho/Cs/Li/La/ $Y_2O_3$ | Ho/Cs/Li/La/ MgO |
| Cs/La/Na | Cs/La/Na/ $Ln1_{4-x}Ln2_xO_6$ | Cs/La/Na/ $La_{4-x}Ln1_xO_6$ | Cs/La/Na/ $Y_2O_3$ | Cs/La/Na/ MgO |
| La/S/Sr | La/S/Sr/ $Ln1_{4-x}Ln2_xO_6$ | La/S/Sr/ $La_{4-x}Ln1_xO_6$ | La/S/Sr/ $Y_2O_3$ | La/S/Sr/ MgO |
| K/La/Zr/Ag | K/La/Zr/Ag/ $Ln1_{4-x}Ln2_xO_6$ | K/La/Zr/Ag/ $La_{4-x}Ln1_xO_6$ | K/La/Zr/Ag/ $Y_2O_3$ | K/La/Zr/Ag/ MgO |
| Lu/Tl | Lu/Tl/ $Ln1_{4-x}Ln2_xO_6$ | Lu/Tl/ $La_{4-x}Ln1_xO_6$ | Lu/Tl/ $Y_2O_3$ | Lu/Tl/ MgO |
| Pr/Zn | Pr/Zn/ $Ln1_{4-x}Ln2_xO_6$ | Pr/Zn/ $La_{4-x}Ln1_xO_6$ | Pr/Zn/ $Y_2O_3$ | Pr/Zn/ MgO |
| Rb/Sr/La | Rb/Sr/La/ $Ln1_{4-x}Ln2_xO_6$ | Rb/Sr/La/ $La_{4-x}Ln1_xO_6$ | Rb/Sr/La/ $Y_2O_3$ | Rb/Sr/La/ MgO |
| Na/Sr/Eu/Ca | Na/Sr/Eu/Ca/ $Ln1_{4-x}Ln2_xO_6$ | Na/Sr/Eu/Ca/ $La_{4-x}Ln1_xO_6$ | Na/Sr/Eu/Ca/ $Y_2O_3$ | Na/Sr/Eu/Ca/ MgO |
| K/Cs/Sr/La | K/Cs/Sr/La/ $Ln1_{4-x}Ln2_xO_6$ | K/Cs/Sr/La/ $La_{4-x}Ln1_xO_6$ | K/Cs/Sr/La/ $Y_2O_3$ | K/Cs/Sr/La/ MgO |
| Na/Sr/Lu | Na/Sr/Lu/ $Ln1_{4-x}Ln2_xO_6$ | Na/Sr/Lu/ $La_{4-x}Ln1_xO_6$ | Na/Sr/Lu/ $Y_2O_3$ | Na/Sr/Lu/ MgO |
| Sr/Eu/Dy | Sr/Eu/Dy/ $Ln1_{4-x}Ln2_xO_6$ | Sr/Eu/Dy/ $La_{4-x}Ln1_xO_6$ | Sr/Eu/Dy/ $Y_2O_3$ | Sr/Eu/Dy/ MgO |
| Lu/Nb | Lu/Nb/ $Ln1_{4-x}Ln2_xO_6$ | Lu/Nb/ $LLa_{4-x}Ln1_xO_6$ | Lu/Nb/ $Y_2O_3$ | Lu/Nb/ MgO |
| La/Dy/Gd | La/Dy/Gd/ $Ln1_{4-x}Ln2_xO_6$ | La/Dy/Gd/ $La_{4-x}Ln1_xO_6$ | La/Dy/Gd/ $Y_2O_3$ | La/Dy/Gd/ MgO |
| Na/Mg/Tl/P | Na/Mg/Tl/P/ $Ln1_{4-x}Ln2_xO_6$ | Na/Mg/Tl/P/ $La_{4-x}Ln1_xO_6$ | Na/Mg/Tl/P/ $Y_2O_3$ | Na/Mg/Tl/P/ MgO |
| Na/Pt | Na/Pt/ $Ln1_{4-x}Ln2_xO_6$ | Na/Pt/ $La_{4-x}Ln1_xO_6$ | Na/Pt/ $Y_2O_3$ | Na/Pt/ MgO |

TABLE 4-continued

CATALYSTS (CAT) DOPED WITH SPECIFIC DOPANTS (DOP)

| Dop\Cat | $Ln1_{4-x}Ln2_xO_6$ | $La_{4-x}Ln1_xO_6$ | $Y_2O_3$ | MgO |
|---|---|---|---|---|
| Gd/Li/K | Gd/Li/K/ $Ln1_{4-x}Ln2_xO_6$ | Gd/Li/K/ $La_{4-x}Ln1_xO_6$ | Gd/Li/K/ $Y_2O_3$ | Gd/Li/K/ MgO |
| Rb/K/Lu | Rb/K/Lu/ $Ln1_{4-x}Ln2_xO_6$ | Rb/K/Lu/ $La_{4-x}Ln1_xO_6$ | Rb/K/Lu/ $Y_2O_3$ | Rb/K/Lu/ MgO |
| Sr/La/Dy/S | Sr/La/Dy/S/ $Ln1_{4-x}Ln2_xO_6$ | Sr/La/Dy/S/ $La_{4-x}Ln1_xO_6$ | Sr/La/Dy/S/ $Y_2O_3$ | Sr/La/Dy/S/ MgO |
| Na/Ce/Co | Na/Ce/Co/ $Ln1_{4-x}Ln2_xO_6$ | Na/Ce/Co/ $La_{4-x}Ln1_xO_6$ | Na/Ce/Co/ $Y_2O_3$ | Na/Ce/Co/ MgO |
| Na/Ce | Na/Ce/ $Ln1_{4-x}Ln2_xO_6$ | Na/Ce/ $La_{4-x}Ln1_xO_6$ | Na/Ce/ $Y_2O_3$ | Na/Ce/ MgO |
| Na/Ga/Gd/Al | Na/Ga/Gd/Al/ $Ln1_{4-x}Ln2_xO_6$ | Na/Ga/Gd/Al/ $La_{4-x}Ln1_xO_6$ | Na/Ga/Gd/Al/ $Y_2O_3$ | Na/Ga/Gd/Al/ MgO |
| Ba/Rh/Ta | Ba/Rh/Ta/ $Ln1_{4-x}Ln2_xO_6$ | Ba/Rh/Ta/ $La_{4-x}Ln1_xO_6$ | Ba/Rh/Ta/ $Y_2O_3$ | Ba/Rh/Ta/ MgO |
| Ba/Ta | Ba/Ta/ $Ln1_{4-x}Ln2_xO_6$ | Ba/Ta/ $La_{4-x}Ln1_xO_6$ | Ba/Ta/ $Y_2O_3$ | Ba/Ta/ MgO |
| Na/Al/Bi | Na/Al/Bi/ $Ln1_{4-x}Ln2_xO_6$ | Na/Al/Bi/ $La_{4-x}Ln1_xO_6$ | Na/Al/Bi/ $Y_2O_3$ | Na/Al/Bi/ MgO |
| Cs/Eu/S | Cs/Eu/S/ $Ln1_{4-x}Ln2_xO_6$ | Cs/Eu/S/ $La_{4-x}Ln1_xO_6$ | Cs/Eu/S/ $Y_2O_3$ | Cs/Eu/S/ MgO |
| Sm/Tm/Yb/Fe | Sm/Tm/Yb/Fe/ $Ln1_{4-x}Ln2_xO_6$ | Sm/Tm/Yb/Fe/ $La_{4-x}Ln1_xO_6$ | Sm/Tm/Yb/Fe/ $Y_2O_3$ | Sm/Tm/Yb/Fe/ MgO |
| Sm/Tm/Yb | Sm/Tm/Yb/ $Ln1_{4-x}Ln2_xO_6$ | Sm/Tm/Yb/ $La_{4-x}Ln1_xO_6$ | Sm/Tm/Yb/ $Y_2O_3$ | Sm/Tm/Yb/ MgO |
| Hf/Zr/Ta | Hf/Zr/Ta/ $Ln1_{4-x}Ln2_xO_6$ | Hf/Zr/Ta/ $La_{4-x}Ln1_xO_6$ | Hf/Zr/Ta/ $Y_2O_3$ | Hf/Zr/Ta/ MgO |
| Rb/Gd/Li/K | Rb/Gd/Li/K/ $Ln1_{4-x}Ln2_xO_6$ | Rb/Gd/Li/K/ $La_{4-x}Ln1_xO_6$ | Rb/Gd/Li/K/ $Y_2O_3$ | Rb/Gd/Li/K/ MgO |
| Gd/Ho/Al/P | Gd/Ho/Al/P/ $Ln1_{4-x}Ln2_xO_6$ | Gd/Ho/Al/P/ $La_{4-x}Ln1_xO_6$ | Gd/Ho/Al/P/ $Y_2O_3$ | Gd/Ho/Al/P/ MgO |
| Na/Ca/Lu | Na/Ca/Lu/ $Ln1_{4-x}Ln2_xO_6$ | Na/Ca/Lu/ $La_{4-x}Ln1_xO_6$ | Na/Ca/Lu/ $Y_2O_3$ | Na/Ca/Lu/ MgO |
| Cu/Sn | Cu/Sn/ $Ln1_{4-x}Ln2_xO_6$ | Cu/Sn/ $La_{4-x}Ln1_xO_6$ | Cu/Sn/ $Y_2O_3$ | Cu/Sn/ MgO |
| Ag/Au | Ag/Au/ $Ln1_{4-x}Ln2_xO_6$ | Ag/Au/ $La_{4-x}Ln1_xO_6$ | Ag/Au/ $Y_2O_3$ | Ag/Au/ MgO |
| Al/Bi | Al/Bi/ $Ln1_{4-x}Ln2_xO_6$ | Al/Bi/ $La_{4-x}Ln1_xO_6$ | Al/Bi/ $Y_2O_3$ | Al/Bi/ MgO |
| Al/Mo | Al/Mo/ $Ln1_{4-x}Ln2_xO_6$ | Al/Mo/ $La_{4-x}Ln1_xO_6$ | Al/Mo/ $Y_2O_3$ | Al/Mo/ MgO |
| Al/Nb | Al/Nb/ $Ln1_{4-x}Ln2_xO_6$ | Al/Nb/ $La_{4-x}Ln1_xO_6$ | Al/Nb/ $Y_2O_3$ | Al/Nb/ MgO |
| Au/Pt | Au/Pt/ $Ln1_{4-x}Ln2_xO_6$ | Au/Pt/ $La_{4-x}Ln1_xO_6$ | Au/Pt/ $Y_2O_3$ | Au/Pt/ MgO |
| Ga/Bi | Ga/Bi/ $Ln1_{4-x}Ln2_xO_6$ | Ga/Bi/ $La_{4-x}Ln1_xO_6$ | Ga/Bi/ $Y_2O_3$ | Ga/Bi/ MgO |
| Mg/W | Mg/W/ $Ln1_{4-x}Ln2_xO_6$ | Mg/W/ $La_{4-x}Ln1_xO_6$ | Mg/W/ $Y_2O_3$ | Mg/W/ MgO |
| Pb/Au | Pb/Au/ $Ln1_{4-x}Ln2_xO_6$ | Pb/Au/ $La_{4-x}Ln1_xO_6$ | Pb/Au/ $Y_2O_3$ | Pb/Au/ MgO |
| Sn/Mg | Sn/Mg/ $Ln1_{4-x}Ln2_xO_6$ | Sn/Mg/ $La_{4-x}Ln1_xO_6$ | Sn/Mg/ $Y_2O_3$ | Sn/Mg/ MgO |
| Zn/Bi | Zn/Bi/ $Ln1_{4-x}Ln2_xO_6$ | Zn/Bi/ $La_{4-x}Ln1_xO_6$ | Zn/Bi/ $Y_2O_3$ | Zn/Bi/ MgO |
| Sr/Ta | Sr/Ta/ $Ln1_{4-x}Ln2_xO_6$ | Sr/Ta/ $La_{4-x}Ln1_xO_6$ | Sr/Ta/ $Y_2O_3$ | Sr/Ta/ MgO |
| Na | Na/ $Ln1_{4-x}Ln2_xO_6$ | Na/ $La_{4-x}Ln1_xO_6$ | Na/ $Y_2O_3$ | Na/ MgO |
| Sr | Sr/ $Ln1_{4-x}Ln2_xO_6$ | Sr/ $La_{4-x}Ln1_xO_6$ | Sr/ $Y_2O_3$ | Sr/ MgO |
| Ca | Ca/ $Ln1_{4-x}Ln2_xO_6$ | Ca/ $La_{4-x}Ln1_xO_6$ | Ca/ $Y_2O_3$ | Ca/ MgO |
| Yb | Yb/ $Ln1_{4-x}Ln2_xO_6$ | Yb/ $La_{4-x}Ln1_xO_6$ | Yb/ $Y_2O_3$ | Yb/ MgO |
| Cs | Cs/ $Ln1_{4-x}Ln2_xO_6$ | Cs/ $La_{4-x}Ln1_xO_6$ | Cs/ $Y_2O_3$ | Cs/ MgO |
| Sb | Sb/ $Ln1_{4-x}Ln2_xO_6$ | Sb/ $La_{4-x}Ln1_xO_6$ | Sb/ $Y_2O_3$ | Sb/ MgO |
| Gd/Ho | Gd/Ho/ $Ln1_{4-x}Ln2_xO_6$ | Gd/Ho/ $La_{4-x}Ln1_xO_6$ | Gd/Ho/ $Y_2O_3$ | Gd/Ho/ MgO |
| Zr/Bi | Zr/Bi/ $Ln1_{4-x}Ln2_xO_6$ | Zr/Bi/ $La_{4-x}Ln1_xO_6$ | Zr/Bi/ $Y_2O_3$ | Zr/Bi/ MgO |
| Ho/Sr | Ho/Sr/ $Ln1_{4-x}Ln2_xO_6$ | Ho/Sr/ $La_{4-x}Ln1_xO_6$ | Ho/Sr/ $Y_2O_3$ | Ho/Sr/ MgO |
| Gd/Ho/Sr | Gd/Ho/Sr/ $Ln1_{4-x}Ln2_xO_6$ | Gd/Ho/Sr/ $La_{4-x}Ln1_xO_6$ | Gd/Ho/Sr/ $Y_2O_3$ | Gd/Ho/Sr/ MgO |

TABLE 4-continued

CATALYSTS (CAT) DOPED WITH SPECIFIC DOPANTS (DOP)

| Dop\Cat | $Ln1_{4-x}Ln2_xO_6$ | $La_{4-x}Ln1_xO_6$ | $Y_2O_3$ | MgO |
|---|---|---|---|---|
| Ca/Sr | Ca/Sr/$Ln1_{4-x}Ln2_xO_6$ | Ca/Sr/$La_{4-x}Ln1_xO_6$ | Ca/Sr/$Y_2O_3$ | Ca/Sr/MgO |
| Ca/Sr/W | Ca/Sr/W/$Ln1_{4-x}Ln2_xO_6$ | Ca/Sr/W/$La_{4-x}Ln1_xO_6$ | Ca/Sr/W/$Y_2O_3$ | Ca/Sr/W/MgO |
| Na/Zr/Eu/Tm | Na/Zr/Eu/Tm/$Ln1_{4-x}Ln2_xO_6$ | Na/Zr/Eu/Tm/$La_{4-x}Ln1_xO_6$ | Na/Zr/Eu/Tm/$Y_2O_3$ | Na/Zr/Eu/Tm/MgO |
| Sr/Ho/Tm/Na | Sr/Ho/Tm/Na/$Ln1_{4-x}Ln2_xO_6$ | Sr/Ho/Tm/Na/$La_{4-x}Ln1_xO_6$ | Sr/Ho/Tm/Na/$Y_2O_3$ | Sr/Ho/Tm/Na/MgO |
| Sr/Pb | Sr/Pb/$Ln1_{4-x}Ln2_xO_6$ | Sr/Pb/$La_{4-x}Ln1_xO_6$ | Sr/Pb/$Y_2O_3$ | Sr/Pb/MgO |
| Sr/W/Li | Sr/W/Li/$Ln1_{4-x}Ln2_xO_6$ | Sr/W/Li/$La_{4-x}Ln1_xO_6$ | Sr/W/Li/$Y_2O_3$ | Sr/W/Li/MgO |
| Ca/Sr/W | Ca/Sr/W/$Ln1_{4-x}Ln2_xO_6$ | Ca/Sr/W/$La_{4-x}Ln1_xO_6$ | Ca/Sr/W/$Y_2O_3$ | Ca/Sr/W/MgO |
| Sr/Hf | Sr/Hf/$Ln1_{4-x}Ln2_xO_6$ | Sr/Hf/$La_{4-x}Ln1_xO_6$ | Sr/Hf/$Y_2O_3$ | Sr/Hf/MgO |
| Au/Re | Au/Re/$Ln1_{4-x}Ln2_xO_6$ | Au/Re/$La_{4-x}Ln1_xO_6$ | Au/Re/$Y_2O_3$ | Au/Re/MgO |
| Sr/W | Sr/W/$Ln1_{4-x}Ln2_xO_6$ | Sr/W/$La_{4-x}Ln1_xO_6$ | Sr/W/$Y_2O_3$ | Sr/W/MgO |
| La/Nd | La/Nd/$Ln1_{4-x}Ln2_xO_6$ | La/Nd/$La_{4-x}Ln1_xO_6$ | La/Nd/$Y_2O_3$ | La/Nd/MgO |
| La/Sm | La/Sm/$Ln1_{4-x}Ln2_xO_6$ | La/Sm/$La_{4-x}Ln1_xO_6$ | La/Sm/$Y_2O_3$ | La/Sm/MgO |
| La/Ce | La/Ce/$Ln1_{4-x}Ln2_xO_6$ | La/Ce/$La_{4-x}Ln1_xO_6$ | La/Ce/$Y_2O_3$ | La/Ce/MgO |
| La/Sr | La/Sr/$Ln1_{4-x}Ln2_xO_6$ | La/Sr/$La_{4-x}Ln1_xO_6$ | La/Sr/$Y_2O_3$ | La/Sr/MgO |
| La/Nd/Sr | La/Nd/Sr/$Ln1_{4-x}Ln2_xO_6$ | La/Nd/Sr/$La_{4-x}Ln1_xO_6$ | La/Nd/Sr/$Y_2O_3$ | La/Nd/Sr/MgO |
| La/Bi/Sr | La/Bi/Sr/$Ln1_{4-x}Ln2_xO_6$ | La/Bi/Sr/$La_{4-x}Ln1_xO_6$ | La/Bi/Sr/$Y_2O_3$ | La/Bi/Sr/MgO |
| La/Ce/Nd/Sr | La/Ce/Nd/Sr/$Ln1_{4-x}Ln2_xO_6$ | La/Ce/Nd/Sr/$La_{4-x}Ln1_xO_6$ | La/Ce/Nd/Sr/$Y_2O_3$ | La/Ce/Nd/Sr/MgO |
| La/Bi/Ce/Nd/Sr | La/Bi/Ce/Nd/Sr/$Ln1_{4-x}Ln2_xO_6$ | La/Bi/Ce/Nd/Sr/$La_{4-x}Ln1_xO_6$ | La/Bi/Ce/Nd/Sr/$Y_2O_3$ | La/Bi/Ce/Nd/Sr/MgO |
| Eu/Gd | Eu/Gd/$Ln1_{4-x}Ln2_xO_6$ | Eu/Gd/$La_{4-x}Ln1_xO_6$ | Eu/Gd/$Y_2O_3$ | Eu/Gd/MgO |
| Ca/Na | Ca/Na/$Ln1_{4-x}Ln2_xO_6$ | Ca/Na/$La_{4-x}Ln1_xO_6$ | Ca/Na/$Y_2O_3$ | Ca/Na/MgO |
| Eu/Sm | Eu/Sm/$Ln1_{4-x}Ln2_xO_6$ | Eu/Sm/$La_{4-x}Ln1_xO_6$ | Eu/Sm/$Y_2O_3$ | Eu/Sm/MgO |
| Eu/Sr | Eu/Sr/$Ln1_{4-x}Ln2_xO_6$ | Eu/Sr/$La_{4-x}Ln1_xO_6$ | Eu/Sr/$Y_2O_3$ | Eu/Sr/MgO |
| Mg/Sr | Mg/Sr/$Ln1_{4-x}Ln2_xO_6$ | Mg/Sr/$La_{4-x}Ln1_xO_6$ | Mg/Sr/$Y_2O_3$ | Mg/Sr/MgO |
| Ce/Mg | Ce/Mg/$Ln1_{4-x}Ln2_xO_6$ | Ce/Mg/$La_{4-x}Ln1_xO_6$ | Ce/Mg/$Y_2O_3$ | Ce/Mg/MgO |
| Gd/Sm | Gd/Sm/$Ln1_{4-x}Ln2_xO_6$ | Gd/Sm/$La_{4-x}Ln1_xO_6$ | Gd/Sm/$Y_2O_3$ | Gd/Sm/MgO |
| Au/Pb | Au/Pb/$Ln1_{4-x}Ln2_xO_6$ | Au/Pb/$La_{4-x}Ln1_xO_6$ | Au/Pb/$Y_2O_3$ | Au/Pb/MgO |
| Bi/Hf | Bi/Hf/$Ln1_{4-x}Ln2_xO_6$ | Bi/Hf/$La_{4-x}Ln1_xO_6$ | Bi/Hf/$Y_2O_3$ | Bi/Hf/MgO |
| Rb/S | Rb/S/$Ln1_{4-x}Ln2_xO_6$ | Rb/S/$La_{4-x}Ln1_xO_6$ | Rb/S/$Y_2O_3$ | Rb/S/MgO |
| Sr/Nd | Sr/Nd/$Ln1_{4-x}Ln2_xO_6$ | Sr/Nd/$La_{4-x}Ln1_xO_6$ | Sr/Nd/$Y_2O_3$ | Sr/Nd/MgO |
| Eu/Y | Eu/Y/$Ln1_{4-x}Ln2_xO_6$ | Eu/Y/$La_{4-x}Ln1_xO_6$ | Eu/Y/$Y_2O_3$ | Eu/Y/MgO |
| Mg/Nd | Mg/Nd/$Ln1_{4-x}Ln2_xO_6$ | Mg/Nd/$La_{4-x}Ln1_xO_6$ | Mg/Nd/$Y_2O_3$ | Mg/Nd/MgO |
| La/Mg | La/Mg/$Ln1_{4-x}Ln2_xO_6$ | La/Mg/$La_{4-x}Ln1_xO_6$ | La/Mg/$Y_2O_3$ | La/Mg/MgO |
| Mg/Nd/Fe | Mg/Nd/Fe/$Ln1_{4-x}Ln2_xO_6$ | Mg/Nd/Fe/$La_{4-x}Ln1_xO_6$ | Mg/Nd/Fe/$Y_2O_3$ | Mg/Nd/Fe/MgO |
| Rb/Sr/ | Rb/Sr/ Rb/Sr/ | Rb/Sr/ $La_{4-x}Ln1_xO_6$ | Rb/Sr/ $Y_2O_3$ | Rb/Sr/ MgO |

The catalysts of the disclosure may be analyzed by inductively coupled plasma mass spectrometry (ICP-MS) to determine the element content of the catalysts. ICP-MS is a type of mass spectrometry that is highly sensitive and capable of the determination of a range of metals and several non-metals at concentrations below one part in $10^{12}$. ICP is based on coupling together an inductively coupled plasma as a method of producing ions (ionization) with a mass spectrometer as a method of separating and detecting the ions. ICP-MS methods are well known in the art.

As used throughout the specification, a catalyst composition represented by $E^1/E^2/E^3$, etc., wherein $E^1$, $E^2$ and $E^3$ are each independently an element or a compound comprising one or more elements, refers to a catalyst comprised of a mixture of $E^1$, $E^2$ and $E^3$. $E^1$, $E^2$ and $E^3$, etc. are not necessarily present in equal amounts and need not form a bond with one another. For example, a catalyst comprising Li/MgO refers to a catalyst comprising Li and MgO, for example, Li/MgO may refer to MgO doped with Li. By way of another example, a catalyst comprising Na/Mn/W/O refers to a catalyst comprised of a mixture of sodium, manganese, tungsten and oxygen. Generally the oxygen is in the form of a metal oxide.

In some embodiments, dopants are present in the catalysts in, for example, less than 50 at %, less than 25 at %, less than 10 at %, less than 5 at % or less than 1 at %.

In other embodiments of the catalysts, the weight ratio (w/w) of the catalyst base material to the doping element(s) ranges from 1:1 to 10,000:1, 1:1 to 1,000:1 or 1:1 to 500:1.

2. Catalytic Materials

As noted above, the present disclosure includes a catalytic material comprising a plurality of mixed metal oxide catalysts. Typically, the catalytic material comprises a support or carrier. The support is preferably porous and has a high surface area. In some embodiments the support is active (i.e. has catalytic activity). In other embodiments, the support is inactive (i.e. non-catalytic). In some embodiments, the support comprises an inorganic oxide, $Al_2O_3$, $SiO_2$, $TiO_2$, $MgO$, $CaO$, $SrO$, $ZrO_2$, $ZnO$, $LiAlO_2$, $MgAl_2O_4$, $MnO$, $MnO_2$, $Mn_2O_4$, $La_2O_3$, activated carbon, silica gel, zeolites, activated clays, activated $Al_2O_3$, SiC, diatomaceous earth, magnesia, aluminosilicates, calcium aluminate, or combinations thereof. In some embodiments the support comprises $SiO_2$. In other embodiments the support comprises MgO. In yet other embodiments, the support comprises yttrium, for example $Y_2O_3$. In other embodiments the support comprises $ZrO_2$. In yet other embodiments, the support comprises $La_2O_3$.

In still other embodiments, the support comprises $AlPO_4$, $Al_2O_3$, $SiO_2$—$Al_2O_3$, CaO, SrO, $TiO_2$, $ZrO_2$, MgO, $SiO_2$, $Z_2O_2$, $HfO_2$, $In_2O_3$ or combinations thereof. In yet other embodiments, a catalyst may serve as a support for another catalyst. For example, a catalyst may be comprised of catalytic support material and adhered to or incorporated within the support is another catalyst. For example, in some embodiments, the catalytic support may comprise $SiO_2$, MgO, $TiO_2$, $ZrO_2$, $Al_2O_3$, ZnO or combinations thereof.

In still other embodiments, the support material comprises a carbonate. For example, in some embodiments the support material comprises $MgCO_3$, $CaCO_3$, $SrCO_3$, $BaCO_3$, $Y_2(CO_3)_3$, $La_2(CO_3)_3$ or combination thereof.

The optimum amount of catalyst present on the support depends, inter alia, on the catalytic activity of the catalyst. In some embodiments, the amount of catalyst present on the support ranges from 1 to 100 parts by weight of catalyst per 100 parts by weight of support or from 10 to 50 parts by weight of catalyst per 100 parts by weight of support. In other embodiments, the amount of catalyst present on the support ranges from 100-200 parts of catalyst per 100 parts by weight of support, or 200-500 parts of catalyst per 100 parts by weight of support, or 500-1000 parts of catalyst per 100 parts by weight of support.

Typically, heterogeneous catalysts are used either in their pure form or blended with inert support materials, such as silica, alumina, etc. as described above. The blending with inert materials may be used in order to reduce and/or control large temperature non-uniformities within the reactor bed often observed in the case of strongly exothermic (or endothermic) reactions. In the case of complex multistep reactions, such as the reaction to convert methane into ethylene (OCM), typical blending materials can selectively slow down or quench one or more of the desired reactions of the system and promote unwanted side reactions. For example, in the case of the oxidative coupling of methane, silica and alumina can quench the methyl radicals and thus prevent the formation of ethane. In certain aspects, the present disclosure provides a catalytic material which addresses these problems typically associated with catalyst support material. Accordingly, in certain embodiments the catalytic activity of the catalytic material can be tuned by blending two or more catalysts and/or catalyst support materials. The blended catalytic material may comprise a catalyst as described herein in combination with with another catalytic material, for example an additional bulk catalyst or a catalytic nanowire as described in copending U.S. application Ser. No. 13/115,082 which is hereby incorporated by reference in its entirety, and/or inert support material.

The blended catalytic materials comprise any of the catalysts disclosed herein. For example, the blended catalytic materials may comprise a plurality of catalysts, as disclosed herein, and any one or more of catalytic nanowires, bulk materials and inert support materials. The catalytic materials may be undoped or may be doped with any of the dopants described herein.

In one embodiment, the catalyst blend comprises at least one type 1 component and at least one type 2 component. Type 1 components comprise catalysts having a high OCM activity at moderately low temperatures and type 2 components comprise catalysts having limited or no OCM activity at these moderately low temperatures, but are OCM active at higher temperatures. For example, in some embodiments the type 1 component is a catalyst (e.g., mixed oxide of Mn/Mg, Na/Mn/W or rare earth) having high OCM activity at moderately low temperatures. For example, the type 1 component may comprise a C2 yield of greater than 5% or greater than 10% at temperatures less than 8000° C., less than 7000° C. or less than 6000° C. The type 2 component may comprise a C2 yield less than 0.1%, less than 1% or less than 5% at temperatures less than 8000° C., less than 7000° C. or less than 6000° C. The type 2 component may comprise a C2 yield of greater than 0.1%, greater than 1%, greater than 5% or greater than 10% at temperatures greater than 8000° C., greater than 7000° C. or greater than 600° C. Typical type 1 components include any of the catalysts as described herein, while typical type 2 components include other bulk OCM catalysts or catalytic nanowires. The catalyst blend may further comprise inert support materials as described above (e.g., silica, alumina, silicon carbide, etc.).

In certain embodiments, the type 2 component acts as diluent in the same way an inert material does and thus helps reduce and/or control hot spots in the catalyst bed caused by the exothermic nature of the OCM reaction. However, because the type 2 component is an OCM catalyst, albeit not a particularly active one, it may prevent the occurrence of undesired side reactions, e.g. methyl radical quenching. Additionally, controlling the hotspots has the beneficial effect of extending the lifetime of the catalyst.

For example, it has been found that diluting active lanthanide oxide OCM catalysts (e.g., as described above) with as much as a 10:1 ratio of MgO, which by itself is not an active OCM catalyst at the temperature which the lanthanide oxide operates, is a good way to minimize "hot spots" in the reactor catalyst bed, while maintaining the selectivity and yield performance of the catalyst. On the other hand, doing the same dilution with quartz $SiO_2$ is not effective because it appears to quench the methyl radicals which serves to lower the selectivity to C2s.

In yet another embodiment, the type 2 components are good oxidative dehydrogenation (ODH) catalysts at the same temperature that the type 1 components are good OCM catalysts. In this embodiment, the ethylene/ethane ratio of the resulting gas mixture can be tuned in favor of higher ethylene. In another embodiment, the type 2 components are not only good ODH catalysts at the same temperature the type 1 components are good OCM catalysts, but also have limited to moderate OCM activity at these temperatures.

In related embodiments, the catalytic performance of the catalytic material is tuned by selecting specific type 1 and type 2 components of a catalyst blend. In another embodiment, the catalytic performance is tuned by adjusting the ratio of the type 1 and type 2 components in the catalytic material. For example, the type 1 catalyst may be a catalyst for a specific step in the catalytic reaction, while the type 2 catalyst may be specific for a different step in the catalytic reaction. For example, the type 1 catalyst may be optimized for formation of methyl radicals and the type 2 catalyst may be optimized for formation of ethane or ethylene.

In other embodiments, the catalyst material comprises at least two different components (component 1, component 2, component 3, etc.). The different components may comprise different morphologies, e.g. nanowires, nanoparticles, bulk, etc. The different components in the catalyst material can be, but not necessarily, of the same chemical composition and the only difference is in the morphology and/or the size of the particles. This difference in morphology and particle size may result in a difference in reactivity at a specific temperature. Additionally, the difference in morphology and particle size of the catalytic material components is advantageous for creating a homogeneous blend, which can have a beneficial effect on catalyst performance. Also, the difference in morphology and particle size of the blend components would allow for control and tuning of the macro-pore distribution in the reactor bed and thus its catalytic efficiency. An additional level of micro-pore tuning can be attained by blending catalysts with different chemical composition and different morphology and/or particle size. The proximity effect would be advantageous for the reaction selectivity.

For ease of illustration, the above description of catalytic materials often refers to OCM; however, such catalytic materials find utility in other catalytic reactions including but not limited to: oxidative dehydrogenation (ODH) of alkanes to their corresponding alkenes, selective oxidation of alkanes and alkenes and alkynes, oxidation of CO, dry reforming of methane, selective oxidation of aromatics, Fischer-Tropsch, combustion of hydrocarbons, etc.

OCM catalysts may be prone to hotspots due to the very exothermic nature of the OCM reaction. Diluting such catalysts helps to manage the hotspots. However, the diluent needs to be carefully chosen so that the overall performance of the catalyst is not degraded. Silicon carbide for example can be used as a diluent with little impact on the OCM selectivity of the blended catalytic material whereas using silica as a diluent may significantly reduce OCM selectivity. The good heat conductivity of SiC is also beneficial in minimizing hot spots.

Use of a catalyst diluent or support material that is itself OCM active has significant advantages over more traditional diluents such as silica and alumina, which can quench methyl radicals and thus reduce the OCM performance of the catalyst. An OCM active diluent is not expected to have any adverse impact on the generation and lifetime of methyl radicals and thus the dilution should not have any adverse impact on the catalyst performance. Thus embodiments of the invention include catalyst compositions comprising an OCM catalyst (e.g., any of the disclosed catalysts) in combination with a diluent or support material that is also OCM active. Methods for use of the same in an OCM reaction are also provided.

In some embodiments, the above diluent comprises alkaline earth metal compounds, for example alkaline metal oxides, carbonates, sulfates or phosphates. Examples of diluents useful in various embodiments include, but are not limited to, $MgO$, $MgCO_3$, $MgSO_4$, $Mg_3(PO_4)_2$, $MgAl_2O_4$, $CaO$, $CaCO_3$, $CaSO_4$, $Ca_3(PO_4)_2$, $CaAl_2O_4$, $SrO$, $SrCO_3$, $SrSO_4$, $Sr_3(PO_4)_2$, $SrAl_2O_4$, $BaO$, $BaCO_3$, $BaSO_4$, $Ba_3(PO_4)_2$, $BaAl_2O_4$ and the like. Most of these compounds are very cheap, especially $MgO$, $CaO$, $MgCO_3$, $CaCO_3$, $SrO$, $SrCO_3$ and thus very attractive for use as diluents from an economic point of view. Additionally, the magnesium, calcium and strontium compounds are also environmentally friendly. Accordingly, an embodiment of the invention provides a catalytic material comprising a catalyst in combination with a diluent selected from one or more of $MgO$, $MgCO_3$, $MgSO_4$, $Mg_3(PO_4)_2$, $CaO$, $CaCO_3$, $CaSO_4$, $Ca_3(PO_4)_2$, $SrO$, $SrCO_3$, $SrSO_4$, $Sr_3(PO_4)_2$, $BaO$, $BaCO_3$, $BaSO_4$, $Ba_3(PO_4)_2$. In some specific embodiments the diluents is $MgO$, $CaO$, $SrO$, $MgCO_3$, $CaCO_3$, $SrCO_3$ or combination thereof. Methods for use of the foregoing catalytic materials in an OCM reaction are also provided. The methods comprise converting methane to ethane and/or ethylene in the presence of the catalytic materials.

The above diluents and supports may be employed in any number of methods. For example, in some embodiments a support (e.g., $MgO$, $CaO$, $CaCO_3$, $SrCO_3$) may be used in the form of a pellet or monolith (e.g., honeycomb) structure, and the catalysts may be impregnated or supported thereon. In other embodiments, a core/shell arrangement is provided and the support material may form part of the core or shell. For example, a core of $MgO$, $CaO$, $CaCO_3$ or $SrCO_3$ may be coated with a shell of any of the disclosed catalyst compositions.

In some embodiments, the diluent has a morphology selected from bulk (e.g. commercial grade), nano (nanowires, for example as described in copending U.S. application Ser. No. 13/115,082, which is hereby incorporated by reference in its entirety, nanorods, nanoparticles, etc.) or combinations thereof.

In some embodiments, the diluent has zero to moderate catalytic activity at the temperature the OCM catalyst is operated. In some other embodiments, the diluent has moderate to large catalytic activity at a temperature higher than the temperature the OCM catalyst is operated. In yet some other embodiments, the diluent has zero to moderate catalytic activity at the temperature the OCM catalyst is operated and moderate to large catalytic activity at temperatures higher than the temperature the OCM catalyst is operated. Typical temperatures for operating an OCM reaction according to the present disclosure are 800° C. or lower, 750° C. or lower, 700° C. or lower, 650° C. or lower, 600° C. or lower and 550° C. or lower.

For example, $CaCO_3$ is a relatively good OCM catalyst at T>750° C. (50% selectivity, >20% conversion) but has essentially no activity below 700° C. Accordingly, dilution of OCM catalysts with a $CaCO_3$ (or $SrO_3$) material is expected to result in no degradation of OCM performance and, in some cases, even better performance than the neat catalyst.

In some embodiments, the diluent portion in the catalyst/diluent mixture is 0.01%, 10%, 30%, 50%, 70%, 90% or 99.99% (weight percent) or any other value between 0.01% and 99.9%. In some embodiments, the dilution is performed with the OCM catalyst ready to go, e.g. after calcination. In some other embodiments, the dilution is performed prior to the final calcination of the catalyst, i.e. the catalyst and the diluent are calcined together. In yet some other embodiments, the dilution can be done during the synthesis as well, so that, for example, a mixed oxide is formed.

In some embodiments, the catalyst/diluent mixture comprises more than one catalyst and/or more than one diluent. In some other embodiments, the catalyst/diluent mixture is pelletized and sized, or made into shaped extrudates or deposited on a monolith or foam, or is used as it is. Methods of the invention include taking advantage of the very exothermic nature of OCM by diluting the catalyst with another catalyst that is (almost) inactive in the OCM reaction at the operating temperature of the first catalyst but active at higher temperature. In these methods, the heat generated by the hotspots of the first catalyst will provide the necessary heat for the second catalyst to become active.

3. Preparation of Catalysts and Catalytic Materials

The catalytic materials can be prepared according to any number of methods known in the art. For example, the catalytic materials can be prepared after preparation of the individual components by mixing the individual components in their dry form, e.g. blend of powders, and optionally, ball milling can be used to reduce particle size and/or increase mixing. Each component can be added together or one after the other to form layered particles. Alternatively, the individual components can be mixed prior to calcination, after calcination or by mixing already calcined components with uncalcined components. The catalytic materials may also be prepared by mixing the individual components in their dry form and optionally pressing them together into a "pill" followed by calcination to above 800° C., or above 900° C.

The foregoing catalysts may be doped prior to, or after formation of the mixed oxide. In one embodiment, one or more metal salts are mixed to form a solution or a slurry which is dried and then calcined in a range of 400° C. to 900° C., or between 500° C. and 700° C. In another embodiment, the mixed oxide is formed first through calcination of a metal salt followed by contact with a solution comprising the doping element followed by drying and/or calcination between 300° C. and 800° C., or between 400° C. and 700° C.

In other examples, the catalytic materials are prepared by mixing the individual components with one or more solvents into a suspension or slurry, and optional mixing and/or ball milling can be used to maximize uniformity and reduce particle size. Examples of slurry solvents useful in this context include, but are not limited to: water, alcohols, ethers, carboxylic acids, ketones, esters, amides, aldehydes, amines, alkanes, alkenes, alkynes, aromatics, etc. In other embodiments, the individual components are deposited on a supporting material such as silica, alumina, magnesia, activated carbon, and the like, or by mixing the individual components using a fluidized bed granulator. Combinations of any of the above methods may also be used.

The catalytic materials may optionally comprise a dopant as described in more detail herein. In this respect, doping material(s) may be added during preparation of the individual components, after preparation of the individual components but before drying of the same, after the drying step but before calcinations or after calcination. If more than one doping material is used, each dopant can be added together or one after the other to form layers of dopants.

Doping material(s) may also be added as dry components and optionally ball milling can be used to increase mixing. In other embodiments, doping material(s) are added as a liquid (e.g. solution, suspension, slurry, etc.) to the dry individual catalyst components or to the blended catalytic material. The amount of liquid may optionally be adjusted for optimum wetting of the catalyst, which can result in optimum coverage of catalyst particles by doping material. Mixing and/or ball milling can also be used to maximize doping coverage and uniform distribution. Alternatively, doping material(s) are added as a liquid (e.g. solution, suspension, slurry, etc.) to a suspension or slurry of the catalyst in a solvent. Incorporation of dopants can also be achieved using any of the methods described elsewhere herein.

As noted herein, an optional calcination step usually follows an optional drying step at T<200° C. (typically 60-120° C.) in a regular oven or in a vacuum oven. Calcination may be performed on the individual components of the catalytic material or on the blended catalytic material. Calcination is generally performed in an oven/furnace at a temperature higher than the minimum temperature at which at least one of the components decomposes or undergoes a phase transformation and can be performed in inert atmosphere (e.g. $N_2$, Ar, He, etc.), oxidizing atmosphere (air, $O_2$, etc.) or reducing atmosphere ($H_2$, $H_2/N_2$, $H_2/Ar$, etc.). The atmosphere may be a static atmosphere or a gas flow and may be performed at ambient pressure, at p<1 atm, in vacuum or at p>1 atm. High pressure treatment (at any temperature) may also be used to induce phase transformation including amorphous to crystalline.

Calcination is generally performed in any combination of steps comprising ramp up, dwell and ramp down. For example, ramp to 500° C., dwell at 500° C. for 5 h, ramp down to RT. Another example includes ramp to 100° C., dwell at 100° C. for 2 h, ramp to 300° C., dwell at 300° C. for 4 h, ramp to 550° C., dwell at 550° C. for 4 h, ramp down to RT. Calcination conditions (pressure, atmosphere type, etc.) can be changed during the calcination. In some embodiments, calcination is performed before preparation of the blended catalytic material (i.e., individual components are calcined), after preparation of the blended catalytic material but before doping, after doping of the individual components or blended catalytic material. Calcination may also be performed multiple times, e.g. after catalyst preparation and after doping and may also be performed by microwave heating.

The catalytic materials may be incorporated into a reactor bed for performing any number of catalytic reactions (e.g., OCM, ODH and the like). Accordingly, in one embodiment the present disclosure provides a catalytic material as disclosed herein in contact with a reactor and/or in a reactor bed. For example, the reactor may be for performing an OCM reaction, may be a fixed bed reactor and may have a diameter greater than 1 inch. In this regard, the catalytic material may be packed neat (without diluents) or diluted with an inert material (e.g., sand, silica, alumina, etc.) The catalyst components may be packed uniformly forming a homogeneous reactor bed.

The particle size of the individual components within a catalytic material may also alter the catalytic activity, and other properties, of the same. Accordingly, in one embodiment, the catalyst is milled to a target average particle size or the catalyst powder is sieved to select a particular particle size. In some aspects, the catalyst powder may be pressed into pellets and the catalyst pellets can be optionally milled and or sieved to obtain the desired particle size distribution.

In some embodiments, the catalyst materials, alone or with binders and/or diluents, can be configured into larger aggregate forms, such as pellets, extrudates, or other aggregations of catalyst particles. For ease of discussion, such larger forms are generally referred to herein as "pellets". Such pellets may optionally include a binder and/or support material.

Catalytic materials also include any of the disclosed catalysts disposed on or adhered to a solid support. For example, the catalysts may be adhered to the surface of a monolith support. Monoliths include honeycomb-type structures, foams and other catalytic support structures derivable by one skilled in the art. In one embodiment, the support is a honeycomb matrix formed from silicon carbide, and the support further comprises the disclosed catalysts disposed on the surface.

As the OCM reaction is very exothermic, it can be desirable to reduce the rate of conversion per unit volume of reactor in order to avoid run away temperature rise in the catalyst bed that can result in hot spots affecting performance and catalyst life. One way to reduce the OCM reaction rate per unit volume of reactor is to spread the active catalyst onto an inert support with interconnected large pores as in ceramic or metallic foams (including metal alloys having reduced reactivity with hydrocarbons under OCM reaction conditions) or having arrays of channel as in honeycomb structured ceramic or metal assembly.

In one embodiment, a catalytic material comprising a catalyst as disclosed herein supported on a structured support is provided. Examples of such structure supports include, but are not limited to, metal foams, Silicon Carbide or Alumina foams, corrugated metal foil arranged to form channel arrays, extruded ceramic honeycomb, for example Cordierite (available from Corning or NGK ceramics, USA), Silicon Carbide or Alumina.

Active catalyst loading on the structured support ranges from 1 to 500 mg per ml of support component, for example from 5 to 100 mg per ml of structure support. Cell densities on honeycomb structured support materials may range from 100 to 900 CPSI (cell per square inch), for example 200 to 600 CPSI. Foam densities may range from 10 to 100 PPI (pore per inch), for example 20 to 60 PPI.

In other embodiments, the exotherm of the OCM reaction may be at least partially controlled by blending the active catalytic material with catalytically inert material, and pressing or extruding the mixture into shaped pellets or extrudates. In some embodiments, these mixed particles may then be loaded into a pack-bed reactor. The Extrudates or pellets comprise between 30% to 70% pore volume with 5% to 50% active catalyst weight fraction. Useful inert materials in this regard include, but are not limited to MgO, CaO, $Al_2O_3$, SiC and cordierite.

In addition to reducing the potential for hot spots within the catalytic reactor, another advantage of using a structured ceramic with large pore volume as a catalytic support is reduced flow resistance at the same gas hourly space velocity versus a pack-bed containing the same amount of catalyst.

Yet another advantage of using such supports is that the structured support can be used to provide features difficult to obtain in a pack-bed reactor. For example the support structure can improve mixing or enabling patterning of the active catalyst depositions through the reactor volume. Such patterning can consist of depositing multiple layers of catalytic materials on the support in addition to the OCM active component in order to affect transport to the catalyst or combining catalytic functions such as adding O2-ODH activity, CO2-OCM activity or CO2-ODH activity to the system in addition to O2-OCM active material. Another patterning strategy can be to create bypass within the structure catalyst essentially free of active catalyst to limit the overall conversion within a given supported catalyst volume.

Yet another advantage is reduced heat capacity of the bed of the structured catalyst over a pack bed a similar active catalyst loading therefore reducing startup time.

Alternatively, such catalyst on support or in pellet form approaches can be used for other reactions besides OCM, such as ODH, dry methane reforming, FT, and all other catalytic reactions.

In yet another embodiment, the catalysts are packed in bands forming a layered reactor bed. Each layer is composed of either a catalyst of a particular type, morphology or size or a particular blend of catalysts. In one embodiment, the catalysts blend may have better sintering properties, i.e. lower tendency to sinter, then a material in its pure form. Better sintering resistance is expected to increase the catalyst's lifetime and improve the mechanical properties of the reactor bed.

One skilled in the art will recognize that various combinations or alternatives of the above methods are possible, and such variations are also included within the scope of the present disclosure.

4. Structure/Physical Characteristics of the Disclosed Catalysts

Typically, a catalytic material described herein comprises a plurality of metal oxide particles. In certain embodiments, the catalytic material may further comprise a support material. The total surface area per gram of a catalytic material may have an effect on the catalytic performance. Pore size distribution may affect the catalytic performance as well. Surface area and pore size distribution of the catalytic material can be determined by BET (Brunauer, Emmett, Teller) measurements. BET techniques utilize nitrogen adsorption at various temperatures and partial pressures to determine the surface area and pore sizes of catalysts. BET techniques for determining surface area and pore size distribution are well known in the art.

In some embodiments the catalytic material comprises a surface area of between 0.1 and 100 $m^2/g$, between 1 and 100 $m^2/g$, between 1 and 50 $m^2/g$, between 1 and 20 $m^2/g$, between 1 and 10 $m^2/g$, between 1 and 5 $m^2/g$, between 1 and 4 $m^2/g$, between 1 and 3 $m^2/g$, or between 1 and 2 $m^2/g$.

Catalytic Reactions

The present disclosure provides heterogenous catalysts having better catalytic properties than a corresponding undoped catalyst. The catalysts disclosed herein are useful in any number of reactions catalyzed by a heterogeneous catalyst. Examples of reactions wherein the disclosed catalysts may be employed are disclosed in Farrauto and Bartholomew, "Fundamentals of Industrial Catalytic Processes" Blackie Academic and Professional, first edition, 1997, which is hereby incorporated in its entirety. Other non-limiting examples of reactions wherein the catalysts may be employed include: the oxidative coupling of methane (OCM) to ethane and ethylene; oxidative dehydrogenation (ODH) of alkanes to the corresponding alkenes, for example oxidative dehydrogenation of ethane or propane to ethylene or propylene, respectively; selective oxidation of alkanes, alkenes, and alkynes; oxidation of CO, dry reforming of methane, selective oxidation of aromatics; Fischer-Tropsch, hydrocarbon cracking; and the like. Reactions catalyzed by the disclosed catalysts are discussed in more detail below. While an embodiment of the invention is described in greater detail below in the context of the OCM reaction and other reactions described herein, the catalysts are not in any way limited to the particularly described reactions.

The disclosed catalysts are generally useful in methods for converting a first carbon-containing compound (e.g., a hydrocarbon, CO or $CO_2$) to a second carbon-containing compound. In some embodiments the methods comprise contacting a disclosed catalyst, or material comprising the same, with a gas comprising a first carbon-containing compound and an oxidant to produce a second carbon-containing compound. In some embodiments, the first carbon-containing compound is a hydrocarbon, CO, $CO_2$, methane, ethane, propane, hexane, cyclohexane, octane or combinations thereof. In other embodiments, the second carbon-containing compound is a hydrocarbon, CO, $CO_2$, ethane, ethylene, propane, propylene, hexane, hexene, cyclohexane, cyclohexene, bicyclohexane, octane, octene or hexadecane. In some embodiments, the oxidant is oxygen, ozone, nitrous oxide, nitric oxide, water, carbon dioxide or combinations thereof.

In other embodiments of the foregoing, the method for conversion of a first carbon-containing compound to a second carbon-containing compound is performed at a temperature below 100° C., below 200° C., below 300° C., below 400° C., below 500° C., below 600° C., below 700° C., below 800° C., below 900° C. or below 1000° C. In certain embodiments, the method is OCM and the method is performed at a temperature below 600° C., below 700° C., below 800° C., or below 900° C. In other embodiments, the method for conversion of a first carbon-containing compound to a second carbon-containing compound is performed at a pressure above 0.5 ATM, above 1 ATM, above 2 ATM, above 5 ATM, above 10 ATM, above 25 ATM or above 50 ATM.

The catalytic reactions described herein can be performed using standard laboratory equipment known to those of skill in the art, for example as described in U.S. Pat. No. 6,350,716, which is incorporated herein in its entirety.

As noted above, the catalysts disclosed herein have better catalytic activity than a corresponding undoped catalyst. In some embodiments, the selectivity, yield, conversion, or combinations thereof, of a reaction catalyzed by the catalysts is better than the selectivity, yield, conversion, or combinations thereof, of the same reaction catalyzed by a corresponding undoped catalyst under the same conditions. For example, in some embodiments, the catalyst possesses a catalytic activity such that yield of product in a reaction catalyzed by the catalyst is greater than 1.1 times, greater than 1.25 times, greater than 1.5 times, greater than 2.0 times, greater than 3.0 times or greater than 4.0 times the yield of product in the same reaction catalyzed by a corresponding undoped catalyst (i.e., a catalyst comprising the same base material but different or no dopants).

In other embodiments, the catalyst possesses a catalytic activity such that selectivity for the desired product(s) in a reaction catalyzed by the catalyst is greater than 1.1 times, greater than 1.25 times, greater than 1.5 times, greater than 2.0 times, greater than 3.0 times or greater than 4.0 times the yield of product in the same reaction catalyzed by a corresponding undoped catalyst.

In yet other embodiments, the catalyst possesses a catalytic activity such that conversion of reactant in a reaction catalyzed by the catalyst is greater than 1.1 times, greater than 1.25 times, greater than 1.5 times, greater than 2.0 times, greater than 3.0 times or greater than 4.0 times the yield of product in the same reaction catalyzed by a corresponding undoped catalyst.

In yet other embodiments, the catalysts possess a catalytic activity such that the activation temperature of a reaction catalyzed by the catalyst is at least 25° C. lower, at least 50° C. lower, at least 75° C. lower, or at least 100° C. lower than the temperature of the same reaction under the same conditions but catalyzed by a corresponding undoped bulk catalyst.

Production of unwanted oxides of carbon (e.g., CO and $CO_2$) is a problem that reduces overall yield of desired product and results in an environmental liability. Accordingly, in one embodiment the present disclosure addresses this problem and provides catalysts with a catalytic activity such that the selectivity for CO and/or $CO_2$ in a reaction catalyzed by the catalysts is less than the selectivity for CO and/or $CO_2$ in the same reaction under the same conditions but catalyzed by an undoped catalyst. Accordingly, in one embodiment, the present disclosure provides a catalyst which possesses a catalytic activity such that selectivity for $CO_x$, wherein x is 1 or 2, in a reaction catalyzed by the catalyst is less than at least 0.9 times, less than at least 0.8 times, less than at least 0.5 times, less than at least 0.2 times or less than at least 0.1 times the selectivity for $CO_x$ in the same reaction under the same conditions but catalyzed by a corresponding undoped catalyst (i.e., a catalyst comprising the same base material bu different or no dopants).

In some embodiments, the absolute selectivity, yield, conversion, or combinations thereof, of a reaction catalyzed by the catalysts disclosed herein is better than the absolute selectivity, yield, conversion, or combinations thereof, of the same reaction under the same conditions but catalyzed by a corresponding undoped catalyst. For example, in some embodiments the yield of desired product(s) in a reaction catalyzed by the catalysts is greater than 10%, greater than 20%, greater than 30%, greater than 50%, greater than 75%, or greater than 90%. In some embodiments, the reaction is OCM and the yield of product is greater than 10%, greater than 20%, greater than 30% or greater than 40%. In other embodiments, the selectivity for product in a reaction catalyzed by the catalysts is greater than 10%, greater than 20%, greater than 30%, greater than 50%, greater than 75%, or greater than 90%. In other embodiments, the conversion of reactant to product in a reaction catalyzed by the catalysts is greater than 10%, greater than 20%, greater than 30%, greater than 50%, greater than 75%, or greater than 90%.

1. Oxidative Coupling of Methane (OCM)

As noted above, the present disclosure provides catalysts having catalytic activity and related approaches to catalyst design and preparation for improving the yield, selectivity and/or conversion of any number of catalyzed reactions, including the OCM reaction. As mentioned above, there exists a tremendous need for catalyst technology capable of addressing the conversion of methane into high value chemicals (e.g., ethylene and products prepared therefrom) using a direct route that does not go though syngas. Accomplishing this task will dramatically impact and redefine a non-petroleum based pathway for feedstock manufacturing and liquid fuel production yielding reductions in GHG emissions, as well as providing new fuel sources.

Ethylene has the largest carbon footprint compared to all industrial chemical products in part due to the large total volume consumed into a wide range of downstream important industrial products including plastics, surfactants and pharmaceuticals. In 2008, worldwide ethylene production exceeded 120 M metric tons while growing at a robust rate of 4% per year. The United States represents the largest single producer at 28% of the world capacity. Ethylene is primarily manufactured from high temperature cracking of naphtha (e.g., oil) or ethane that is separated from natural gas. The true measurement of the carbon footprint can be difficult as it depends on factors such as the feedstock and the allocation as several products are made and separated during the same process. However, some general estimates can be made based on published data.

Cracking consumes a significant portion (about 65%) of the total energy used in ethylene production and the remainder is for separations using low temperature distillation and compression. The total tons of $CO_2$ emission per ton of ethylene are estimated at between 0.9 to 1.2 from ethane cracking and 1 to 2 from naphtha cracking. Roughly, 60% of ethylene produced is from naphtha, 35% from ethane and 5% from others sources (Ren, T.; Patel, M. *Res. Conserv. Recycl.* 53:513, 2009). Therefore, based on median averages, an estimated amount of $CO_2$ emissions from the cracking process is 114M tons per year (based on 120M tons produced). Separations would then account for an additional 61M tons $CO_2$ per year.

The catalysts of this disclosure provide an alternative to the need for the energy intensive cracking step. Additionally, because of the high selectivity of the catalysts, downstream separations are dramatically simplified, as compared to cracking which yields a wide range of hydrocarbon products. The reaction is also exothermic so it can proceed via an autothermal process mechanism. Overall, it is estimated that up to a potential 75% reduction in $CO_2$ emission compared to conventional methods could be achieved. This would equate to a reduction of one billion tons of $CO_2$ over a ten-year period and would save over 1M barrels of oil per day.

The catalysts of this disclosure also permit converting ethylene into liquid fuels such as gasoline or diesel, given ethylene's high reactivity and numerous publications demonstrating high yield reactions, in the lab setting, from ethylene to gasoline and diesel. On a life cycle basis from well to wheel, recent analysis of methane to liquid (MTL) using F-T process derived gasoline and diesel fuels has shown an emission profile approximately 20% greater to that of petroleum based production (based on a worst case scenario) (Jaramillo, P., Griffin, M., Matthews, S., *Env. Sci. Tech* 42:7559, 2008). In the model, the $CO_2$ contribution from plant energy was a dominating factor at 60%. Thus, replacement of the cracking and F-T process would be expected to provide a notable reduction in net emissions, and could be produced at lower $CO_2$ emissions than petroleum based production.

Furthermore, a considerable portion of natural gas is found in regions that are remote from markets or pipelines. Most of this gas is flared, re-circulated back into oil reservoirs, or vented given its low economic value. The World Bank estimates flaring adds 400M metric tons of $CO_2$ to the atmosphere each year as well as contributing to methane emissions. The catalysts of this disclosure also provide economic and environmental incentive to stop flaring. Also, the conversion of methane to fuel has several environmental advantages over petroleum-derived fuel. Natural gas is the cleanest of all fossil fuels, and it does not contain a number of impurities such as mercury and other heavy metals found in oil. Additionally, contaminants including sulfur are also easily separated from the initial natural gas stream. The resulting fuels burn much cleaner with no measurable toxic pollutants and provide lower emissions than conventional diesel and gasoline in use today.

The selective, catalytic oxidative coupling of methane to ethylene (i.e. the OCM reaction) is shown by the following reaction (1):

$$2CH_4 + O_2 \rightarrow CH_2CH_2 + 2H_2O \qquad (1)$$

This reaction is exothermic (Heat of Reaction −67 kcals/mole) and usually occurs at very high temperatures (>700° C.). During this reaction, it is believed that the methane ($CH_4$) is first oxidatively coupled into ethane ($C_2H_6$), and subsequently the ethane ($C_2H_6$) is oxidatively dehydrogenated into ethylene ($C_2H_4$). Because of the high temperatures used in the reaction, it has been suggested that the ethane is produced mainly by the coupling in the gas phase of the surface-generated methyl ($CH_3$) radicals. Reactive metal oxides (oxygen type ions) are apparently required for the activation of $CH_4$ to produce the $CH_3$ radicals. The yield of $C_2H_4$ and $C_2H_6$ is limited by further reactions in the gas phase and to some extent on the catalyst surface. A few of the possible reactions that occur during the oxidation of methane are shown below as reactions (2) through (8):

$$CH_4 \rightarrow CH_3 \text{ radical} \qquad (2)$$

$$CH_3 \text{ radical} \rightarrow C_2H_6 \qquad (3)$$

$$CH_3 \text{ radical} + 2.5O_2 \rightarrow CO_2 + 1.5H_2O \qquad (4)$$

$$C_2H_6 \rightarrow C_2H_4 + H_2 \qquad (5)$$

$$C_2H_6 + 0.5\ O_2 \rightarrow C_2H_4 + H_2O \qquad (6)$$

$$C_2H_4 + 3\ O_2 \rightarrow 2CO_2 + 2H_2O \qquad (7)$$

$$CH_3 \text{ radical} + C_xH_y + O_2 \rightarrow \text{Higher HC's-Oxidation/} \\ CO_2 + H_2O \qquad (8)$$

With conventional heterogeneous catalysts and reactor systems, the reported performance is generally limited to <25% $CH_4$ conversion at <80% combined $C_2$ selectivity at high temperatures (~850° C. or higher), with the performance characteristics of high selectivity at low conversion, or the low selectivity at high conversion. In contrast, the catalysts of this disclosure are highly active and can optionally operate at a lower temperature. In one embodiment, the catalysts disclosed herein enable efficient conversion of methane to ethylene in the OCM reaction at temperatures less than when other known catalysts are used. For example, in one embodiment, the catalysts disclosed herein enable efficient conversion (i.e., high yield, conversion, and/or selectivity) of methane to ethylene at temperatures of less than 800° C., less than 700° C. or less than 600° C. In other embodiments, the use of staged oxygen addition, designed heat management, rapid quench and/or advanced separations may also be employed.

Typically, the OCM reaction is run in a mixture of oxygen and nitrogen or other inert gas. Such gasses are expensive and increase the overall production costs associated with preparation of ethylene or ethane from methane. However, the present inventors have now discovered that such expensive gases are not required and high yield, conversion, selectivity, etc. can be obtained when air is used as the gas mixture instead of pre-packaged and purified sources of oxygen and other gases. Accordingly, in one embodiment the disclosure provides a method for performing the OCM reaction using air as the oxidizer source.

Accordingly, in one embodiment a stable, very active, high surface area, multifunctional catalyst is disclosed having active sites that are isolated and precisely engineered with the catalytically active metal centers/sites in the desired proximity (see, e.g., FIG. 1) for facilitating the OCM reaction, as well as other reactions.

The exothermic heats of reaction (free energy) follows the order of reactions depicted above and, because of the proximity of the active sites, will mechanistically favor ethylene formation while minimizing complete oxidation reactions that form CO and $CO_2$. Representative catalyst compositions useful for the OCM reaction include, but are not limited to the catalyst compositions described herein.

As noted above, the presently disclosed catalysts comprise a catalytic performance better than corresponding undoped catalysts, for example in one embodiment the catalytic performance of the catalysts in the OCM reaction is better than the catalytic performance of a corresponding undoped catalyst. In this regard, various performance criteria may define the "catalytic performance" of the catalysts in the OCM (and other reactions). In one embodiment, catalytic performance is defined by C2 selectivity in the OCM reaction, and the C2 selectivity of the catalysts in the OCM reaction is >5%, >10%, >15%, >20%, >25%, >30%, >35%, >40%, >45%, >50%, >55%, >60%, >65%, >70%, >75% or >80%.

Other important performance parameters used to measure the catalysts' catalytic performance in the OCM reaction are selected from single pass methane conversion percentage (i.e., the percent of methane converted on a single pass over the catalyst or catalytic bed, etc.), reaction inlet gas temperature, reaction operating temperature, total reaction pressure, methane partial pressure, gas-hour space velocity (GHSV), $O_2$ source, catalyst stability and ethylene to ethane ratio. In certain embodiments, improved catalytic performance is defined in terms of the catalysts' improved performance (relative to a corresponding undoped catalyst) with respect to at least one of the foregoing performance parameters.

The reaction inlet gas temperature in an OCM reaction catalyzed by the disclosed catalysts can generally be maintained at a lower temperature, while maintaining better performance characteristics (e.g., conversion, C2 yield, C2 selectivity and the like) compared to the same reaction catalyzed by a corresponding undoped catalyst under the same reaction conditions. In certain embodiments, the inlet gas temperature in an OCM reaction catalyzed by the disclosed catalysts is <700° C., <675° C., <650° C., <625° C., <600° C., <593° C., <580° C., <570° C., <560° C., <550° C., <540° C., <530° C., <520° C., <510° C., <500° C., <490° C., <480° C. or even <470° C.

The reaction operating temperature in an OCM reaction catalyzed by the disclosed catalysts can generally be maintained at a lower temperature, while maintaining better performance characteristics compared to the same reaction catalyzed by a corresponding bulk catalyst under the same reaction conditions. In certain embodiments, the reaction operating temperature in an OCM reaction catalyzed by the disclosed catalysts is <700° C., <675° C., <650° C., <625° C., <600° C., <593° C., <580° C., <570° C., <560° C., <550° C., <540° C., <530° C., <520° C., <510° C., <500° C., <490° C., <480° C., <470° C.

The single pass methane conversion in an OCM reaction catalyzed by the catalysts is also generally better compared to the single pass methane conversion in the same reaction catalyzed by a corresponding undoped catalyst under the same reaction conditions. For single pass methane conversion it is preferably >5%, >10%, >15%, >20%, >25%, >30%, >35%, >40%, >45%, >50%, >55%, >60%, >65%, >70%, >75%, >80%.

In certain embodiments, the total reaction pressure in an OCM reaction catalyzed by the catalysts is >1 atm, >1.1 atm, >1.2 atm, >1.3 atm, >1.4 atm, >1.5 atm, >1.6 atm, >1.7 atm, >1.8 atm, >1.9 atm, >2 atm, >2.1 atm, >2.1 atm, >2.2 atm, >2.3 atm, >2.4 atm, >2.5 atm, >2.6 atm, >2.7 atm, >2.8 atm, >2.9 atm, >3.0 atm, >3.5 atm, >4.0 atm, >4.5 atm, >5.0 atm, >5.5 atm, >6.0 atm, >6.5 atm, >7.0 atm, >7.5 atm, >8.0 atm, >8.5 atm, >9.0 atm, >10.0 atm, >11.0 atm, >12.0 atm, >13.0 atm, >14.0 atm, >15.0 atm, >16.0 atm, >17.0 atm, >18.0 atm, >19.0 atm or >20.0 atm.

In certain other embodiments, the total reaction pressure in an OCM reaction catalyzed by the catalysts ranges from about 1 atm to about 10 atm, from about 1 atm to about 7 atm, from about 1 atm to about 5 atm, from about 1 atm to about 3 atm or from about 1 atm to about 2 atm.

In some embodiments, the methane partial pressure in an OCM reaction catalyzed by the catalysts is >0.3 atm, >0.4 atm, >0.5 atm, >0.6 atm, >0.7 atm, >0.8 atm, >0.9 atm, >1 atm, >1.1 atm, >1.2 atm, >1.3 atm, >1.4 atm, >1.5 atm, >1.6 atm, >1.7 atm, >1.8 atm, >1.9 atm, >2.0 atm, >2.1 atm, >2.2 atm, >2.3 atm, >2.4 atm, >2.5 atm, >2.6 atm, >2.7 atm, >2.8 atm, >2.9 atm, >3.0 atm, >3.5 atm, >4.0 atm, >4.5 atm, >5.0 atm, >5.5 atm, >6.0 atm, >6.5 atm, >7.0 atm, >7.5 atm, >8.0 atm, >8.5 atm, >9.0 atm, >10.0 atm, >11.0 atm, >12.0 atm, >13.0 atm, >14.0 atm, >15.0 atm, >16.0 atm, >17.0 atm, >18.0 atm, >19.0 atm or >20.0 atm.

In some embodiments, the GSHV in an OCM reaction catalyzed by the catalysts is >20,000/hr, >50,000/hr, >75,000/hr, >100,000/hr, >120,000/hr, >130,000/hr, >150,000/hr, >200,000/hr, >250,000/hr, >300,000/hr, >350,000/hr, >400,000/hr, >450,000/hr, >500,000/hr, >750,000/hr, >1,000,000/hr, >2,000,000/hr, >3,000,000/hr, >4,000,000/hr.

In contrast to other OCM reactions, the present inventors have discovered that OCM reactions catalyzed by the disclosed catalysts can be performed (and still maintain high C2 yield, C2 selectivity, conversion, etc.) using $O_2$ sources other than pure $O_2$. For example, in some embodiments the $O_2$ source in an OCM reaction catalyzed by the disclosed catalysts is air, enriched oxygen, pure oxygen, oxygen diluted with nitrogen (or another inert gas) or oxygen diluted with $CO_2$. In certain embodiments, the $O_2$ source is $O_2$ diluted by >99%, >98%, >97%, >96%, >95%, >94%, >93%, >92%, >91%, >90%, >85%, >80%, >75%, >70%, >65%, >60%, >55%, >50%, >45%, >40%, >35%, >30%, >25%, >20%, >15%, >10%, >9%, >8%, >7%, >6%, >5%, >4%, >3%, >2% or >1% with $CO_2$ or an inert gas, for example nitrogen.

The disclosed catalysts are also very stable under conditions required to perform any number of catalytic reactions, for example the OCM reaction. The stability of the catalysts is defined as the length of time a catalyst will maintain its catalytic performance without a significant decrease in performance (e.g., a decrease >20%, >15%, >10%, >5%, or greater than 1% in C2 yield, C2 selectivity or conversion, etc.). In some embodiments, the disclosed catalysts have stability under conditions required for the OCM reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

In some embodiments, the ratio of ethylene to ethane in an OCM reaction catalyzed by the catalysts is better than the ratio of ethylene to ethane in an OCM reaction catalyzed by a corresponding undoped catalyst under the same conditions. In some embodiments, the ratio of ethylene to ethane in an OCM reaction catalyzed by the catalysts is >0.3, >0.4, >0.5, >0.6, >0.7, >0.8, >0.9, >1, >1.1, >1.2, >1.3, >1.4, >1.5, >1.6, >1.7, >1.8, >1.9, >2.0, >2.1, >2.2, >2.3, >2.4, >2.5, >2.6, >2.7, >2.8, >2.9, >3.0, >3.5, >4.0, >4.5, >5.0, >5.5, >6.0, >6.5, >7.0, >7.5, >8.0, >8.5, >9.0, >9.5, >10.0.

As noted above, the OCM reaction employing known catalysts suffers from poor yield, selectivity, or conversion. In contrast, the presently disclosed catalysts posses a catalytic activity in the OCM reaction such that the yield, selectivity, and/or conversion is better than when the OCM reaction is catalyzed by a corresponding undoped catalyst. In one embodiment, the disclosure provides a catalyst having a catalytic activity such that the conversion of methane in the oxidative coupling of methane reaction is greater than at least 1.1 times, 1.25 times, 1.50 times, 2.0 times, 3.0 times, or 4.0 times the conversion of methane compared to the same reaction under the same conditions but performed with a corresponding undoped catalyst. In other embodiments, the conversion of methane in an OCM reaction catalyzed by the catalyst is greater than 10%, greater than 15%, greater than 20%, greater than 25%, greater than 30% greater than 40% or greater than 50%. In some embodiments the conversion of methane is determined when the catalyst is employed as a heterogenous catalyst in the oxidative coupling of methane at a temperature of 750° C. or less, 700° C. or less, 650° C. or less or even 600° C. or less. The conversion of methane may also be determined based on a single pass of a gas comprising methane over the catalyst or may be determined based on multiple passes over the catalyst.

In another embodiment, the disclosure provides a catalyst having a catalytic activity such that the C2 yield in the oxidative coupling of methane reaction is greater than at least 1.1 times, 1.25 times, 1.50 times, 2.0 times, 3.0 times, or 4.0 times the C2 yield compared to the same reaction under the same conditions but performed with a corresponding undoped catalyst. In some embodiments the C2 yield in an OCM reaction catalyzed by the catalyst is greater than 10%, greater than 15%, greater than 20%, greater than 25%, greater than 30%, greater than 50%, greater than 75%, or greater than 90%. In some embodiments the C2 yield is determined when the catalyst is employed as a heterogenous catalyst in the oxidative coupling of methane at a temperature of 750° C. or less, 700° C. or less, 650° C. or less or even 600° C. or less. The C2 yield may also be determined based on a single pass of a gas comprising methane over the catalyst or may be determined based on multiple passes over the catalyst.

In another embodiment, the disclosure provides a catalyst having a catalytic activity such that the C2 selectivity in the oxidative coupling of methane reaction is greater than at least 1.1 times, 1.25 times, 1.50 times, 2.0 times, 3.0 times, or 4.0 times the C2 selectivity compared to the same reaction under the same conditions but performed with a corresponding undoped catalyst. In other embodiments, the C2 selectivity in an OCM reaction catalyzed by the catalyst is greater than 10%, greater than 20%, greater than 30%, greater than 40%, greater than 50%, greater than 60%, greater than 65%, greater than 75%, or greater than 90%. In some embodiments the C2 selectivity is determined when the catalyst is employed as a heterogenous catalyst in the oxidative coupling of methane at a temperature of 750° C. or less, 700° C. or less, 650° C. or less or even 600° C. or less. The C2 selectivity may also be determined based on a single pass of a gas comprising methane over the catalyst or may be determined based on multiple passes over the catalyst.

In another embodiment, the disclosure provides a catalyst having a catalytic activity such that the selectivity for CO or $CO_2$ in the oxidative coupling of methane reaction is less than at least 0.9 times, 0.8 times, 0.5 times, 0.2 times, or 0.1 times the selectivity for CO or $CO_2$ compared to the same reaction under the same conditions but performed with a corresponding undoped catalyst.

In other embodiments, the above selectivity, conversion and yield values are determined at a temperature of less than 850° C., less than 800° C., less than 750° C., less than 700° C. or less than 650° C.

In addition to air or $O_2$ gas, the presently disclosed catalysts and associated methods provide for use of other sources of oxygen in the OCM reaction. In this respect, an alternate source of oxygen such a $CO_2$, $H_2O$, $SO_2$ or $SO_3$ may be used either in place of, or in addition to, air or oxygen as the oxygen source. Such methods have the potential to increase the efficiency of the OCM reaction, for example by consuming a reaction byproduct (e.g., $CO_2$ or $H_2O$) and controlling the OCM exotherm as described below.

As noted above, in the OCM reaction, methane is oxidatively converted to methyl radicals, which are then coupled to form ethane, which is subsequently oxidized to ethylene. In traditional OCM reactions, the oxidation agent for both the methyl radical formation and the ethane oxidation to ethylene is oxygen. In order to minimize full oxidation of methane or ethane to carbon dioxide, i.e. maximize C2 selectivity, the methane to oxygen ratio is generally kept at 4 (i.e. full conversion of methane into methyl radicals) or above. As a result, the OCM reaction is typically oxygen limited and thus the oxygen concentration in the effluent is zero.

Accordingly, in one embodiment the present disclosure provides a method for increasing the methane conversion and increasing, or in some embodiments, not reducing, the C2 selectivity in an OCM reaction. The disclosed methods include adding to a traditional OCM catalyst another OCM catalyst that uses an oxygen source other than molecular oxygen. In some embodiments, the alternate oxygen source is $CO_2$, $H_2O$, $SO_2$, $SO_3$ or combinations thereof. For example in some embodiments, the alternate oxygen source is $CO_2$. In other embodiments the alternate oxygen source is $H_2O$.

Because C2 selectivity is typically between 50% and 80% in the OCM reaction, OCM typically produces significant amounts of $CO_2$ as a byproduct ($CO_2$ selectivity can typically range from 20-50%). Additionally, $H_2O$ is produced in copious amounts, regardless of the C2 selectivity. Therefore both $CO_2$ and $H_2O$ are attractive oxygen sources for OCM in an $O_2$ depleted environment. Accordingly, one embodiment of the present disclosure provides a catalyst (and related methods for use thereof) which is catalytic in the OCM reaction and which uses $CO_2$, $H_2O$, $SO_2$, $SO_3$ or another alternative oxygen source or combinations thereof as a source of oxygen. Other embodiments, provide a catalytic material comprising two or more catalysts, wherein the catalytic material comprises at least one catalyst which is catalytic in the OCM reaction and uses $O_2$ for at least one oxygen source and at least one catalysts which is catalytic in the OCM reaction and uses at least of $CO_2$, $H_2O$, $SO_2$, $SO_3$ or another alternative oxygen source. Methods for performing the OCM reaction with such catalytic materials are also provided. Such catalysts comprise any of the compositions disclosed herein and are effective as catalysts in an OCM reaction using an alternative oxygen source at temperatures of 900° C. or lower, 850° C. or lower, 800° C. or lower, 750° C. or lower, 700° C. or lower or even 650° C. or lower.

Examples of OCM catalysts that use $CO_2$ or other oxygen sources rather than $O_2$ include, but are not limited to, catalysts comprising $La_2O_3$/ZnO, $CeO_2$/ZnO, CaO/ZnO, CaO/$CeO_2$, CaO/$Cr_2O_3$, CaO/$MnO_2$, SrO/ZnO, SrO/$CeO_2$, SrO/$Cr_2O_3$, SrO/$MnO_2$, $SrCO_3$/$MnO_2$, BaO/ZnO, BaO/$CeO_2$, BaO/$Cr_2O_3$, BaO/$MnO_2$, CaO/MnO/$CeO_2$, $Na_2WO_4$/Mn/$SiO_2$, $Pr_2O_3$, or $Tb_2O_3$.

Some embodiments provide a method for performing OCM, wherein a mixture of an OCM catalyst which use $O_2$ as an oxygen source (referred to herein as an $O_2$-OCM catalyst) and an OCM catalyst which use $CO_2$ as an oxygen source (referred to herein as a $CO_2$—OCM catalyst) is employed as the catalytic material, for example in a catalyst bed. Such methods have certain advantages. For example, the $CO_2$—OCM reaction is endothermic and the $O_2$-OCM reaction is exothermic, and thus if the right mixture and/or arrangement of $CO_2$—OCM and $O_2$-OCM catalysts is used, the methods are particularly useful for controlling the exotherm of the OCM reaction. In some embodiments, the catalyst bed comprises a mixture of $O_2$-OCM catalyst and $CO_2$—OCM catalysts. The mixture may be in a ratio of 1:99 to 99:1. The two catalysts work synergistically as the $O_2$-OCM catalyst supplies the $CO_2$—OCM catalyst with the necessary carbon dioxide and the endothermic nature of the $C_2$-OCM reaction serves to control the exotherm of the overall reaction. Alternatively, the $CO_2$ source may be external to the reaction (e.g., fed in from a $CO_2$ tank, or other source) and/or the heat required for the $CO_2$—OCM reaction is supplied from an external source (e.g., heating the reactor).

Since the gas composition will tend to become enriched in $CO_2$ as it flows through the catalyst bed (i.e., as the OCM reaction proceeds, more $CO_2$ is produced), some embodiments of the present invention provide an OCM method wherein the catalyst bed comprises a gradient of catalysts which changes from a high concentration of $O_2$-OCM catalysts at the front of the bed to a high concentration of $CO_2$—OCM catalysts at the end of the catalyst bed.

The $O_2$-OCM catalyst and $CO_2$ OCM catalyst may have the same or different compositions. For example, in some embodiments the $O_2$-OCM catalyst and $CO_2$—OCM catalyst have the same composition but different morphologies (e.g., nanowire, bent nanowire, bulk, etc.). In other embodiments the $O_2$-OCM and the $CO_2$—OCM catalyst have different compositions.

Furthermore, $CO_2$—OCM catalysts will typically have higher selectivity, but lower yields than an $O_2$-OCM catalyst. Accordingly, in one embodiment the methods comprise use of a mixture of an $O_2$-OCM catalyst and a $CO_2$—OCM catalyst and performing the reaction in $O_2$ deprived environment so that the $CO_2$-OCM reaction is favored and the selectivity is increased. Under appropriate conditions the yield and selectivity of the OCM reaction can thus be optimized.

In some other embodiments, the catalyst bed comprises a mixture of one or more low temperature $O_2$-OCM catalyst (i.e., a catalyst active at low temperatures, for example less than 700° C.) and one or more high temperature $CO_2$—OCM catalyst (i.e., a catalyst active at high temperatures, for example 800° C. or higher). Here, the required high temperature for the $CO_2$—OCM may be provided by the hotspots produced by the $O_2$-OCM catalyst. In such a scenario, the mixture may be sufficiently coarse such that the hotspots are not being excessively cooled down by excessive dilution effect.

In other embodiments, the catalyst bed comprises alternating layers of $O_2$-OCM and $CO_2$—OCM catalysts. The catalyst layer stack may begin with a layer of $O_2$-OCM catalyst, so that it can supply the next layer (e.g., a $CO_2$—OCM layer) with the necessary $CO_2$. The $O_2$-OCM layer thickness may be optimized to be the smallest at which O2 conversion is 100% and thus the $CH_4$ conversion of the layer is maximized. The catalyst bed may comprise any number of catalyst layers, for example the overall number of layers may be optimized to maximize the overall $CH_4$ conversion and C2 selectivity.

In some embodiments, the catalyst bed comprises alternating layers of low temperature $O_2$-OCM catalysts and high temperature $CO_2$—OCM catalysts. Since the $CO_2$—OCM reaction is endothermic, the layers of $CO_2$—OCM catalyst may be sufficiently thin such that in can be "warmed up" by the hotspots of the $O_2$-OCM layers. The endothermic nature of the $CO_2$—OCM reaction can be advantageous for the overall thermal management of an OCM reactor. In some embodiments, the $CO_2$—OCM catalyst layers act as "internal" cooling for the $O_2$-OCM layers, thus simplifying the requirements for the cooling, for example in a tubular reactor. Therefore, an interesting cycle takes place with the endothermic reaction providing the necessary heat for the endothermic reaction and the endothermic reaction providing the necessary cooling for the exothermic reaction.

Accordingly, one embodiment of the present invention is a method for the oxidative coupling of methane, wherein the method comprises conversion of methane to ethane and/or ethylene in the presence of a catalytic material, and wherein the catalytic material comprises a bed of alternating layers of $O_2$-OCM catalysts and $CO_2$—OCM catalysts. In other embodiments the bed comprises a mixture (i.e., not alternating layers) of $O_2$-OCM catalysts and $CO_2$—OCM catalysts.

In other embodiments, the OCM methods include use of a jacketed reactor with the exothermic $O_2$-OCM reaction in the core and the endothermic $CO_2$—OCM reaction in the mantel. In other embodiments, the unused $CO_2$ can be recycled and reinjected into the reactor, optionally with the recycled $CH_4$. Additional $CO_2$ can also be injected to increase the overall methane conversion and help reduce greenhouse gases.

In other embodiments, the reactor comprises alternating stages of $O_2$-OCM catalyst beds and $CO_2$—OCM catalyst beds. The $CO_2$ necessary for the $CO_2$—OCM stages is provided by the $O_2$-OCM stage upstream. Additional $CO_2$ may also be injected. The $O_2$ necessary for the subsequent $O_2$-OCM stages is injected downstream from the $CO_2$—OCM stages. The $CO_2$—OCM stages may provide the necessary cooling for the $O_2$-OCM stages. Alternatively, separate cooling may be provided. Likewise, if necessary the inlet gas of the $CO_2$—OCM stages can be additionally heated, the $CO_2$—OCM bed can be heated or both.

In related embodiments, the $CO_2$ naturally occurring in natural gas is not removed prior to performing the OCM, alternatively CO2 is added to the feed with the recycled methane. Instead the $CO_2$ containing natural gas is used as a feedstock for $CO_2$—OCM, thus potentially saving a separation step. The amount of naturally occurring $CO_2$ in natural gas depends on the well and the methods can be adjusted accordingly depending on the source of the natural gas.

The foregoing methods can be generalized as a method to control the temperature of very exothermic reactions by coupling them with an endothermic reaction that uses the same feedstock (or byproducts of the exothermic reaction) to make the same product (or a related product). This concept can be reversed, i.e. providing heat to an endothermic reaction by coupling it with an exothermic reaction. This will also allow a higher per pass yield in the OCM reactor.

For purpose of simplicity, the above description relating to the use of $O_2$-OCM and $CO_2$—OCM catalysts was described in reference to the oxidative coupling of methane (OCM); however, the same concept is applicable to other catalytic reactions including but not limited to: oxidative dehydrogenation (ODH) of alkanes to their corresponding alkenes, selective oxidation of alkanes and alkenes and alkynes, etc. For example, in a related embodiment, a catalyst capable of using an alternative oxygen source (e.g., $CO_2$, $H_2O$, $SO_2$, $SO_3$ or combinations thereof) to catalyze the oxidative dehydrogenation of ethane is provided. Such catalysts, and uses thereof are described in more detail below.

Furthermore, the above methods are applicable for creating novel catalysts by blending catalysts that use different reactants for the same catalytic reactions, for example different oxidants for an oxidation reaction and at least one oxidant is a byproduct of one of the catalytic reactions. In addition, the methods can also be generalized for internal temperature control of reactors by blending catalysts that catalyze reactions that share the same or similar products but are exothermic and endothermic, respectively. These two concepts can also be coupled together.

2. Oxidative Dehydrogenation

Worldwide demand for alkenes, especially ethylene and propylene, is high. The main sources for alkenes include steam cracking, fluid-catalytic-cracking and catalytic dehydrogenation. The current industrial processes for producing alkenes, including ethylene and propylene, suffer from some of the same disadvantages described above for the OCM reaction. Accordingly, a process for the preparation of alkenes which is more energy efficient and has higher yield, selectivity, and conversion than current processes is needed. The catalysts disclosed herein fulfill this need and provide related advantages.

In one embodiment, the catalysts are useful for the oxidative dehydrogenation (ODH) of hydrocarbons (e.g. alkanes, alkenes, and alkynes). For example, in one embodiment the catalysts are useful in an ODH reaction for the conversion of ethane or propane to ethylene or propylene, respectively. Reaction scheme (9) depicts the oxidative dehydrogenation of hydrocarbons:

$$C_xH_y + \tfrac{1}{2}O_2 \rightarrow C_xH_{y-2} + H_2O \tag{9}$$

Representative catalysts useful for the ODH reaction include, but are not limited to any of the catalysts disclosed herein.

As noted above, improvements to the yield, selectivity, and/or conversion in the ODH reaction employing bulk catalysts are needed. Accordingly, in one embodiment, the catalysts posses a catalytic activity in the ODH reaction such that the yield, selectivity, and/or conversion is better than when the ODH reaction is catalyzed by a corresponding undoped catalyst. In one embodiment, the disclosure provides a catalyst having a catalytic activity such that the conversion of hydrocarbon to alkene in the ODH reaction is greater than at least 1.1 times, 1.25 times, 1.50 times, 2.0 times, 3.0 times, or 4.0 times the conversion of methane to ethylene compared to the same reaction under the same conditions but performed with a corresponding undoped catalyst. In other embodiments, the conversion of alkanes in an ODH reaction catalyzed by the catalyst is greater than 10%, greater than 15%, greater than 20%, greater than 25%, greater than 30%, greater than 50%, greater than 75%, or greater than 90%.

In another embodiment, the disclosure provides a catalyst having a catalytic activity such that the yield of alkene in an ODH reaction is greater than at least 1.1 times, 1.25 times, 1.50 times, 2.0 times, 3.0 times, or 4.0 times the yield of ethylene compared to the same reaction under the same conditions but performed with a corresponding undoped catalyst. In some embodiments the yield of alkene in an ODH reaction catalyzed by the catalyst is greater than 10%, greater than 20%, greater than 30%, greater than 50%, greater than 75%, or greater than 90%.

In another embodiment, the disclosure provides a catalyst having a catalytic activity such that the selectivity for alkenes in an ODH reaction is greater than at least 1.1 times, 1.25 times, 1.50 times, 2.0 times, 3.0 times, or 4.0 times the selectivity for alkenes compared to the same reaction under the same conditions but performed with a corresponding undoped catalyst. In other embodiments, the selectivity for alkenes in an ODH reaction catalyzed by the catalyst is greater than 50%, greater than 60%, greater than 70%, greater than 75%, greater than 80%, greater than 85%, greater than 90%, or greater than 95%.

In another embodiment, the disclosure provides a catalyst having a catalytic activity such that the selectivity for CO or $CO_2$ in an ODH reaction is less than at least 0.9 times, 0.8 times, 0.5 times, 0.2 times, or 0.1 times the selectivity for CO or $CO_2$ compared to the same reaction under the same conditions but performed with a corresponding undoped catalyst.

In one embodiment, the catalysts disclosed herein enable efficient conversion of hydrocarbon to alkene in the ODH reaction at temperatures less than when a corresponding undoped catalyst is used. For example, in one embodiment, the catalysts disclosed herein enable efficient conversion (i.e. high yield, conversion, and/or selectivity) of hydrocarbon to alkene at temperatures of less than 800° C., less than 700° C., less than 600° C., less than 500° C., less than 400° C., or less than 300° C.

One embodiment of the present disclosure is directed to a catalyst capable of using an alternative oxygen source (e.g., $CO_2$, $H_2O$, $SO_2$, $SO_3$ or combinations thereof) to catalyze the oxidative dehydrogenation of ethane. For example, the ODH reaction may proceed according to the following reaction (10):

$$CO_2 + C_xH_y \rightarrow C_xH_{y-2} + CO + H_2O \tag{10}$$

wherein x is an integer and Y is 2x+2. Compositions useful in this regard include $Fe_2O_3$, $Cr_2O_3$, $MnO_2$, $Ga_2O_3$, $Cr/SiO_2$, $Cr/SO_4$—$SiO_2$, Cr—$K/SO_4$—$SiO_2$, $Na_2WO_4$—$Mn/SiO_2$, Cr-HZSM-5, Cr/Si-MCM-41 (Cr-HZSM-5 and Cr/Si-MCM-41 refer to known zeolites) and $MoC/SiO_2$. In some embodiments, any of the foregoing catalyst compositions may be supported on $SiO_2$, $ZrO_2$, $Al_2O_3$, $TiO_2$ or combinations thereof.

The catalysts having ODH activity with alternative oxygen sources (e.g., $CO_2$, referred to herein as a $CO_2$—ODH catalyst) have a number of advantages. For example, in some embodiments a method for converting methane to ethylene comprises use of an $O_2$-OCM catalyst in the presence of a $CO_2$—ODH catalyst is provided. Catalytic materials comprising at least one $O_2$-OCM catalyst and at least one $CO_2$—ODH catalyst are also provided in some embodiments. This combination of catalysts results in a higher yield of ethylene (and/or ratio of ethylene to ethane) since the $CO_2$ produced by the OCM reaction is consumed and used to convert ethane to ethylene.

In one embodiment, a method for preparation of ethylene comprises converting methane to ethylene in the presence of two or more catalysts, wherein at least one catalyst is an $O_2$-OCM catalyst and at least one catalyst is a $CO_2$—ODH catalyst. Such methods have certain advantages. For example, the CO2-ODH reaction is endothermic and the $O_2$-OCM reaction is exothermic, and thus if the right mixture and/or arrangement of $CO_2$—ODH and $O_2$—OCM catalysts is used, the methods are particularly useful for controlling the exotherm of the OCM reaction. In some embodiments, the catalyst bed comprises a mixture of $O_2$-OCM catalyst and CO2-ODH catalysts. The mixture may be in a ratio of 1:99 to 99:1. The two catalysts work synergistically as the $O_2$-OCM catalyst supplies the $CO_2$—ODH catalyst with the necessary carbon dioxide and the endothermic nature of the $C_2$-OCM reaction serves to control the exotherm of the overall reaction.

Since the gas composition will tend to become enriched in $CO_2$ as it flows through the catalyst bed (i.e., as the OCM reaction proceeds, more $CO_2$ is produced), some embodiments of the present invention provide an OCM method wherein the catalyst bed comprises a gradient of catalysts which changes from a high concentration of $O_2$-OCM catalysts at the front of the bed to a high concentration of $CO_2$—ODH catalysts at the end of the catalyst bed.

The $O_2$-ODH catalyst and $CO_2$—ODH catalyst may have the same or different compositions. For example, in some embodiments the $O_2$-ODH catalyst and $CO_2$—ODH catalyst have the same composition but different morphologies (e.g., catalyst, bent catalyst, bulk, etc.). In other embodiments the $O_2$-ODH and the $CO_2$—ODH catalyst have different compositions.

In other embodiments, the catalyst bed comprises alternating layers of $O_2$-OCM and $CO_2$—ODH catalysts. The catalyst layer stack may begin with a layer of $O_2$-OCM catalyst, so that it can supply the next layer (e.g., a CO2-ODH layer) with the necessary $CO_2$. The $O_2$-OCM layer thickness may be optimized to be the smallest at which O2 conversion is 100% and thus the $CH_4$ conversion of the layer is maximized. The catalyst bed may comprise any number of catalyst layers, for example the overall number of layers may be optimized to maximize the overall $CH_4$ conversion and C2 selectivity.

In some embodiments, the catalyst bed comprises alternating layers of low temperature $O_2$-OCM catalysts and high temperature $CO_2$—ODH catalysts. Since the $CO_2$—ODH reaction is endothermic, the layers of $CO_2$—ODH catalyst may be sufficiently thin such that in can be "warmed up" by the hotspots of the $O_2$-OCM layers. The endothermic nature of the $CO_2$—ODH reaction can be advantageous for the overall thermal management of an OCM reactor. In some embodiments, the $CO_2$—ODH catalyst layers act as "internal" cooling for the $O_2$-OCM layers, thus simplifying the requirements for the cooling, for example in a tubular reactor. Therefore, an interesting cycle takes place with the endothermic reaction providing the necessary heat for the endothermic reaction and the endothermic reaction providing the necessary cooling for the exothermic reaction.

Accordingly, one embodiment of the present invention is a method for the oxidative coupling of methane, wherein the method comprises conversion of methane to ethane and/or ethylene in the presence of a catalytic material, and wherein the catalytic material comprises a bed of alternating layers of $O_2$-OCM catalysts and $CO_2$—ODH catalysts. In other embodiments the bed comprises a mixture (i.e., not alternating layers) of $O_2$-OCM catalysts and $CO_2$—ODH catalysts. Such methods increase the ethylene yield and/or ratio of ethylene to ethane compared to other known methods.

In other embodiments, the OCM methods include use of a jacketed reactor with the exothermic $O_2$-OCM reaction in the core and the endothermic $CO_2$—ODH reaction in the mantel. In other embodiments, the unused $CO_2$ can be recycled and reinjected into the reactor, optionally with the recycled $CH_4$. Additional $CO_2$ can also be injected to increase the overall methane conversion and help reduce greenhouse gases.

In other embodiments, the reactor comprises alternating stages of $O_2$-OCM catalyst beds and $CO_2$—ODH catalyst beds. The $CO_2$ necessary for the $CO_2$—ODH stages is provided by the $O_2$-OCM stage upstream. Additional $CO_2$ may also be injected. The $O_2$ necessary for the subsequent O2-OCM stages is injected downstream from the $CO_2$—ODH stages. The $CO_2$—ODH stages may provide the necessary cooling for the $O_2$-OCM stages. Alternatively, separate cooling may be provided. Likewise, if necessary the inlet gas of the $CO_2$—ODH stages can be additionally heated, the $CO_2$—ODH bed can be heated or both.

In related embodiments, the $CO_2$ naturally occurring in natural gas is not removed prior to performing the OCM, alternatively $CO_2$ is added to the feed with the recycled methane. Instead the $CO_2$ containing natural gas is used as a feedstock for $CO_2$—ODH, thus potentially saving a separation step. The amount of naturally occurring $CO_2$ in natural gas depends on the well and the methods can be adjusted accordingly depending on the source of the natural gas.

3. Carbon Dioxide Reforming of Methane

Carbon dioxide reforming (CDR) of methane is an attractive process for converting $CO_2$ in process streams or naturally occurring sources into the valuable chemical product, syngas (a mixture of hydrogen and carbon monoxide). Syngas can then be manufactured into a wide range of hydrocarbon products through processes such as the Fischer-Tropsch synthesis (discussed below) to form liquid fuels including methanol, ethanol, diesel, and gasoline. The result is a powerful technique to not only remove $CO_2$ emissions but also create a new alternative source for fuels that are not derived from petroleum crude oil. The CDR reaction with methane is exemplified in reaction scheme (11).

$$CO_2 + CH_4 \rightarrow 2CO + 2H_2 \quad (11)$$

Unfortunately, no established industrial technology for CDR exists today in spite of its tremendous potential value. While not wishing to be bound by theory, it is thought that the primary problem with CDR is due to side-reactions from catalyst deactiviation induced by carbon deposition via the Boudouard reaction (reaction scheme (12)) and/or methane cracking (reaction scheme (13)) resulting from the high temperature reaction conditions. The occurrence of the coking effect is intimately related to the complex reaction mechanism, and the associated reaction kinetics of the catalysts employed in the reaction.

$$2CO \rightarrow C + CO_2 \quad (12)$$

$$CH_4 \rightarrow C + 2H_2 \quad (13)$$

Figure 3:
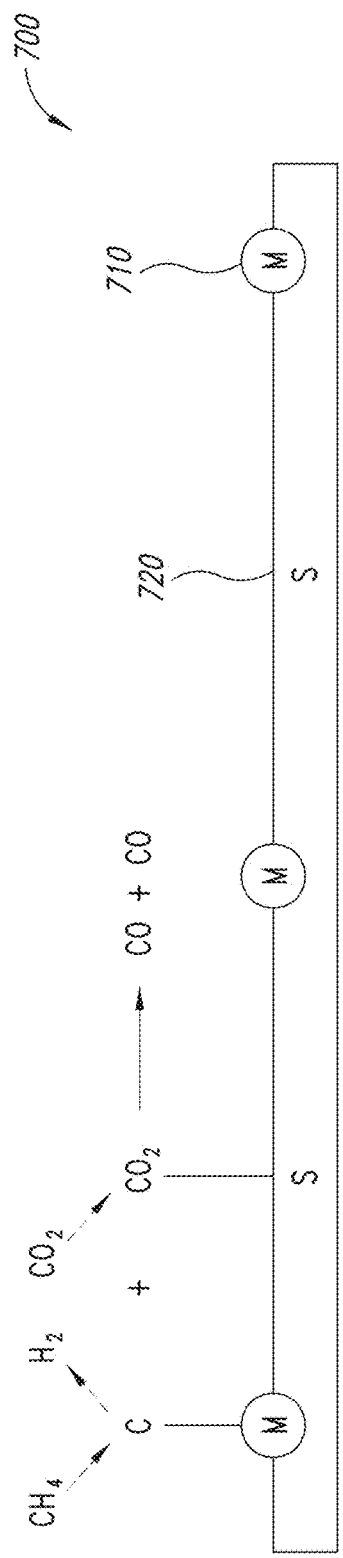
FIG. 3 schematically depicts a carbon dioxide reforming reaction on a catalytic surface.

While not wishing to be bound by theory, the CDR reaction is thought to proceed through a multistep surface reaction mechanism. FIG. 3 schematically depicts a CDR reaction 700, in which activation and dissociation of $CH_4$ occurs on the metal catalyst surface 710 to form intermediate "M-C". At the same time, absorption and activation of $CO_2$ takes place at the oxide support surface 720 to provide intermediate "S—$CO_2$", since the carbon in a $CO_2$ molecule as a Lewis acid tends to react with the Lewis base center of an oxide. The final step is the reaction between the M-C species and the activated S—$CO_2$ to form CO.

In one embodiment, the catalysts disclosed herein are useful as catalysts for the carbon dioxide reforming of methane. For example, in one embodiment the catalysts are useful as catalysts in a CDR reaction for the production of syn gas.

Improvements to the yield, selectivity, and/or conversion in the CDR reaction employing bulk catalysts are needed. Accordingly, in one embodiment, the catalysts posses a catalytic activity in the CDR reaction such that the yield, selectivity, and/or conversion is better than when the CDR reaction is catalyzed by a corresponding undoped catalyst. In one embodiment, the disclosure provides a catalyst having a catalytic activity such that the conversion of $CO_2$ to CO in the CDR reaction is greater than at least 1.1 times, 1.25 times, 1.50 times, 2.0 times, 3.0 times, or 4.0 times the conversion of $CO_2$ to CO compared to the same reaction under the same conditions but performed with a corresponding undoped catalyst. In other embodiments, the conversion of $CO_2$ to CO in a CDR reaction catalyzed by the catalyst is greater than 10%, greater than 15%, greater than 20%, greater than 25%, greater than 30%, greater than 50%, greater than 75%, or greater than 90%.

In another embodiment, the disclosure provides a catalyst having a catalytic activity such that the yield of CO in a CDR reaction is greater than at least 1.1 times, 1.25 times, 1.50 times, 2.0 times, 3.0 times, or 4.0 times the yield of CO compared to the same reaction under the same conditions but performed with a corresponding undoped catalyst. In some embodiments the yield of CO in a CDR reaction catalyzed by the catalyst is greater than 10%, greater than 20%, greater than 30%, greater than 50%, greater than 75%, or greater than 90%.

In another embodiment, the disclosure provides a catalyst having a catalytic activity such that the selectivity for CO in a CDR reaction is greater than at least 1.1 times, 1.25 times, 1.50 times, 2.0 times, 3.0 times, or 4.0 times the selectivity for CO compared to the same reaction under the same conditions but performed with a corresponding undoped catalyst. In other embodiments, the selectivity for CO in a CDR reaction catalyzed by the catalyst is greater than 10%, greater than 20%, greater than 30%, greater than 40%, greater than 50%, greater than 65%, greater than 75%, or greater than 90%.

In one embodiment, the catalysts disclosed herein enable efficient conversion of $CO_2$ to CO in the CDR reaction at temperatures less than when a corresponding undoped catalyst. For example, in one embodiment, the catalysts enable efficient conversion (i.e., high yield, conversion, and/or selectivity) of $CO_2$ to CO at temperatures of less than 900° C., less than 800° C., less than 700° C., less than 600° C., or less than 500° C.

4. Fischer-Tropsch Synthesis

Fischer-Tropsch synthesis (FTS) is a valuable process for converting synthesis gas (i.e., CO and $H_2$) into valuable hydrocarbon fuels, for example, light alkenes, gasoline, diesel fuel, etc. FTS has the potential to reduce the current reliance on the petroleum reserve and take advantage of the abundance of coal and natural gas reserves. Current FTS processes suffer from poor yield, selectivity, conversion, catalyst deactivation, poor thermal efficiency and other related disadvantages. Production of alkanes via FTS is shown in reaction scheme (14), wherein n is an integer.

$$CO + 2H_2 \rightarrow (1/n)(C_nCH_{2n}) + H_2O \quad (14)$$

In one embodiment, the catalysts are useful as catalysts in FTS processes. For example, in one embodiment the catalysts are useful as catalysts in a FTS process for the production of alkanes.

Improvements to the yield, selectivity, and/or conversion in FTS processes employing bulk catalysts are needed. Accordingly, in one embodiment, the catalysts posses a catalytic activity in an FTS process such that the yield, selectivity, and/or conversion is better than when the FTS process is catalyzed by a corresponding undoped catalyst. In one embodiment, the disclosure provides a catalyst having a catalytic activity such that the conversion of CO to alkane in an FTS process is greater than at least 1.1 times, 1.25 times, 1.50 times, 2.0 times, 3.0 times, or 4.0 times the conversion of CO to alkane compared to the same reaction under the same conditions but performed with a corresponding undoped catalyst. In other embodiments, the conversion of CO to alkane in an FTS process catalyzed by the catalyst is greater than 10%, greater than 15%, greater than 20%, greater than 25%, greater than 30%, greater than 50%, greater than 75%, or greater than 90%.

In another embodiment, the disclosure provides a catalyst having a catalytic activity such that the yield of alkane in a FTS process is greater than at least 1.1 times, 1.25 times, 1.50 times, 2.0 times, 3.0 times, or 4.0 times the yield of alkane compared to the same reaction under the same conditions but performed with a corresponding undoped catalyst. In some embodiments the yield of alkane in an FTS process catalyzed by the catalyst is greater than 10%, greater than 20%, greater than 30%, greater than 40%, greater than 50%, greater than 65%, greater than 75%, or greater than 90%.

In another embodiment, the disclosure provides a catalyst having a catalytic activity such that the selectivity for alkanes in an FTS process is greater than at least 1.1 times, 1.25 times, 1.50 times, 2.0 times, 3.0 times, or 4.0 times the selectivity for alkanes compared to the same reaction under the same conditions but performed with a corresponding undoped catalyst. In other embodiments, the selectivity for alkanes in an FTS process catalyzed by the catalyst is greater than 10%, greater than 20%, greater than 30%, greater than 50%, greater than 75%, or greater than 90%.

In one embodiment, the catalysts disclosed herein enable efficient conversion of CO to alkanes in a CDR process at temperatures less than when a corresponding undoped catalyst is used. For example, in one embodiment, the catalysts enable efficient conversion (i.e., high yield, conversion, and/or selectivity) of CO to alkanes at temperatures of less than 400° C., less than 300° C., less than 250° C., less than 200° C., less the 150° C., less than 100° C. or less than 50° C.

5. Oxidation of CO

Carbon monoxide (CO) is a toxic gas and can convert hemoglobin to carboxyhemoglobin resulting in asphyxiation. Dangerous levels of CO can be reduced by oxidation of CO to $CO_2$ as shown in reaction scheme 15:

$$CO + \tfrac{1}{2}O_2 \rightarrow CO_2 \quad (15)$$

Catalysts for the conversion of CO into $CO_2$ have been developed but improvements to the known catalysts are needed. Accordingly in one embodiment, the present disclosure provides catalysts useful as catalysts for the oxidation of CO to $CO_2$.

In one embodiment, the catalysts posses a catalytic activity in a process for the conversion of CO into $CO_2$ such that the yield, selectivity, and/or conversion is better than when the oxidation of CO into $CO_2$ is catalyzed by a corresponding undoped catalyst. In one embodiment, the disclosure provides a catalyst having a catalytic activity such that the conversion of CO to $CO_2$ is greater than at least 1.1 times, 1.25 times, 1.50 times, 2.0 times, 3.0 times, or 4.0 times the conversion of CO to $CO_2$ compared to the same reaction under the same conditions but performed with a corresponding undoped catalyst. In other embodiments, the conversion of CO to $CO_2$ catalyzed by the catalyst is greater than 10%, greater than 15%, greater than 20%, greater than 25%, greater than 30%, greater than 50%, greater than 75%, or greater than 90%.

In another embodiment, the disclosure provides a catalyst having a catalytic activity such that the yield of $CO_2$ from the oxidation of CO is greater than at least 1.1 times, 1.25 times, 1.50 times, 2.0 times, 3.0 times, or 4.0 times the yield of $CO_2$ compared to the same reaction under the same conditions but performed with a corresponding undoped catalyst. In some embodiments the yield of $CO_2$ from the oxidation of CO catalyzed by the catalyst is greater than 10%, greater than 20%, greater than 30%, greater than 50%, greater than 75%, or greater than 90%.

In another embodiment, the disclosure provides a catalyst having a catalytic activity such that the selectivity for $CO_2$ in the oxidation of CO is greater than at least 1.1 times, 1.25 times, 1.50 times, 2.0 times, 3.0 times, or 4.0 times the selectivity for $CO_2$ compared to the same reaction under the same conditions but performed with a corresponding undoped catalyst. In other embodiments, the selectivity for $CO_2$ in the oxidation of CO catalyzed by the catalyst is greater than 10%, greater than 20%, greater than 30%, greater than 40%, greater than 50%, greater than 65%, greater than 75%, or greater than 90%.

In one embodiment, the catalysts disclosed herein enable efficient conversion of CO to $CO_2$ at temperatures less than when a corresponding undoped catalyst is used as a catalyst. For example, in one embodiment, the catalysts enable efficient conversion (i.e., high yield, conversion, and/or selectivity) of CO to $CO_2$ at temperatures of less than 500° C., less than 400° C., less than 300° C., less than 200° C., less than 100° C., less than 50° C. or less than 20° C.

Although various reactions have been described in detail, the disclosed catalysts are useful as catalysts in a variety of other reactions. In general, the disclosed catalysts find utility in any reaction utilizing a heterogeneous catalyst and have a catalytic activity such that the yield, conversion, and/or selectivity in reaction catalyzed by the catalysts is better than the yield, conversion and/or selectivity in the same reaction catalyzed by a corresponding undoped catalyst.

6. Evaluation of Catalytic Properties

To evaluate the catalytic properties of the catalysts in a given reaction, for example those reactions discussed above, various methods can be employed to collect and process data including measurements of the kinetics and amounts of reactants consumed and the products formed. In addition to allowing for the evaluation of the catalytic performances, the data can also aid in designing large scale reactors, experimentally validating models and optimizing the catalytic process.

One exemplary methodology for collecting and processing data is depicted in FIG. 4. Three main steps are involved. The first step (block 750) comprises the selection of a reaction and catalyst. This influences the choice of reactor and how it is operated, including batch, flow, etc. (block 754). Thereafter, the data of the reaction are compiled and analyzed (block 760) to provide insights to the mechanism, rates and process optimization of the catalytic reaction. In addition, the data provide useful feed backs for further design modifications of the reaction conditions. Additional methods for evaluating catalytic performance in the laboratory and industrial settings are described in, for example, Bartholomew, C. H. et al. *Fundamentals of Industrial Catalytic Processes*, Wiley-AIChE; 2Ed (1998).

As an example, in a laboratory setting, an Altamira Benchcat 200 can be employed using a 4 mm ID diameter quartz tube with a 0.5 mm ID capillary downstream. Catalysts are tested in a number of different dilutions and amounts. In some embodiments, the range of testing is between 10 and 300 mg. In some embodiments, the catalysts are diluted with quartz ($SiO_2$) or one of the other support materials discussed above to minimize hot spots and provide an appropriate loading into the reactor.

In a typical procedure, 100 mg is the total charge of catalyst, optionally including quartz sand. On either side of the catalysts a small plug of glass wool is loaded to keep the catalysts in place. A thermocouple is placed on the inlet side of the catalyst bed into the glass wool to monitor the temperature at the catalyst bed. Another thermocouple can be placed on the downstream end of the catalyst bed to measure the exotherms, if any.

When blending the catalyst with quartz silica, the following exemplary procedure may be used: x (usually 10-50) mg of the catalyst, for example a magnesium oxide based catalyst, is blended with (100-x) mg of quartz ($SiO_2$). Thereafter, about 2 ml of ethanol or water is added to form a slurry mixture, which is then sonicated for about 10 minutes. The slurry is then dried in an oven at about 140° C. for 2 hours to remove solvent. The resulting solid mixture is then scraped out and loaded into the reactor between the plugs of quartz wool.

Once loaded into the reactor, the reactor is inserted into the Altamira instrument and furnace and then a temperature and flow program is started. In some embodiment, the total flow is 50 to 100 sccm of gases but this can be varied and programmed with time. In one embodiment, the temperatures range from 500° C. to 900° C. The reactant gases comprise oxygen (diluted with nitrogen) and methane in the case of the OCM reaction and gas mixtures comprising ethane and/or propane with oxygen for oxidative dehydrogenation (ODH) reactions. Other gas mixtures are used for other reactions.

The primary analysis of these oxidation catalysis runs is the Gas Chromatography (GC) analysis of the feed and effluent gases. From these analyses, the conversion of the oxygen and alkane feed gases can easily be attained and estimates of yields and selectivities of the products and by-products can be determined.

The GC method developed for these experiments employs 4 columns and 2 detectors and a complex valve switching system to optimize the analysis. Specifically, a flame ionization detector (FID) is used for the analysis of the hydrocarbons only. It is a highly sensitive detector that produces accurate and repeatable analysis of methane, ethane, ethylene, propane, propylene and all other simple alkanes and alkenes up to five carbons in length and down to ppm levels.

There are two columns in series to perform this analysis, the first is a stripper column (alumina) which traps polar materials (including the water by-product and any oxygenates generated) until back-flushed later in the cycle. The second column associated with the FID is a capillary alumina column known as a PLOT column which performs the actual separation of the light hydrocarbons. The water and oxygenates are not analyzed in this method.

For the analysis of the light non-hydrocarbon gases, a Thermal Conductivity Detector (TCD) may be employed which also employees two columns to accomplish its analysis. The target molecules for this analysis are $CO_2$, ethylene, ethane, hydrogen, oxygen, nitrogen, methane and CO. The two columns used here are a porous polymer column known as the Hayes Sep N which performs some of the separation for the $CO_2$, ethylene and ethane. The second column is a molecular sieve column which uses size differentiation to perform the separation. It is responsible for the separation of $H_2$, $O_2$, $N_2$, methane and CO.

There is a sophisticated and timing sensitive switching between these two columns in the method. In the first 2 minutes or so, the two columns are operating in series but at about 2 minutes, the molecular sieve column is by-passed and the separation of the first 3 components is completed. At about 7 minutes, the columns are then placed back in series and the light gases come off of the sieve according to their molecular size.

The end result is an accurate analysis of all of the aforementioned components from these fixed beds, gas phase reactions. Analysis of other reactions and gases not specifically described above can be performed in a similar manner known to those of skill in the art.

7. Downstream Products

Figure 5:
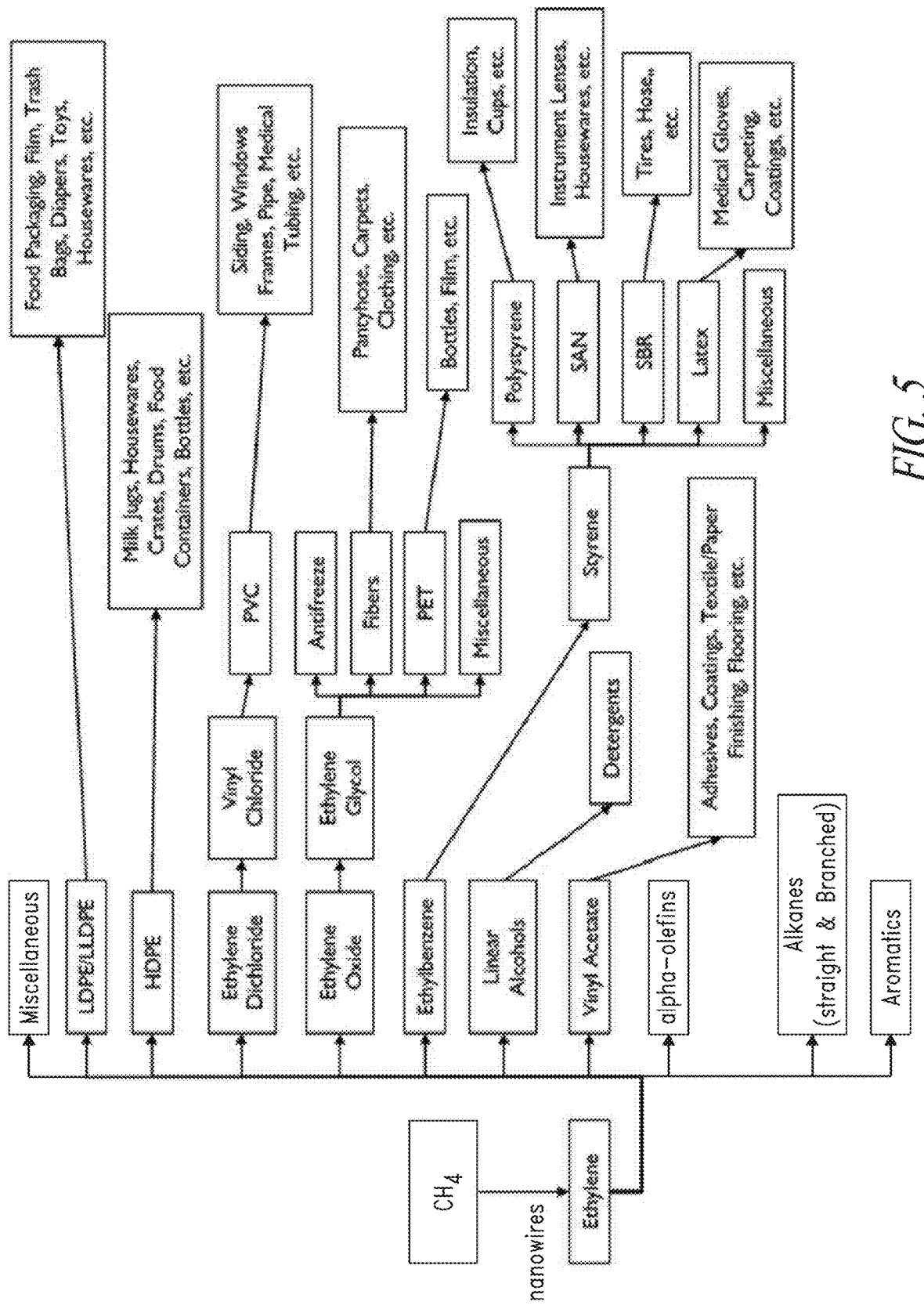
FIG. 5 is a chart showing various downstream products of ethylene.

As noted above, the catalysts disclosed herein are useful in reactions for the preparation of a number of valuable hydrocarbon compounds. For example, in one embodiment the catalysts are useful for the preparation of ethylene from methane via the OCM reaction. In another embodiment, the catalysts are useful for the preparation of ethylene or propylene via oxidative dehydrogenation of ethane or propane respectively. Ethylene and propylene are valuable compounds which can be converted into a variety of consumer products. For example, as shown in FIG. 5, ethylene can be converted into many various compounds including low density polyethylene, high density polyethylene, ethylene dichloride, ethylene oxide, ethylbenzene, linear alcohols, vinyl acetate, alkanes, alpha olefins, various hydrocarbon-based fuels, ethanol and the like. These compounds can then be further processed using methods well known to one of ordinary skill in the art to obtain other valuable chemicals and consumer products (e.g. the downstream products shown in FIG. 5). Propylene can be analogously converted into various compounds and consumer goods including polypropylenes, propylene oxides, propanol, and the like.

Accordingly, in one embodiment the invention is directed to a method for the preparation of C2 hydrocarbons via the OCM reaction, the method comprises contacting a catalyst as described herein with a gas comprising methane. In some embodiments the C2 hydrocarbons are selected from ethane and ethylene. In other embodiments the disclosure provides a method of preparing downstream products of ethylene. The method comprises converting ethylene into a downstream product of ethylene, wherein the ethylene has been prepared via a catalytic reaction employing a catalyst disclosed herein (e.g., OCM). In some embodiments, the downstream product of ethylene is low density polyethylene, high density polyethylene, ethylene dichloride, ethylene oxide, ethylbenzene, ethanol or vinyl acetate. In other embodiments, the downstream product of ethylene is natural gasoline. In still other embodiments, the downstream product of ethylene comprises 1-hexene, 1-octene, hexane, octane, benzene, toluene, xylene or combinations thereof.

In another embodiment, a process for the preparation of ethylene from methane comprising contacting a mixture comprising oxygen and methane at a temperature below 900° C., below 850° C., below 800° C., below 750° C., below 700° C. or below 650° C. with a catalyst as disclosed herein is provided.

In another embodiment, the disclosure provides a method of preparing a product comprising low density polyethylene, high density polyethylene, ethylene dichloride, ethylene oxide, ethylbenzene, ethanol or vinyl acetate or combinations thereof. The method comprises converting ethylene into low density polyethylene, high density polyethylene, ethylene dichloride, ethylene oxide, ethylbenzene, ethanol or vinyl acetate, wherein the ethylene has been prepared via a catalytic reaction employing a catalyst disclosed herein.

In more specific embodiments of the above methods, the ethylene is produced via an OCM or ODH reaction.

In one particular embodiment, the disclosure provides a method of preparing a downstream product of ethylene and/or ethane. For example, the downstream product of ethylene may be a hydrocarbon fuel such as natural gasoline or a $C_4$-$C_{14}$ hydrocarbon, including alkanes, alkenes and aromatics. Some specific examples include 1-butene, 1-hexene, 1-octene, hexane, octane, benzene, toluene, xylenes and the like. The method comprises converting methane into ethylene, ethane or combinations thereof by use of a catalyst, for example any of the catalysts disclosed herein, and further oligomerizing the ethylene and/or ethane to prepare a downstream product of ethylene and/or ethane. For example, the methane may be converted to ethylene, ethane or combinations thereof via the OCM reaction as discussed above.

Figure 6:
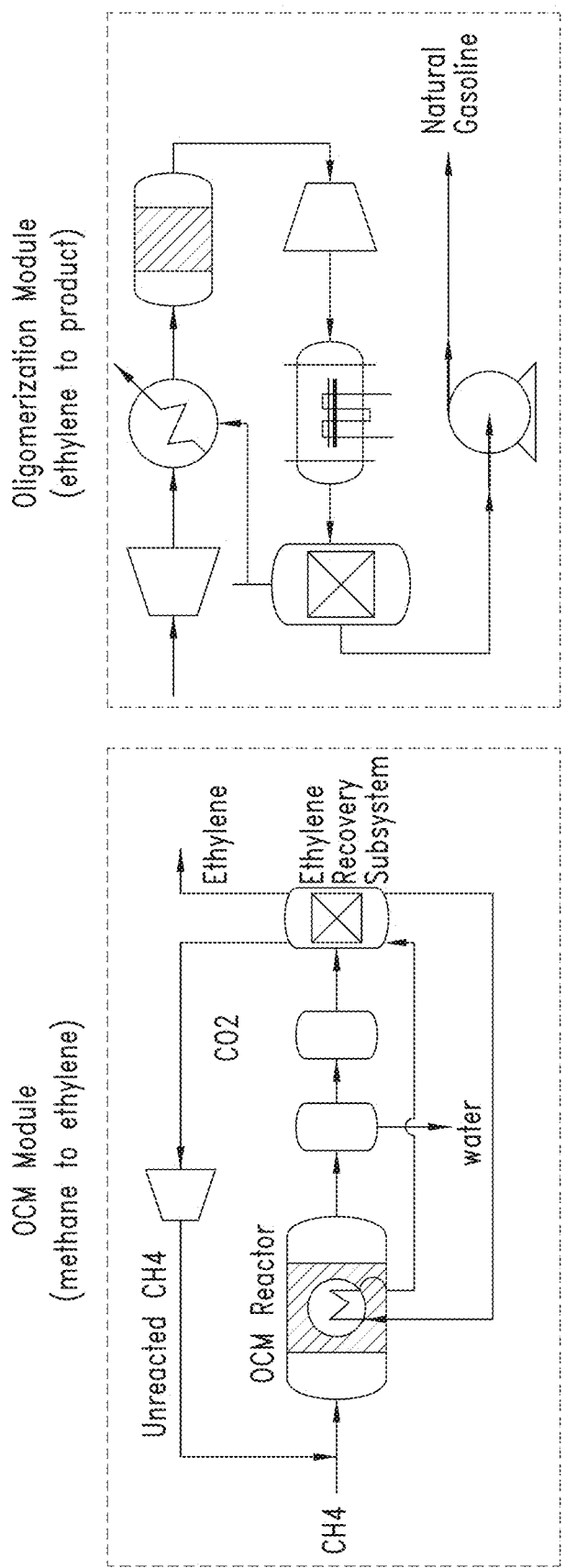
FIG. 6 shows an OCM and ethylene oligomerization module.

As depicted in FIG. 6, the method begins with charging methane (e.g., as a component in natural gas) into an OCM reactor. The OCM reaction may then be performed utilizing a catalyst under any variety of conditions. Water and $CO_2$ are optionally removed from the effluent and unreacted methane is recirculated to the OCM reactor.

Ethylene is recovered and charged to an oligomerization reactor. Optionally the ethylene stream may contain $CO_2$, $H_2O$, $N_2$, ethane, C3's and/or higher hydrocarbons. Oligomerization to higher hydrocarbons (e.g., $C_4$-$C_{14}$) then proceeds under any number of conditions known to those of skill in the art. For example oligomerization may be effected by use of any number of catalysts known to those skilled in the art. Examples of such catalysts include catalytic zeolites, crystalline borosilicate molecular sieves, homogeneous metal halide catalysts, Cr catalysts with pyrrole ligands or other catalysts. Exemplary methods for the conversion of ethylene into higher hydrocarbon products are disclosed in the following references: Catalysis Science & Technology (2011), 1(1), 69-75; Coordination Chemistry Reviews (2011), 255(7-8), 861-880; Eur. Pat. Appl. (2011), EP 2287142 A1 20110223; Organometallics (2011), 30(5), 935-941; Designed Monomers and Polymers (2011), 14(1), 1-23; Journal of Organometallic Chemistry 689 (2004) 3641-3668; Chemistry—A European Journal (2010), 16(26), 7670-7676; Acc. Chem. Res. 2005, 38, 784-793; Journal of Organometallic Chemistry, 695 (10-11): 1541-1549 May 15, 2010; Catalysis Today Volume 6, Issue 3, January 1990, Pages 329-349; U.S. Pat. Nos. 5,968,866; 6,800,702; 6,521,806; 7,829,749; 7,867,938; 7,910,670; 7,414,006 and Chem. Commun., 2002, 858-859, each of which are hereby incorporated in their entirety by reference.

In certain embodiments, the exemplary OCM and oligomerization modules depicted in FIG. 6 may be adapted to be at the site of natural gas production, for example a natural gas field. Thus the natural gas can be efficiently converted to more valuable and readily transportable hydrocarbon commodities without the need for transport of the natural gas to a processing facility.

Referring to FIG. 6, "natural gasoline" refers to a mixture of oligomerized ethylene products. In this regard, natural gasoline comprises hydrocarbons containing 5 or more carbon atoms. Exemplary components of natural gasoline include linear, branched or cyclic alkanes, alkenes and alkynes, as well as aromatic hydrocarbons. For example, in some embodiments the natural gasoline comprises 1-pentene, 1-hexene, cyclohexene, 1-octene, benzene, toluene, dimethyl benzene, xylenes, napthalene, or other oligomerized ethylene products or combinations thereof. In some embodiments, natural gasoline may also include C3 and C4 hydrocarbons dissolved within the liquid natural gasoline. This mixture finds particular utility in any number of industrial applications, for example natural gasoline is used as feedstock in oil refineries, as fuel blend stock by operators of fuel terminals, as diluents for heavy oils in oil pipelines and other applications. Other uses for natural gasoline are well-known to those of skill in the art.

The following examples are provided for purposes of illustration, not limitation.

EXAMPLES

Example 1

Preparation of a Catalyst Comprising La, Nd and Sr

Equimolar aqueous solutions of strontium nitrate, neodymium nitrate, and lanthanum nitrate were prepared. Aliquots of each solution were mixed together to prepare a desired formulation of $La_xNd_ySr_z$ where x, y, z represent mole fractions of total metal content in moles. Representative examples of formulations are: $La_{50}Nd_{30}Sr_{20}$, $La_{52}Nd_{45}Sr_{05}$, $La_{75}Nd_{22}Sr_{03}$, and the like. A solution of citric acid was added to the metal salt mixture so that citric acid mole/metal mole ratio was 3:1. Ethylene glycol was then added to the citric acid/metal salt solution so that the ethylene glycol/citric acid mole ratio was 1:1. The solution was stirred at room temperature for 1 h. The solution was placed in a 130° C. oven for 15 h to remove water and to promote resin formation. After 15 h, a hard dark resin was observed. The resin was placed in a furnace and heated to 500° C. for 8 h. The remaining material was heated to 650° C. for 2 h to yield the desired product.

Other catalysts are prepared according to an analogous procedure. For example, catalysts comprising La and Sm as well as catalysts comprising La and Ce can be prepared according to the above general procedure. Furthermore, catalysts comprising La/Ce/Nd/Sr, La/Bi/Sr, Nd/Sr, La/Sr, La/Bi/Ce/Nd/Sr can also be prepared in this manner.

Catalysts comprising support materials can also be prepared by coprecipitation according to the above method. For example, rare earth oxides on on MgO, CaO or $AlPO_4$ supports can be prepared. Specific examples include, Nd/Sr/CaO (i.e., a catalyst comprising Nd and Sr on a CaO support).

Example 2

Preparation of a Sr Doped $Nd_2O_3$ Catalyst

To prepare this catalyst at a level of 20 mole % Sr (based on total moles of $Nd_2O_3$), 3.0 g of $Nd_2O_3$ bulk from Alfa Chemicals was slurried in a solution formed by dissolving 0.378 g of $Sr(NO_3)_2$ in about 20 ml of DI water. The slurry was stirred at room temperature for about 30 minutes to ensure that the $Sr(NO_3)_2$ dissolved. The slurry was then moved to an evaporating dish and placed into an oven at 100-140° C. for 2-3 hours to ensure dryness. The solids were then calcined in a furnace by ramping up to 350° C. at 5° C./min and holding for 2 hours and then ramping again at the same rate to 700° C. and holding for 4 hours. It was then cooled to room temperature, ground and sieved to a particle size range of 180 μm to 250 μm.

Example 3

Preparation of a LiMgMnB Catalyst

The following fine powders were mixed together: 1.072 g of Mn2O3 (325 mesh); 1.418 g of MgO (325 mesh); 0.384 g Boric acid powder and 0.164 g LiOH anhydrous. This corresponds to an approximate molar ratio of Li:B:Mn:Mg of 1:1:2:5. The powders were then added to about 20 ml of water, resulting in a black slurry. This slurry was stirred for about an hour to dissolve all of the LiOH and boric acid and then dried for several hours at about 120° C. In a crucible, the resulting powder was ground as fine as possible and calcined according to the following schedule. Ramp to 350° C. at 5° C./min and hold for 120 minutes. Ramp to 950° C. at 5° C./min and hold for at least 8 hours. Cool to room temperature and repeat grinding. In certain embodiments, the catalyst was sieved to between 150-300 μm to minimize pressure drop and then the catalyst was ready for catalyst testing.

Example 4

Preparation of Doped LiMgMnB Catalysts

Four doped samples of the LiMgMnB catalyst prepared according to Example 3 were prepared as follows:

1. 1.00 g (+−0.1 g) of uncalcined LiMgMnB were weighed into a small beaker. 0.060 g (+−0.01 g) of NaCl and 0.240 g of cobalt chloride were added to this beaker. Approximately 15 ml of DI water was added and the resulting slurry was stirred for 20 minutes. The slurry was placed in a ceramic evaporating dish (small) and dried in an oven at about 110-140° C. overnight.

2. Sample 2 was prepared in a manner analogous to sample one, except that 0.060 g of cobalt chloride was used.

3. Sample 3 was prepared in a manner analogous to sample one, except that 0.015 g (+−0.01 g) NaCl was used.

4. Sample 4 was prepared in a manner analogous to sample one, except that 0.015 g (+−0.01 g) NaCl and 0.060 g of cobalt chloride were used.

After the 4 dishes were dry, they were placed in the muffle furnace and programmed to run at 350° C. for 2 hours followed by 650° C. for 2 hours followed by 950° C. for 8 hours before cooling to near room temperature. After cooling the dishes, the solids were ground with a pestle in the dish and run through a Gilson sieve shaker. The sieves used were, from top to bottom, 300 um, 212 μm, 106 μm and 75 μm. The 106 fraction was collected and put in a vial, and the combined other fractions were placed in another vial.

Example 5

Preparation of NaMnW Catalysts 0.2 g of Davisil 645 Silica was mixed with 0.0365 g of Manganese nitrate tetrahydrate ($Mn(NO_3)_2$) and 0.0179 g of Sodium tungstate ($Na_2WO_4$) in a beaker with enough water to make a stirrable slurry. The mixture was stirred on a hotplate at about 60-80° C. for 3 hours, adding water as necessary to keep from drying. The resultant slurry was placed in a 100-140° C. oven overnight to dry prior to calcining in a ceramic evaporating dish with the following schedule: ramp 5° C./min to 400° C. and hold for 2 hours, ramp 5° C./min to 850° C. and hold for 8 hours.

0.410 g of $ZrO_2$ powder were mixed with 0.0365 g of Manganese nitrate tetrahydrate ($Mn(NO_3)_2$) and 0.0179 g of Sodium tungstate ($Na_2WO_4$) in a beaker with enough water to make a stirrable slurry. The mixture was stirred on hotplate at about 60-80° C. for 3 hours, adding water as necessary to keep from drying. The resultant slurry was placed in a 100-140° C. oven overnight to dry prior to calcining in a ceramic evaporating dish with the following schedule: ramp 5° C./min to 400° C. and hold for 2 hours, ramp 5° C./min to 850° C. and hold for 8 hours.

Example 6

Figure 7:
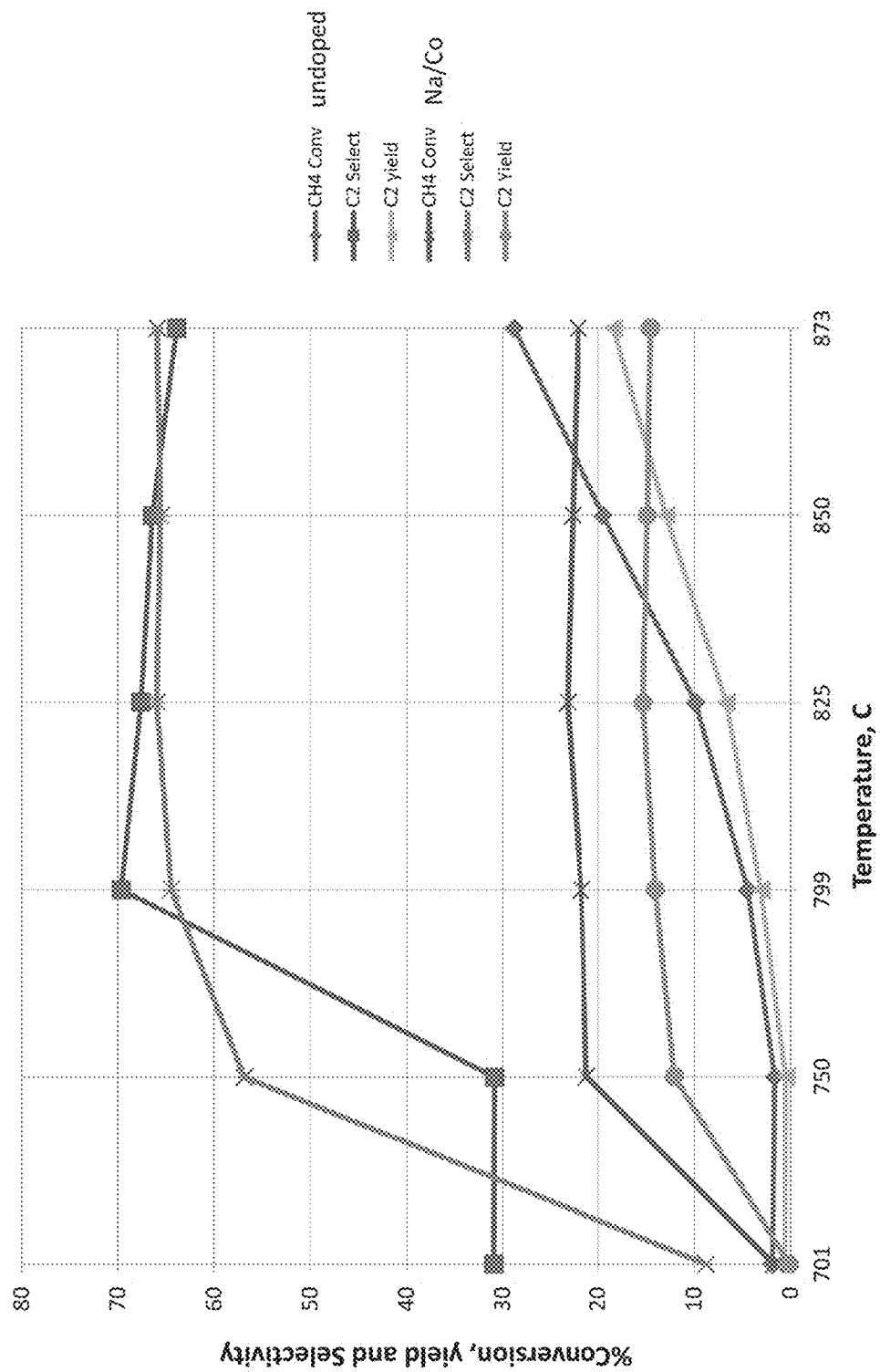
FIG. 7 is a plot of conversion, selectivity and yield of an OCM reaction catalyzed with a doped and undoped catalyst.

OCM Catalyzed with LiMgMnB Mixed Oxide and Na—Co Doped LiMgMnB Mixed Oxide 50 mg of prepared samples from examples 3 and 4 were placed into a reactor tube (4 mm ID diameter quartz tube with a 0.5 mm ID capillary downstream), which was then tested in an Altamira Benchcat 200. The gas flows were held constant at 46 sccm methane and 54 sccm air, which correspond to a $CH_4/O_2$ ratio of 4 and a feed gas-hour space velocity (GHSV) of about 130000 $h^{-1}$. The reactor temperature was varied from 700° C. to 750° C. in a 50° C. increment and from 750° C. to 875° C. in 25° C. increments. The vent gases were analyzed with gas chromatography (GC) at each temperature level. FIG. 7 shows the onset of OCM between 700° C. and 750° C. for the Na/Co doped LiMnMgB mixed oxide sample whereas the onset of the OCM is between 800° C. and 825° C. for the undoped LiMnMgB mixed oxide catalyst. The C2 selectivity, methane conversion and C2 yield at 750° C. for the doped catalyst were 57%, 22% and 12%, respectively. The undoped LiMnMgB mixed oxide catalyst reached 12% C2 yield at 850° C.

Example 7

Figure 8:
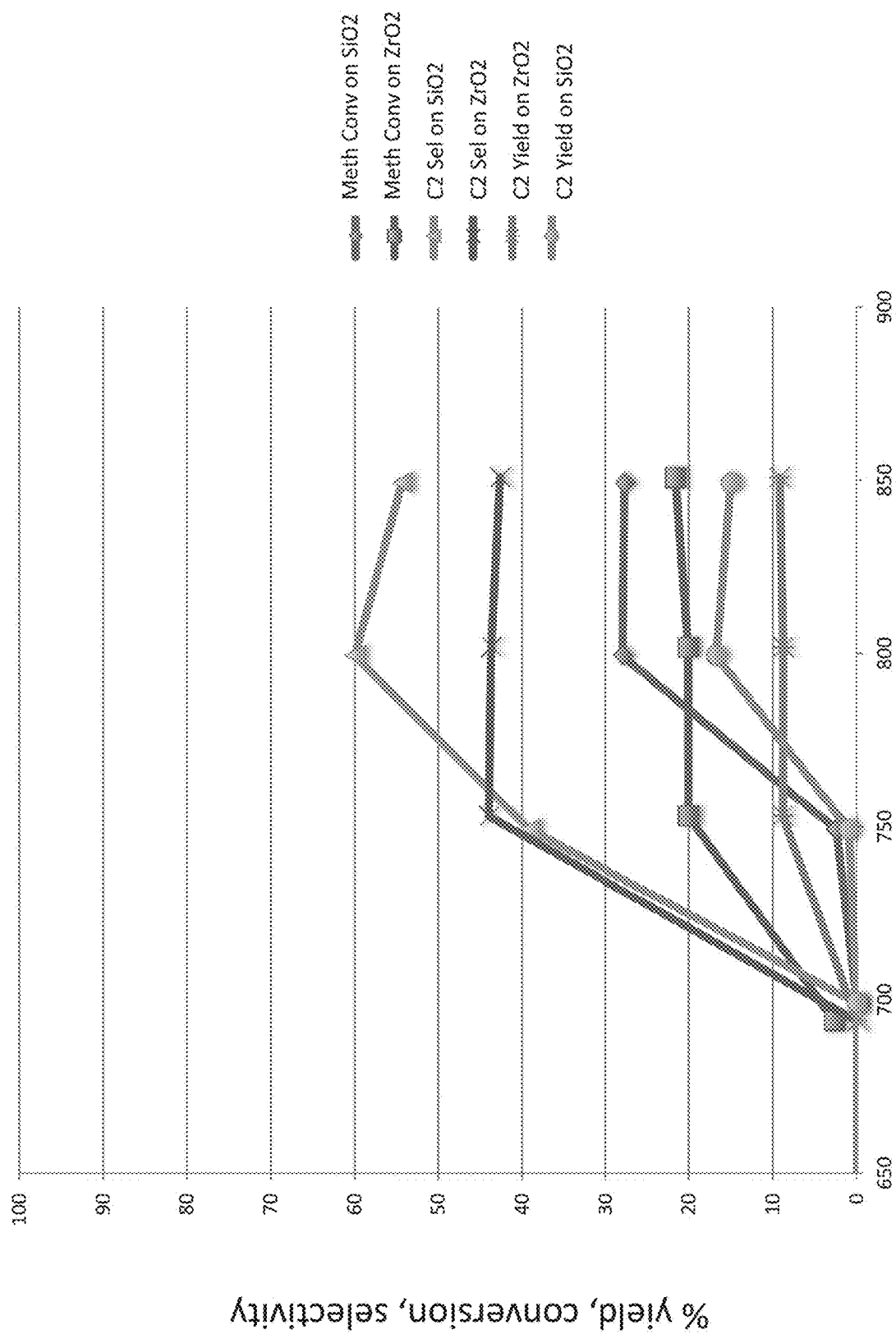
FIG. 8 is a plot of conversion, selectivity and yield of an OCM reaction catalyzed comparing a catalyst on two different supports.

OCM Using a $NaMnWO_4$ Catalyst Supported on Silica or Zirconia 50 mg of each sample from example 5 were placed into a reactor tube (4 mm ID diameter quartz tube with a 0.5 mm ID capillary downstream), which was then tested in an Altamira Benchcat 200. The gas flows were held constant at 46 sccm methane and 54 sccm air, which correspond to a $CH_4/O_2$ ratio of 4 and a feed gas-hour space velocity (GHSV) of about 130000 $h^{-1}$. The reactor temperature was varied from 650° C. to 900° C. in a 50° C. increment. The vent gases were analyzed with gas chromatography (GC) at each temperature level. FIG. 8 shows the onset of OCM between 700° C. and 750° C. for the $NaMnWO_4$ supported on Zirconia whereas the onset of the OCM is between 750° C. and 800° C. for the $NaMnWO_4$ supported on Silica. The C2 selectivity, methane conversion and C2 yield at 750° C. for the Zirconia supported catalyst were 45%, 20% and 9%, respectively.

Example 8

High Throughput Screening of OCM Catalyzed by Catalyst Libraries

The effect of doping of bulk rare earth oxides or other mixed oxides was evaluated by preparing libraries of doped catalysts on a quartz wafer etched to form a 16×16 well area (4 ml per well) in which about 1 mg of the base catalyst (e.g., bulk rare earth oxide) is added. These oxides were first suspended in slurries with Butanol then the slurries were distributed to the wells using automated liquid dispensing. The wafer library was then dried.

Aqueous salt solutions of 49 different metals were prepared and added to the wells in a pre-set pattern design with 4 repeats of each doping in 4 different area of the wafer. The list of metal salts evaluated was as follows: $Al(NO_3)_3$, $CuCl$, $CsCl$, $BaCl_2$, $CeCl_3$, $Ga(NO_3)_3$, $InCl_3$, $HfCl_2O$, $Fe(NO_3)_3$, $CrCl_3$, $LaCl_3$, $RuCl_3$, $SmCl_3$, $EuCl_3$, $YCl_3$, $Sr(NO_3)_2$, $ZrOC_2$, $TaCl_5$, $RhAcAc$, $Be(NO_3)_2$, $AuCl_4H$, $NaCl$, $NiCl_2$, $CoCl_2$, $SbCl_3$, $Ba(NO_3)_2$, $VCl_3$, $PrCl_3$, $AgNO_3$, $TeCl_4$, $ErCl_3$, $Tb(NO_3)_3$, $HfCl_2O$, $NaO_4W$, $IrCl_3$, $Mn(NO_3)_2$, $Gd(NO_3)_3$, $LiOH$, $Rb(NO_3)$, $Ca(NO_3)_2$, $Lu(NO_3)_3$, $KNO_3$, $Yb(NO_3)_3$, $H_3BO_3$, $(NH_4)_6Mo_7O_{24}$, $ScCl_3$, $NdCl_3$, $Pd(NO_3)_2$, $Mg(NO_3)_2$, $Te(OH)_4$, $(NH_4)_2TiO(C_2O_4)_2$, $NbCl_5$ The wafer was calcined again after doping at 700° C. for 4 hours. Testing of the activity of the doped catalysts was conducted in a Scanning Mass Spectrometer, which allows to heat up at set temperature individual wells on the wafer while flowing a reactant mixture on top of the heated well. Reaction products were aspirated through a glass capillary and analysed using a mass spectrometer. The gas mixture in contact with the catalytic material was comprised of Methane, Oxygen, Argon with a 4/1/1 molar ratio.

The products analysed with the mass spectrometer were: $H_2O$, $CO_2$, $CO$, $C_2H_6$, $O_2H_4$, $CH_4$ and $O_2$. Test temperatures were typically varied from 600° C. to 800° C. in 50° C. increment with a one minute hold at each temperature.

In the following examples the relative Ethane and $CO_2$ concentrations are plotted for the gas effluent collected at different temperatures for different catalyst compositions. These graphs provide the ability to quickly compare the activity and selectivity of multiple catalysts within a catalyst library. The higher the ethane concentration at a given $CO_2$ concentration the more selective the catalyst is. The lower the $CO_2$ concentration at a given ethane concentration the more selective the catalyst is. The undoped samples results are shown in grey for comparison in FIGS. 10 to 14 for comparison.

Example 8-a

Figure 9:
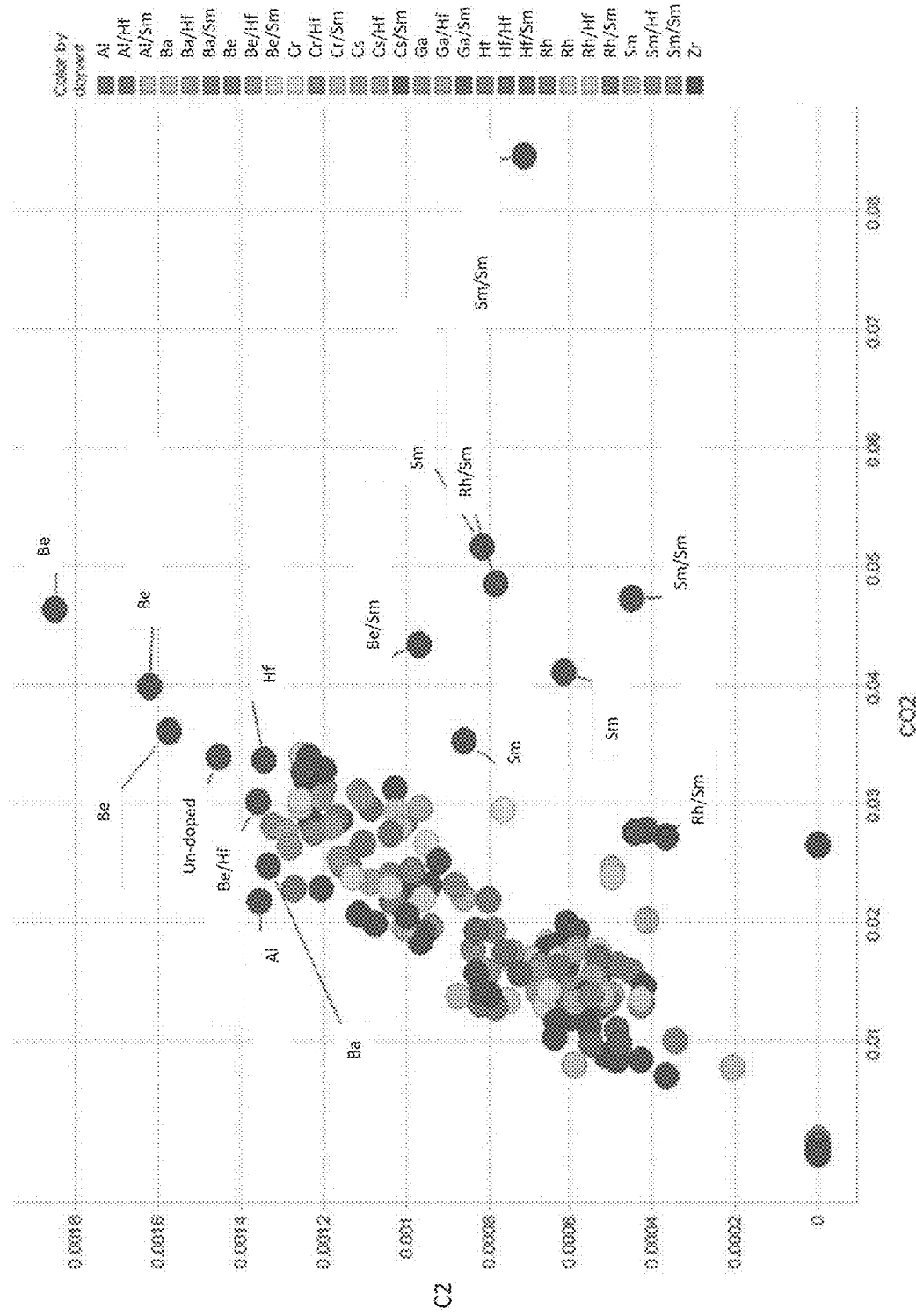
FIG. 9 depicts the results of high-throughput screening on a doped Co/Na/LiMnMgB library.
Figure 10:
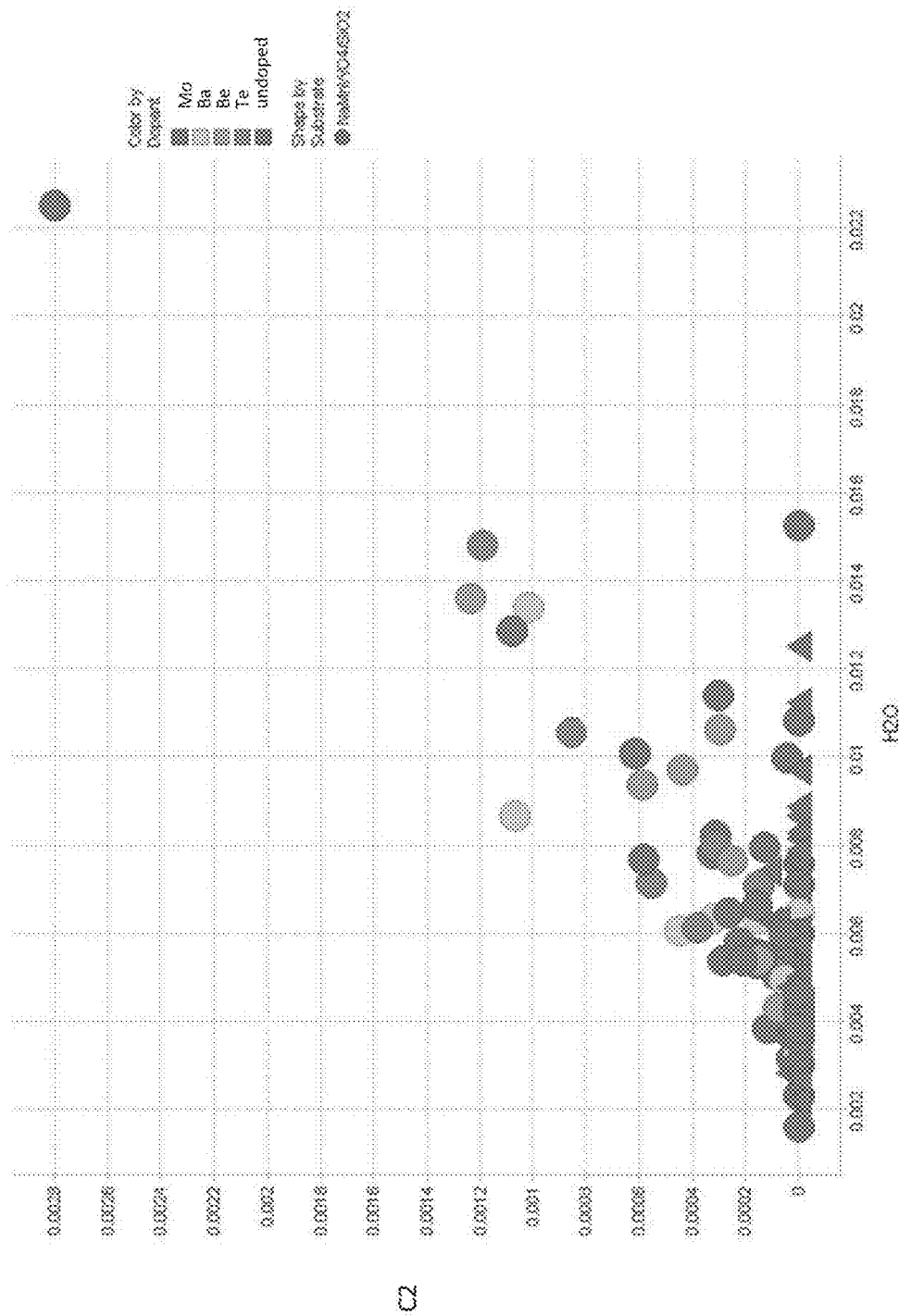
FIG. 10 depicts the results of high-throughput screening on a doped $MnWO_4$ on silica library.
Figure 11:
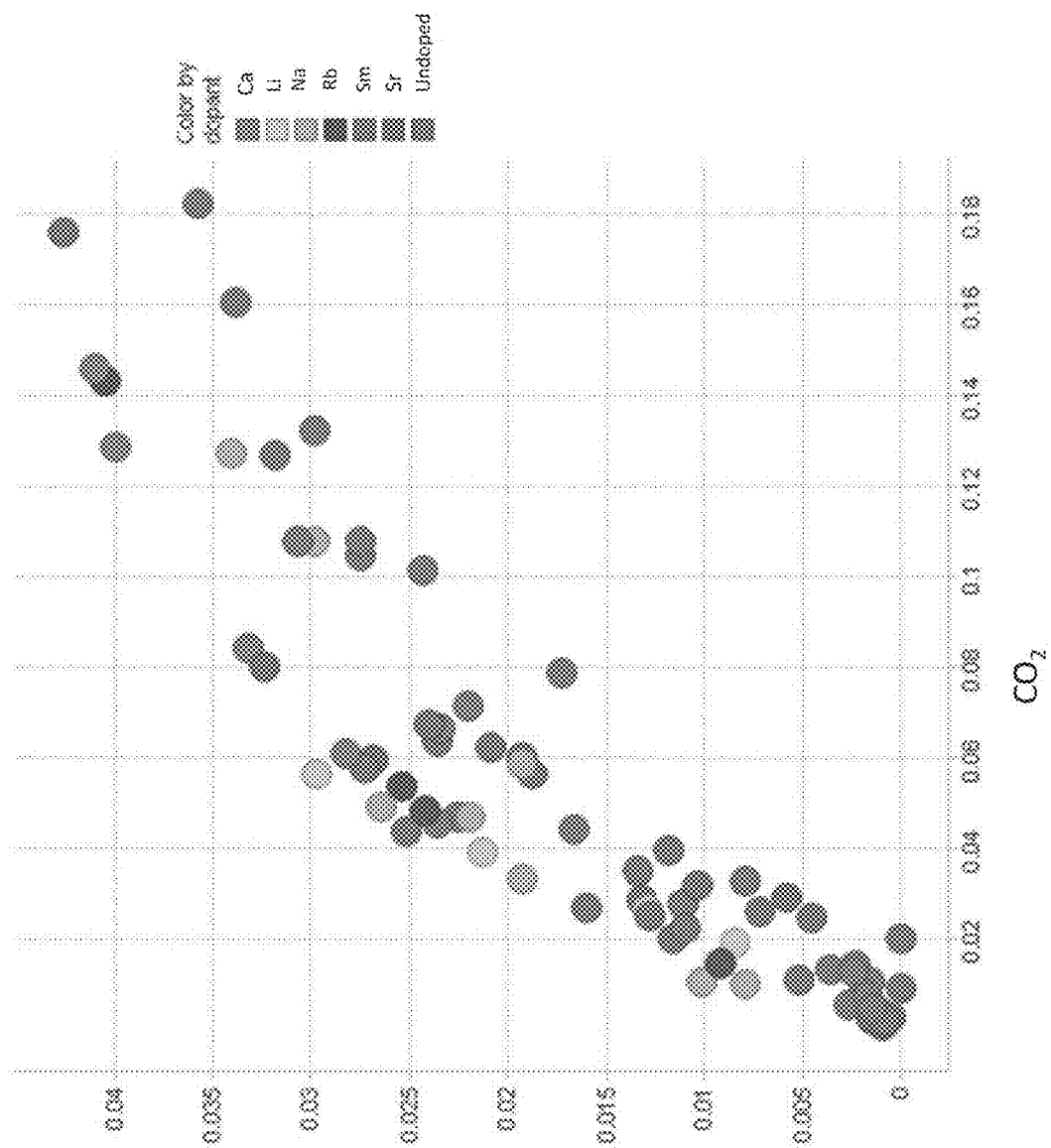
FIG. 11 depicts the results of high-throughput screening on a doped $Nd_2O_3$ library.
Figure 12:
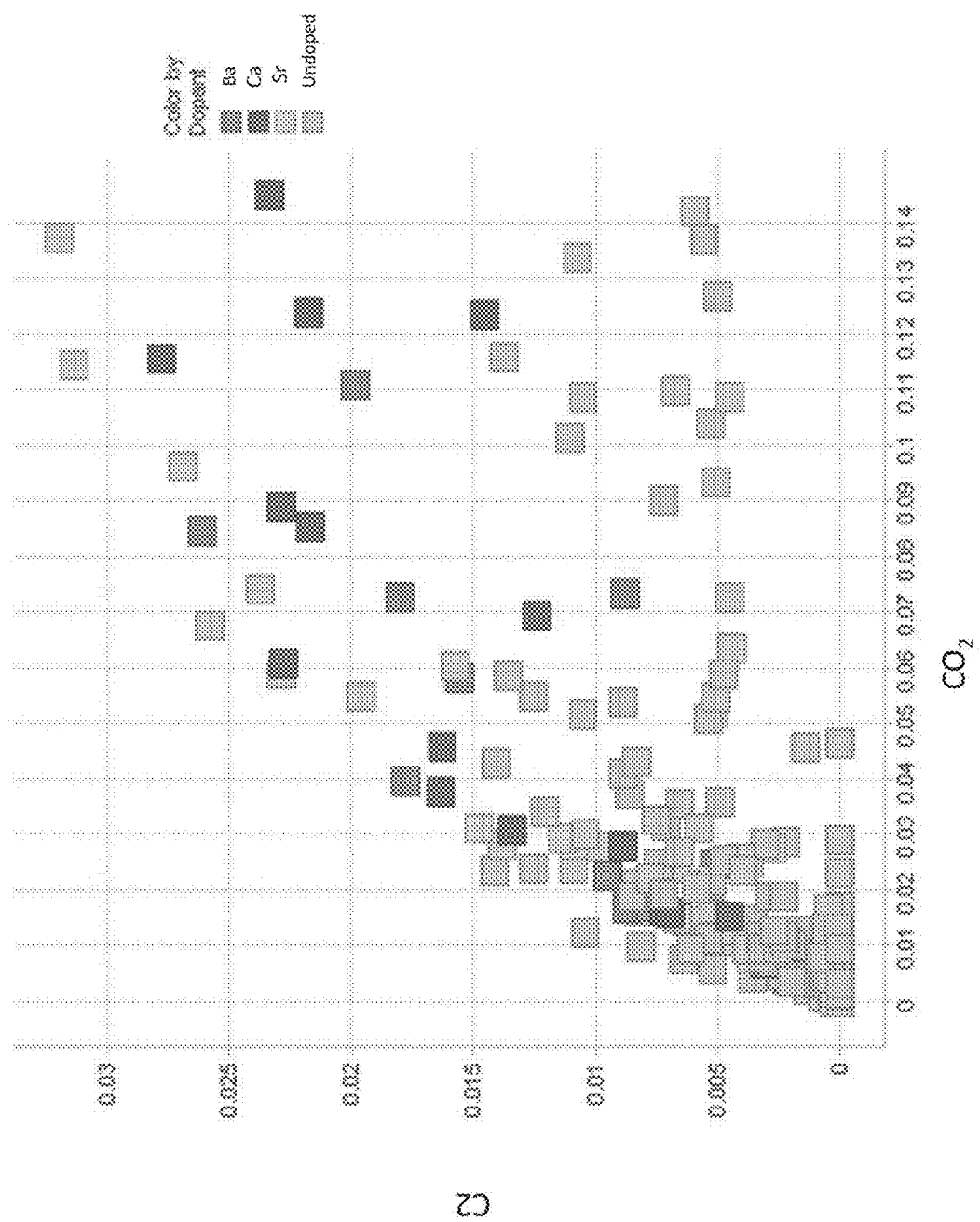
FIG. 12 depicts the results of high-throughput screening on a doped $Yb_2O_3$ library.
Figure 13:
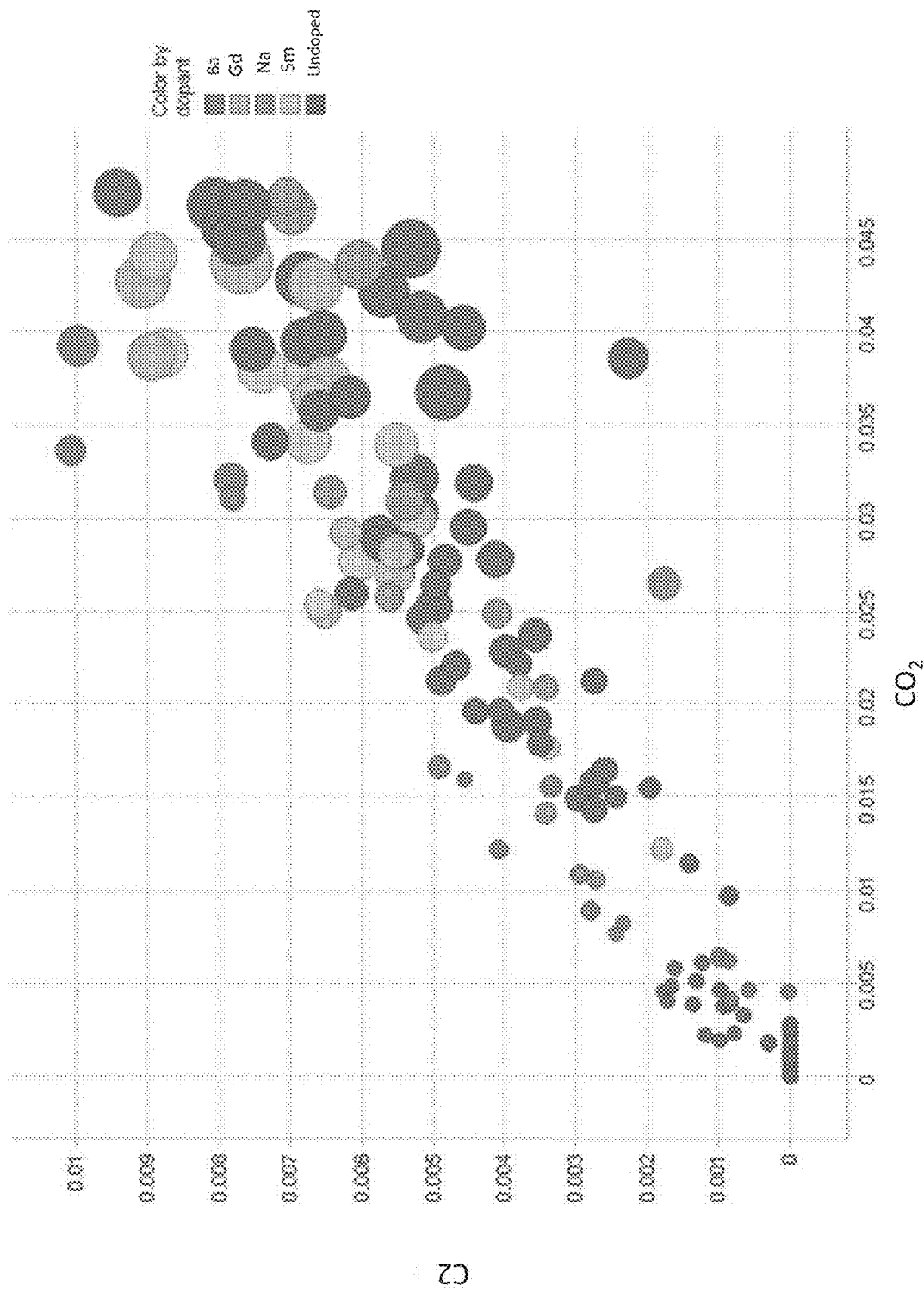
FIG. 13 depicts the results of high-throughput screening on a doped $Eu_2O_3$ library.
Figure 14:
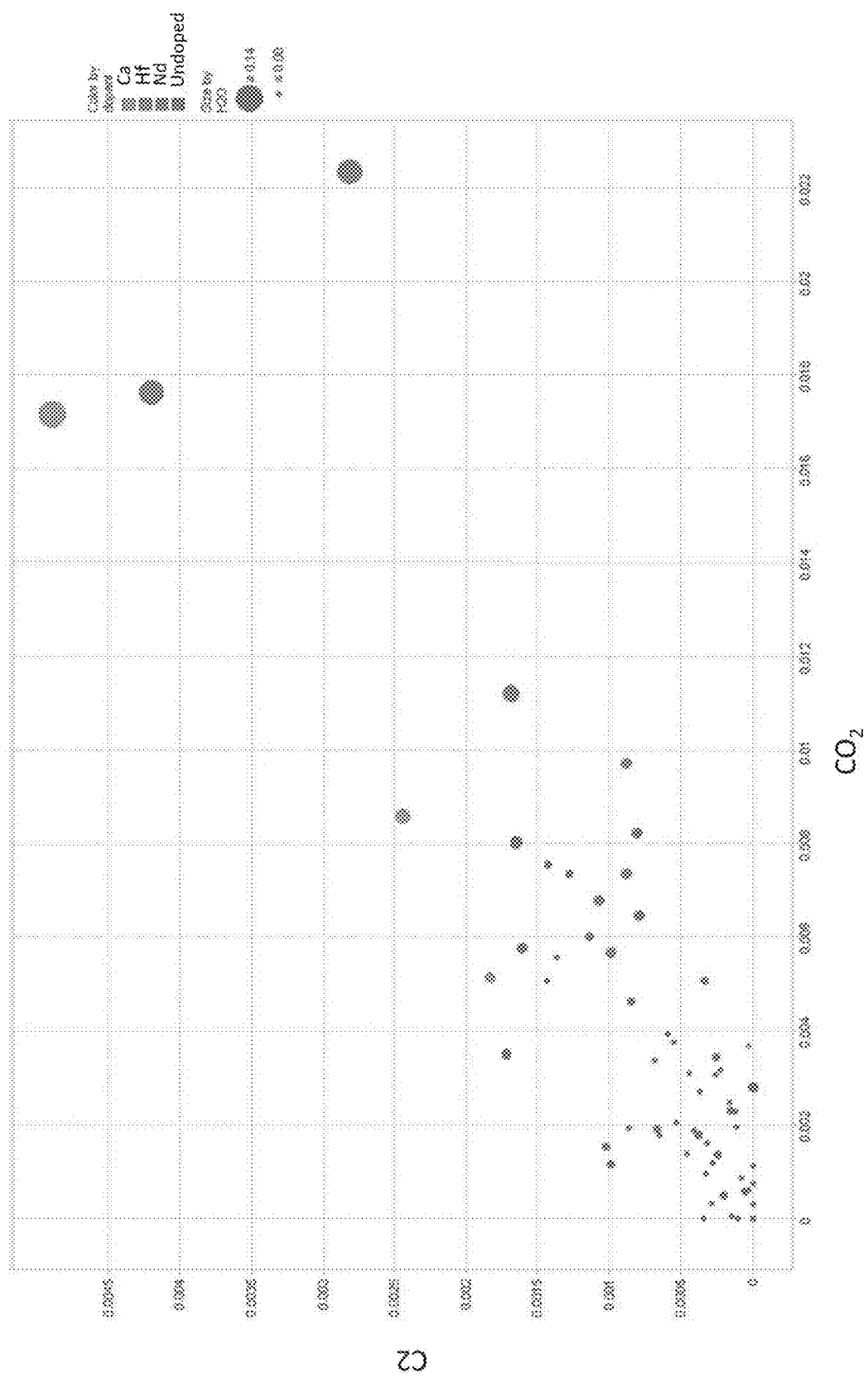
FIG. 14 depicts the results of high-throughput screening on a doped $La_2O_3$ library.

Doped Co/Na/LiMnMgB library. A SMS wafer with a base oxide from example 4-1 was prepared and tested as described above. The results of the test are presented in FIG. 9. Be, Ba, Al, Hf dopants were found to promote the Co/Na/LiMnMgB catalyst activity further without affecting the selectivity towards higher hydrocarbons.

Example 8-b

Doping of MnW on Silica library. A SMS wafer with a silica supported oxide from Example 5 was prepared and tested as described above. The results of the test are presented in FIG. 10. Mo, Be, Ba, Te dopants were found to promote the OCM activity of the MnW on Silica catalyst.

Example 8-c

Doping of $Nd_2O_3$ library. A SMS wafer with bulk $Nd_2O_3$ was prepared and tested as described above. The results of the test are presented in FIG. 11. Ca, Li, Na, Rb, Sm, Sr dopants were found to promote the OCM activity of the $Nd_2O_3$ catalyst and improved higher hydrocarbon selectivity compared to undoped $Nd_2O_3$ catalyst tested under the same conditions.

Example 8-d

Doping of $Yb_2O_3$ library. A SMS wafer with bulk $Yb_2O_3$ was prepared and tested as described above. The results of the test are presented in FIG. 12. Ba, Ca, Sr dopants were found to promote the OCM activity of the $Yb_2O_3$ catalyst and improved higher hydrocarbon selectivity compared to undoped $Yb_2O_3$ catalyst tested under the same conditions.

Example 8-e

Doping of Eu2O3 library. A SMS wafer with bulk $Eu_2O_3$ was prepared and tested as described above. The results of the test are presented in FIG. 13. Na, Ba, Gd, Sm dopants were found to promote the OCM activity of the $Eu_2O_3$ catalyst compared to undoped $Eu_2O_3$ catalyst tested under the same conditions.

Example 8-f

Doping of $La_2O_3$ library. A SMS wafer with bulk $La_2O_3$ was prepared and tested as described above. The results of the test are presented in FIG. 14. Ca, Sr, Nd, Hf dopants were found to promote the OCM activity of the $La_2O_3$ catalyst compared to undoped $La_2O_3$ catalyst tested under the same conditions. In addition to the list of OCM activators, Rh, Fe, Pr, Mn, Ir doping was found to promote unselective oxidation of methane whereas Ba, Te, V, Li doping was found to suppress methane activation.

Example 9

OCM Activity of Various Catalysts

Exemplary catalysts comprising $La_2O_3$, $Nd_2O_3$ or $La_3NdO_6$ with one, two, three or four different dopants selected from Eu, Na, Sr, Ho, Tm, Zr, Ca, Mg, Sm, W, La, K, Ba, Zn, and Li, were prepared and tested for their OCM activity according to the general procedures described in the above examples. Each of the exemplary catalysts produced a C2 yield above 10%, a C2 selectivity above 50%, and a $CH_4$ conversion above 20%, when tested as OCM catalysts at 650° C. or lower at pressures ranging from 1 to 10 atm.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A catalyst comprising a mixed oxide of a lanthanide and tungsten, wherein the catalyst further comprises a sodium dopant and at least one doping element from groups 2, 4-15, lanthanides or combinations thereof, wherein the catalyst comprises a $C_2$ selectivity of greater than 50% and a methane conversion of greater than 20% when the catalyst is employed as a heterogeneous catalyst in the oxidative coupling of methane at a temperature of 750° C. or less.

2. The catalyst of claim 1, wherein the lanthanide is Ce, Pr, Nd, La, Eu, Sm or Yb.

3. The catalyst of claim 1, wherein the at least one doping element is Fe, Co, Mn, Cu, Ni, Sr, Ga, Zr, Pb, Zn, Cr, Pt, Al, Nb, La, Ba, Bi, Sn, In, Ru, P or combinations thereof.

4. The catalyst of claim 1, wherein the $C_2$ selectivity is greater than 60% when the catalyst is employed as a heterogeneous catalyst in the oxidative coupling of methane at a temperature of 750° C. or less.

5. The catalyst of claim 1, wherein the $C_2$ yield is greater than 10% when the catalyst is employed as a heterogeneous catalyst in the oxidative coupling of methane at a temperature of 750° C. or less.

6. The catalyst of claim 1, wherein the $C_2$ yield is greater than 15% when the catalyst is employed as a heterogeneous catalyst in the oxidative coupling of methane at a temperature of 750° C. or less.

7. The catalyst of claim 1, wherein the methane conversion is greater than 30% when the catalyst is employed as a heterogeneous catalyst in the oxidative coupling of methane at a temperature of 750° C. or less.

8. The catalyst of claim 1, wherein the oxidative coupling of methane is performed at a temperature of 700° C. or less.

9. The catalyst of claim 1, wherein the oxidative coupling of methane is performed at total reaction pressures ranging from 1 atm to 10 atm.

10. The catalyst of claim 1 in combination with a support material.

11. The catalyst of claim 10, wherein the support material comprises $AlPO_4$, $Al_2O_3$, $SiO_2$—$Al_2O_3$, CaO, $TiO_2$, $ZrO_2$, MgO, $SiO_2$, $ZrO_2$, $HfO_2$, $In_2O_3$, SiC or combinations thereof.

12. A method for preparing a downstream product of ethylene, the method comprising converting ethylene into a downstream product of ethylene, wherein the ethylene has been prepared via a reaction employing a catalyst according to claim 1.

13. The method of claim 12, wherein the downstream product of ethylene is low density polyethylene, high density polyethylene, ethylene dichloride, ethylene oxide, ethylbenzene, ethanol or vinyl acetate.

14. The method of claim 12, wherein the downstream product of ethylene comprises 1-hexene, 1-octene, hexane, octane, benzene, toluene, xylene or combinations thereof.

15. A method for the preparation of a downstream product of ethane, ethylene or combinations thereof, the method comprising converting methane into ethane, ethylene or combinations thereof in the presence of the catalyst of claim 1 and further oligomerizing the ethylene to prepare a downstream product of ethylene.

16. The method of claim 15, wherein the downstream product of ethylene is low density polyethylene, high density polyethylene, ethylene dichloride, ethylene oxide, ethylbenzene, ethanol or vinyl acetate.

17. The method of claim 15, wherein the downstream product of ethylene comprises 1-hexene, 1-octene, hexane, octane, benzene, toluene, xylene or combinations thereof.

18. A method for the preparation of ethane, ethylene or combinations thereof, the method comprising contacting the catalyst of claim 1 with a gas comprising methane at a temperature of 750° C. or less.

19. A catalyst comprising a rare earth oxide and two or more dopants, wherein the catalyst comprises a $C_2$ selectivity of greater than 50% and a methane conversion of greater than 20% when the catalyst is employed as a heterogeneous catalyst in the oxidative coupling of methane at a temperature of 750° C. or less, and wherein the dopant comprises Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ca/Cs, Ca/Mg/Na, Hf/Bi, Sr/Sn, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Gd/Ho/Sr, Ca/Sr, Ca/Sr/W, Na/Zr/Eu/Tm, Sr/Ho/Tm/Na, Sr/Pb, Sr/W/Li, Sr/Hf or combinations thereof.

20. The catalyst of claim 19, wherein the rare earth oxide is a rare earth mixed oxide comprising two or more rare earth elements.

21. The catalyst of claim 20, wherein the rare earth elements are selected from the group consisting of La, Nd, Eu, Sm, Yb, Gd and Y.

22. The catalyst of claim 19, where the rare earth oxide comprises a mixed oxide of Y—La, Zr—La, Pr—La, Ce—La or combinations thereof.

23. The catalyst of claim 19, wherein the rare earth oxide comprises $La_{4-x}Ln_xO_6$, wherein x is a number ranging from greater than 0 and less than 4, and Ln is Nd, Eu, Sm, Yb, Gd or Y.

24. The catalyst of claim 23, wherein Ln is Nd.
25. The catalyst of claim 23, wherein Ln is Eu.
26. The catalyst of claim 23, wherein Ln is Sm.
27. The catalyst of claim 23, wherein Ln is Yb.
28. The catalyst of claim 23, wherein Ln is Gd.
29. The catalyst of claim 23, wherein Ln is Y.

30. The catalyst of claim 19, wherein the rare earth oxide comprises $La_2O_3$, $Nd_2O_3$, $Yb_2O_3$, $Eu_2O_3$, $Sm_2O_3$, $Pr_2O_3$ or combinations thereof.

31. The catalyst of claim 19, wherein the catalyst comprises a dopant combination selected from the group consisting of Sr/Sm, Sr/W, Sb/W, Eu/Na, Sr/Na, Mg/Na, Ca/Sr/W, Sr/W/Li and Sr/Sn.

32. The catalyst of claim 31, wherein the dopant is Sr/Sm.
33. The catalyst of claim 31, wherein the dopant is Sr/W.
34. The catalyst of claim 31, wherein the dopant is Sb/W.
35. The catalyst of claim 31, wherein the dopant is Eu/Na.
36. The catalyst of claim 31, wherein the dopant is Sr/Na.
37. The catalyst of claim 31, wherein the dopant is Mg/Na.
38. The catalyst of claim 31, wherein the dopant is Ca/Sr/W.
39. The catalyst of claim 31, wherein the dopant is Sr/W/Li.
40. The catalyst of claim 31, wherein the dopant is Sr/Sn.

41. The catalyst of claim 19 in combination with a support material.

42. The catalyst of claim 41, wherein the support material comprises $AlPO_4$, $Al_2O_3$, $SiO_2$—$Al_2O_3$, CaO, $TiO_2$, $ZrO_2$, MgO, $SiO_2$, $ZrO_2$, $HfO_2$, $In_2O_3$, SiC or combinations thereof.

43. The catalyst of claim 19, wherein the catalyst is a nanowire catalyst.

44. The catalyst of claim 19, wherein the $C_2$ selectivity is greater than 60% when the catalyst is employed as a heterogeneous catalyst in the oxidative coupling of methane at a temperature of 750° C. or less.

45. The catalyst of claim 19, wherein the $C_2$ yield is greater than 10% when the catalyst is employed as a heterogeneous catalyst in the oxidative coupling of methane at a temperature of 750° C. or less.

46. The catalyst of claim 19, wherein the $C_2$ yield is greater than 15% when the catalyst is employed as a heterogeneous catalyst in the oxidative coupling of methane at a temperature of 750° C. or less.

47. The catalyst of claim 19, wherein the methane conversion is greater than 30% when the catalyst is employed as a heterogeneous catalyst in the oxidative coupling of methane at a temperature of 750° C. or less.

48. The catalyst of claim 19, wherein the catalyst comprises a $C_2$ selectivity of greater than 50% and a methane conversion of greater than 20% when the catalyst is employed as a heterogeneous catalyst in the oxidative coupling of methane at an inlet gas temperature of 700° C. or less.

49. A method for preparing a downstream product of ethylene, the method comprising converting ethylene into a downstream product of ethylene, wherein the ethylene has been prepared via a reaction employing a catalyst according to claim 19.

50. The method of claim 49, wherein the downstream product of ethylene is low density polyethylene, high density polyethylene, ethylene dichloride, ethylene oxide, ethylbenzene, ethanol or vinyl acetate.

51. The method of claim 49, wherein the downstream product of ethylene comprises 1-hexene, 1-octene, hexane, octane, benzene, toluene, xylene or combinations thereof.

52. A method for the preparation of a downstream product of ethane, ethylene or combinations thereof, the method comprising converting methane into ethane, ethylene or combinations thereof in the presence of the catalyst of claim 19 and further oligomerizing the ethylene to prepare a downstream product of ethylene.

53. The method of claim 52, wherein the downstream product of ethylene is low density polyethylene, high density polyethylene, ethylene dichloride, ethylene oxide, ethylbenzene, ethanol or vinyl acetate.

54. The method of claim 52, wherein the downstream product of ethylene comprises 1-hexene, 1-octene, hexane, octane, benzene, toluene, xylene or combinations thereof.

55. A method for the preparation of ethane, ethylene or combinations thereof, the method comprising contacting the catalyst of claim 19 with a gas comprising methane at a temperature of 750° C. or less.

56. A catalyst comprising a mixed oxide of a rare earth element and a Group 13 element, wherein the catalyst further comprises one or more Group 2 elements, wherein the catalyst comprises a $C_2$ selectivity of greater than 50% and a methane conversion of greater than 20% when the catalyst is employed as a heterogeneous catalyst in the oxidative coupling of methane at an inlet gas temperature of 700° C. or less.

57. The catalyst of claim 49, wherein the Group 13 element is selected from the group consisting of B, Ga and In.

58. The catalyst of claim 49, wherein the catalyst comprises a $C_2$ selectivity of greater than 50% and a methane conversion of greater than 20% when the catalyst is employed as a heterogeneous catalyst in the oxidative coupling of methane at a temperature of 750° C. or less.

59. A method for preparing a downstream product of ethylene, the method comprising converting ethylene into a downstream product of ethylene, wherein the ethylene has been prepared via a reaction employing a catalyst according to claim 56.

60. The method of claim 59, wherein the downstream product of ethylene is low density polyethylene, high density polyethylene, ethylene dichloride, ethylene oxide, ethylbenzene, ethanol or vinyl acetate.

61. The method of claim 59, wherein the downstream product of ethylene comprises 1-hexene, 1-octene, hexane, octane, benzene, toluene, xylene or combinations thereof.

62. A method for the preparation of a downstream product of ethane, ethylene or combinations thereof, the method comprising converting methane into ethane, ethylene or combinations thereof in the presence of the catalyst of claim 56 and further oligomerizing the ethylene to prepare a downstream product of ethylene.

63. The method of claim 62, wherein the downstream product of ethylene is low density polyethylene, high density polyethylene, ethylene dichloride, ethylene oxide, ethylbenzene, ethanol or vinyl acetate.

64. The method of claim 62, wherein the downstream product of ethylene comprises 1-hexene, 1-octene, hexane, octane, benzene, toluene, xylene or combinations thereof.

65. A method for the preparation of ethane, ethylene or combinations thereof, the method comprising contacting the catalyst of claim 56 with a gas comprising methane at a temperature of 750° C. or less.

* * * * *

UNITED STATES PATENT AND TRADEMARK OFFICE
CERTIFICATE OF CORRECTION

PATENT NO. : 10,654,769 B2
APPLICATION NO. : 15/944665
DATED : May 19, 2020
INVENTOR(S) : Joel M. Cizeron et al.

It is certified that error appears in the above-identified patent and that said Letters Patent is hereby corrected as shown below:

In the Claims

Column 113, Claim 57, Line 19:
"The catalyst of claim 49" should be: -- The catalyst of claim 56 --.

Column 113, Claim 58, Line 22:
"The catalyst of claim 49" should be: -- The catalyst of claim 56 --.

Signed and Sealed this
Eighth Day of September, 2020

Andrei Iancu
*Director of the United States Patent and Trademark Office*